(12) United States Patent
Naidu et al.

(10) Patent No.: US 8,906,929 B2
(45) Date of Patent: Dec. 9, 2014

(54) INHIBITORS OF HUMAN IMMUNODEFICIENCY VIRUS REPLICATION

(71) Applicant: Bristol-Myers Squibb Company, Princeton, NJ (US)

(72) Inventors: B. Narasimhulu Naidu, Durham, CT (US); Manoj Patel, Berlin, CT (US); Stanley D'Andrea, Wallingford, CT (US); Zhizhen Barbara Zheng, Cheshire, CT (US); Timothy P. Connolly, Portland, CT (US); David R. Langley, Meriden, CT (US); Kevin Peese, Haddam, CT (US); Zhongyu Wang, Tolland, CT (US); Michael A. Walker, Durham, CT (US); John F. Kadow, Wallingford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 13/959,268

(22) Filed: Aug. 5, 2013

(65) Prior Publication Data
US 2014/0051692 A1 Feb. 20, 2014

Related U.S. Application Data

(60) Provisional application No. 61/818,572, filed on May 2, 2013, provisional application No. 61/683,772, filed on Aug. 16, 2012.

(51) Int. Cl.
| | |
|---|---|
| C07D 471/04 | (2006.01) |
| C07D 471/22 | (2006.01) |
| C07D 487/04 | (2006.01) |
| A61K 31/535 | (2006.01) |
| A01N 37/18 | (2006.01) |
| A61K 38/00 | (2006.01) |
| A61P 31/18 | (2006.01) |
| C07D 267/22 | (2006.01) |
| C07D 491/22 | (2006.01) |
| A61K 31/5383 | (2006.01) |
| A61K 31/519 | (2006.01) |
| C07D 498/16 | (2006.01) |
| C07D 487/16 | (2006.01) |
| A61K 45/06 | (2006.01) |
| C07D 498/22 | (2006.01) |

(52) U.S. Cl.
CPC .......... *A61K 31/5383* (2013.01); *C07D 491/22* (2013.01); *A61K 31/519* (2013.01); *C07D 498/16* (2013.01); *C07D 487/16* (2013.01); *A61K 45/06* (2013.01); *C07D 498/22* (2013.01)
USPC .......... 514/257; 514/229.5; 514/3.8; 540/469

(58) Field of Classification Search
None
See application file for complete search history.

(56) References Cited

U.S. PATENT DOCUMENTS

| | | | |
|---|---|---|---|
| 7,939,545 B2 | 5/2011 | Tsantrizos et al. | |
| 7,956,068 B2 * | 6/2011 | Carson et al. ................. | 514/301 |
| 8,338,441 B2 | 12/2012 | Yoakim et al. | |
| 8,354,429 B2 | 1/2013 | Tsantrizos et al. | |
| 8,377,960 B2 | 2/2013 | Tsantrizos et al. | |
| 8,461,180 B2 | 6/2013 | Tsantrizos et al. | |
| 8,629,276 B2 | 1/2014 | Walker et al. | |
| 8,633,200 B2 | 1/2014 | Pendri et al. | |
| 2011/0207626 A1 | 8/2011 | Inazawa et al. | |
| 2012/0129840 A1 | 5/2012 | Chaltin et al. | |
| 2012/0316161 A1 | 12/2012 | Carlens et al. | |
| 2013/0203748 A1 | 8/2013 | Naidu et al. | |
| 2013/0231331 A1 | 9/2013 | Pendri et al. | |
| 2013/0237499 A1 | 9/2013 | Zheng et al. | |
| 2014/0051692 A1 | 2/2014 | Naidu et al. | |

FOREIGN PATENT DOCUMENTS

WO  WO 2012/033735     3/2012
WO  WO 2012/033735 A1 *  3/2012

OTHER PUBLICATIONS

Borisy, A.A. et al., "Systematic discovery of multicomponent therapeutics", Proc. Natl. Acad. Sci., vol. 100, No. 13, pp. 7977-7982 (2003).
Bristol-Myers Squibb Company, International Patent Application No. PCT/US14/17070, filed Feb. 19, 2014.
Bristol-Myers Squibb Company, International Patent Application No. PCT/US14/21867, filed Mar. 7, 2014.
Bristol-Myers Squibb Company, International Patent Application No. PCT/US14/22354, filed Mar. 10, 2014.
Bristol-Myers Squibb Company, International Patent Application No. PCT/US14/22405, filed Mar. 10, 2014.

(Continued)

*Primary Examiner* — Jason Sims
*Assistant Examiner* — Tori M Strong
(74) *Attorney, Agent, or Firm* — James Epperson

(57) ABSTRACT

The disclosure generally relates to compounds of formula I, including compositions and methods for treating human immunodeficiency virus (HIV) infection. The disclosure provides novel inhibitors of HIV, pharmaceutical compositions containing such compounds, and methods for using these compounds in the treatment of HIV infection.

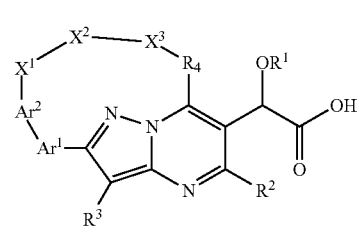

15 Claims, No Drawings

(56) References Cited

OTHER PUBLICATIONS

Bristol-Myers Squibb Company, International Patent Application No. PCT/US14/22501, filed Mar. 10, 2014.
Bristol-Myers Squibb Company, International Patent Application No. PCT/US14/25525, filed Mar. 13, 2014.
Eastman et al., U.S. Appl. No. 61/941,619, filed Feb. 19, 2014.
Naidu, U.S. Appl. No. 61/942,207, filed Feb. 20, 2014.
Naidu, U.S. Appl. No. 61/942,244, filed Feb. 20, 2014.
Naidu et al., U.S. Appl. No. 61/938,856, filed Feb. 12, 2014.
Naidu et al., U.S. Appl. No. 61/940,912, filed Feb. 18, 2014.
Naidu et al., U.S. Appl. No. 61/940,952, filed Feb. 18, 2014.
Naidu et al., U.S. Appl. No. 61/941,931, filed Feb. 19, 2014.
Peese et al., U.S. Appl. No. 61/938,959, filed Feb. 12, 2014.
Peese et al., U.S. Appl. No. 61/941,004, filed Feb. 18, 2014.

\* cited by examiner

INHIBITORS OF HUMAN IMMUNODEFICIENCY VIRUS REPLICATION

CROSS-REFERENCE TO RELATED APPLICATIONS

This application claims the benefit of U.S. Provisional Application Ser. No. 61/818,572 filed May 2, 2013 and U.S. Provisional Application Ser. No. 61/683,772 filed Aug. 16, 2012.

BACKGROUND OF THE INVENTION

The disclosure generally relates to compounds, compositions, and methods for the treatment of human immunodeficiency virus (HIV) infection. The disclosure provides novel inhibitors of HIV, pharmaceutical compositions containing such compounds, and methods for using these compounds in the treatment of HIV infection.

Human immunodeficiency virus (HIV) has been identified as the etiological agent responsible for acquired immune deficiency syndrome (AIDS), a fatal disease characterized by destruction of the immune system and the inability to fight off life threatening opportunistic infections. Recent statistics indicate that as many as 33.3 million people worldwide are infected with the virus (UNAIDS Report on the Global AIDS Epidemic 2010). In addition to the large number of individuals already infected, the virus continues to spread. Estimates from 1998 point to close to 6 million new infections in that year alone. In the same year there were approximately 2.5 million deaths associated with HIV and AIDS.

There are currently a number of antiviral drugs available to combat the infection. These drugs can be divided into classes based on the viral protein they target or their mode of action. In particular, saquinavir, indinavir, ritonavir, nelfinavir atazanavir darunavir, amprenavir, fosamprenavir, lopinavir and tipranavir are competitive inhibitors of the aspartyl protease expressed by HIV. Zidovudine, didanosine, stavudine, lamivudine, zalcitabine, emtricitibine, tenofovir and abacavir are nucleos(t)ide reverse transcriptase inhibitors that behave as substrate mimics to halt viral cDNA synthesis. The non-nucleoside reverse transcriptase inhibitors nevirapine, delavirdine, efavirenz and etravirine inhibit the synthesis of viral cDNA via a non-competitive (or uncompetitive) mechanism. Enfuvirtide and maraviroc inhibit the entry of the virus into the host cell. An HIV integrase inhibitor, raltegravir (MK-0518, Isentress®), has also been approved for use in treatment experienced patients, and it is clear that this class of inhibitors is very effective as part of a combination regimen containing HIV inhibitors of different classes.

Used alone, these drugs are effective in reducing viral replication: However, the effect is only temporary as the virus readily develops resistance to all known agents used as monotherapy. On the other hand, combination therapy has proven very effective at both reducing virus and suppressing the emergence of resistance in a number of patients. In the US, where combination therapy is widely available, the number of HIV-related deaths has dramatically declined (Palella, F. J.; Delany, K. M.; Moorman, A. C.; Loveless, M. O.; Further, J.; Satten, G. A.; Aschman, D. J.; Holmberg, S. D. *N Engl. J. Med.* 1998, 338, 853-860).

Unfortunately, not all patients are responsive and a large number fail this therapy. In fact, initial studies suggest that approximately 30-50% of patients ultimately fail at least one drug in the suppressive combination. Treatment failure in most cases is caused by the emergence of viral resistance. Viral resistance in turn is caused by the replication rate of HIV-1 during the course of infection combined with the relatively high viral mutation rate associated with the viral polymerase and the lack of adherence of HIV-infected individuals in taking their prescribed medications. Clearly, there is a need for new antiviral agents, preferably with activity against viruses already resistant to currently approved drugs. Other important factors include improved safety and a more convenient dosing regimen than many of the currently approved drugs.

Compounds which inhibit HIV replication have been disclosed. See WO2007131350, WO2009062285, WO2009062288, WO2009062289, WO2009062308, WO2010130034, WO2010130842, WO2011015641, WO2011076765, WO2012003497, WO2012003498, WO2012033735, WO2012065963 and WO2012066442.

The invention provides technical advantages, for example, the compounds are novel and are useful in the treatment of HIV. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

The invention encompasses compounds of Formula I, including pharmaceutically acceptable salts, their pharmaceutical compositions, and their use in inhibiting HIV integrase and treating those infected with HIV or AIDS.

One aspect of the invention is a compound of Formula I

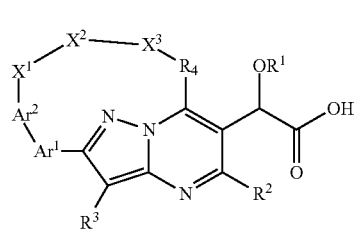

where:
$R^1$ is hydrogen, alkyl, or cycloalkyl;
$R^2$ is hydrogen or alkyl;
$R^3$ is hydrogen, alkyl or halo;
$R^4$ is cycloalkyl or $Ar^3$;
or $R^4$ is azetidinyl, pyrrolidinyl, piperidinyl, piperazinyl, morpholinyl, homopiperidinyl, homopiperazinyl, or homomorpholinyl, and is substituted with 0-3 alkyl substituents;
$R^5$ is hydrogen or alkyl;
$Ar^1$ is phenyl substituted with 0-3 substituents selected from cyano, halo, alkyl, haloalkyl, alkoxy, and haloalkoxy;
$Ar^2$ is phenyl, pyridinyl, pyridazinyl, pyrimidinyl, pyrazinyl, or trizainyl, and is substituted with 0-3 substituents selected from cyano, halo, alkyl, haloalkyl, alkoxy, haloalkoxy, and $CON(R^5)_2$;
$Ar^3$ is phenyl, chromanyl, or dihydrobenzoxazinyl, and is substituted with 0-3 substituents selected from cyano, halo, alkyl, haloalkyl, alkoxy, and haloalkoxy;
$X^1$ is CH, $CH_2$, O, S, or $NR^5$;
$X^2$ is alkylene or alkenylene; and
$X^3$ is CH, $CH_2$, $CH_2O$, O, S, or $NR^5$;
or a pharmaceutically acceptable salt thereof.
Another aspect of the invention is a compound of Formula I
where:
$R^1$ is hydrogen or alkyl;

$R^2$ is hydrogen or alkyl;

$R^3$ is hydrogen, alkyl or halo;

$R^4$ is cycloalkyl or $Ar^3$;

or $R^4$ is azetidinyl, pyrrolidinyl, piperidinyl, piperazinyl, morpholinyl, homopiperidinyl, homopiperazinyl, or homomorpholinyl, and is substituted with 0-3 alkyl substituents;

$R^5$ is hydrogen or alkyl;

$Ar^1$ is phenyl substituted with 0-3 substituents selected from cyano, halo, alkyl, haloalkyl, alkoxy, and haloalkoxy;

$Ar^2$ is phenyl, pyridinyl, pyridazinyl, pyrimidinyl, pyrazinyl, or trizainyl, and is substituted with 0-3 substituents selected from cyano, halo, alkyl, haloalkyl, alkoxy, and haloalkoxy;

$Ar^3$ is phenyl, chromanyl, or dihydrobenzoxazinyl, and is substituted with 0-3 substituents selected from cyano, halo, alkyl, haloalkyl, alkoxy, and haloalkoxy;

$X^1$ is $CH_2$, O, S, or $NR^5$;

$X^2$ is alkylene or alkenylene; and $X^3$ is CH, $CH_2$, O, S, or $NR^5$;

or a pharmaceutically acceptable salt thereof.

Another aspect of the invention is a compound of Formula I where $R^1$ is alkyl; $R^2$ is alkyl; $R^3$ is hydrogen; $R^4$ is $Ar^3$ or is azetidinyl, pyrrolidinyl, piperidinyl, piperazinyl, morpholinyl, homopiperidinyl, homopiperazinyl, or homomorpholinyl substituted with 0-3 alkyl substituents; $Ar^1$ is phenyl substituted with 0-3 substituents selected from cyano, halo, alkyl, haloalkyl, alkoxy, and haloalkoxy; $Ar^2$ is phenyl substituted with 0-3 substituents selected from cyano, halo, alkyl, haloalkyl, alkoxy, and haloalkoxy; $Ar^3$ is dihydrobenzoxazinyl substituted with 0-3 substituents selected from cyano, halo, alkyl, haloalkyl, alkoxy, and haloalkoxy; $X^1$ is $CH_2$ or O; $X^2$ is alkylene or alkenylene; and $X^3$ is CH, $CH_2$ or O; or a pharmaceutically acceptable salt thereof.

Another aspect of the invention is a compound of Formula I where $R^1$ is alkyl; $R^2$ is alkyl; $R^3$ is hydrogen; $R^4$ is $Ar^3$ or is piperidinyl substituted with 0-1 alkyl substituents; $Ar^1$ is phenyl; $Ar^2$ is phenyl; $Ar^3$ is dihydrobenzoxazinyl substituted with 0-1 halo or alkyl substituents; $X^1$ is $CH_2$ or O; $X^2$ is alkylene or alkenylene; and $X^3$ is CH, $CH_2$ or O; or a pharmaceutically acceptable salt thereof.

Another aspect of the invention is a compound of formula I where $R^1$ is alkyl; $R^2$ is alkyl; $R^3$ is hydrogen; $R^4$ is $Ar^3$ or is piperidinyl substituted with 0-1 alkyl substituents; $Ar^1$ is phenyl; $Ar^2$ is phenyl substituted with 0-3 substituents selected from cyano, halo, alkyl, haloalkyl, alkoxy, haloalkoxy, and $CON(R^5)_2$; $Ar^3$ is dihydrobenzoxazinyl substituted with 0-1 halo or alkyl substituents; $X^1$ is $CH_2$ or O; $X^2$ is alkylene or alkenylene; and $X^3$ is CH, $CH_2$ or O; or a pharmaceutically acceptable salt thereof.

Another aspect of the invention is a compound of Formula I where $R^1$ is alkyl, $R^2$ is alkyl and $R^3$ is hydrogen.

Another aspect of the invention is a compound of Formula I where $R^4$ is $Ar^3$ or is azetidinyl, pyrrolidinyl, piperidinyl, piperazinyl, morpholinyl, homopiperidinyl, homopiperazinyl, or homomorpholinyl substituted with 0-3 alkyl substituents.

Another aspect of the invention is a compound of Formula I where $R^4$ is $Ar^3$.

Another aspect of the invention is a compound of Formula I where $R^4$ is azetidinyl, pyrrolidinyl, piperidinyl, piperazinyl, morpholinyl, homopiperidinyl, homopiperazinyl, or homomorpholinyl substituted with 0-3 alkyl substituents.

Another aspect of the invention is a compound of Formula I where $R^4$ is piperidinyl substituted with 0-3 alkyl substituents.

Another aspect of the invention is a compound of Formula I where $Ar^1$ is phenyl substituted with 0-3 substituents selected from cyano, halo, alkyl, haloalkyl, alkoxy, and haloalkoxy.

Another aspect of the invention is a compound of Formula I where $Ar^1$ is phenyl.

Another aspect of the invention is a compound of Formula I where $Ar^2$ is phenyl substituted with 0-3 substituents selected from cyano, halo, alkyl, haloalkyl, alkoxy, haloalkoxy, and $CON(R^5)_2$.

Another aspect of the invention is a compound of Formula I where $Ar^2$ is pyridinyl, pyridazinyl, pyrimidinyl, pyrazinyl, or trizainyl, and is substituted with 0-3 substituents selected from cyano, halo, alkyl, haloalkyl, alkoxy, haloalkoxy, and $CON(R^5)_2$.

Another aspect of the invention is a compound of Formula I where $Ar^3$ is phenyl, chromanyl, or dihydrobenzoxazinyl, and is substituted with 0-3 substituents selected from cyano, halo, alkyl, haloalkyl, alkoxy, and haloalkoxy.

Another aspect of the invention is a compound of Formula I where $Ar^3$ is phenyl substituted with 0-3 substituents selected from cyano, halo, alkyl, haloalkyl, alkoxy, and haloalkoxy.

Another aspect of the invention is a compound of Formula I where $X^1$ is $CH_2$ or O; $X^2$ is alkylene or alkenylene; and $X^3$ is CH, $CH_2$ or O.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Alkylene" means a straight or branched divalent alkyl group composed of 1 to 6 carbons. "Alkenylene" means a straight or branched divalent alkene group composed of 2 to 6 carbons with at least one double bond. "Cycloalkyl" means a monocyclic ring system composed of 3 to 7 carbons. "Hydroxyalkyl," "alkoxy" and other terms with a substituted alkyl moiety include straight and branched isomers composed of 1 to 6 carbon atoms for the alkyl moiety. "Alkyleneoxy" means a straight or branched divalent alkyloxy group composed of 1 to 6 carbons, for example, —$CH_2CH_2CH_2O$—. "Alkenyleneoxy" means a straight or branched divalent alkeneoxy group composed of 2 to 6 carbons with at least one double bond, for example, —CH=$CHCH_2O$—. "Halo" includes fluoro, chloro, bromo, and iodo. "Halo" includes all halogenated isomers from monohalo substituted to perhalo substituted in substituents defined with halo, for example, "Haloalkyl" "haloalkoxy", "halophenyl", and "halophenoxy." "Aryl" includes carbocyclic and heterocyclic aromatic substituents. Substituents which are illustrated by chemical drawing to bond at variable positions on a multiple ring system (for example a bicyclic ring system) are intended to bond to the ring where they are drawn to append. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereomers. Methods of making and separating stereoisomers are known in the art. The invention includes all tautomeric forms of the compounds. The invention includes atropisomers and rotational isomers.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Biological Methods

Inhibition of HIV Replication. A recombinant NL-Rluc virus was constructed in which a section of the nef gene from NL4-3 was replaced with the *Renilla* Luciferase gene. The NL-RLuc virus was prepared by co-transfection of two plasmids, pNLRLuc and pVSVenv. The pNLRLuc contains the NL-Rluc DNA cloned into pUC18 at the PvuII site, while the pVSVenv contains the gene for VSV G protein linked to an LTR promoter. Transfections were performed at a 1:3 ratio of pNLRLuc to pVSVenv in 293T cells using the LipofectAMINE PLUS kit from Invitrogen (Carlsbad, Calif.) according to the manufacturer, and the pseudotype virus generated was titered in MT-2 cells. For susceptibility analyses, the titrated virus was used to infect MT-2 cells in the presence of compound, and after 5 days of incubation, cells were processed and quantitated for virus growth by the amount of expressed luciferase. This provides a simple and easy method for quantitating the extent of virus growth and consequently, the antiviral activity of test compounds. Luciferase was quantitated using the Dual Luciferase kit from Promega (Madison, Wis.).

Susceptibility of viruses to compounds was determined by incubation in the presence of serial dilutions of the compound. The 50% effective concentration ($EC_{50}$) was calculated by using the exponential form of the median effect equation where $(Fa)=1/[1+(ED_{50}/\text{drug conc.})^m]$ (Johnson V A, Byington R T. Infectivity Assay. In *Techniques in HIV Research*. ed. Aldovini A, Walker B D. 71-76. New York: Stockton Press. 1990). The anti-viral activity of compounds was evaluated under two serum conditions, 10% FBS, or 45 mg/ml human serum albumin/10% FBS, and the results from at least 2 experiments were used to calculate the $EC_{50}$ values. The anti-viral activity shown in Table 1 was determined in 10% FBS.

TABLE 1

| Example | $EC_{50}$ µM |
|---|---|
| 1 | 0.853 |
| 2 | 0.722 |
| 3 | 0.418 |
| 4 | 0.125 |
| 5 | 0.030 |
| 6 | 0.054 |
| 7 | 3.51 |
| 8 | 0.051 |
| 9 | 3.676 |
| 10 | 0.237 |
| 11 | 1.269 |
| 12 | 0.007 |
| 13 | 0.216 |
| 14 | 0.383 |
| 15 | 0.004 |
| 16 | 0.177 |
| 17 | 0.145 |
| 18 | 0.016 |
| 19 | 0.021 |
| 20 | 0.005 |
| 21 | 0.007 |
| 22 | 0.036 |
| 23 | 0.011 |
| 24 | 0.008 |
| 25 | 0.038 |
| 26 | 0.041 |
| 27 | 0.010 |
| 28 | 0.040 |
| 29 | 0.018 |
| 30 | 0.027 |
| 31 | 0.006 |
| 32 | 0.009 |
| 33 | 0.008 |
| 34 | 0.014 |
| 35 | 0.010 |
| 36 | 0.034 |
| 37 | 0.002 |
| 38 | 0.002 |
| 39 | 0.118 |
| 40 | 0.034 |
| 41 | 0.180 |
| 42 | 0.035 |
| 43 | 0.134 |
| 44 | 0.041 |
| 45 | 0.033 |
| 46 | 0.010 |
| 47 | 0.014 |
| 48 | 0.011 |
| 49 | 0.009 |
| 50 | 0.006 |
| 51 | 0.006 |
| 52 | 0.005 |
| 53 | 0.010 |
| 54 | 0.13 |
| 55 | 0.014 |
| 56 | 0.351 |
| 57 | 0.300 |
| 58 | 0.074 |
| 59 | 0.008 |
| 60 | 0.084 |
| 61 | 0.010 |
| 62 | 0.007 |
| 63 | 0.007 |
| 64 | 0.026 |
| 65 | 0.043 |
| 66 | 0.043 |
| 67 | 0.109 |
| 68 | 0.009 |
| 69 | 0.021 |
| 70 | 0.019 |
| 71 | 0.003 |
| 72 | 0.015 |
| 73 | 0.006 |
| 74 | 0.036 |
| 75 | 0.034 |
| 76 | 0.029 |
| 77 | 0.021 |
| 78 | 0.031 |

TABLE 1-continued

| Example | EC$_{50}$ µM |
|---|---|
| 79 | 0.038 |
| 80 | n.d. |
| 81 | 0.013 |
| 82 | 0.020 |
| 83 | 0.025 |
| 84 | 0.012 |
| 85 | 0.021 |
| 86 | 0.052 |
| 87 | 0.009 |
| 88 | 0.086 |
| 89 | 0.110 |
| 90 | 0.157 |
| 91 | 0.047 |
| 92 | 0.968 |
| 93 | 0.095 |
| 94 | 0.035 |
| 95 | 0.036 |
| 96 | 0.036 |
| 97 | 0.041 |
| 98 | n.d. |
| 99 | 0.020 |
| 100 | n.d. |
| 101 | n.d. |
| 102 | n.d. |
| 103 | 0.025 |
| 104 | 0.026 |
| 105 | 0.028 |
| 106 | 0.089 | n.d. = not determined

Pharmaceutical Composition and Methods of Use

The compounds of this invention inhibit HIV replication. Accordingly, another aspect of the invention is a method for treating HIV infection in a human patient comprising administering a therapeutically effective amount of a compound of Formula I, or a pharmaceutically acceptable salt thereof, with a pharmaceutically acceptable carrier.

Another aspect of the invention is the use of a compound of formula I in the manufacture of a medicament for the treatment of AIDS or HIV infection.

Another aspect of the invention is a method for treating HIV infection in a human patient comprising the administration of a therapeutically effective amount of a compound of Formula I, or a pharmaceutically acceptable salt thereof, with a therapeutically effective amount of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

Another aspect of the invention is a method wherein the agent is a nucleoside HIV reverse transcriptase inhibitor.

Another aspect of the invention is a method wherein the nucleoside HIV reverse transcriptase inhibitor is selected from the group consisting of abacavir, didanosine, emtricitabine, lamivudine, stavudine, tenofovir, zalcitabine, and zidovudine, or a pharmaceutically acceptable salt thereof.

Another aspect of the invention is a method wherein the agent is a non-nucleoside HIV reverse transcriptase inhibitor.

Another aspect of the invention is a method wherein the non-nucleoside HIV reverse transcriptase inhibitor is selected from the group consisting of delavirdine, efavirenz, and nevirapine, or a pharmaceutically acceptable thereof.

Another aspect of the invention is a method wherein the agent is an HIV protease inhibitor.

Another aspect of the invention is a method wherein the HIV protease inhibitor is selected from the group consisting of amprenavir, atazanavir, indinavir, lopinavir, nelfinavir, ritonavir, saquinavir and fosamprenavir, or a pharmaceutically acceptable salt thereof.

Another aspect of the invention is a method wherein the agent is an HIV fusion inhibitor.

Another aspect of the invention is a method wherein the HIV fusion inhibitor is enfuvirtide or T-1249, or a pharmaceutically acceptable salt thereof.

Another aspect of the invention is a method wherein the agent is an HIV attachment inhibitor.

Another aspect of the invention is a method wherein the agent is a CCR5 inhibitor.

Another aspect of the invention is a method wherein the CCR5 inhibitor is selected from the group consisting of Sch-C, Sch-D, TAK-220, PRO-140, and UK-427,857, or a pharmaceutically acceptable salt thereof Another aspect of the invention is a method wherein the agent is a CXCR4 inhibitor.

Another aspect of the invention is a method wherein the CXCR4 inhibitor is AMD-3100, or a pharmaceutically acceptable salt thereof.

Another aspect of the invention is a method wherein the agent is an HIV budding or maturation inhibitor.

Another aspect of the invention is a method wherein the budding or maturation inhibitor is PA-457, or a pharmaceutically acceptable salt thereof.

Another aspect of the invention is a method wherein the agent is an HIV integrase inhibitor.

Another aspect of the invention is a pharmaceutical composition comprising a therapeutically effective amount of a compound of Formula I, or a pharmaceutically acceptable salt thereof, with at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors, and a pharmaceutically acceptable carrier.

Another aspect of the invention is the composition wherein the agent is a nucleoside HIV reverse transcriptase inhibitor.

Another aspect of the invention is the composition wherein the nucleoside HIV transcriptase inhibitor is selected from the group consisting of abacavir, didanosine, emtricitabine, lamivudine, stavudine, tenofovir, zalcitabine, and zidovudine, or a pharmaceutically acceptable salt thereof.

Another aspect of the invention is the composition wherein the agent is a non-nucleoside HIV reverse transcriptase inhibitor.

Another aspect of the invention is the composition wherein the non-nucleoside HIV reverse transcriptase inhibitor is selected from the group consisting of delavirdine, efavirenz, and nevirapine, or a pharmaceutically acceptable salt thereof.

Another aspect of the invention is the composition wherein the agent is an HIV protease inhibitor.

Another aspect of the invention is the composition wherein the HIV protease inhibitor is selected from the group consisting of amprenavir, atazanavir, indinavir, lopinavir, nelfinavir, ritonavir, saquinavir and fosamprenavir, or a pharmaceutically acceptable salt thereof.

Another aspect of the invention is the composition wherein the agent is an HIV fusion inhibitor.

Another aspect of the invention is the composition method wherein the HIV fusion inhibitor is enfuvirtide or T-1249, or a pharmaceutically acceptable salt thereof.

Another aspect of the invention is the composition wherein the agent is an HIV attachment inhibitor.

Another aspect of the invention is the composition wherein the agent is a CCR5 inhibitor.

Another aspect of the invention is the composition wherein the CCR5 inhibitor is selected from the group consisting of Sch-C, Sch-D, TAK-220, PRO-140, and UK-427,857, or a pharmaceutically acceptable salt thereof Another aspect of the invention is a method wherein the agent is a CXCR4 inhibitor.

Another aspect of the invention is a method wherein the CXCR4 inhibitor is AMD-3100 or a pharmaceutically acceptable salt thereof.

Another aspect of the invention is the composition wherein the agent is an HIV budding or maturation inhibitor.

Another aspect of the invention is the composition wherein the budding or maturation inhibitor is PA-457, or a pharmaceutically acceptable salt thereof.

Another aspect of the invention is the composition wherein the agent is an HIV integrase inhibitor.

"Combination," "coadministration," "concurrent" and similar terms referring to the administration of a compound of Formula I with at least one anti-HIV agent mean that the components are part of a combination antiretroviral therapy or highly active antiretroviral therapy (HAART) as understood by practitioners in the field of AIDS and HIV infection.

"Therapeutically effective" means the amount of agent required to provide a meaningful patient benefit as understood by practitioners in the field of AIDS and HIV infection. In general, the goals of treatment are suppression of viral load, restoration and preservation of immunologic function, improved quality of life, and reduction of HIV-related morbidity and mortality.

"Patient" means a person infected with the HIV virus and suitable for therapy as understood by practitioners in the field of AIDS and HIV infection.

"Treatment," "therapy," "regimen," "HIV infection," "ARC," "AIDS" and related terms are used as understood by practitioners in the field of AIDS and HIV infection.

The compounds of this invention are generally given as pharmaceutical compositions comprised of a therapeutically effective amount of a compound of Formula I or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, Remington's Pharmaceutical Sciences, 17th edition, Mack Publishing Company, Easton, Pa. (1985).

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other antiretroviral agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other antiretroviral agents will be present in a unit range similar to agents of that class used clinically. Typically, this is 1-100 mg/mL.

The invention encompasses all conventional modes of administration; oral and parenteral methods are preferred. Generally, the dosing regimen will be similar to other antiretroviral agents used clinically. Typically, the daily dose will be 1-100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating AIDS and HIV infection. Some of these agents include HIV attachment inhibitors, CCR5 inhibitors, CXCR4 inhibitors, HIV cell fusion inhibitors, HIV integrase inhibitors, HIV nucleoside reverse transcriptase inhibitors, HIV non-nucleoside reverse transcriptase inhibitors, HIV protease inhibitors, budding and maturation inhibitors, immunomodulators, and anti-infectives. In these combination methods, the compound of Formula I will generally be given in a daily dose of 1-100 mg/kg body weight daily in conjunction with other agents. The other agents generally will be given in the amounts used therapeutically. The specific dosing regime, however, will be determined by a physician using sound medical judgement.

Synthetic Methods

The compounds of this invention can be made by various methods known in the art including those of the following schemes and in the specific embodiments section. The structure numbering and variable numbering shown in the synthetic schemes are distinct from, and should not be confused with, the structure or variable numbering in the claims or the rest of the specification. The variables in the schemes are meant only to illustrate how to make some of the compounds of this invention.

The disclosure is not limited to the foregoing illustrative examples and the examples should be considered in all respects as illustrative and not restrictive, reference being made to the appended claims, rather than to the foregoing examples, and all changes which come within the meaning and range of equivalency of the claims are therefore intended to be embraced.

Abbreviations used in the schemes and examples generally follow conventions used in the art. Chemical abbreviations used in the specification and examples are defined as follows: "KHMDS" for potassium bis(trimethylsilyl)amide; "DMF" for N,N-dimethylformamide; "HATU" for O-(t-Azabenzotriazol-1-yl)-N,N,N',N'-tetramethyluronium hexafluorophosphate, "MeOH" for methanol; "Ar" for aryl; "TFA" for trifluoroacetic acid, "DMSO" for dimethylsulfoxide; "h" for hours; "rt" for room temperature or retention time (context will dictate); "min" for minutes; "EtOAc" for ethyl acetate; "THF" for tetrahydrofuran; "Et$_2$O" for diethyl ether; "DMAP" for 4-dimethylaminopyridine; "DCM" for dichloromethane, "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "DEAD" for diethyl azodicarboxylate and "DIAD" for diisopropyl azodicarboxylate.

Abbreviations as used herein, are defined as follows: "1 x" for once, "2 x" for twice, "3 x" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Some compounds can be synthesized from an appropriately substituted heterocycle I-1 according to Scheme I, Compound I-1 and I-2 are commercially available or synthesized by reactions known in the art. Intermediates I-3 can be prepared by procedure known in the art or as set forth in the examples below using compound I-1 and compound I-2. Intermediates I-3 can be transformed to intermediates I-5 via intermediates I-4 using conditions known to those skilled in the art. Intermediates I-5 can be oxidized to intermediates I-6 by reactions known in the art, including Davis oxidation. Intermediates I-6 can be oxidized to intermediates I-7 by known conditions, including Dess-Martin oxidation. Intermediates I-7 can be reduced to chiral intermediates I-8 using known conditions in the presence of catalytic chiral ligands. Intermediates I-8 can be converted to the intermediates I-9 by known conditions, including tertiary-butyl acetate and perchloric acid. Sequential coupling of aryl groups to Intermediates I-9 using conditions known in the art, including Suzuki coupling, can provide intermediates 10 and 11. Boronate or boronic acid coupling reagents are commercially availible or are prepared by reactions known in the art (for example, PCT Appln. WO20090662285). Intermediates I-11 can be converted to intermediates I-12 by conditions known in the art, including ring closing metathesis. Hydrolysis of intermediates I-12 can provide products I-13 which can be converted to I-14 using conditions known in the art.

Scheme I.

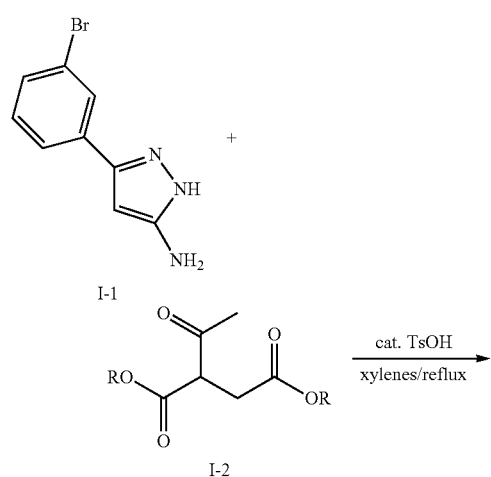

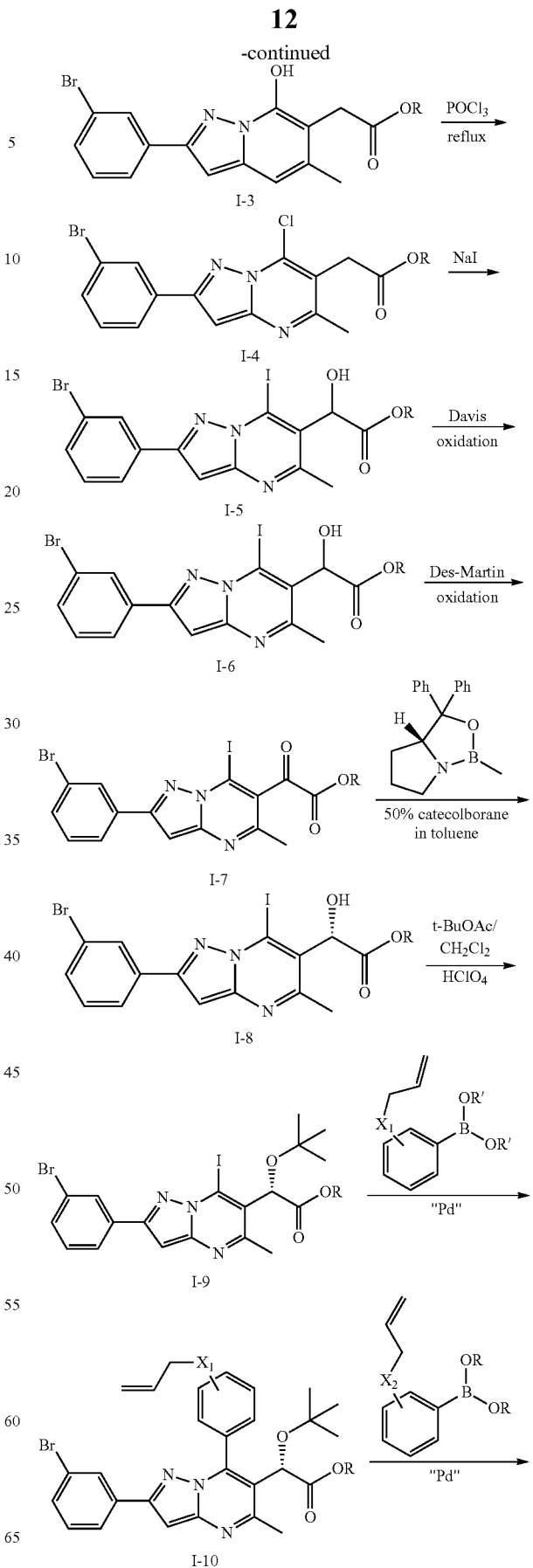

13
-continued
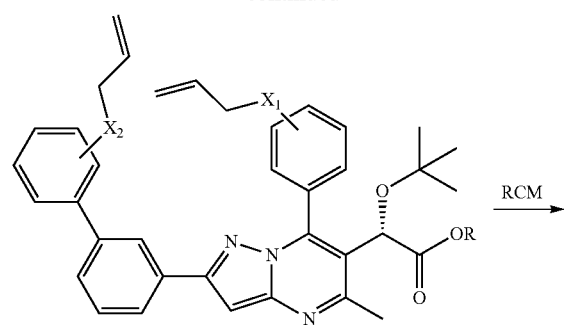
I-11
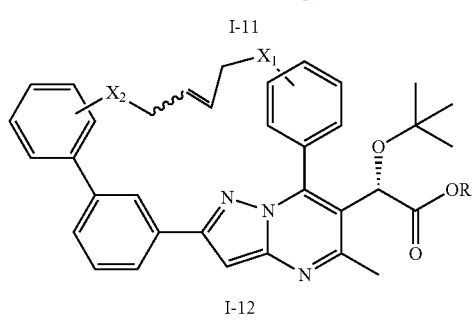
I-12
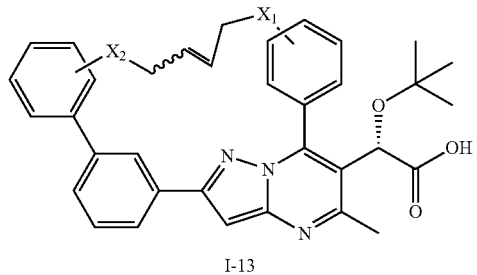
I-13
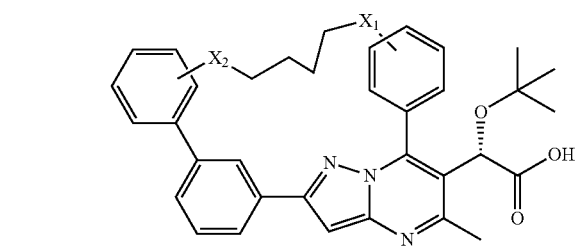
Intermediate I-4 can be transformed to final compounds II-5 and II-6 by methods known in the art as outlined in Scheme II.
Scheme II
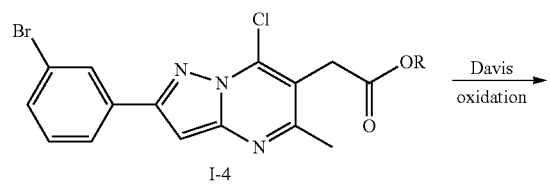
I-4
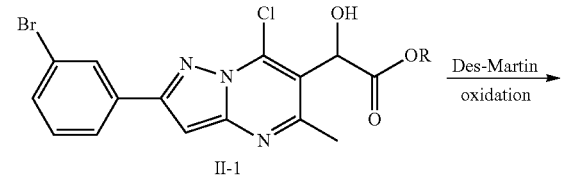
II-1
14
-continued
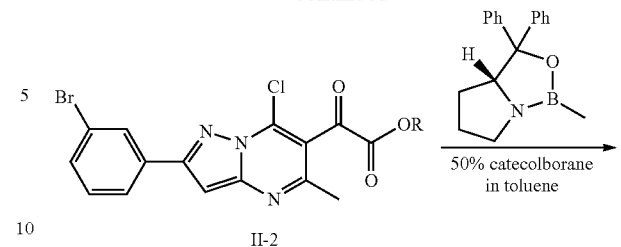
II-2
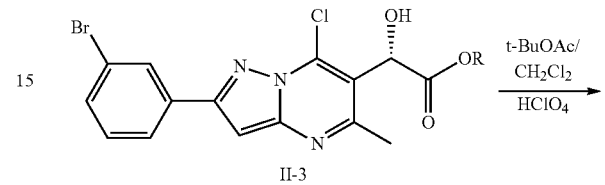
II-3
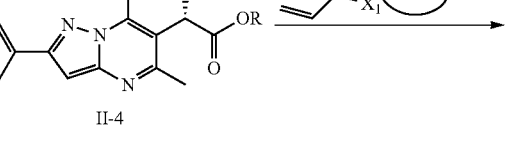
II-4
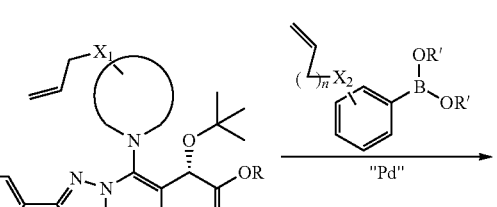
II-5
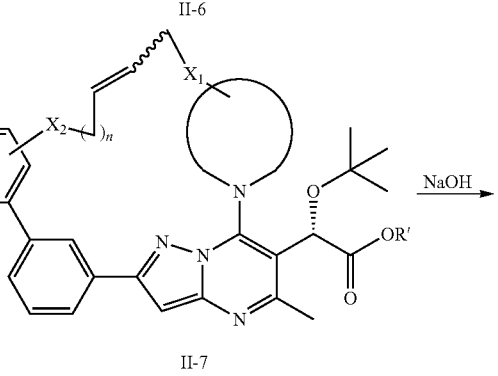
II-6
II-7

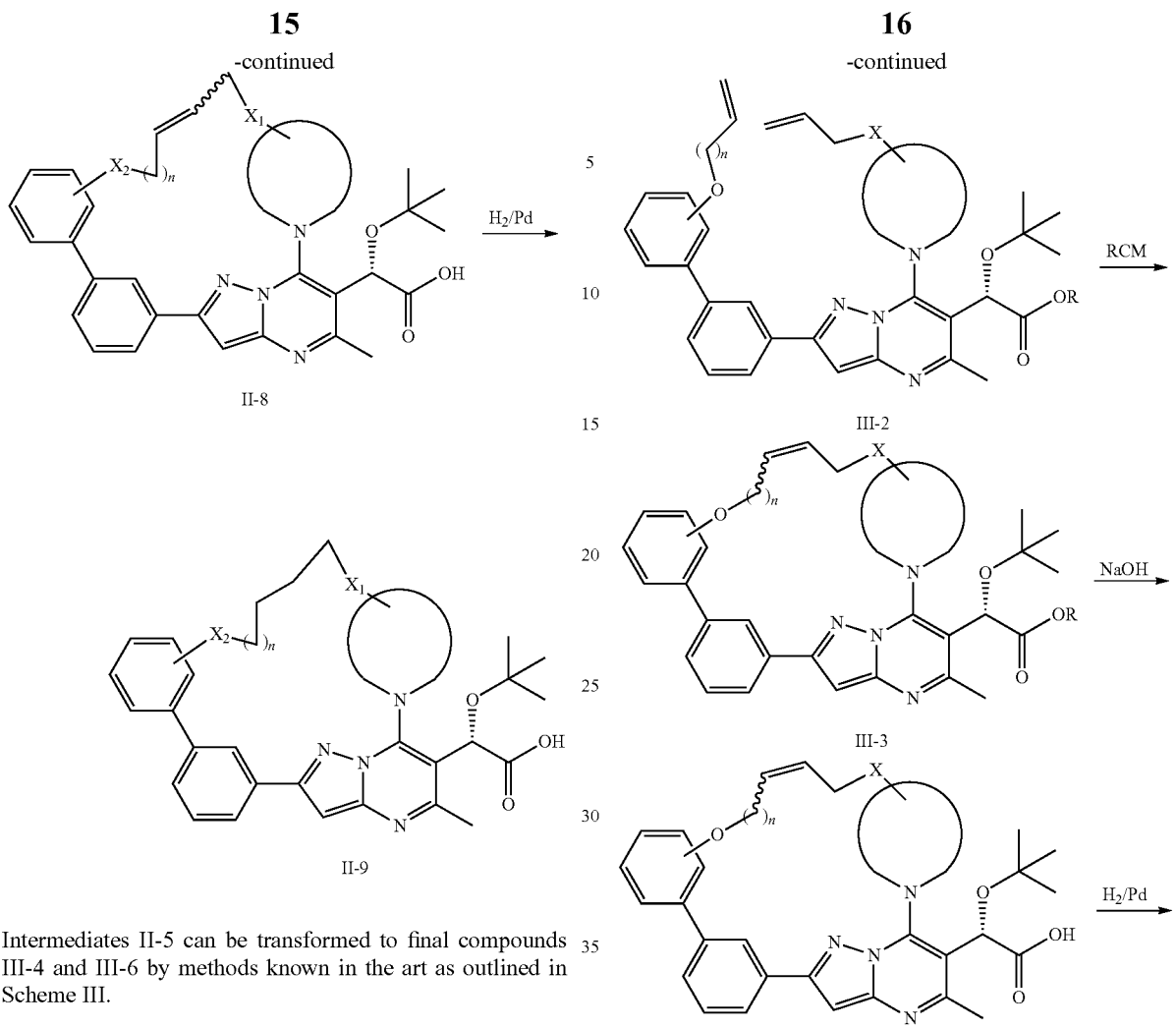
Intermediates II-5 can be transformed to final compounds III-4 and III-6 by methods known in the art as outlined in Scheme III.
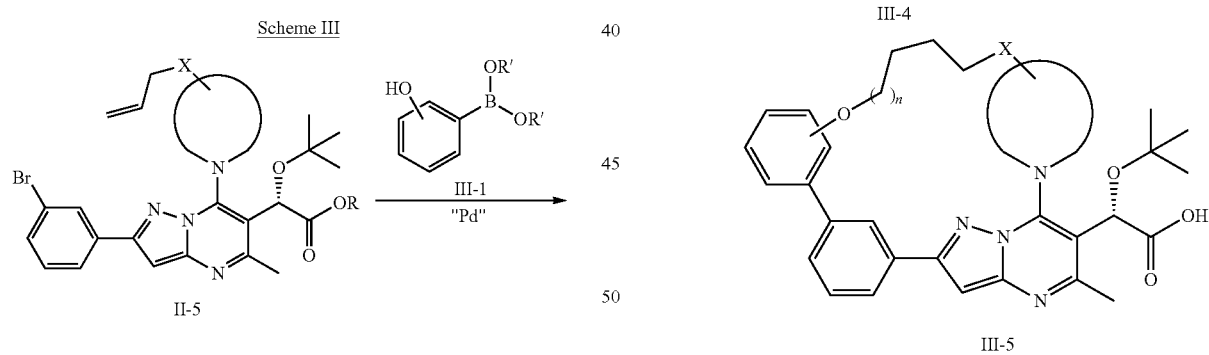
Intermediates I-4 can be transformed to final compounds IV-5 and IV-6 by methods known in the art as outlined in Scheme IV.
Scheme IV
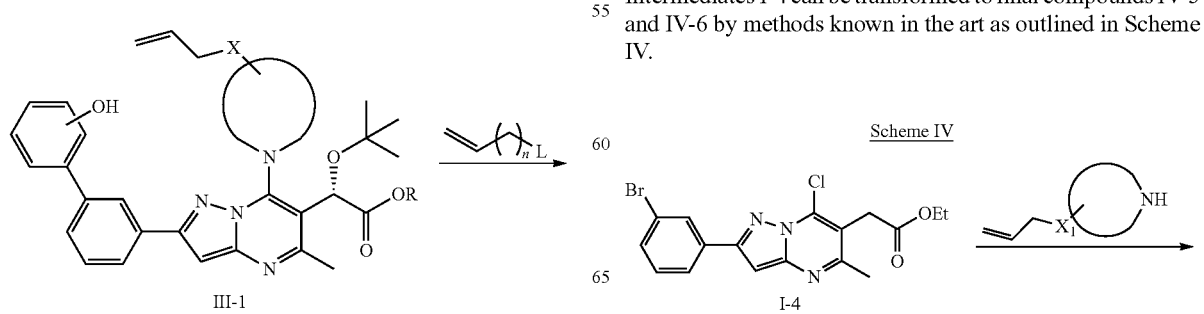

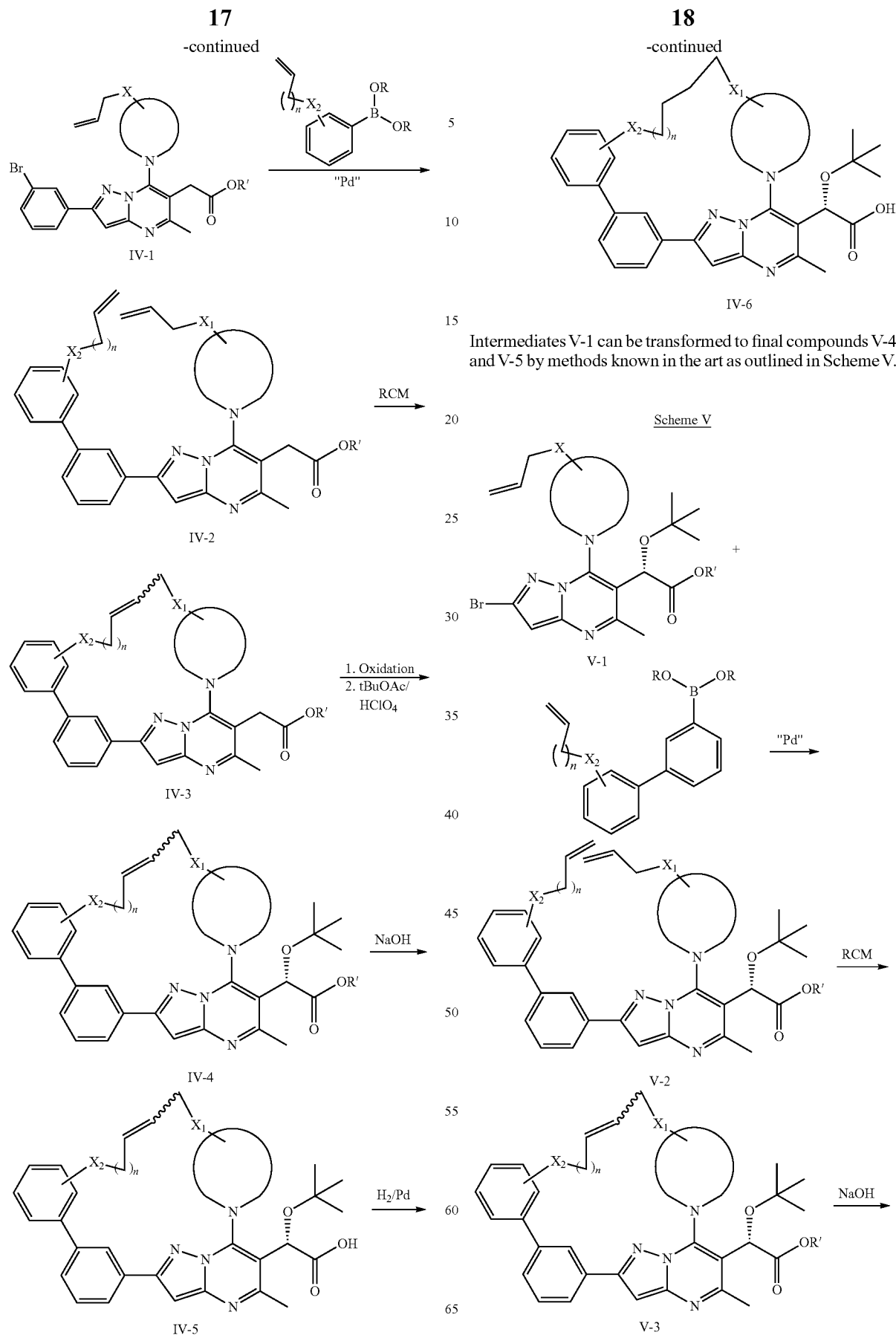
Intermediates V-1 can be transformed to final compounds V-4 and V-5 by methods known in the art as outlined in Scheme V.
Scheme V -continued

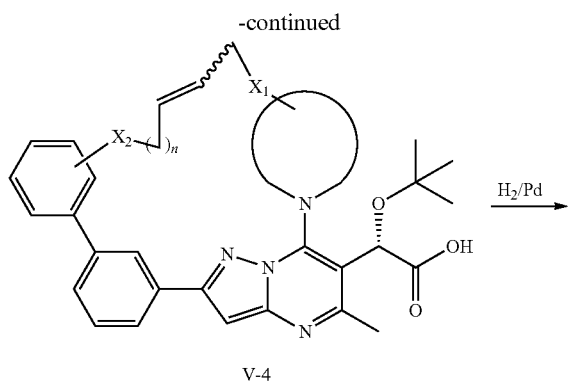

V-4

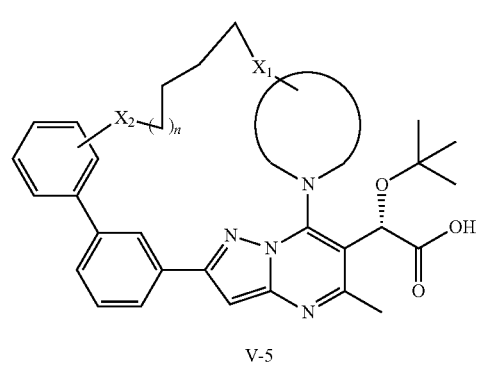

V-5

The compounds described herein were purified by the methods known to those skilled in art by normal phase column chromatography on silica gel column using appropriate solvent systems. Preparative HPLC purifications mentioned in this experimentation section were carried out by gradient elution on C18 prep-columns (5 µm) using either mobile phase A: 9:1 H$_2$O/acetonitrile with 10 mM NH$_4$OAc and mobile phase B:A: 9:1 acetonitrile/H$_2$O with: 10 mM NH$_4$OAc or mobile phase A: 95:5 H$_2$O/MeOH with 20 mM NH$_4$OAc and mobile phase B: 95:5 MeOH/H$_2$O with 20 mM NH$_4$OAc.

Intermediate 1

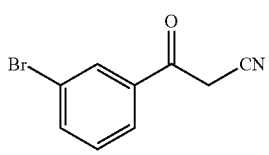

3-(3-bromophenyl)-3-oxopropanenitrile: Acetonitrile (21.86 mL, 419 mmol) was added to a stirred suspension of 60% NaH (7.25 g, 181 mmol) in THF (150 mL). Then, methyl 3-bromobenzoate (30 g, 140 mmol) was added and the mixture was heated at 75° C. for 4 h. After cooling to room temperature, water followed by 1N HCl (200 mL) was added and the mixture was extracted with ethyl acetate (500 mL), washed with sat .NaHCO$_3$ solution (200 mL), dried (Na$_2$SO$_4$), filtered and concentrated to afford 3-(3-bromophenyl)-3-oxopropanenitrile (29 g, 129 mmol, 93% yield) as light yellow solid. $^1$H NMR (500 MHz, CDCl$_3$) δ 8.09 (t, J=1.7 Hz, 1H), 7.90-7.86 (m, 1H), 7.83 (ddd, J=8.0, 2.0, 1.1 Hz, 1H), 7.45 (t, J=7.9 Hz, 1H), 4.08 (s, 2H).

Intermediate 2

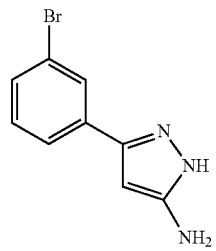

3-(3-bromophenyl)-1H-pyrazol-5-amine: A mixture of 3-(3-bromophenyl)-3-oxopropanenitrile (35 g, 156 mmol) and hydrazine hydrate (11.34 mL, 234 mmol) in ethanol (600 mL) was refluxed for 16 h. Mixture was then cooled and concentrated in vacuuo. Crude product was diluted with dichloromethane and stirred for 5 min. Solids were filtered and dried to afford 3-(3-bromophenyl)-1H-pyrazol-5-amine (30 g, 126 mmol, 81% yield) as off-white solid. $^1$H NMR (400 MHz, DMSO-d$_6$) δ 12.02 (br. s., 0.4H), 11.66 (br. s., 0.6H), 7.86 (t, J=1.6 Hz, 1H), 7.67 (d, J=7.5 Hz, 1H), 7.45 (d, J=6.8 Hz, 1H), 7.37-7.18 (m, 1H), 5.78 (br. s., 1H), 5.08 (br. s., 1.2H), 4.68 (br. s., 0.8H). LCMS (M+H)=240.1.

Intermediate 3

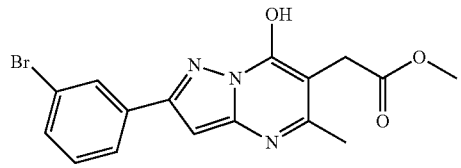

Methyl 2-(2-(3-bromophenyl)-7-hydroxy-5-methylpyrazolo[1,5-a]pyrimidin-6-yl)acetate: A 3-lit three neck flask was fitted with a mechanical stirrer and a heating mantle. A suspension of 3-(3-bromophenyl)-1H-pyrazol-5-amine (84.9 g, 357 mmol), dimethyl 2-acetylsuccinate (73.8 g, 392 mmol) and tosic acid monohydrate (1.357 g, 7.13 mmol) in o-xylene (1500 mL) was heated to refluxed (135° C. measured internal temp) for 3.5 h. The heating was turned off, the reaction was diluted with hexanes (1000 mL) and was allowed to cool slowly overnight. The solids were collected by filtration. The filter cake was washed with hexanes and dried under vacuum overnight to afford methyl 2-(2-(3-bromophenyl)-7-hydroxy-5-methylpyrazolo[1,5-a]pyrimidin-6-yl)acetate (132.21 g, 334 mmol, 94% yield) as a white powdery solid. $^1$H NMR (500 MHz, DMSO-d$_6$) δ: 12.47 (s, 1H), 8.18 (t, J=1.7 Hz, 1H), 8.02 (dt, J=7.1, 1.3 Hz, 1H), 7.65-7.60 (m, 1H), 7.45 (t, J=7.9 Hz, 1H), 6.69 (s, 1H), 3.63 (s, 3H), 3.58 (s, 2H), 2.34 (s, 3H). LCMS (M+H)=376.4.

Intermediate 4

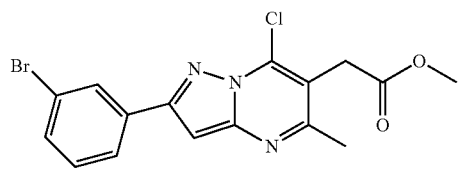

2-(2-(3-Bromophenyl)-7-chloro-5-methylpyrazolo[1,5-d]pyrimidin-6-yl)acetate: A mixture of methyl 2-(2-(3-bromophenyl)-7-hydroxy-5-methylpyrazolo[1,5-a]pyrimidin-6-yl)acetate (133 g, 354 mmol) and N,N-dimethylaniline (62.7 ml, 495 mmol) in POCl$_3$ (450 ml) was heated (120° C. oil bath) for 2.5 h. The reaction was cooled, then concentrated under reduced pressure. The residue was dried from toluene (3×300 mL), and the residue, suspended in EtOAc (600 mL) was poured onto ice water at a rate that maintained the cold temperature. The emulsion was then diluted (EtOAc, 300 mL) and the combined layers were pulled through a filter paper to collect solids. The solids were washed with several portions of EtOAc, then air dried. The filtered solids were suspended in EtOAc and hexanes (500 mL of each) and stirred for 10 min, then filtered. The filter cake was washed with hexanes and dried under vacuum to afford methyl 24243-bromophenyl)-7-chloro-5-methylpyrazolo[1,5-a]pyrimidin-6-yl)acetate (121.7 g, 300 mmol, 85% yield) as pale green solid. $^1$H NMR (500 MHz, DMSO-d$_6$) δ: 8.25 (t, J=1.8 Hz, 1H), 8.09 (dt, J=7.8, 1.3 Hz, 1H), 7.63-7.70 (m, 1H), 7.45-7.54 (m, 1H), 7.40 (s, 1H), 4.04 (s, 2H), 3.71 (s, 3H), 2.58 (s, 3H). LC/MS (085-04, M+H)=396.1.

Intermediate 5

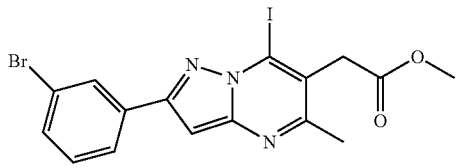

Methyl 2-(2-(3-bromophenyl)-7-iodo-5-methylpyrazolo[1,5-a]pyrimidin-6-yl)acetate:Methyl 2-(2-(3-bromophenyl)-7-chloro-5-methylpyrazolo[1,5-a]pyrimidin-6-yl)acetate (1 g, 2.53 mmol) and NaI (1.519 g, 10.14 mmol) were suspended in acetonitrile (10 mL) and the resulting mixture was heated at 80° C. for 5 h. After cooling to room temp, mixture was diluted with ethyl acetate (50 mL) and washed with water (25 mL) and aqueous Na$_2$S$_2$O$_3$ (25 mL), dried (Na$_2$SO$_4$), filtered and concentrated. Crude was then triturated with ethyl acetate/hexane to afford methyl 2-(2-(3-bromophenyl)-7-iodo-5-methylpyrazolo[1,5-a]pyrimidin-6-yl)acetate (1 g, 2.057 mmol, 81% yield) as off white solid. $^1$H NMR (400 MHz, CDCl$_3$) δ: 8.20 (t, J=1.8 Hz, 1H), 7.95 (dt, J=7.8, 1.3 Hz, 1H), 7.55 (ddd, J=8.0, 2.0, 1.0 Hz, 1H), 7.36 (t, J=7.9 Hz, 1H), 7.08 (s, 1H), 4.02 (s, 2H), 3.79 (s, 3H), 2.66 (s, 3H). LCMS (M+H)=486.1.

Intermediate 6

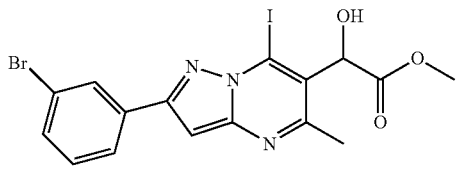

Methyl 2-(2-(3-bromophenyl)-7-iodo-5-methylpyrazolo[1,5-a]pyrimidin-6-yl)-2-hydroxyacetate: To a stirred solution of 0.9M KHMDS/THF (2.55 mL, 2.297 mmol) in THF (8 mL) at −78° C. was added dropwise a THF (10 mL) solution of methyl 2-(2-(3-bromophenyl)-7-iodo-5-methylpyrazolo[1,5-a]pyrimidin-6-yl)acetate (859 mg, 1.767 mmol) over 5 min. After 30 min, a THF (10 mL) solution of 3-phenyl-2-(phenylsulfonyl)-1,2-oxaziridine (600 mg, 2.297 mmol) was added to the resulting red reaction mixture and stirred for additional 30 min at −78° C. Then, the resulting orange reaction mixture was quenched with sat. NH$_4$Cl (50 mL), diluted with EtOAc (200 mL), washed with water (100 mL), brine (100 mL), dried (Na$_2$SO$_4$), filtered and concentrated to give light solid. This solid was triturated with small amount of ethyl acetate and solids were filtered, washed with hexanes and dried under high vacuo to afford methyl 2-(2-(3-bromophenyl)-7-iodo-5-methylpyrazolo[1,5-a]pyrimidin-6-yl)-2-hydroxyacetate (600 mg, 1.195 mmol, 67.6% yield) as light yellow solid. $^1$H NMR (500 MHz, CDCl$_3$) δ: 8.21 (t, J=1.7 Hz, 1H), 7.96 (dt, J=7.8, 1.2 Hz, 1H), 7.59-7.55 (m, 1H), 7.37 (t, J=7.8 Hz, 1H), 7.09 (s, 1H), 5.78 (s, 1H), 3.87 (s, 3H), 3.54 (br. s., 1H), 2.61 (s, 3H). LCMS (M+H)=504.05.

Intermediate 7

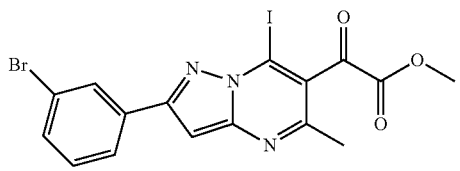

Methyl 2-(2-(3-bromophenyl)-7-iodo-5-methylpyrazolo[1,5-d]pyrimidin-6-yl)-2-oxoacetate: To a mixture of methyl 2-(2-(3-bromophenyl)-7-iodo-5-methylpyrazolo[1,5-a]pyrimidin-6-yl)-2-hydroxyacetate (2.6 g, 5.18 mmol) in CH$_2$Cl$_2$ (100 mL) was added Dess-Martin Periodinane (2.196 g, 5.18 mmol) and the resulting mixture was stirred at room temperature for 1 h. The reaction mixture was diluted with ethyl acetate (500 mL), washed with sat. NaHCO$_3$ solution (100 mL), dried (Na$_2$SO$_4$), filtered and concentrated. The residue was purified by silica gel chromatography (5-70% EtOAc/hexane) to afford desired methyl 2-(2-(3-bromophenyl)-7-iodo-5-methylpyrazolo[1,5-a]pyrimidin-6-yl)-2-oxoacetate (1.7 g, 3.40 mmol, 65.6% yield) as off-white solid. $^1$H NMR (500 MHz, CDCl$_3$) δ: 8.21 (t, J=1.7 Hz, 1H), 7.96 (dt, J=7.7, 1.3 Hz, 1H), 7.61-7.58 (m, 1H), 7.39 (t, J=7.9 Hz, 1H), 7.14 (s, 1H), 4.03 (s, 3H), 2.57 (s, 3H). LCMS (M+H)=501.0.

Intermediate 8

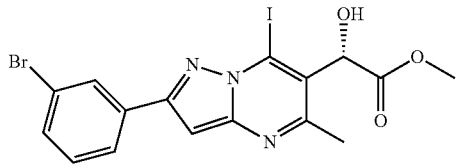

(S)-Methyl 2-(2-(3-bromophenyl)-7-iodo-5-methylpyrazolo[1,5-a]pyrimidin-6-yl)-2-hydroxyacetate: To a stirred yellow solution of methyl 2-(2-(3-bromophenyl)-7-iodo-5-methylpyrazolo[1,5-a]pyrimidin-6-yl)-2-oxoacetate (1.7 g, 3.40 mmol) in anhydrous toluene (100 mL) was added 1.1M (R)-1-methyl-3,3-diphenylhexahydropyrrolo[1,2-c][1,3,2]oxazaborole/toluene (1.236 mL, 1.360 mmol). The mixture was cooled to −35° C. and a solution of catechoborane/toluene (1.166 mL, 4.76 mmol) was added over 5 min. After 30 min, the reaction mixture was slowly warmed to −15° C. and stirred for additional 2 h. and diluted with EtOAc (600 mL) and sat. Na$_2$CO$_3$ (100 mL). The mixture was stirred vigorously for 30 min, and the organic phase washed with sat Na$_2$CO$_3$ (2×100 mL), dried (Na$_2$SO$_4$), filtered, concentrated and the residue was purified by silica gel chromatography (5-100% EtOAc/hexane) to afford desired (S)-methyl 2-(2-(3-bromophenyl)-7-iodo-5-methylpyrazolo[1,5-a]pyrimidin-6-yl)-2-hydroxyacetate (1 g, 1.992 mmol, 58.6% yield) as off-white solid. ¹H NMR (500 MHz, CDCl₃) δ: 8.21 (t, J=1.7 Hz, 1H), 7.96 (dt, J=7.8, 1.2 Hz, 1H), 7.59-7.55 (m, 1H), 7.37 (t, J=7.8 Hz, 1H), 7.09 (s, 1H), 5.78 (s, 1H), 3.87 (s, 3H), 3.54 (br. s., 1H), 2.61 (s, 3H). LCMS (M+H)=504.05.

Intermediate 9

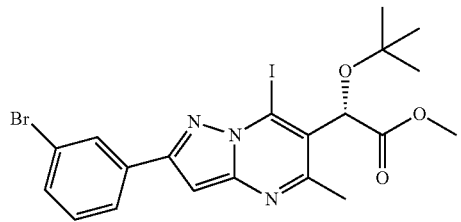

(S)-Methyl 2-(2-(3-bromophenyl)-7-iodo-5-methylpyrazolo[1,5-a]pyrimidin-6-yl)-2-(tert-butoxy)acetate: To a stirred solution of (S)-methyl 2-(2-(3-bromophenyl)-7-iodo-5-methylpyrazolo[1,5-a]pyrimidin-6-yl)-2-hydroxyacetate (1 g, 1.992 mmol) in CH₂Cl₂ (30 mL) and t-butyl acetate (21.00 mL) at rt was added 70% perchloric acid (0.513 mL, 5.97 mmol). After 3 h, the reaction mixture was diluted with CH₂Cl₂ (100 mL), carefully quenched with sat. NaHCO₃ (50 mL), organic layer separated and washed with brine (100 mL), dried (Na₂SO₄), filtered and concentrated to give yellow liquid. This was purified by flash column chromatograpgy on silica gel column using (10-50% EtOAc/Hex as eluant) to afford (S)-methyl 2-(2-(3-bromophenyl)-7-iodo-5-methylpyrazolo[1,5-a]pyrimidin-6-yl)-2-(tert-butoxy)acetate (800 mg, 1.433 mmol, 72.0% yield) as yellow solid. ¹H NMR (500 MHz, CDCl₃) δ: 8.20 (s, 1H), 7.95 (d, J=7.7 Hz, 1H), 7.56 (d, J=7.9 Hz, 1H), 7.37 (t, J=7.9 Hz, 1H), 7.08 (s, 1H), 5.59 (s, 1H), 3.76 (s, 3H), 2.70 (s, 3H), 1.32 (s, 9H). LCMS (M+H)=560.15.

Intermediate 10

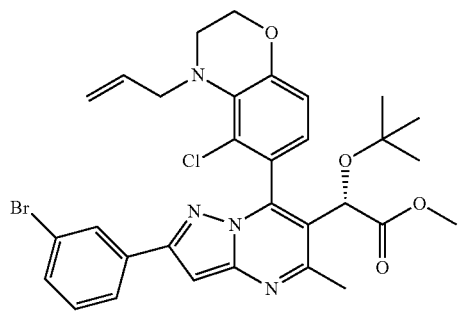

(2S)-Methyl 2-(7-(4-allyl-5-chloro-3,4-dihydro-2H-benzo[b][1,4]oxazin-6-yl)-2-(3-bromophenyl)-5-methylpyrazolo[1,5-d]pyrimidin-6-yl)-2-(tert-butoxy)acetate: A mixture of (S)-methyl 2-(2-(3-bromophenyl)-7-iodo-5-methylpyrazolo[1,5-a]pyrimidin-6-yl)-2-(tert-butoxy)acetate (350 mg, 0.627 mmol), 4-allyl-5-chloro-6-(4,4,5,5-tetramethyl-1,3,2-dioxaborolan-2-yl)-3,4-dihydro-2H-benzo[b][1,4]oxazine (231 mg, 0.690 mmol) and 2M Na₂CO₃ (0.627 mL, 1.254 mmol) in DMF (5 mL) was degassed for 15 min.

tetrakis(triphenylphosphine)pallafium(0) (50.7 mg, 0.044 mmol) was then added and the degassing was continue for another 5 min. The mixture was then heated at 90° C. for 16 h. After cooling to room temperature, water (10 mL) was added and the mixture was extracted with ethyl acetate (50 mL), washed with water (25 mL), brine (25 mL), dried (Na₂SO₄), filtered and concentrated. Crude was then purified by Biotage using 5-50% EtOAc/hexane to afford (2S)-methyl 2-(7-(4-allyl-5-chloro-3,4-dihydro-2H-benzo[b][1,4]oxazin-6-yl)-2-(3-bromophenyl)-5-methylpyrazolo[1,5-a]pyrimidin-6-yl)-2-(tert-butoxy)acetate (260 mg, 0.406 mmol, 64.8% yield) as light yellow solid. ¹H NMR (500 MHz, CDCl₃) δ: 8.00 (t, J=1.7 Hz, 1H), 7.77 (dt, J=8.0, 1.2 Hz, 1H), 7.46 (ddd, J=8.0, 2.0, 0.9 Hz, 1H), 7.26 (t, J=7.9 Hz, 1H), 7.03 (d, J=8.4 Hz, 1H), 6.97 (d, J=8.4 Hz, 1H), 6.87 (s, 1H), 6.06 (dd, J=17.2, 10.2 Hz, 1H), 5.37 (dd, J=17.2, 1.7 Hz, 1H), 5.28 (dd, J=10.2, 1.7 Hz, 1H), 5.07 (s, 1H), 4.34-4.24 (m, 2H), 3.71 (dd, J=12.2, 6.1 Hz, 2H), 3.67 (s, 3H), 3.29-3.18 (m, 2H), 2.86 (s, 3H), 1.18 (s, 9H). LCMS (M+H)=641.3.

Intermediate 11

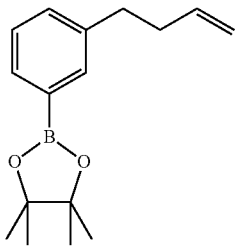

2-(3-(But-3-en-1-yl)phenyl)-4,4,5,5-tetramethyl-1,3,2-dioxaborolane: To a solution of 1-bromo-3-(but-3-en-1-yl)benzene (2.5 g, 11.84 mmol) in anhydrous DMF (60 mL) was added bis(pinacolato)diborane (3.31 g, 13.03 mmol), potassium acetate (3.49 g, 35.5 mmol) and the mixture was degassed for 15 min. To the degassed solution was added PdCl₂(dppf) (0.867 g, 1.184 mmol) and degassing continued for a further 5 min, after which the reaction was heated at 90° C. for 3 h. After cooling to room temperature, water (50 mL) was added and the mixture was extracted with ether (2×100 mL), washed with brine (50 mL), dried (Na₂SO₄), filtered and concentrated. Crude was then purified by biotage using 0-15% EtOAc/hexane to afford 2-(3-(but-3-en-1-yl)phenyl)-4,4,5,5-tetramethyl-1,3,2-dioxaborolane (2 g, 7.75 mmol, 65.4% yield) as light yellow oil. ¹H NMR (500 MHz, CDCl₃) δ: 7.69-7.65 (m, 2H), 7.34-7.31 (m, 2H), 5.89 (ddt, J=17.1, 10.3, 6.6 Hz, 1H), 5.07 (dq, J=17.2, 1.7 Hz, 1H), 5.02-4.97 (m, 1H), 2.77-2.70 (m, 2H), 2.45-2.38 (m, 2H), 1.38 (s, 12H).

Intermediate 12

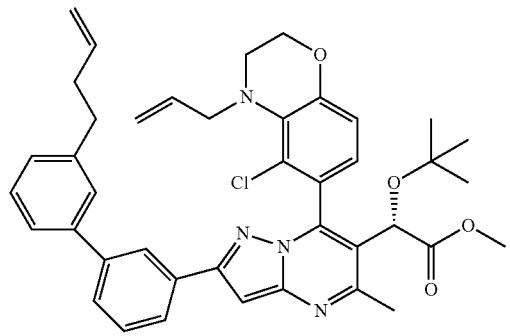

(2S)-Methyl 2-(7-(4-allyl-5-chloro-3,4-dihydro-2H-benzo[b][1,4]oxazin-6-yl)-2-(3'-(but-3-en-1-yl)-[1,1'-biphenyl]-3-yl)-5-methylpyrazolo[1,5-a]pyrimidin-6-yl)-2-(tert-butoxy)acetate: A mixture of (2S)-methyl 2-(7-(4-allyl-5-chloro-3,4-dihydro-2H-benzo[b][1,4]oxazin-6-yl)-2-(3-bromophenyl)-5-methylpyrazolo[1,5-a]pyrimidin-6-yl)-2-(tert-butoxy)acetate (75 mg, 0.117 mmol), 2-(3-(but-3-en-1-yl)phenyl)-4,4,5,5-tetramethyl-1,3,2-dioxaborolane (45.4 mg, 0.176 mmol) and 2N Na$_2$CO$_3$ (0.117 mL, 0.234 mmol) in DMF (1 mL) was degassed for 15 min. tetrakis(triphenylphosphine)pallafium(0) (9.48 mg, 8.20 μmol) was then added and the degassing was continue for another 5 min. The mixture was then heated at 90° C. for 16 h. After cooling to room temperature, water was added and the mixture was extracted with ether (2×25 mL), washed with brine (15 mL), dried (Na$_2$SO$_4$), filtered and concentrated. Crude was then purified by biotage (0-15% EtOAc/hexane) to afford (2S)-methyl 2-(7-(4-allyl-5-chloro-3,4-dihydro-2H-benzo[b][1,4]oxazin-6-yl)-2-(3'-(but-3-en-1-yl)-[1,1'-biphenyl]-3-yl)-5-methylpyrazolo[1,5-a]pyrimidin-6-yl)-2-(tert-butoxy)acetate (50 mg, 0.072 mmol, 61.7% yield) as light yellow solid. $^1$H NMR (500 MHz, CDCl$_3$) δ: 8.05 (t, J=1.6 Hz, 1H), 7.85-7.82 (m, 1H), 7.57-7.54 (m, 1H), 7.45 (dd, J=4.6, 2.5 Hz, 3H), 7.41-7.35 (m, 1H), 7.21 (d, J=7.6 Hz, 1H), 7.00 (d, J=5.0 Hz, 2H), 6.95-6.93 (m, 1H), 6.11-6.00 (m, 1H), 5.91 (ddt, J=17.0, 10.3, 6.6 Hz, 1H), 5.35 (dd, J=17.2, 1.6 Hz, 1H), 5.26 (dd, J=10.2, 1.6 Hz, 1H), 5.12-5.07 (m, 2H), 5.04-5.00 (m, 1H), 4.27 (t, J=4.4 Hz, 2H), 3.79-3.72 (m, 1H), 3.67 (s, 3H), 3.63 (dd, J=15.1, 6.1 Hz, 1H), 3.28-3.17 (m, 2H), 2.86 (s, 3H), 2.83-2.78 (m, 2H), 2.49-2.41 (m, 2H), 1.20 (s, 9H). LCMS (M+H)=691.5.

INTERMEDIATES 13 AND 14

A mixture of (2S)-methyl 2-(7-(4-allyl-5-chloro-3,4-dihydro-2H-benzo[b][1,4]oxazin-6-yl)-2-(3'-(but-3-en-1-yl)-[1,1'-biphenyl]-3-yl)-5-methylpyrazolo[1,5-a]pyrimidin-6-yl)-2-(tert-butoxy)acetate (40 mg, 0.058 mmol) and Hoveyda-Grubbs 2nd generation catalyst (4.91 mg, 5.79 μmol) catalyst in DCE (2 mL) was heated at 85° C. for 2 h. Mixture was then cooled, concentrated and purified by prep HPLC to afford cis and trans ester.

Intermediate 13

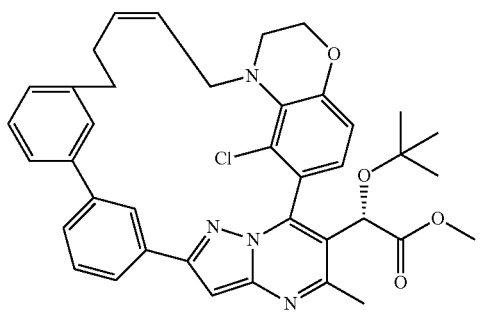

Methyl (2S)-2-(tert-butoxy)-2-[(22Z)-32-chloro-4-methyl-28-oxa-5,7,8,25-tetraazaheptacyclo[23.6.2. 1$^{6,9}$.1$^{10,14}$.1$^{15,19}$.0$^{2,7}$.0$^{29,33}$]hexatriaconta-1(31),2,4,6(36), 8,10(35),11,13,15 (34),16,18,22,29,32-tetradecaen-3-yl]acetate: First eluting cis isomer. $^1$H NMR (400 MHz, CDCl$_3$) δ: 8.08 (s, 1H), 7.75 (d, J=7.5 Hz, 1H), 7.56-7.52 (m, 1H), 7.51-7.46 (m, 1H), 7.41-7.34 (m, 3H), 7.17 (d, J=7.0 Hz, 1H), 6.99 (s, 2H), 6.90 (s, 1H), 5.78-5.60 (m, 2H), 5.29 (s, 1H), 4.55 (d, J=15.6 Hz, 1H), 4.34-4.22 (m, 2H), 3.65 (d, J=8.5 Hz, 1H), 3.63 (s, 3H), 3.48 (dd, J=15.6, 7.8 Hz, 1H), 3.40-3.24 (m, 1H), 3.05-2.95 (m, 1H), 2.88 (s, 3H), 2.87-2.74 (m, 1H), 2.58 (d, J=5.0 Hz, 2H), 1.26 (s, 9H). LCMS (M+H)=663.4.

Intermediate 14

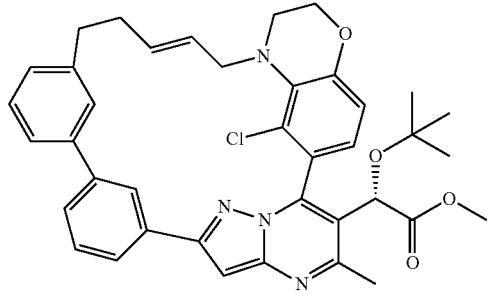

Methyl (2S)-2-(tert-butoxy)-2-[(22E)-32-chloro-4-methyl-28-oxa-5,7,8,25-tetraazaheptacyclo[23.6.2. 1$^{6,9}$.1$^{10,14}$.1$^{15,19}$.0$^{2,7}$.0$^{29,33}$]hexatriaconta-1(31),2,4,6(36), 8,10(35),11,13, 15(34), 16,18,22,29,32-tetradecaen-3-yl]acetate" Second eluting trans isomer. $^1$H NMR (400 MHz, CDCl$_3$) δ: 8.05-8.02 (m, 1H), 7.72 (dt, J=7.0, 1.8 Hz, 1H), 7.52-7.45 (m, 2H), 7.42-7.32 (m, 3H), 7.17-7.11 (m, 1H), 7.00-6.97 (m, 2H), 6.88-6.86 (m, 1H), 5.83-5.65 (m, 2H), 5.34 (s, 1H), 4.31-4.06 (m, 2H), 3.85 (dd, J=15.6, 6.8 Hz, 1H), 3.64 (s, 3H), 3.39-3.18 (m, 2H), 3.06-2.97 (m, 1H), 2.88 (s, 3H), 2.75-2.55 (m, 2H), 1.26 (s, 9H). LCMS (M+H)=663.4.

EXAMPLES 1 AND 2

Both cis (intermediate 13) and trans (intermediate 14) isomers were individually hydrolyzed with 1N NaOH (0.174 mL, 0.174 mmol) in MeOH (2.000 mL) at 50° C. for 3 h and purified by prep-HPLC to afford the desired product.

EXAMPLE 1

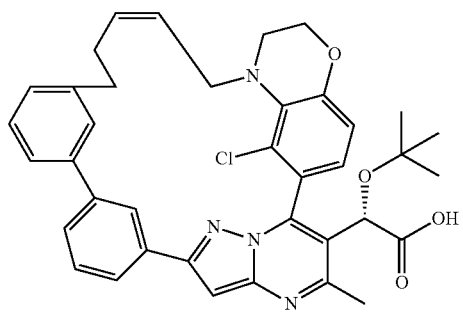 [SMILES: Cc1nc2cc3nn2c(c1[C@H](OC(C)(C)C)C(=O)O)-c1ccc2c(c1Cl)N(C/C=C\CCc1cccc(c1)-c1cccc-3c1)CCO2]

(2S)-2-(tert-Butoxy)-2-[(22Z)-32-chloro-4-methyl-28-oxa-5,7,8,25-tetraazaheptacyclo[23.6.2. 1$^{6,9}$.1$^{10,14}$.1$^{15,19}$.0$^{2,7}$.0$^{29,33}$]hexatriaconta-1(31),2,4,6(36), 8,10(35), 11,13,15(34), 16,18,22,29,32-tetradecaen-3-yl] acetic acid Cis isomer (1.4 mg, 2.049 μmol, 3.54% yield). $^1$H NMR (500 MHz, CDCl$_3$) δ: 8.13 (s, 1H), 7.76 (d, J=7.6 Hz, 1H), 7.55 (d, J=7.9 Hz, 1H), 7.49 (t, J=7.6 Hz, 1H), 7.41-7.33 (m, 3H), 7.17 (d, J=7.3 Hz, 1H), 6.99-6.92 (m, 2H), 6.89-6.85 (m, 1H), 5.76-5.62 (m, 2H), 5.34 (s, 1H), 4.52 (d, J=15.9 Hz, 1H), 4.34-4.14 (m, 2H), 3.46 (dd, J=15.4, 6.7 Hz, 1H), 3.27 (br. s., 2H), 3.00 (dt, J=7.5, 3.6 Hz, 1H), 2.90 (s, 3H), 2.82-2.73 (m, 1H), 2.65-2.50 (m, 2H), 1.20 (s, 9H). LCMS (M+H)=649.4.

EXAMPLE 2

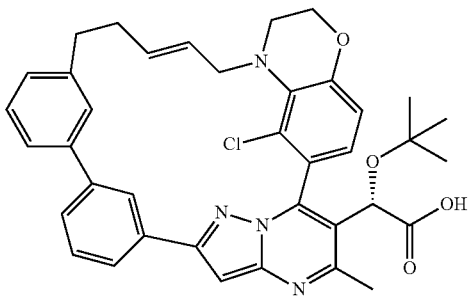 [SMILES: Cc1nc2cc3nn2c(c1[C@H](OC(C)(C)C)C(=O)O)-c1ccc2c(c1Cl)N(C/C=C/CCc1cccc(c1)-c1cccc-3c1)CCO2]

(2S)-2-(tert-Butoxy)-2-[(22E)-32-chloro-4-methyl-28-oxa-5,7,8,25-tetraazaheptacyclo[23.6.2.1$^{6,9}$.1$^{10,14}$.1$^{15,19}$.0$^{2,7}$.0$^{29,33}$]hexatriaconta-1(31),2,4,6(36),8,10(35),11,13,15(34),16,18,22,29,32-tetradecaen-3-yl]acetic acid: Trans isomer (1.9 mg, 2.78 μmol, 4.8% yield). $^1$H NMR (500 MHz, CDCl$_3$) δ: 8.08 (s, 1H), 7.73 (d, J=7.4 Hz, 1H), 7.55-7.47 (m, 2H), 7.44-7.32 (m, 3H), 7.15 (d, J=7.3 Hz, 1H), 6.95-6.87 (m, 3H), 5.78-5.66 (m, 2H), 5.37 (s, 1H), 4.28-4.16 (m, 2H), 4.10 (d, J=14.2 Hz, 1H), 3.87 (dd, J=14.9, 6.9 Hz, 1H), 3.34 (d, J=14.3 Hz, 1H), 3.23-3.15 (m, 1H), 3.02-2.94 (m, 1H), 2.90 (s, 3H), 2.71 (dt, J=14.0, 7.0 Hz, 1H), 2.66-2.56 (m, 2H), 1.21 (s, 9H). LCMS (M+H)=649.4.

Intermediate 15

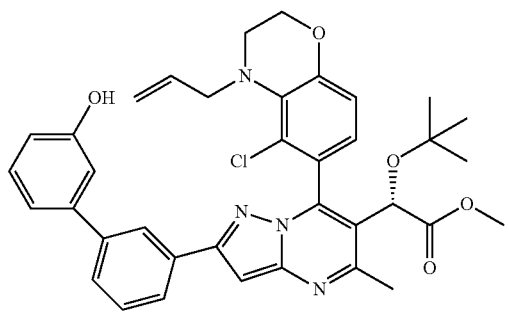

(2S)-Methyl 2-(7-(4-allyl-5-chloro-3,4-dihydro-2H-benzo[b][1,4]oxazin-6-yl)-2-(3'-hydroxy-[1,1'-biphenyl]-3-yl)-5-methylpyrazolo[1,5-a]pyrimidin-6-yl)-2-(tert-butoxy)acetate: A mixture of (2S)-methyl 2-(7-(4-allyl-5-chloro-3,4-dihydro-2H-benzo[b][1,4]oxazin-6-yl)-2-(3-bromophenyl)-5-methylpyrazolo[1,5-a]pyrimidin-6-yl)-2-(tert-butoxy)acetate (120 mg, 0.188 mmol), 3-(4,4,5,5-tetramethyl-1,3,2-dioxaborolan-2-yl)phenol (61.9 mg, 0.281 mmol) and 2M Na$_2$CO$_3$ (0.188 mL, 0.375 mmol) in DMF (2 mL) was degassed for 15 min by bubbling N$_2$ through the reaction mixture. Then, tetrakis(triphenylphosphine)palladium(0) (15.17 mg, 0.013 mmol) was added and the degassing was continue for another 5 min. The mixture was then heated at 90° C. for 16 h. After cooling to room temperature, water was added and the mixture was extracted with ether (2×50 mL), washed with brine (25 mL), dried (Na$_2$SO$_4$), filtered and concentrated. The residue was then purified by biotage (10-40% EtOAc/hexane) to afford (2S)-methyl 2-(7-(4-allyl-5-chloro-3,4-dihydro-2H-benzo[b][1,4]oxazin-6-yl)-2-(3'-hydroxy-[1,1'-biphenyl]-3-yl)-5-methylpyrazolo[1,5-a]pyrimidin-6-yl)-2-(tert-butoxy)acetate (90 mg, 0.138 mmol, 73.5% yield) as off-white solid. $^1$H NMR (500 MHz, CDCl$_3$) δ: 8.02 (t, J=1.6 Hz, 1H), 7.82 (dt, J=7.6, 1.4 Hz, 1H), 7.54-7.51 (m, 1H), 7.47-7.43 (m, 1H), 7.33-7.29 (m, 1H), 7.19-7.13 (m, 1H), 7.10 (t, J=8.1 Hz, 1H), 7.02-7.00 (m, 1H), 6.98 (s, 2H), 6.93 (s, 1H), 6.81 (ddd, J=8.0, 2.5, 0.9 Hz, 1H), 6.42 (dd, J=8.1, 2.3 Hz, 2H), 6.39-6.35 (m, 1H), 6.10-5.98 (m, 1H), 5.40-5.30 (m, 2H), 5.07 (s, 1H), 4.29-4.18 (m, 2H), 3.67 (s, 3H), 3.18 (t, J=4.4 Hz, 2H), 2.87 (s, 3H), 1.18 (s, 9H). LCMS (M+H)=653.4.

Intermediate 16

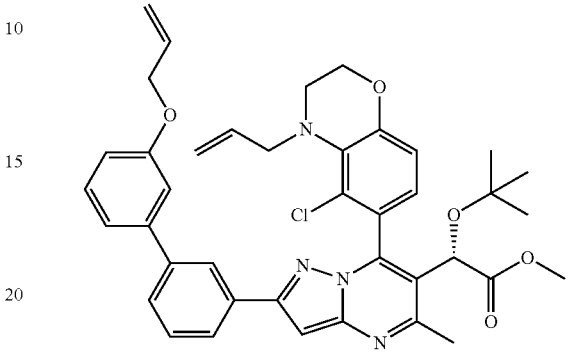

(2S)-Methyl 2-(7-(4-allyl-5-chloro-3,4-dihydro-2H-benzo[b][1,4]oxazin-6-yl)-2-(3'-(allyloxy)-[1,1'-biphenyl]-3-yl)-5-methylpyrazolo[1,5-a]pyrimidin-6-yl)-2-(tert-butoxy)acetate: To a solution of (2S)-methyl 2-(7-(4-allyl-5-chloro-3,4-dihydro-2H-benzo[b][1,4]oxazin-6-yl)-2-(3'-hydroxy-[1,1'-biphenyl]-3-yl)-5-methylpyrazolo[1,5-a]pyrimidin-6-yl)-2-(tert-butoxy)acetate (90 mg, 0.138 mmol) in DMF (2 mL) was added K$_2$CO$_3$ (38.1 mg, 0.276 mmol) followed by 3-bromoprop-1-ene (0.017 mL, 0.207 mmol) and the resulting mixture was heated at 50° C. for 16 h. After cooling to room temperature, water was added and the mixture was extracted with ether (50 mL), washed with brine, dried (Na$_2$SO$_4$), filtered and concentrated. Crude was then purified by biotage (5-30% EtOAc/hexane) to afford (2S)-methyl 2-(7-(4-allyl-5-chloro-3,4-dihydro-2H-benzo[b][1,4]oxazin-6-yl)-2-(3'-(allyloxy)-[1,1'-biphenyl]-3-yl)-5-methylpyrazolo[1,5-a]pyrimidin-6-yl)-2-(tert-butoxy)acetate (40 mg, 0.058 mmol, 41.9% yield) as white solid. 28 mg of starting material was also recovered. $^1$H NMR (500 MHz, CDCl$_3$) δ: 8.05 (t, J=1.6 Hz, 1H), 7.84 (dt, J=7.7, 1.4 Hz, 1H), 7.57-7.53 (m, 1H), 7.45 (t, J=7.6 Hz, 1H), 7.37 (t, J=7.9 Hz, 1H), 7.23-7.20 (m, 1H), 7.19-7.16 (m, 1H), 7.03-6.97 (m, 2H), 6.96-6.92 (m, 1H), 6.17-6.00 (m, 2H), 5.50-5.44 (m, 1H), 5.39-5.29 (m, 3H), 5.25 (dd, J=10.2, 1.6 Hz, 1H), 5.09 (s, 1H), 4.62 (dt, J=5.3, 1.4 Hz, 2H), 4.27 (t, J=4.4 Hz, 2H), 3.67 (s, 3H), 3.27-3.17 (m, 2H), 2.86 (s, 3H), 1.19 (s, 9H). LCMS (M+H)=693.4.

Intermediate 17

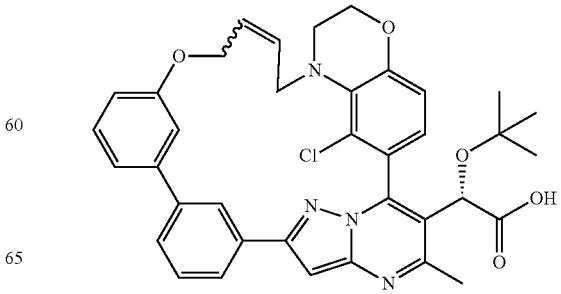

(2S)-2-(tert-Butoxy)-2-[32-chloro-4-methyl-20,28-dioxa-5,7,8,25-tetraazaheptacyclo[23.6.2. 1⁶,⁹.1¹⁰,¹⁴.1¹⁵,¹⁹.0²,⁷.0²⁹,³³]hexatriaconta-1(31),2,4,6(36), 8,10(35), 11,13,15(34), 16,18,22,29,32-tetradecaen-3-yl] acetic acid: A mixture of (2S)-methyl 2-(7-(4-allyl-5-chloro-3,4-dihydro-2H-benzo[b][1,4]oxazin-6-yl)-2-(3'-(allyloxy)-[1,1'-biphenyl]-3-yl)-5-methylpyrazolo[1,5-a]pyrimidin-6-yl)-2-(tert-butoxy)acetate (40 mg, 0.058 mmol) and Hoveyda-Grubbs 2nd generation catalyst (4.90 mg, 5.77 µmol) catalyst in DCE (2 mL) was heated at 50° C. for 5 h. Mixture was then cooled to room temp and concentrated under reduced pressure. Mixture was then treated with 1N NaOH (0.173 mL, 0.173 mmol) in MeOH (2.0 mL) at 50° C. for 3 h. Mixture was then cooled to room temp and purified by prep-HPLC to afford desired product (10 mg, 0.015 mmol, 26.6% yield) as inseparable mixture of cis and trans isomers. Used as is in the next step without further purification. LCMS (M+H)=651.3.

EXAMPLE 3

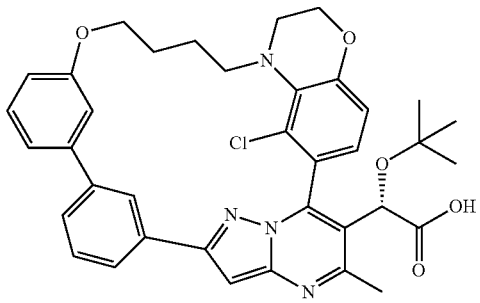 [SMILES: Cc1nc2cc3nn2c(c1[C@H](OC(C)(C)C)C(=O)O)-c1ccc2c(c1Cl)N(CCCCOc1cccc(c1)-c1cccc-3c1)CCO2]

(2S)-2-(tert-Butoxy)-2-{32-chloro-4-methyl-20,28-dioxa-5,7,8,25-tetraazaheptacyclo[23.6.2. 1⁶,⁹.1¹⁰,¹⁴.1¹⁵,¹⁹.0²,⁷.0²⁹,³³]hexatriaconta-1(31), 2,4, 6(36), 8, 10(35), 11, 13, 15 (34), 16,18,29,32-tridecaen-3-yl}acetic acid: To a solution of intermediate 17 (10 mg, 0.015 mmol) in EtOAc (1 mL) was added 10% Pd/C (1.634 mg, 1.536 µmol) and the mixture was stirred under balloon hydrogen atmosphere for 1 h. At this point, LCMS indicated no desired product was formed, so 0.5 mL of MeOH was added and the mixture was stirred under balloon hydrogen atmosphere for 2 h. At this point, LCMS indicated desired product as the major component along with small amount of open form and starting material. Mixture was then filtered and purified by prep HPLC to afford example 3 (4.5 mg, 6.55 µmol, 42.6% yield) as white solid. ¹H NMR (500 MHz, CDCl₃) δ: 8.12 (t, J=1.6 Hz, 1H), 7.71-7.66 (m, 2H), 7.54-7.50 (m, 1H), 7.37-7.33 (m, 1H), 7.28-7.22 (m, 2H), 6.94-6.87 (m, 3H), 6.82 (d, J=8.4 Hz, 1H), 5.31 (s, 1H), 4.36-4.17 (m, 4H), 3.44-3.28 (m, 2H), 3.20 (ddd, J=14.3, 11.1, 3.2 Hz, 1H), 2.90 (s, 3H), 2.16-2.07 (m, 2H), 1.97 (dt, J=11.9, 5.9 Hz, 1H), 1.88-1.71 (m, 2H), 1.20 (s, 9H). LCMS (M+H)=653.3.

Intermediate 18

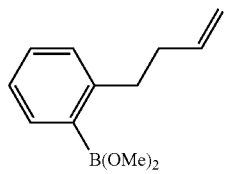

Dimethyl (2-(but-3-en-1-yl)phenyl)boronate: This intermediate was synthesized according to the procedure described by Kuznetsov, N.Yu.; Russ.Chem.Bull., Int.Ed., 2005, 54(3), 678-683. 1-Bromo-2-(but-3-en-1-yl)benzene (1 g, 4.74 mmol) was dissolved in THF (5 mL) and cooled to −78° C. under an atmosphere of N2. BuLi (3.26 mL, 5.21 mmol) was added all at once. This light yellow solution was stirred for 15 min at which time B(OMe)₃ (0.794 mL, 7.11 mmol) was added all at once. This mixture was stirred and allowed to warm to 0° C. Once at this temperature, TMS-Cl (0.787 mL, 6.16 mmol) was added and the reaction was allowed to warm to rt. The reaction mixture was concentrated in vacuo to give 1.2 g of crude product as a colorless oil. Kugelrohr distillation (1 mm, 100-150° C.) gave three fractions (original flask residue, first bulb, and 2nd bulb). The first bulb yielded 60 mg which appeared to be the desired product (90% pure; colorless liquid which crystallized on standing). Used in subsequent reactions without further purification. ¹H NMR (500 MHz, CDCl₃) δ: 7.31 (td, J=1.7, 7.0 Hz, 2H), 7.21-7.25 (m, 2H), 5.86-5.92 (m, 1H), 4.99-5.11 (m, 2H), 3.64 (s, 6H), 2.72-2.76 (t, J=7.4 Hz, 2H), 2.38 (dt, J=1.1, 7.4 Hz, 2H).

Intermediate 19

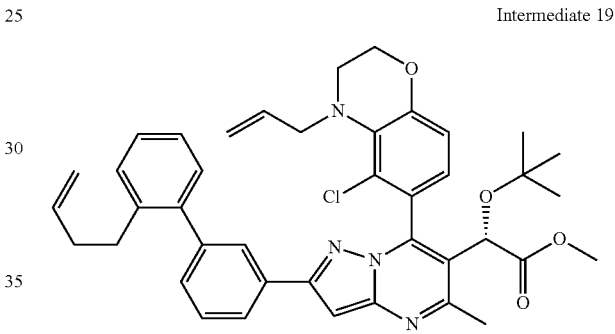

(2S)-Methyl 2-(7-(4-allyl-5-chloro-3,4-dihydro-2H-benzo[b][1,4]oxazin-6-yl)-2-(2'-(but-3-en-1-yl)-[1,1'-biphenyl]-3-yl)-5-methylpyrazolo[1,5-a]pyrimidin-6-yl)-2-(tert-butoxy)acetate: To a 2-5 ml microwave tube was added (2S)-methyl 2-(7-(4-allyl-5-chloro-3,4-dihydro-2H-benzo[b][1,4]oxazin-6-yl)-2-(3-bromophenyl)-5-methylpyrazolo[1,5-a]pyrimidin-6-yl)-2-(tert-butoxy)acetate (0.060 g, 0.094 mmol), dimethyl (2-(but-3-en-1-yl)phenyl)boronate (0.029 g, 0.141 mmol), and 2.0 M aqueous K₂CO₃ (0.094 ml, 0.188 mmol) in DMF (1 ml). The reaction was sparged with nitrogen for 10 minutes, treated with Pd(Ph₃P)₄ (10.83 mg, 9.38 pmol), then sparged for 15 min. The reaction tube was sealed and then heated (90° C., heating block) for 2.5 h. The reaction was cooled, then diluted with Et₂O (20 mL) and washed with water, then brine (20 mL). The organic layer was dried (Na₂SO₄), filtered, and concentrated under reduced pressure to an orange oil (~80 mg). The crude was purified by Biotage column chromatography, and product fractions were pooled and concentrated under reduced pressure, to afford (2S)-methyl 2-(7-(4-allyl-5-chloro-3,4-dihydro-2H-benzo[b][1,4]oxazin-6-yl)-2-(2'-(but-3-en-1-yl)-[1,1'-biphenyl]-3-yl)-5-methylpyrazolo[1,5-a]pyrimidin-6-yl)-2-(tert-butoxy)acetate (0.039 g, 0.056 mmol, 60.2% yield). ¹H NMR (500 MHz, CDCl₃) δ: 7.85 (d, J=7.8 Hz, 1H), 7.78-7.82 (m, 1H), 7.42 (t, J=7.7 Hz, 1H), 7.30-7.35 (m, 2H), 7.25 (t, J=3.4 Hz, 2H), 6.93-7.01 (m, 2H), 6.89 (s, 1H), 5.97-6.10 (m, 1H), 5.69 (ddt, J=16.9, 10.3, 6.7 Hz, 1H), 5.32 (m, J=17.2, 1.4 Hz, 1H), 5.23 (m, J=10.3, 1.3 Hz, 1H), 4.81-4.94 (m, 2H), 4.25 (t, J=4.4 Hz, 2H), 3.66-3.75 (m, 1H), 3.65 (s, 3H), 3.55-3.62 (m, 1H), 3.19 (q, J=3.9 Hz, 2H), 2.84 (s, 3H), 2.64-2.71 (m, 2H), 2.18-2.28 (m, 2H), 1.25-1.33 (m, 1H), 1.17 (s, 9H). LCMS (M+H)=691.5.

Intermediate 20

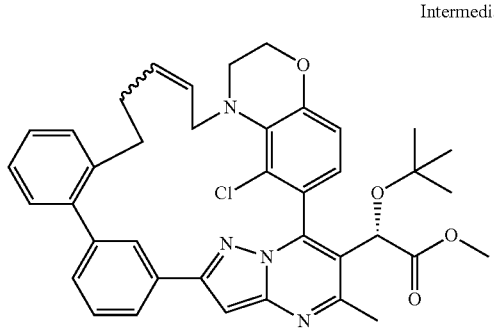

Methyl (2S)-2-(tert-butoxy)-2-[(33-chloro-4-methyl-29-oxa-5,7,8,26-tetraazaheptacyclo[24.6.2.1$^{6,9}$.1$^{10,14}$.1$^{15,19}$.0$^{2,7}$.0$^{29,33}$]hexatriaconta-1(32),2,4,6(36), 8,10(35), 11, 13, 15 (20), 16,18,23,30,33-tetradecaen-3-yl] acetate: A mixture of (2S)-methyl 2-(7-(4-allyl-5-chloro-3,4-dihydro-2H-benzo[b][1,4]oxazin-6-yl)-2-(2'-(but-3-en-1-yl)-[1,1'-biphenyl]-3-yl)-5-methylpyrazolo[1,5-a]pyrimidin-6-yl)-2-(tert-butoxy)acetate (0.039 g, 0.056 mmol) and Hoveyda-Grubbs 2nd generation catalyst (4.79 mg, 5.64 μmol) in DCE (2 mL) was heated at 50° C. for 1 h. The reaction was cooled, then the entire mixture was loaded onto a small plug of silica gel in a Pasteur pipette, and eluted with CH$_2$Cl$_2$ (~5 mL), followed separately by 20% EtOAc in hexanes (~5 mL). The later eluant was concentrated under reduced pressure to afford a gummy oil. The oil was loaded onto a prep-HPLC for purification. The product fraction was concentrated under reduced pressure and the residue containing water was dissolved in CH$_2$Cl$_2$ and dried (Na$_2$SO$_4$), filtered, and concentrated under reduced pressure to afford the product (0.0099 g, 0.015 mmol, 26.5% yield) as a yellow film. $^1$H NMR (500 MHz, CDCl$_3$) δ: 7.98 (s, 1H), 7.82 (d, J=7.9 Hz, 1H), 7.54 (t, J=7.6 Hz, 1H), 7.34 (d, J=7.7 Hz, 1H), 7.19-7.28 (m, 4H), 7.14 (s, 1H), 6.90-6.97 (m, 2H), 5.57-5.63 (m, 2H), 5.11 (s, 1H), 4.30-4.41 (m, 2H), 3.67 (s, 3H), 3.53-3.63 (m, 1H), 3.46-3.54 (m, 1H), 3.34-3.43 (m, 1H), 2.95 (s, 3H), 2.63 (t, J=8.3 Hz, 2H), 2.34-2.40 (m, 5H), 1.21 (s, 9H). LCMS (M+H)=663.3.

EXAMPLE 4

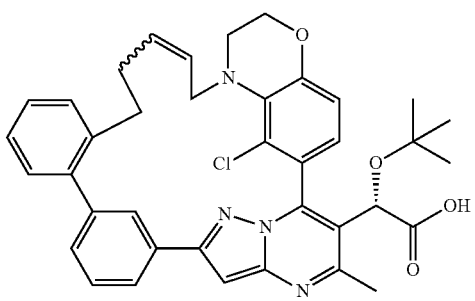 [SMILES: Cc1nc2cc3nn2c(c1[C@H](OC(C)(C)C)C(=O)O)-c1ccc2c(c1Cl)N(CC=CCCc1ccccc1-c1cccc-3c1)CCO2]

(2S)-2-(tert-Butoxy)-2-[(33-chloro-4-methyl-29-oxa-5,7, 8,26-tetraazaheptacyclo[24.6.2.1$^{6,9}$.1$^{10,14}$.0$^{2,7}$.0$^{15,20}$.0$^{30,34}$] hexatriaconta-1(32), 2,4,6(36),8,10(35), 11,13,15(20), 16,18,23,30,33-tetradecaen-3-yl]acetic acid: A solution of intermediate 20 (0.0099 g, 0.015 mmol) and 1N NaOH (0.045 mL, 0.045 mmol) in MeOH (1.0 mL) was stirred with heating (50° C. oil bath) for 18 h. The reaction was cooled, concentrated under reduced pressure and the residue was partitioned between CH$_2$Cl$_2$ and 1N HCl. The organic layer was dried (Na$_2$SO$_4$), filtered, and concentrated under reduced pressure. The residue was dissolved in THF (1 mL), treated with activated carbon, filtered and the filtrate was concentrated under reduced pressure. The white residue was dried under vacuum to afford the desired product (0.0065 g, 8.98 mmol, 58.3%) as a white solid. $^1$H NMR (500 MHz, MeOD) δ: 7.92 (s, 1H), 7.84 (d, J=7.9 Hz, 1H), 7.53 (t, J=7.7 Hz, 1H), 7.26-7.31 (m, 3H), 7.19-7.26 (m, 2H), 7.00 (s, 1H), 6.88-6.99 (m, 2H), 5.63-5.71 (m, 1H), 5.50-5.59 (m, 1H), 5.13 (s, 1H), 4.87 (s, 12H), 4.59 (dd, J=14.9, 9.1 Hz, 1H), 4.26-4.34 (m, 2H), 3.48-3.55 (m, 1H), 3.35-3.45 (m, 2H), 2.83-2.86 (m, 3H), 2.48-2.61 (m, 2H), 2.28-2.42 (m, 1H), 2.16-2.27 (m, 1H), 1.28-1.35 (m, 2H), 1.17-1.22 (m, 9H). LCMS (M+H)=649.4.

Intermediate 21

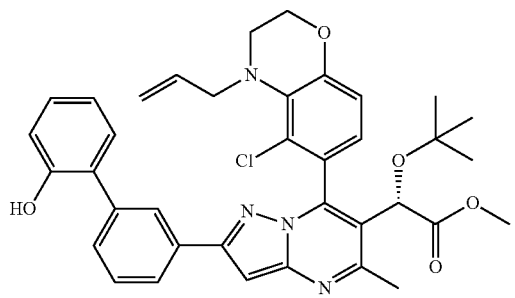

(2S)-Methyl 2-(7-(4-allyl-5-chloro-3,4-dihydro-2H-benzo[b][1,4]oxazin-6-yl)-2-(2'-hydroxy-[1,1'-biphenyl]-3-yl)-5-methylpyrazolo[1,5-d]pyrimidin-6-yl)-2-(tert-butoxy) acetate: To a 2-5 ml microwave tube was added (2S)-methyl 2-(7-(4-allyl-5-chloro-3,4-dihydro-2H-benzo[b][1,4]oxazin-6-yl)-2-(3-bromophenyl)-5-methylpyrazolo[1,5-a]pyrimidin-6-yl)-2-(tert-butoxy)acetate (0.240 g, 0.375 mmol), 2-(4,4,5,5-tetramethyl-1,3,2-dioxaborolan-2-yl)phenol (0.124 g, 0.563 mmol), and 2M aqueous K$_2$CO$_3$ (0.375 ml, 0.750 mmol) in 1,4-dioxane (3.0 ml) and water (0.75 ml). The reaction was sparged with nitrogen for 10 minutes, treated with Pd(Ph$_3$P)$_4$ (0.043 g, 0.038 mmol), then sparged for 15 min. The reaction tube was sealed and heated (90° C., heating block) for 90 min. The reaction was cooled, diluted with water (5 mL) and extracted with Et$_2$O. The ether layer was washed with brine, dried (Na$_2$SO$_4$), filtered, and concentrated under reduced pressure. The residue was adsorbed onto silica gel, then purified by biotage column chromatography (5%-55% EtOAc in hexanes). The product fractions were pooled and concentrated under reduced pressure to afford (2S)-methyl 2-(7-(4-allyl-5-chloro-3,4-dihydro-2H-benzo[b][1,4] oxazin-6-yl)-2-(2'-hydroxy-[1,1'-biphenyl]-3-yl)-5-methylpyrazolo[1,5-a]pyrimidin-6-yl)-2-(tert-butoxy)acetate. $^1$H NMR (500 MHz, CDCl$_3$) δ 7.94 (t, J=1.5 Hz, 1H), 7.86 (dt, J=7.7, 1.4 Hz, 1H), 7.47-7.52 (m, 1H), 7.39-7.45 (m, 1H), 7.25 (s, 1H), 6.95-7.02 (m, 5H), 6.88-6.92 (m, 1H), 5.96-6.10 (m, 1H), 5.51 (br. s., 1H), 5.29-5.37 (m, 1H), 5.24 (dd, J=10.3, 1.5 Hz, 1H), 5.04-5.09 (m, 1H), 4.24 (t, J=4.4 Hz, 2H), 3.67-3.76 (m, 1H), 3.65 (s, 2H), 3.58 (dd, J=15.2, 6.1 Hz, 1H), 3.16-3.23 (m, 2H), 2.84 (s, 3H), 1.95 (s, 1H), 1.17 (s, 9H). LCMS (M+H)=653.4.

Intermediate 22

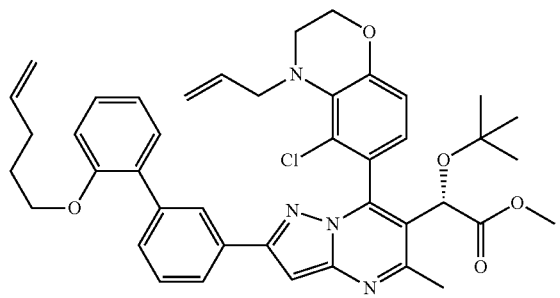

(2S)-Methyl 2-(7-(4-allyl-5-chloro-3,4-dihydro-2H-benzo[b][1,4]oxazin-6-yl)-5-methyl-2-(2'-(pent-4-en-1-yloxy)-[1,1'-biphenyl]-3-yl)-pyrazolo[1,5-a]pyrimidin-6-yl)-2-(tert-butoxy)acetate: A solution of (2S)-methyl 2-(7-(4-allyl-5-chloro-3,4-dihydro-2H-benzo[b][1,4]oxazin-6-yl)-2-(2'-hydroxy-[1,1'-biphenyl]-3-yl)-5-methylpyrazolo[1,5-a]pyrimidin-6-yl)-2-(tert-butoxy)acetate (0.058 g, 0.089 mmol) and $K_2CO_3$ (0.042 g, 0.304 mmol) in dry acetone (5 mL) was treated with 5-bromopent-1-ene (0.026 g, 0.174 mmol), and the reaction was stirred with heating (70° C. oil bath) for 16 h. The reaction was cooled, then concentrated under reduced pressure. The residue was taken up in $CH_2Cl_2$ (5 mL) and washed with 1N HCl (5 mL), dried ($Na_2SO_4$), filtered, and concentrated under reduced pressure. The residue was purified by biotage column chromatography (5%-50% EtOAc in hexanes). Product fractions were pooled and concentrated under reduced pressure. The product, (2S)-methyl 2-(7-(4-allyl-5-chloro-3,4-dihydro-2H-benzo[b][1,4]oxazin-6-yl)-5-methyl-2-(2'-(pent-4-en-1-yloxy)-[1,1'-biphenyl]-3-yl)pyrazolo[1,5-a]pyrimidin-6-yl)-2-(tert-butoxy)acetate (0.031 g, 0.040 mmol, 45.4% yield) was isolated as a clear film. $^1$H NMR (400 MHz, $CDCl_3$) δ 8.04-7.99 (m, 1H), 7.85-7.79 (m, 1H), 7.54-7.49 (m, 1H), 7.44-7.38 (m, 1H), 7.36 (dd, J=7.5, 1.8 Hz, 1H), 7.31 (td, J=7.8, 1.6 Hz, 1H), 7.03 (td, J=7.5, 0.9 Hz, 1H), 7.01-6.94 (m, 3H), 6.90 (s, 1H), 6.03 (ddt, J=16.9, 10.5, 6.0 Hz, 1H), 5.74 (ddt, J=17.0, 10.3, 6.7 Hz, 1H), 5.33 (dd, J=17.1, 1.5 Hz, 1H), 5.24 (d, J=10.0 Hz, 1H), 5.05 (s, 1H), 4.96-4.86 (m, 2H), 4.26 (t, J=4.4 Hz, 2H), 3.96 (t, J=6.4 Hz, 2H), 3.78-3.69 (m, 1H), 3.65 (s, 3H), 3.64-3.55 (m, 1H), 3.20 (q, J=4.2 Hz, 2H), 2.84 (s, 3H), 2.11 (q, J=6.9 Hz, 2H), 1.83-1.71 (m, 2H), 1.63 (s, 1H), 1.17 (s, 9H). LCMS (M+H)=721.5.

Intermediate 23

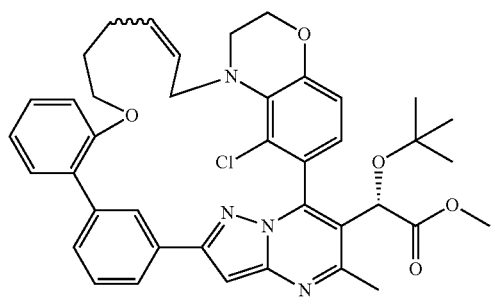

Methyl (2S)-2-(tert-butoxy)-2-[(35-chloro-4-methyl-21,31-dioxa-5,7,8,28-tetraazaheptacyclo[26.6.2. 1⁶,⁹.1¹⁰,¹⁴.0²,⁷.0¹⁵,²⁰.0³²,³⁶]octatriaconta-1(34),2,4,6(38),8, 10(37), 11, 13, 15(20), 16,18,25,32,35-tetradecaen-3-yl]acetate: A mixture of (2S)-methyl 2-(7-(4-allyl-5-chloro-3,4-dihydro-2H-benzo[b][1,4]oxazin-6-yl)-5-methyl-2-(2'-(pent-4-en-1-yloxy)-[1,1'-biphenyl]-3-yl)pyrazolo[1,5-a]pyrimidin-6-yl)-2-(tert-butoxy)acetate (0.039 g, 0.054 mmol) and Hoveyda-Grubbs 2nd generation catalyst (4.59 mg, 5.41 μmol) in DCE (2 mL) was sparged wtih nitrogen, then heated at 50° C. for 3 h. The reaction was cooled, then the entire mixture was loaded onto a small plug of silica gel in a Pasteur pipette, and eluted with $CH_2Cl_2$ (~5 mL), followed separately by 20%-50% EtOAc in hexanes (~5 mL each step, 10% steps). The later eluant was concentrated under reduced pressure to afford a gummy oil. The product (0.020 g, 0.029 mmol, 53.4% yield) was used immediately in the following step. LCMS (M+H)=693.4.

Intermediate 24

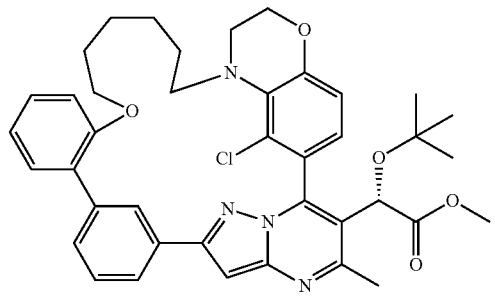

Methyl (2S)-2-(tert-butoxy)-2-{35-chloro-4-methyl-21,31-dioxa-5,7,8,28-tetraazaheptacyclo[26.6.2. 1⁶,⁹.1¹⁰,¹⁴.0²,⁷.0¹⁵,²⁰.0³²,³⁶]octatriaconta-1(34),2,4,6(38),8, 10(37), 11, 13, 15 (20), 16,18,32,35-tridecaen-3-yl}acetate: A solution of intermediate 23 (0.020 g, 0.029 mmol) in MeOH (2 mL) and $CH_2Cl_2$ (0.5 mL) was treated with 10 wt % Pd/C (3.07 mg, 0.029 mmol) and the sealed flask was twice evacuated and back-filled with hydrogen gas (balloon). The reaction was stirred for 14.5 h. The reaction was filtered through celite, washing with several portions of MeOH, and the filtrate was concentrated under reduced pressure, affording a white film, which was used immediately in the following step. LCMS (M+H)=695.5.

EXAMPLE 5

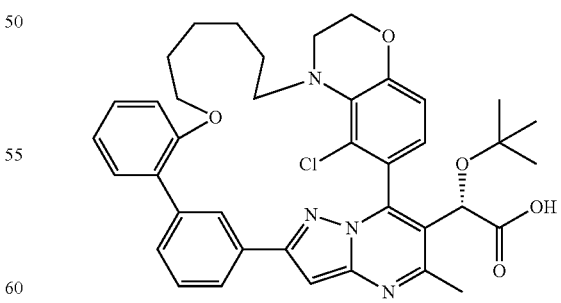

(2S)-2-(tert-Butoxy)-2-{35-chloro-4-methyl-21,31-dioxa-5,7,8,28-tetraazaheptacyclo[26.6.2. 1⁶,⁹.1¹⁰,¹⁴.0²,⁷.0¹⁵,²⁰0³²,³⁶]octatriaconta-1(34),2,4,6(38),8, 10(37), 11, 13, 15 (20), 16,18,32,35-tridecaen-3-yl}acetic acid: A solution of intermediate 24 (0.020 g, 0.029 mmol) in MeOH (1 mL) was treated with 1N NaOH (0.086 mL, 0.086 mmol), and the reaction was heated (50° C. heating block) for 10 h, then cooled to room temperature and quenched with 1M HCl (0.086 mL, 0.086 mmol). The reaction was diluted with water (1.5 mL), resulting in a cloudy suspension. The product was extracted with $CH_2Cl_2$ (3×1 mL), and the combined extracts were dried ($Na_2SO_4$), filtered, and concentrated under reduced pressure. The residue was dried once from $Et_2O$ to afford example 5 (0.0021 g, 2.81 μmol, 9.78% yield) as a white powdery solid. $^1H$ NMR (500 MHz, $CDCl_3$) δ 8.14 (t, J=1.5 Hz, 1H), 7.76 (dt, J=7.8, 1.4 Hz, 1H), 7.47 (t, J=7.7 Hz, 1H), 7.30-7.33 (m, 1H), 7.25-7.28 (m, 1H), 7.22 (dd, J=7.4, 1.7 Hz, 1H), 6.95-7.02 (m, 3H), 6.91 (d, J=8.4 Hz, 1H), 6.82 (d, J=8.4 Hz, 1H), 5.27 (s, 1H), 4.24-4.30 (m, 1H), 4.10-4.18 (m, 2H), 3.86 (dt, J=10.3, 5.3 Hz, 1H), 3.26-3.36 (m, 1H), 3.21 (d, J=14.3 Hz, 1H), 3.03-3.12 (m, 1H), 2.86 (s, 3H), 2.58-2.67 (m, 1H), 1.74-1.89 (m, 4H), 1.50-1.71 (m, 6H), 1.19 (s, 9H). LCMS (M+H)=681.5.

Intermediate 25

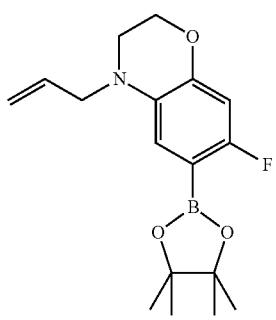

4-Allyl-7-fluoro-6-(4,4,5,5-tetramethyl-1,3,2-dioxaborolan-2-yl)-3,4-dihydro-2H-benzo[b][1,4]oxazine: A solution of 7-fluoro-6-(4,4,5,5-tetramethyl-1,3,2-dioxaborolan-2-yl)-3,4-dihydro-2H-benzo[b][1,4]oxazine (0.503 g, 1.802 mmol, Ref. WO20100130034) and $K_2CO_3$ (0.504 g, 3.65 mmol) in dry DMF (5 mL) was sparged with $N_2$ for 5 min, then treated with allyl bromide (0.8 mL, 9.17 mmol). The reaction tube was sealed then heated (70° C.) for 22 h. The reaction was diluted with water (50 mL) and extracted into EtOAc (50 mL). The organic layer was washed with water, brine, and then dried ($Na_2SO_4$), filtered, and concentrated. The residue was purified by biotage (4 g $SiO_2$, 5% (3 CV), 5-40% (15 CV), 40% (2 CV), EtOAc in hexanes), affording the desired product (0.430 g, 1.347 mmol, 74.8% yield) as a clear viscous oil. $^1H$ NMR (500 MHz, $CDCl_3$) δ 7.03 (6, J=5.7 Hz, 1H), 6.51 (d, J=9.9 Hz, 1H), 5.84-5.94 (m, 1H), 5.26-5.31 (m, 1H), 5.24 (m, 1H), 4.25-4.32 (m, 2H), 3.87 (m, 2H), 3.19-3.25 (m, 2H), 1.34 (s, 12H). LCMS (M+H)=319.7.

Intermediate 26

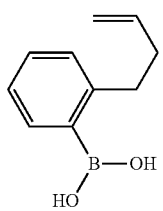

(2-(But-3-en-1-yl)phenyl)boronic acid: Ref Li, W., Nelson, D. P., Jensen, M. S., Hoerrner, R. S., Cai, D., Larsen, R. D., Reider, P. J. *J. Org. Chem.*, 2002, 67, 5394-5397. A solution of 1-bromo-2-(but-3-en-1-yl)benzene (9.46 g, 44.8 mmol) in dry THF (44.8 ml) was cooled (−78° C.) and treated with 2.5 M n-BuLi in hexanes (19.7 ml, 49.3 mmol). The mixture was stirred for 20 min, and then treated with triisopropyl borate (51.5 ml, 224 mmol). After 90 min, the reaction mixture was warmed to room temperature over 1 h. Then, the reaction was quenched with 2.0 N aq. HCl (240 mL), diluted with $Et_2O$ (120 mL), and the layers were stirred vigorously for several minutes. The resulting white precipitate was removed by filtration and then the filtrate layers were separated. The organic layer was dried ($Na_2SO_4$), filtered, and concentrated, affording a pale yellow oil which partially solidified upon standing. These solids were triturated with hexanes and then dried under vacuum. The decantate was concentrated to an oil, dissolved in fresh hexanes (~15 mL) and stored (−40° C.) for 16 h. A second crop of solid was collected, washing with a small volume of hexanes, and dried under vacuum Both crops were combined to afford the desired product (5.46 g, 31.0 mmol, 69.2% yield) as a white crystalline solid. $^1H$ NMR (500 MHz, $CDCl_3$) δ 8.24 (dd, J=7.8, 1.3 Hz, 1H), 7.52 (td, J=7.5, 1.4 Hz, 1H), 7.30-7.36 (m, 2H), 5.96 (ddt, J=17.0, 10.3, 6.5 Hz, 1H), 5.04-5.10 (m, 1H), 5.02 (dd, J=10.2, 1.6 Hz, 1H), 3.29-3.40 (m, 2H), 2.50 (td, J=7.9, 6.6 Hz, 2H). LCMS (M−H)=175.11.

Intermediate 27

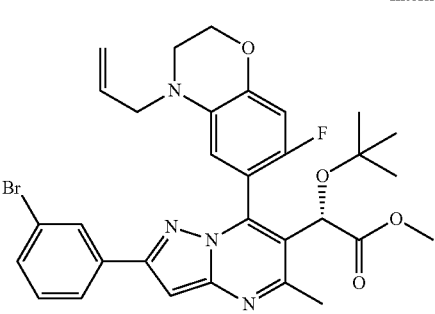

(2S)-Methyl 2-(7-(4-allyl-7-fluoro-3,4-dihydro-2H-benzo[b][1,4]oxazin-6-yl)-2-(3-bromophenyl)-5-methylpyrazolo[1,5-a]pyrimidin-6-yl)-2-(tert-butoxy)acetate: A solution of (S)-methyl 2-(2-(3-bromophenyl)-7-iodo-5-methylpyrazolo[1,5-a]pyrimidin-6-yl)-2-(tert-butoxy)acetate (0.100 g, 0.179 mmol), 4-allyl-7-fluoro-6-(4,4,5,5-tetramethyl-1,3,2-dioxaborolan-2-yl)-3,4-dihydro-2H-benzo[b][1,4]oxazine (0.060 g, 0.188 mmol) and 2.0 M aq. $Na_2CO_3$ (0.179 mL, 0.358 mmol) in DMF (4 mL) was sparged with $N_2$ for 5 min, treated with $Pd(Ph_3P)_4$ (0.014 g, 0.013 mmol), sparged for 2 minutes, then sealed and heated (90° C.) for 6 h. The reaction was filtered (0.45 μm syringe tip filter), and purified by prep-HPLC, affording the desired product (0.033 g, 0.053 mmol, 29.5% yield), as a yellow oily film. $^1H$ NMR (500 MHz, $CDCl_3$) δ 8.05 (s, 1H), 7.83 (d, J=7.6 Hz, 1H), 7.45-7.50 (m, 1H), 7.28-7.33 (m, 1H), 6.97 (br. s., 1H), 6.83 (d, J=6.3 Hz, 1H), 6.74-6.81 (m, 1H), 5.73-5.84 (m, 1H), 5.14-5.30 (m, 3H), 4.35-4.46 (m, 2H), 3.95 (m, 1H), 3.79 (s, 3H), 3.69-3.76 (m, 1H), 3.41-3.50 (m, 1H), 3.36 (m, 1H), 2.67-2.76 (m, 3H), 1.00-1.05 (m, 9H). LCMS (M+H)=625.3.

Intermediate 28

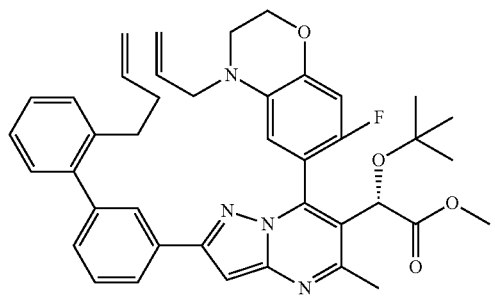

(2S)-Methyl 2-(7-(4-allyl-7-fluoro-3,4-dihydro-2H-benzo[b][1,4]oxazin-6-yl)-2-(2'-(but-3-en-1-yl)-[1,1'-biphenyl]-3-yl)-5-methylpyrazolo[1,5-d]pyrimidin-6-yl)-2-(tert-butoxy)acetate: A solution of (2S)-methyl 2-(7-(4-allyl-7-fluoro-3,4-dihydro-2H-benzo[b][1,4]oxazin-6-yl)-2-(3-bromophenyl)-5-methylpyrazolo[1,5-a]pyrimidin-6-yl)-2-(tert-butoxy)acetate (0.033 g, 0.053 mmol), (2-(but-3-en-1-yl)phenyl)boronic acid (0.019 g, 0.106 mmol) and 2.0 M aq. $Na_2CO_3$ (0.066 mL, 0.132 mmol) in DMF (3.0 mL) was sparged with $N_2$ for 15 min, then treated with $Pd(Ph_3P)_4$ (4.28 mg, 3.70 µmol), sparged for 5 min, then heated (90° C.) for 5 h. The reaction was cooled, filtered, and purified by prep-HPLC to afford the desired product (0.016 g, 0.024 mmol, 44.8% yield) as a yellow film. $^1$H NMR (500 MHz, $CDCl_3$) δ 7.92 (dt, J=7.7, 1.3 Hz, 1H), 7.87 (t, J=1.6 Hz, 1H), 7.46 (t, J=7.7 Hz, 1H), 7.32-7.37 (m, 3H), 7.30 (d, J=1.4 Hz, 2H), 6.91 (s, 1H), 6.85 (d, J=6.3 Hz, 1H), 6.76 (d, J=10.1 Hz, 1H), 5.67-5.85 (m, 2H), 5.27 (s, 1H), 5.14-5.24 (m, 2H), 4.84-4.95 (m, 2H), 4.37-4.43 (m, 2H), 3.96 (dd, J=16.9, 4.7 Hz, 1H), 3.79 (s, 3H), 3.68-3.75 (m, 1H), 3.31-3.48 (m, 2H), 2.68-2.73 (m, 2H), 2.66 (s, 3H), 2.27 (q, J=7.5 Hz, 2H), 1.04 (s, 9H). LCMS (M+H)=675.5.

Intermediate 29

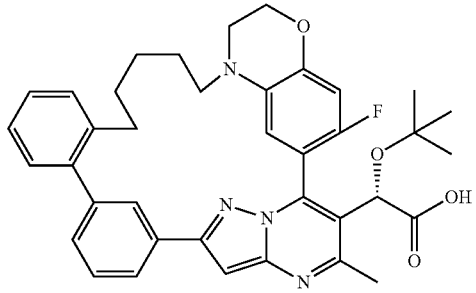 [SMILES: Cc1nc2cc3nn2c(c1[C@H](OC(C)(C)C)C(=O)O)-c1cc2c(cc1F)OCCN2CCCCCc1ccccc1-c1cccc-3c1]

Methyl (2S)-2-(tert-butoxy)-2-[(32-fluoro-4-methyl-29-oxa-5,7,8,26-tetraazaheptacyclo[24.6.2.1$^{6,9}$.1$^{10,14}$.0$^{2,7}$.0$^{15,20}$.0$^{30,34}$]hexatriaconta-1 (32), 2,4,6(36), 8,10(35),11, 13, 15 (20), 16,18,23,30,33-tetradecaen-3-yl]acetate: A solution of (2S)-methyl 2-(7-(4-allyl-7-fluoro-3,4-dihydro-2H-benzo[b][1,4]oxazin-6-yl)-2-(2'-(but-3-en-1-yl)-[1,1'-biphenyl]-3-yl)-5-methylpyrazolo[1,5-a]pyrimidin-6-yl)-2-(tert-butoxy)acetate (0.024 g, 0.036 mmol) in DCE (10 mL) was heated (70° C.) under $N_2$ atmosphere, and then treated with Hoveyda-Grubbs Catalyst 2nd Gen. (2.2 mg, 3.6 µmol). The reaction was stirred for 90 min. The reaction was cooled, concentrated, and the crude intermediate was used immediately in the following step. LCMS (M+H)=647.5.

Intermediate 30

Methyl (2S)-2-(tert-butoxy)-2-{32-fluoro-4-methyl-29-oxa-5,7,8,26-tetraazaheptacyclo[24.6.2.1$^{6,9}$.1$^{10,14}$.0$^{2,7}$.0$^{15,20}$.0$^{30,34}$]hexatriaconta-1 (32), 2,4, 6(36), 8, 10(35), 11, 13, 15(20),16,18,30,33-tridecaen-3-yl}acetate: A solution of methyl (2S)-2-(tert-butoxy)-2-[32-fluoro-4-methyl-29-oxa-5,7,8,26-tetraazaheptacyclo[24.6.2.1$^{6,9}$.1$^{10,14}$.0$^{2,7}$.0$^{15,20}$.0$^{30,34}$]hexatriaconta-1 (32),2,4,6(36),8,10(35),11,13,15 (20),16,18,23,30,33-tetradecaen-3-yl]acetate (0.023 g, 0.036 mmol) in MeOH (5 mL) was treated with 10 wt % Pd/C (4 mg, 0.04 mmol), evacuated and hydrogen back-filled three times, then stirred under hydrogen atmosphere for 18 h. The crude mixture was filtered (0.45 µm syringe tip filter) and the filtrate solution was used immediately in the following step. LCMS (M+H)= 649.5.

EXAMPLE 6

(2S)-2-(tert-Butoxy)-2-{32-fluoro-4-methyl-29-oxa-5,7, 8,26-tetraazaheptacyclo[24.6.2.1$^{6,9}$.1$^{10,14}$.0$^{2,7}$.0$^{15,20}$.0$^{30,34}$] hexatriaconta-1(32),2,4,6(36),8,10(35), 11, 13, 15(20), 16,18,30,33-tridecaen-3-yl}acetic acid: A solution of methyl (2S)-2-(tert-butoxy)-2-{32-fluoro-4-methyl-29-oxa-5,7,8, 26-tetraazaheptacyclo[24.6.2.1$^{6,9}$.1$^{10,14}$.0$^{2,7}$.0$^{15,20}$.0$^{30,34}$] hexatriaconta-1(32),2,4,6(36),8,10(35),11,13,15(20),16,18, 30,33-tridecaen-3-yl}acetate (0.023 g, 0.036 mmol) in MeOH (~2 mL) was treated with 1.0 N aq. NaOH (0.360 ml, 0.360 mmol) and heated (70° C. oil bath) for 4 h, then temperature was lowered to 50° C. and stirring continued for 16 h. The reaction was cooled and purified by prep-HPLC to afford desired product. $^1$H NMR (500 MHz, DMSO-$d_6$) δ 7.98-7.83 (m, 2H), 7.59-7.49 (m, 1H), 7.40-7.29 (m, 2H), 7.29-7.20 (m, 2H), 7.17 (br. s., 2H), 7.00 (d, J=6.4 Hz, 1H), 6.82 (d, J=10.4 Hz, 1H), 4.84 (br. s., 1H), 4.19 (br. s., 3H), 2.94-2.79 (m, 2H), 2.72 (d, J=12.2 Hz, 2H), 2.62 (br. s., 3H), 1.69 (br. s., 1H), 1.59-1.18 (m, 6H), 0.92 (br. s., 9H). UPLC-MS (M+H)=635.4.

Intermediate 31

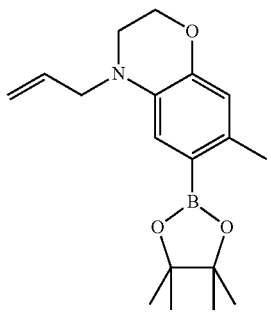

4-Allyl-7-methyl-6-(4,4,5,5-tetramethyl-1,3,2-dioxaborolan-2-yl)-3,4-dihydro-2H-benzo[b][1,4]oxazine: A solution of 7-methyl-6-(4,4,5,5-tetramethyl-1,3,2-dioxaborolan-2-yl)-3,4-dihydro-2H-benzo[b][1,4]oxazine (0.488 g, 1.774 mmol, prepared according to the procedures outlined for related compounds in Ref. WO20100130034) and $K_2CO_3$ (0.490 g, 3.55 mmol) in dry DMF (5 mL) was sparged with $N_2$ for 5 min, treated with allyl bromide (0.773 mL, 8.87 mmol), then heated (70° C.) for 22 h. The reaction was diluted with water (50 mL) and extracted into EtOAc (50 mL) and washed with water, brine and then dried ($Na_2SO_4$), filtered, and concentrated. The crude was purified by biotage column chromatography (12 g $SiO_2$, 0% (3 CV), 0-40% (10 CV), 40% (2 CV), EtOAc in hexanes). Product rich fractions were re-purified by biotage (0% (3 CV), 0-40% (15 CV), 40% (2 CV), EtOAc in hexanes) to afford the desired product (0.345 g, 0.938 mmol, 52.9% yield), as a colorless viscous oil. $^1$H NMR (500 MHz, $CDCl_3$) δ 7.20 (s, 1H), 6.62 (d, J=0.5 Hz, 1H), 5.92 (ddt, J=16.9, 10.4, 5.9 Hz, 1H), 5.29 (dq, J=17.2, 1.6 Hz, 1H), 5.23 (dq, J=10.2, 1.4 Hz, 1H), 4.30-4.24 (m, 2H), 3.89 (dt, J=5.9, 1.3 Hz, 2H), 3.27-3.18 (m, 2H), 2.43 (s, 3H), 1.33 (s, 12H).

Intermediate 32

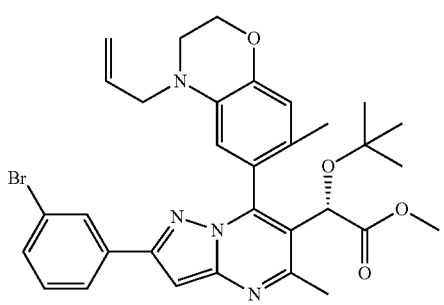

(2S)-Methyl 2-(7-(4-allyl-7-methyl-3,4-dihydro-2H-benzo[b][1,4]oxazin-6-yl)-2-(3-bromophenyl)-5-methylpyrazolo[1,5-a]pyrimidin-6-yl)-2-(tert-butoxy)acetate: A solution of (S)-methyl 2-(2-(3-bromophenyl)-7-iodo-5-methylpyrazolo[1,5-a]pyrimidin-6-yl)-2-(tert-butoxy)acetate (0.100 g, 0.179 mmol), 4-allyl-7-methyl-6-(4,4,5,5-tetramethyl-1,3,2-dioxaborolan-2-yl)-3,4-dihydro-2H-benzo[b][1,4]oxazine (0.062 g, 0.197 mmol) and 2.0 M $Na_2CO_3$ (0.179 mL, 0.358 mmol) in dry DMF (3 mL) was sparged with $N_2$ for 10 min, treated with Pd(Ph$_3$P)$_4$ (0.014 g, 0.013 mmol), sparged for 5 minutes, then heated (90° C.) for 48 h. The reaction was cooled, filtered (0.45 μm syringe tip filter) and purified by prep-HPLC to afford the desired product (0.028 g, 0.045 mmol, 25.2% yield) as a yellow oily film. $^1$H NMR (500 MHz, $CDCl_3$) δ 7.99 (t, J=1.7 Hz, 1H), 7.78 (dt, J=7.7, 1.3 Hz, 1H), 7.49-7.42 (m, 1H), 7.26-7.22 (m, 1H), 6.87-6.80 (m, 2H), 6.61 (s, 1H), 5.86-5.73 (m, 1H), 5.22 (dd, J=17.2, 1.6 Hz, 1H), 5.17 (dd, J=10.2, 1.4 Hz, 1H), 5.11 (s, 1H), 4.42-4.30 (m, 2H), 3.87-3.78 (m, 1H), 3.75-3.68 (m, 1H), 3.66 (s, 3H), 3.42-3.34 (m, 1H), 3.32-3.24 (m, 1H), 2.76 (s, 3H), 1.90 (s, 3H), 1.17 (s, 9H). LCMS (M+H)=621.3.

Intermediate 33

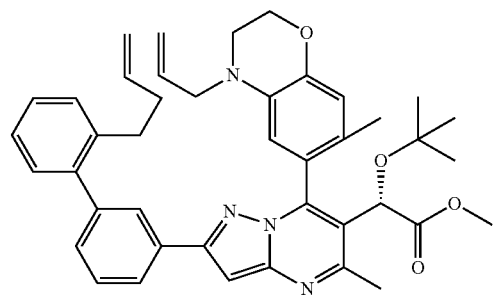

(2S)-Methyl 2-(7-(4-allyl-7-methyl-3,4-dihydro-2H-benzo[b][1,4]oxazin-6-yl)-2-(2'-(but-3-en-1-yl)-[1,1'-biphenyl]-3-yl)-5-methylpyrazolo[1,5-a]pyrimidin-6-yl)-2-(tert-butoxy)acetate: A solution of (2S)-methyl 2-(7-(4-allyl-7-methyl-3,4-dihydro-2H-benzo[b][1,4]oxazin-6-yl)-2-(3-bromophenyl)-5-methylpyrazolo[1,5-a]pyrimidin-6-yl)-2-(tert-butoxy)acetate (0.028 g, 0.045 mmol), (2-(but-3-en-1-yl)phenyl)boronic acid (0.016 g, 0.090 mmol) and 2.0 M aq. $Na_2CO_3$ (0.056 ml, 0.113 mmol) in dry DMF (2.5 ml) was sparged with $N_2$ for 15 min, then treated with Pd(Ph$_3$P)$_4$ (3.7 mg, 3.2 μmol), sparged for another 5 min, then heated (90° C.) for 16 h. The reaction was cooled, filtered (0.45 μm syringe tip filter), and purified by prep-HPLC to afford the desired product. $^1$H NMR (500 MHz, $CDCl_3$) δ 7.88 (dt, J=7.9, 1.3 Hz, 1H), 7.83 (t, J=1.5 Hz, 1H), 7.44 (t, J=7.6 Hz, 1H), 7.32-7.36 (m, 2H), 7.29-7.31 (m, 1H), 7.26-7.28 (m, 2H), 6.88 (s, 1H), 6.81 (s, 1H), 6.64 (s, 1H), 5.65-5.85 (m, 2H), 5.21 (dd, J=17.2, 1.6 Hz, 1H), 5.10-5.15 (m, 2H), 4.85-4.94 (m, 2H), 4.33-4.38 (m, 2H), 3.78-3.86 (m, 1H), 3.68-3.76 (m, 1H), 3.67 (s, 3H), 3.23-3.40 (m, 2H), 2.78 (s, 3H), 2.66-2.74 (m, 2H), 2.26 (td, J=7.9, 6.7 Hz, 2H), 1.92 (s, 3H), 1.20 (s, 9H). LCMS (M+H)=671.5.

Intermediate 34

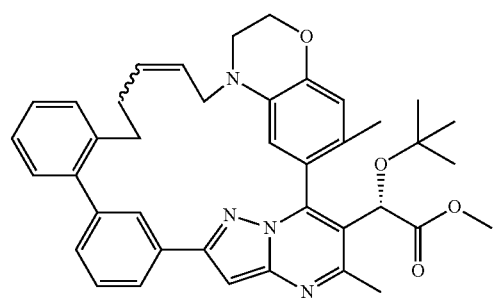

Methyl (2S)-2-(tert-butoxy)-2-[4,32-dimethyl-29-oxa-5,7,8,26-tetraazaheptacyclo[24.6.2. 1$^{6,9}$.1$^{10,14}$.0$^{2,7}$.0$^{15,20}$.0$^{30,34}$]hexatriaconta-1(32), 2,4,6(36),8,10(35),11, 13, 15(20), 16,18,23,30,33-tetradecaen-3-yl]acetate: A solution of (2S)-methyl 2-(7-(4-allyl-7-methyl-3,4-dihydro-2H-benzo[b][1,4]oxazin-6-yl)-2-(2'-

(but-3-en-1-yl)-[1,1'-biphenyl]-3-yl)-5-methylpyrazolo[1,5-a]pyrimidin-6-yl)-2-(tert-butoxy)acetate (0.030 g, 0.045 mmol) in dry DCE (5 mL) was heated (70° C. oil bath) and then treated with Hoveyda-Grubbs Cat. 2nd Gen. (3 mg, 5 μmol). The reaction was stirred for 90 min. The solvent was removed and the intermediate was used immediately in the following step. LCMS (M+H)=643.4.

Intermediate 35

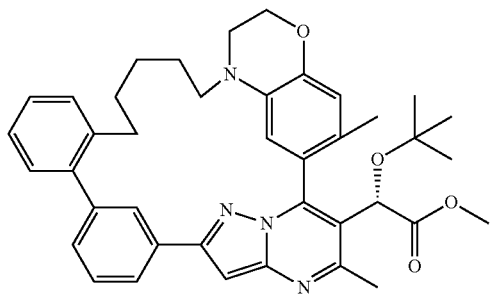

Methyl (2S)-2-(tert-butoxy)-2-{4,32-dimethyl-29-oxa-5,7,8,26-tetraazaheptacyclo[24.6.2.1$^{6,9}$.1$^{10,14}$.0$^{2,7}$.0$^{15,20}$.0$^{30,34}$]hexatriaconta-1(32), 2,4,6(36),8,10(35), 11,13, 15(20),16,18,30,33-tridecaen-3-yl}acetate: A solution of methyl (2S)-2-(tert-butoxy)-2-[4,32-dimethyl-29-oxa-5,7,8,26-tetraazaheptacyclo[24.6.2.1$^{6,9}$.1$^{10,14}$.0$^{2,7}$.0$^{15,20}$.0$^{30,34}$]hexatriaconta-1(32),2,4,6(36),8,10(35), 11,13,15 (20),16,18,23,30,33-tetradecaen-3-yl]acetate in MeOH (4 mL), was treated with 10 wt % Pd/C (5 mg, 0.05 mmol), evacuated and hydrogen purged three times, then stirred under hydrogen atmosphere for 18 h. The reaction was filtered (0.45 μm syringe tip filter), concentrated to a film, and the residue was used immediately in the following step. LCMS (M+H)=645.4.

EXAMPLE 7

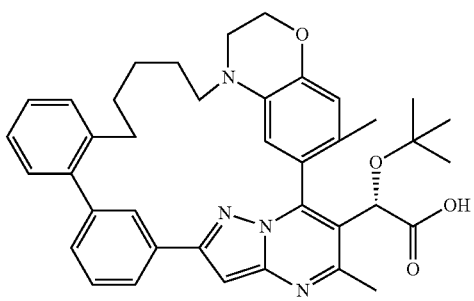 [SMILES: Cc1cc2c3cc1-c1c([C@H](OC(C)(C)C)C(=O)O)c(C)nc4cc(nn14)-c1cccc(c1)-c1ccccc1CCCCCN3CCO2]

(2S)-2-(tert-Butoxy)-2-{4,32-dimethyl-29-oxa-5,7,8,26-tetraazaheptacyclo[24.6.2.1$^{6,9}$.1$^{10,14}$.0$^{2,7}$.0$^{15,20}$.0$^{30,34}$]hexatriaconta-1(32), 2,4,6(36),8,10(35), 11, 13, 15(20), 16,18,30,33-tridecaen-3-yl}acetic acid: A solution of methyl (2S)-2-(tert-butoxy)-2-{4,32-dimethyl-29-oxa-5,7,8,26-tetraazaheptacyclo[24.6.2.1$^{6,9}$1$^{10,14}$.0$^{2,7}$.0$^{15,20}$.0$^{30,34}$]hexatriaconta-1(32),2,4,6(36),8,10(35),11,13,15(20),16,18, 30,33-tridecaen-3-yl}acetate (0.029 g, 0.045 mmol) in MeOH (2 mL) was treated with NaOH (0.225 mL, 0.225 mmol) and the mixture was heated (70° C.) for 11 h, then stirred at 50° C. for an additional 60 h. The reaction mixture was purified by prep HPLC to afford desired product (0.0041 g, 6.5 μmol, 14.4% yield). $^1$H NMR (500 MHz, DMSO-d$_6$) δ: 7.87 (d, J=7.0 Hz, 1H), 7.82 (br. s., 1H), 7.53 (t, J=7.5 Hz, 1H), 7.40-7.30 (m, 2H), 7.29-7.20 (m, 2H), 7.17 (d, J=7.6 Hz, 1H), 7.12 (s, 1H), 6.67 (d, J=4.9 Hz, 2H), 4.85 (s, 1H), 4.12 (br, 3H), 2.61 (s, 3H), 1.98-1.86 (m, 3H), 1.72 (br. s., 1H), 1.47 (br. s., 3H), 1.36-1.18 (m, 2H), 0.94 (s, 9H). Note: some proton signals are solvent obscured. LCMS (M+H)=631.4.

Intermediate 36

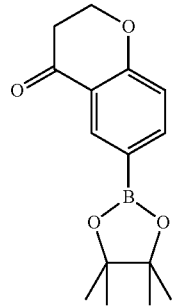

6-(4,4,5,5-Tetramethyl-1,3,2-dioxaborolan-2-yl)chroman-4-one: A mixture of 6-bromochroman-4-one (3.75 g, 16.52 mmol), bis(pinacolato)diborane (4.40 g, 17.34 mmol) and KOAc (4.86 g, 49.5 mmol) in 1,4-dioxane (100 mL) was sparged with N$_2$ for 15 min. Then, 1,1-bis(diphenylphosphino)ferrocene]dichloropalladium(II) CH$_2$Cl$_2$ complex (0.674 g, 0.826 mmol) was added, sparged for 5 min and heated (95° C.) for 16 h. The reaction was cooled, diluted with Et$_2$O (250 mL), washed with water (2×100 mL), brine (25 mL), dried (MgSO$_4$), filtered and concentrated. The residue was purified by biotage (120 g SiO$_2$, 0% (3 CV), 0-60% (15 CV), EtOAc in hexanes) to afford the desired product (3.626 g, 13.23 mmol, 80% yield) as an pale yellow viscous oil. $^1$H NMR (500 MHz, CDCl$_3$) δ 8.40 (d, J=1.6 Hz, 1H), 7.89 (dd, J=8.3, 1.7 Hz, 1H), 6.96 (dd, J=8.4, 0.3 Hz, 1H), 4.59-4.53 (m, 2H), 2.83 (dd, J=6.8, 6.1 Hz, 2H), 1.34 (s, 12H). LCMS (M+H)=275.15.

Intermediate 37

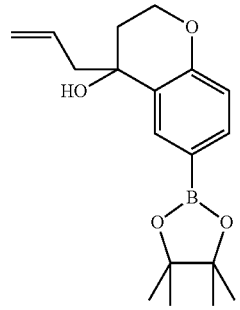

4-Allyl-6-(4,4,5,5-tetramethyl-1,3,2-dioxaborolan-2-Achroman-4-ol: A cold (−78° solution of 6-(4,4,5,5-tetramethyl-1,3,2-dioxaborolan-2-yl)chroman-4-one (1.21 g, 4.41 mmol) in dry THF (20 ml) was treated with 1.0 M allylmagnesium bromide in Et$_2$O (6.62 ml, 6.62 mmol) by dropwise addition over 2 min. The reaction was stirred for 10 min, allowed to warm to room temperature and stirred for 90 min, then quenched with sat'd aq. NH$_4$Cl (2 mL). The mixture was diluted with Et$_2$O (50 mL), washed with water (10 mL), brine (10 mL), dried (MgSO$_4$), filtered and concentrated. The residue was purified by biotage (40 g SiO$_2$, 0% (3 CV), 0-60%

(15 CV), EtOAc in hexanes) to afford the desired product (0.864 g, 2.73 mmol, 61.9% yield) as a colorless viscous oil. $^1$H NMR (400 MHz, CDCl$_3$) δ 7.94 (d, J=1.5 Hz, 1H), 7.64 (dd, J=8.2, 1.6 Hz, 1H), 6.83 (d, J=8.3 Hz, 1H), 5.81 (ddt, J=17.2, 10.2, 7.3 Hz, 1H), 5.21-5.17 (m, 1H), 5.15 (s, 1H), 4.29-4.24 (m, 2H), 2.84 (dd, J=14.1, 7.5 Hz, 1H), 2.66 (dd, J=14.1, 7.0 Hz, 1H), 2.14 (ddd, J=13.9, 7.9, 5.5 Hz, 1H), 2.01 (s, 1H), 2.00-1.91 (m, 1H), 1.34 (d, J=1.0 Hz, 12H). LCMS (M+H—H$_2$O)=299.2.

Intermediate 38

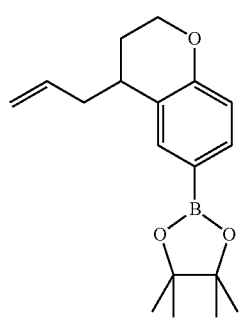

2-(4-Allylchroman-6-yl)-4,4,5,5-tetramethyl-1,3,2-dioxaborolane: A stirred solution of 4-allyl-6-(4,4,5,5-tetramethyl-1,3,2-dioxaborolan-2-yl)chroman-4-ol (1.80 g, 5.69 mmol) and triethylsilane (7.27 ml, 45.5 mmol) in DCE (30 ml) was treated with TFA (14.03 ml, 182 mmol) by rapid addition at ambient temperature. The reaction was stirred for 10 min, then carefully quenched with sat'd. aq. NaHCO$_3$ (200 mL). The organic layer was concentrated and the residue was purified by biotage (80 g SiO$_2$, 0% (3 CV), 0-60% (15 CV), 60% (2 CV), EtOAc in hexanes) to afford the desired product (0.942 g, 3.14 mmol, 55.1% yield) as a viscous clear oil. $^1$H NMR (400 MHz, CDCl$_3$) δ 7.64 (s, 1H), 7.56 (dd, J=8.2, 1.4 Hz, 1H), 6.80 (d, J=8.0 Hz, 1H), 5.90-5.76 (m, 1H), 5.15-5.04 (m, 2H), 4.23-4.14 (m, 2H), 2.89 (dq, J=10.0, 5.0 Hz, 1H), 2.75-2.62 (m, 1H), 2.35-2.22 (m, 1H), 2.09-1.96 (m, 1H), 1.92-1.81 (m, 1H), 1.34 (s, 12H). LCMS (M+H)=301.3.

Intermediate 39

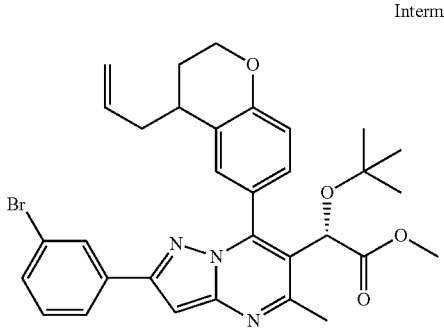

(2S)-Methyl 2-(7-(4-allylchroman-6-yl)-2-(3-bromophenyl)-5-methylpyrazolo[1,5-a]pyrimidin-6-yl)-2-(tert-butoxy)acetate: A solution of (S)-methyl 2-(2-(3-bromophenyl)-7-iodo-5-methylpyrazolo[1,5-a]pyrimidin-6-yl)-2-(tert-butoxy)acetate (0.375 g, 0.374 mmol), 2-(4-allylchroman-6-yl)-4,4,5,5-tetramethyl-1,3,2-dioxaborolane (0.123 g, 0.411 mmol) and 2.0 M Na$_2$CO$_3$ (0.374 ml, 0.747 mmol) in DMF (3.74 ml) was sparged with N$_2$ for 10 min, treated with Pd(Ph$_3$P)$_4$ (0.030 g, 0.026 mmol), sparged for 5 minutes, then heated (90° C.) for 16 h. The reaction was cooled, diluted with water (20 mL) and extracted with EtOAc. The organic layer was dried (MgSO$_4$), filtered, and concentrated and the residue was purified by biotage (40 g SiO$_2$, 0% (3 CV), 0-40% (15 CV), 60% (2 CV), EtOAc in hexanes). Fractions containing desired product combined, concentrated and re-purified (40 g SiO$_2$, 0% (3 CV), 0-60% (15 CV), 60% (2 CV), EtOAc in hexanes) to afford the desired product (0.431 g, 0.713 mmol, 44.6% yield). LCMS (M+H)=606.4.

Intermediate 40

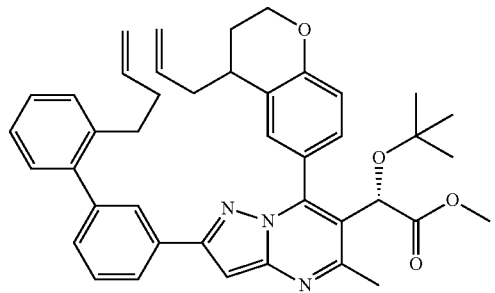

(2S)-Methyl 2-(7-(4-allylchroman-6-yl)-2-(2'-(but-3-en-1-yl)-[1,1'-biphenyl]-3-yl)-5-methylpyrazolo[1,5-d]pyrimidin-6-yl)-2-(tert-butoxy)acetate: A solution of (2S)-methyl 2-(7-(4-allylchroman-6-yl)-2-(3-bromophenyl)-5-methylpyrazolo[1,5-a]pyrimidin-6-yl)-2-(tert-butoxy)acetate (0.070 g, 0.116 mmol) and (2-(but-3-en-1-yl)phenyl)boronic acid (0.041 g, 0.232 mmol) in DMF (3 mL) was treated with 2.0 M aq. Na$_2$CO$_3$ (0.145 mL, 0.289 mmol), and the mixture was sparged with N$_2$ for 10 min, then treated with Pd(Ph$_3$P)$_4$ (9 mg, 8 μmol), sparged for 5 min, then stirred with heating (90° C.) for 90 min. The reaction was cooled, then filtered (0.45 μm syringe tip filter) and purified by biotage column chromatography (4 g SiO$_2$, 5%-45% EtOAc in hexanes,15 CV) to afford the desired product (0.052 g, 0.078 mmol, 67.5% yield), as a clear film. LCMS (H+ M)=656.5.

Intermediate 41

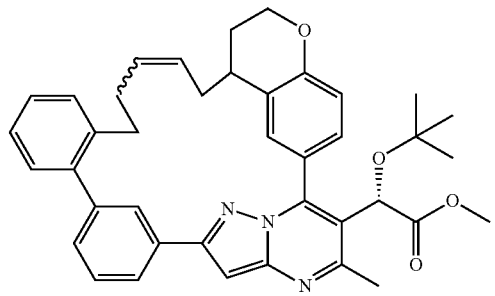

Methyl (2S)-2-(tert-butoxy)-2-[4-methyl-29-oxa-5,7,8-triazaheptacyclo[24.6.2.1$^{6,9}$.1$^{10,14}$.0$^{2,7}$.0$^{15,20}$.0$^{30,34}$] hexatriaconta-1 (32), 2,4,6(36),8,10(35), 11, 13, 15(20), 16,18,23,30,33-tetradecaen-3-yl]acetate: A solution of (2S)-methyl 2-(7-(4-allylchroman-6-yl)-2-(2'-(but-3-en-1-yl)-[1,1'-biphenyl]-3-yl)-5-methylpyrazolo[1,5-a]pyrimidin-6-yl)-2-(tert-butoxy)acetate (0.054 g, 0.082 mmol) in DCE (5.0 mL) was heated (70° C.), then treated with Hoveyda-Grubbs Cat. 2nd Gen. (5 mg, 8 μmol). The reaction was stirred for 90 min. The reaction was cooled, then concentrated and the residue was used immediately in the following step. LCMS (M+H)=628.4.

Intermediate 42

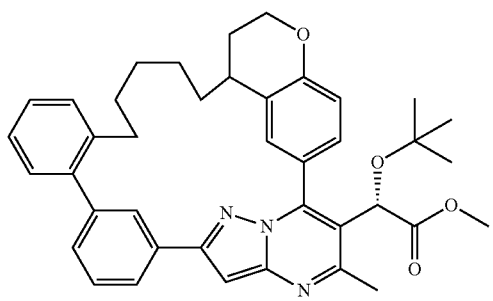

Methyl (2S)-2-(tert-butoxy)-2-{4-methyl-29-oxa-5,7,8-triazaheptacyclo[24.6.2.1$^{6,9}$.1$^{10,14}$.0$^{2,7}$.0$^{15,20}$.0$^{30,34}$]hexatriaconta-1 (32), 2,4, 6(36),8,10(35), 11,13, 15(20),16, 18,30,33-tridecaen-3-yl}acetate: A solution of methyl (2S)-2-(tert-butoxy)-2-[4-methyl-29-oxa-5,7,8-triazaheptacyclo [24.6.2.1$^{6,9}$. 1$^{10,14}$.0$^{2,7}$.0$^{15,20}$.0$^{30,34}$]hexatriaconta-1(32),2, 4,6(36),8,10(35),11,13,15 (20),16,18,23,30,33-tetradecaen-3-yl]acetate (0.051 g, 0.082 mmol) in MeOH (5 mL) was treated with 10 wt % Pd/C (9 mg, 0.08 mmol), then evacuated and hydrogen gas filled three times. The reaction was stirred for 16 h. The reaction mixture was filtered (0.45 nm syringe tip filter) and the filtrate solution was used directly in the following step. LCMS (M+H)=630.5.

EXAMPLES 8-11

A solution of crude methyl (2S)-2-(tert-butoxy)-2-{4-methyl-29-oxa-5,7,8-triazaheptacyclo[24.6.2. 1$^{6,9}$.1$^{10,14}$.0$^{2,7}$.0$^{15,20}$.0$^{30,34}$]hexatriaconta-1(32),2,4,6(36), 8,10(35), 11,13,15(20),16,18,30,33-tridecaen-3-yl}acetate (0.052 g, 0.082 mmol) in MeOH (2 mL) was treated with 1.0 M aq. NaOH (0.4 mL, 0.4 mmol) and heated (70° C.) for 5 h, then cooled and purified by prep-HPLC to afford four products. Note: The mixture was resolved into two diasteriomers as well as two nor-analog diasteriomers.

EXAMPLE 8

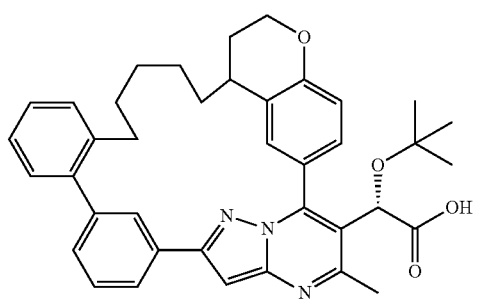 [SMILES: Cc1nc2cc3nn2c(c1[C@H](OC(C)(C)C)C(=O)O)-c1ccc2c(c1)C(CCCCCc1ccccc1-c1cccc-3c1)CCO2]

(2S)-2-(tert-butoxy)-2-{4-methyl-29-oxa-5,7,8-triazaheptacyclo[24.6.2.1$^{6,9}$.1$^{10,14}$. 0$^{2,7}$.0$^{15,20}$.0$^{30,34}$]hexatriaconta-1 (32), 2,4,6(36),8,10(35), 11, 13, 15(20), 16,18,30,33-tridecaen-3-yl}acetic acid: First eluting diasteriomer (0.009 g, 0.014 mmol, 17.5% yield). LCMS (M+H)=616.7.

EXAMPLE 9

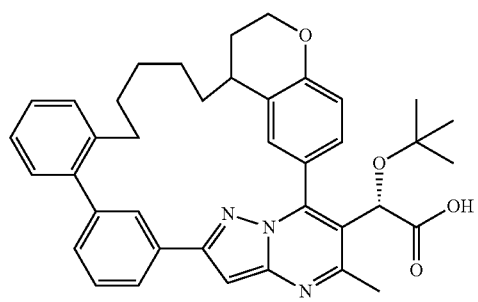

(2S)-2-(tert-butoxy)-2-{4-methyl-29-oxa-5,7,8-triazaheptacyclo[24.6.2.1$^{6,9}$.1$^{10,14}$.0$^{2,7}$.0$^{15,20}$.0$^{30,34}$]hexatriaconta-1 (32), 2,4,6(36),8,10(35), 11, 13, 15 (20),16,18,30,33-tridecaen-3-yl}acetic acid: Second eluting diasteriomer (0.0099 g, 0.016 mmol, 19.6% yield). $^1$H NMR (500 MHz, DMSO-d$_6$) δ 7.94 (d, J=7.6 Hz, 1H), 7.76 (br. s., 1H), 7.59-7.46 (m, 3H), 7.25 (d, J=7.0 Hz, 1H), 7.22-7.12 (m, 4H), 7.05 (d, J=7.0 Hz, 1H), 6.92 (d, J=7.9 Hz, 1H), 4.99 (s, 1H), 4.22-4.07 (m, 2H), 2.72 (d, J=8.9 Hz, 2H), 2.57 (br. s., 3H), 2.26 (br. s., 1H), 2.00-1.89 (m, 2H), 1.77 (d, J=15.9 Hz, 1H), 1.64 (br. s., 1H), 1.43 (br. s., 1H), 1.36-1.11 (m, 5H), 0.91 (br. s., 1H), 0.79 (s, 9H). LCMS (M+H)=616.7.

EXAMPLE 10

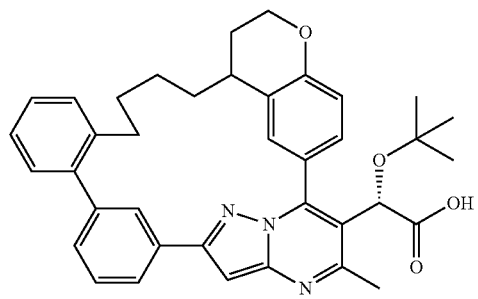

(2S)-2-(tert-Butoxy)-2-{4-methyl-28-oxa-5,7,8-triazaheptacyclo[23.6.2.1$^{6,9}$.1$^{10,14}$.0$^{2,7}$.0$^{15,20}$.0$^{29,33}$]pentatriaconta-1(31), 2,4,6(35),8,10(34), 11, 13, 15 (20), 16,18,29,32-tridecaen-3-yl}acetic acid: First eluting nor-analog diasteriomer (0.0015 g, 2.3 μmol, 2.9% yield). LCMS (M+H)=602.4.

EXAMPLE 11

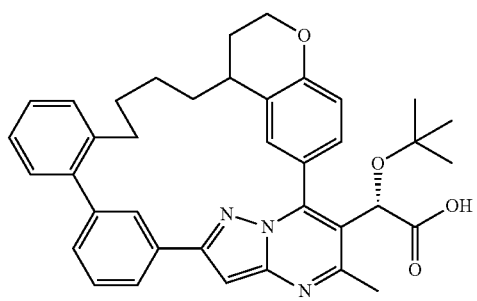 [SMILES: Cc1nc2cc3nn2c(c1[C@H](OC(C)(C)C)C(=O)O)-c1ccc2c(c1)C(CCCCc1ccccc1-c1cccc-3c1)CCO2]

(2S)-2-(tert-Butoxy)-2-{4-methyl-28-oxa-5,7,8-triazaheptacyclo[23.6.2.1$^{6,9}$.1$^{10,14}$.0$^{2,7}$.0$^{15,20}$.0$^{29,33}$]pentatriaconta-1(31),2,4,6(35),8,10(34), 11, 13, 15 (20),16,18,29,32-tridecaen-3-yl}acetic acid: Second eluting nor-analog diasteriomer (0.002 g, 3 μmol, 3.6% yield). $^1$H NMR (500 MHz, CDCl$_3$) δ 7.96 (s, 1H), 7.78 (d, J=1.7 Hz, 1H), 7.69-7.64 (m, 1H), 7.58 (dd, J=8.4, 2.2 Hz, 1H), 7.51 (t, J=7.7 Hz, 1H), 7.37-7.28 (m, 5H), 7.26-7.20 (m, 1H), 6.95 (d, J=8.4 Hz, 1H), 6.88 (s, 1H), 5.36 (s, 1H), 4.49-4.41 (m, 1H), 4.30 (ddd, J=10.9, 6.6, 4.3 Hz, 1H), 2.95 (d, J=4.9 Hz, 1H), 2.81-2.73 (m, 1H), 2.72-2.68 (m, 1H), 2.66 (s, 3H), 2.05-1.97 (m, 2H), 1.95-1.73 (m, 4H), 1.70-1.60 (m, 2H), 0.99 (s, 9H). LCMS (M+H)=602.6.

Intermediate 43

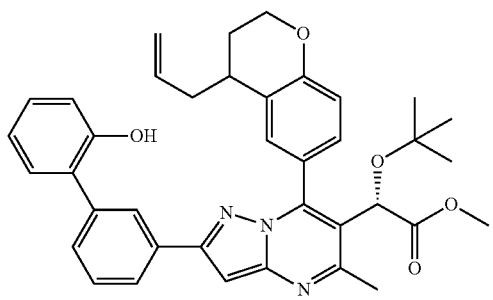

(2S)-Methyl 2-(7-(4-allylchroman-6-yl)-2-(2'-hydroxy-[1,1'-biphenyl]-3-yl)-5-methylpyrazolo[1,5-a]pyrimidin-6-yl)-2-(tert-butoxy)acetate: A solution of ((2S)-methyl 2-(7-(4-allylchroman-6-yl)-2-(3-bromophenyl)-5-methylpyrazolo[1,5-a]pyrimidin-6-yl)-2-(tert-butoxy) acetate (0.430 g, 0.711 mmol), (2-hydroxyphenyl)boronic acid (0.196 g, 1.423 mmol) and 2.0 M aq. Na$_2$CO$_3$ (1.1 ml, 2.1 mmol) in DMF (7 ml) was sparged with nitrogen for 10 min, treated with Pd(Ph$_3$P)$_4$ (0.058 g, 0.050 mmol), then sparged for 5 min. The reaction was stirred for 90 min, then cooled, diluted with water (20 mL) and extracted into Et$_2$O (2×50 mL). The combined extracts were dried (MgSO$_4$), filtered, and concentrated and the residue was purified by biotage (24 g SiO$_2$, 0% (3 CV), 0-60% (15 CV), 60% (2 CV), EtOAc in hexanes) to afford the desired product (0.360 g, 0.572 mmol, 80% yield) as a pale yellow glassy solid. $^1$H NMR (500 MHz, CDCl$_3$) δ: 8.07-7.89 (m, 2H), 7.70 (s, 1H), 7.60-7.49 (m, 2H), 7.49-7.36 (m, 2H), 7.34-7.29 (m, 2H), 7.07-6.97 (m, 3H), 6.95-6.90 (m, 1H), 5.96-5.71 (m, 1H), 5.37-5.19 (m, 2H), 5.16-4.97 (m, 2H), 4.39-4.25 (m, 2H), 3.88-3.79 (m, 3H), 3.12-2.88 (m, 1H), 2.72-2.63 (m, 3H), 2.61-2.32 (m, 1H), 2.22-2.08 (m, 1H), 2.02-1.88 (m, 1H), 1.06-0.92 (m, 9H). LCMS (M+H)=618.5.

Intermediate 44

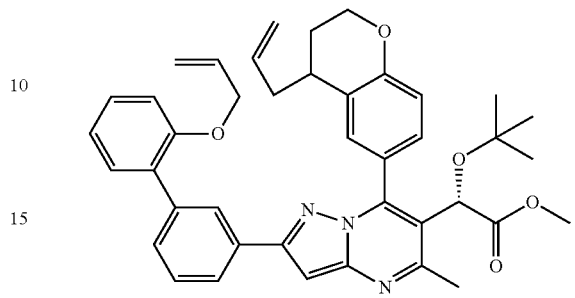

(2S)-Methyl 2-(7-(4-allylchroman-6-yl)-2-(2'-(allyloxy)-[1,1'-biphenyl]-3-yl)-5-methylpyrazolo[1,5-a]pyrimidin-6-yl)-2-(tert-butoxy)acetate: A solution of (2S)-methyl 2-(7-(4-allylchroman-6-yl)-2-(2'-hydroxy-[1,1'-biphenyl]-3-yl)-5-methylpyrazolo[1,5-a]pyrimidin-6-yl)-2-(tert-butoxy) acetate (0.350 g, 0.567 mmol) in dry THF (12 ml) was treated sequentially with allyl alcohol (0.116 ml, 1.700 mmol), Ph$_3$P (0.446 g, 1.700 mmol) and DEAD (0.269 ml, 1.700 mmol), and the reaction was stirred for 2 h. The reaction was concentrated, and the residue was purified by biotage (24 g SiO$_2$, 0% (3 CV), 0-60% (15 CV), 60% (2 CV), EtOAc in hexane). The residue after concentration was taken up in Et$_2$O (20 mL) and washed with water (2×20 mL) to remove residual allyl alcohol, then dried (MgSO$_4$), filtered, and concentrated, affording the desired product (0.4 g, 0.6 mmol, quant.) as a viscous clear oil. $^1$H NMR (500 MHz, CDCl$_3$) δ 8.11-8.04 (m, 1H), 7.90-7.84 (m, 1H), 7.58-7.36 (m, 5H), 7.35-7.29 (m, 1H), 7.06 (t, J=7.4 Hz, 1H), 7.02-6.93 (m, 2H), 6.90 (s, 1H), 6.04-5.91 (m, 1H), 5.90-5.78 (m, 1H), 5.37-5.30 (m, 4H), 5.27-5.13 (m, 4H), 5.12-5.02 (m, 2H), 4.55 (d, J=4.9 Hz, 2H), 4.30 (br. s., 2H), 3.82 (s, 3H), 2.68-2.63 (m, 3H), 1.01-0.93 (m, 9H). LCMS (M+H)=658.6.

Intermediate 45

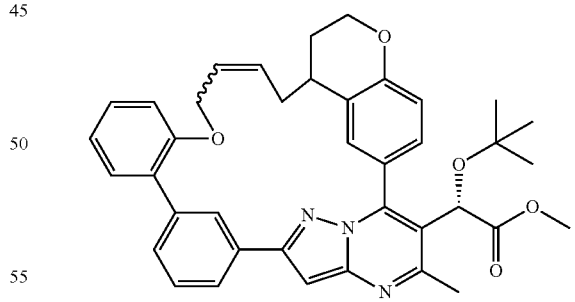

Methyl (2S)-2-(tert-butoxy)-2-[4-methyl-21,29-dioxa-5,7,8-triazaheptacyclo[24.6.2.1$^{6,9}$.1$^{10,14}$.0$^{2,7}$.0$^{15,20}$.0$^{30,34}$]hexatriaconta-1(32),2,4,6(36),8,10(35), 11,13,15 (20),16,18,23,30,33-tetradecaen-3-yl]acetate: A solution of (2S)-methyl 2-(7-(4-allylchroman-6-yl)-2-(2'-(allyloxy)-[1,1'-biphenyl]-3-yl)-5-methylpyrazolo[1,5-a]pyrimidin-6-yl)-2-(tert-butoxy)acetate (0.373 g, 0.567 mmol) in DCE (275 ml) was heated (70° C.) and then treated with Hoveyda-Grubbs cat.2nd gen. (0.025 g, 0.040 mmol). The reaction was stirred for 2.5 hrs, then additional catalyst (0.025 g, 0.040 mmol) was added, the temperature was raised (80° C.) and the reaction was stirred for 30 min. The reaction was cooled, concentrated, and the residue was purified by biotage (24 g SiO$_2$, 0% (3 CV), 0-60% (15 CV), 60% (2 CV), EtOAc in hexanes) to afford the desired product (0.300 g, 0.476 mmol, 84% yield). LCMS (M+H)=630.5.

INTERMEDIATES 46-47

A suspension of methyl (2S)-2-(tert-butoxy)-2-[4-methyl-21,29-dioxa-5,7,8-triazaheptacyclo[24.6.2.1$^{6,9}$.1$^{10,14}$.0$^{2,7}$.0$^{15,20}$0$^{30,34}$]hexatriaconta-1(32),2,4,6(36),8,10(35),11,13,15(20),16,18,23,30,33-tetradecaen-3-yl]acetate (0.196 g, 0.311 mmol) in MeOH (3 mL) was treated with CH$_2$Cl$_2$ (4 mL) and stirred until dissolution occurred. The solution was treated with 10 wt % palladium on carbon (0.040 g, 0.038 mmol) and the reaction was then evacuated and back-filled with hydrogen (balloon) three times. The reaction was stirred for 5 h, then concentrated and dried under vacuum pump for 16 h. The residue was resolved into separate diasteriomers by prep-HPLC.

Intermediate 46

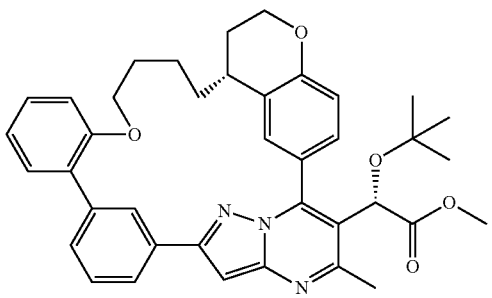

Methyl (2S)-2-(tert-butoxy)-2-[(26R)-4-methyl-21,29-dioxa-5,7,8-triazaheptacyclo[24.6.2.1$^{6,9}$.1$^{10,14}$.0$^{2,7}$.0$^{15,20}$.0$^{30,34}$]hexatriaconta-1(32),2,4,6(36),8,10(35), 11, 13, 15(20),16,18,30,33-tridecaen-3-yl]acetate: Early eluting diasteriomer (0.0544 g, 0.086 mmol, 55.3% yield). LCMS (M+H)=632.4.

Intermediate 46

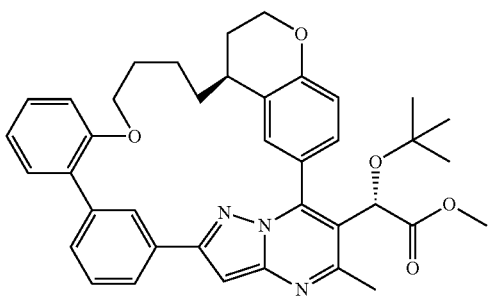

Methyl (2S)-2-(tert-butoxy)-2-[(26S)-4-methyl-21,29-dioxa-5,7,8-triazaheptacyclo[24.6.2.1$^{6,9}$.1$^{10,14}$.0$^{2,7}$0$^{15,20}$.0$^{30,34}$]hexatriaconta-1(32),2,4,6(36),8,10(35), 11, 13, 15(20),16,18,30,33-tridecaen-3-yl]acetate: Later eluting diasteriomer (0.0479 g, 0.076 mmol, 48.7% yield). LCMS (M+H)=632.5.

EXAMPLE 12

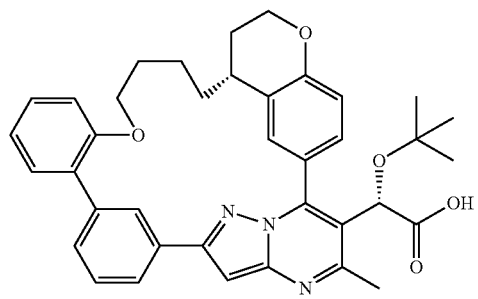 [SMILES: Cc1nc2cc3nn2c(c1[C@H](OC(C)(C)C)C(=O)O)-c1ccc2c(c1)[C@H](CCCCOc1ccccc1-c1cccc-3c1)CCO2]

(2S)-2-(tert-Butoxy)-2-[(26R)-4-methyl-21,29-dioxa-5,7,8-triazaheptacyclo[24.6.2.1$^{6,9}$.1$^{10,14}$.0$^{2,7}$.0$^{15,20}$.0$^{30,34}$]hexatriaconta-1(32), 2,4,6(36),8,10(35), 11, 13, 15 (20),16, 18,30,33-tridecaen-3-yl]acetic acid: A solution of methyl (2S)-2-(tert-butoxy)-2-[(26R)-4-methyl-21,29-dioxa-5,7,8-triazaheptacyclo[24.6.2.1$^{6,9}$.1$^{10,14}$.0$^{2,7}$.0$^{15,20}$0$^{30,34}$]hexatriaconta-1(32),2,4,6(36),8,10(35),11,13,15(20),16,18,30,33-tridecaen-3-yl]acetate (early eluting diasteriomer, 0.045 g, 0.071 mmol) in MeOH (1.5 mL) was treated with 1.0 M aq. NaOH (0.4 mL, 0.400 mmol), and the mixture was heated (65° C.) for 2.5 h, then cooled and concentrated. The residue was partitioned in CH$_2$Cl$_2$ and water (10 mL each) and the organic layer was dried (Na$_2$SO$_4$), filtered, and concentrated under reduced pressure. The film was dried twice from Et$_2$O to afford the desired product (0.031 g, 0.050 mmol, 70.5% yield) as an off white glassy solid. LCMS (M+H)=618.5.

EXAMPLE 13

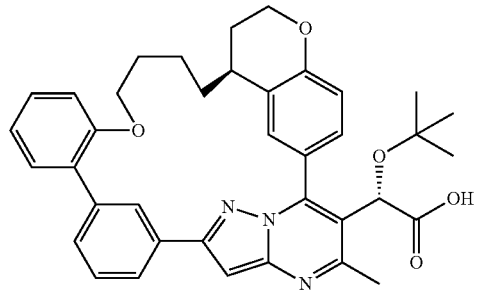 [SMILES: Cc1nc2cc3nn2c(c1[C@H](OC(C)(C)C)C(=O)O)-c1ccc2c(c1)[C@@H](CCCCOc1ccccc1-c1cccc-3c1)CCO2]

(2S)-2-(tert-Butoxy)-2-[(26S)-4-methyl-21,29-dioxa-5,7,8-triazaheptacyclo[24.6.2.1$^{6,9}$.1$^{10,14}$.0$^{2,7}$.0$^{15,20}$.0$^{30,34}$]hexatriaconta-1(32), 2,4,6(36),8,10(35), 11, 13, 15 (20),16, 18,30,33-tridecaen-3-yl]acetic acid: A solution of methyl (2S)-2-(tert-butoxy)-2-[(26S)-4-methyl-21,29-dioxa-5,7,8-triazaheptacyclo[24.6.2.1$^{6,9}$.1$^{10,14}$.0$^{2,7}$.0$^{15,20}$.0$^{30,34}$]hexatriaconta-1(32),2,4,6(36),8,10(35),11,13,15(20),16,18,30,33-tridecaen-3-yl]acetate (later eluting diasteriomer, 0.048 g, 0.076 mmol) in MeOH (2 mL) was treated with 1.0 M aq. NaOH (0.380 mL, 0.380 mmol), and the mixture was heated (65° C.) for 2.5 h, then cooled and concentrated. The residue was partitioned between CH$_2$Cl$_2$ and water (10 mL each) and the organic layer was dried (Na$_2$SO$_4$), filtered, and concentrated under reduced pressure. The residue was suspended in Et$_2$O and collected by vacuum filtration to afford the desired product (0.033 g, 0.052 mmol, 68.1% yield) as an off-white solid. LCMS (M+H)=618.4.

EXAMPLE 14-15

A suspension of methyl (2S)-2-(tert-butoxy)-2-[4-methyl-21,29-dioxa-5,7,8-triazaheptacyclo[24.6.2.1$^{6,9}$.1$^{10,14}$.0$^{2,7}$.0$^{15,20}$.0$^{30,34}$]hexatriaconta-1(32),2,4,6(36),8,10(35),11,13,15(20),16,18,23,30,33-tetradecaen-3-yl]acetate (0.053 g, 0.084 mmol) in MeOH (1.0 mL) was treated with 1.0 M aq. NaOH (0.5 mL, 0.500 mmol), and the mixture was heated (75° C.) for 1 h, then THF (~2 mL) was added and the reaction was stirred for 45 min. The reaction was cooled and concentrated and the remaining aq. suspension was treated with 1.0 N HCl (0.6 mL). Solids were extracted into CH$_2$Cl$_2$ (2×2 mL), then concentrated. The residue was resolved into separate diasteriomers by prep-HPLC.

EXAMPLE 14

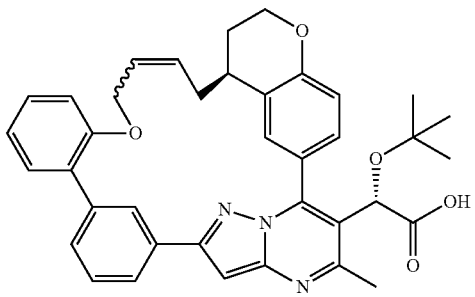 [SMILES: Cc1nc2cc3nn2c(c1[C@H](OC(C)(C)C)C(=O)O)-c1ccc2c(c1)[C@@H](CC=CCOc1ccccc1-c1cccc-3c1)CCO2]

(2S)-2-(tert-Butoxy)-2-[(26S)-4-methyl-21,29-dioxa-5,7,8-triazaheptacyclo[24.6.2.1$^{6,9}$.1$^{10,14}$.0$^{2,7}$.0$^{15,20}$.0$^{30,34}$]hexatriaconta-1(32),2,4,6(36),8,10(35),11,13,15(20),16,18,23,30,33-tetradecaen-3-yl]acetic acid: Early eluting diasteriomer (0.0213 g, 0.034 mmol, 40.7% yield). LCMS (M+H)=616.5.

EXAMPLE 15

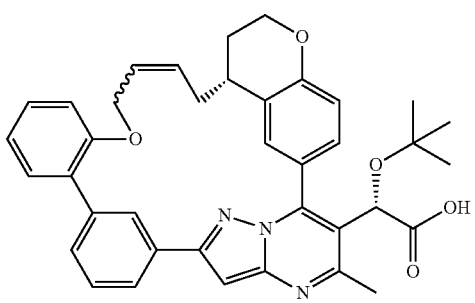 [SMILES: Cc1nc2cc3nn2c(c1[C@H](OC(C)(C)C)C(=O)O)-c1ccc2c(c1)[C@H](CC=CCOc1ccccc1-c1cccc-3c1)CCO2]

(2S)-2-(tert-Butoxy)-2-[(26R)-4-methyl-21,29-dioxa-5,7,8-triazaheptacyclo[24.6.2.1$^{6,9}$.1$^{10,14}$.0$^{2,7}$.0$^{15,20}$.0$^{30,34}$]hexatriaconta-1(32),2,4,6(36),8,10(35), 11,13,15(20),16,18,23,30,33-tetradecaen-3-yl]acetic acid: Later eluting diasteriomer (0.007 g, 0.011 mmol, 13.37% yield). LCMS (M+H)=616.5.

Intermediate 46

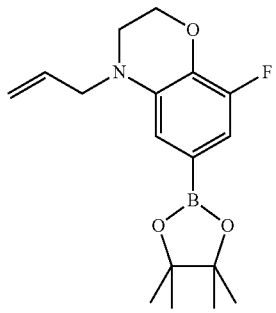

4-Allyl-8-fluoro-6-(4,4,5,5-tetramethyl-1,3,2-dioxaborolan-2-yl)-3,4-dihydro-2H-benzo[b][1,4]oxazine: A solution of 8-fluoro-6-(4,4,5,5-tetramethyl-1,3,2-dioxaborolan-2-yl)-3,4-dihydro-2H-benzo[b][1,4]oxazine (0.507 g, 1.613 mmol, Ref. WO20100130034) and K$_2$CO$_3$ (0.512 g, 3.70 mmol) in dry DMF (5 mL) was sparged with N$_2$ for 5 min, then treated with allyl bromide (0.8 mL, 9.17 mmol). The reaction tube was sealed and then heated (70° C.) for 22 h. The reaction was cooled then diluted with water (50 mL) and extracted into EtOAc (50 mL). The organic layer was then washed with water, brine, dried (Na$_2$SO$_4$), filtered, and concentrated. The residue was purified by biotage column chromatography (12 g SiO$_2$, 0% (3 CV); 0-40% (15 CV), 40% (2 CV), EtOAc in hexanes) to afford the desired product (0.396 g, 1.241 mmol, 77% yield) as a clear viscous oil. $^1$H NMR (500 MHz, CDCl$_3$) δ 6.96-7.01 (m, 2H), 5.84-5.95 (m, 1H), 5.21-5.32 (m, 2H), 4.32-4.38 (m, 2H), 3.94 (d, J=5.8 Hz, 2H), 3.30-3.37 (m, 2H), 1.32 (s, 12H). LCMS (M+H)=320.3.

Intermediate 49

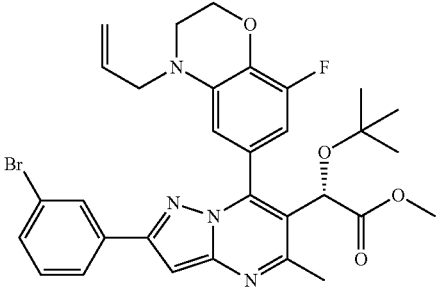

(S)-Methyl 2-(7-(4-allyl-8-fluoro-3,4-dihydro-2H-benzo[b][1,4]oxazin-6-yl)-2-(3-bromophenyl)-5-methylpyrazolo[1,5-d]pyrimidin-6-yl)-2-(tert-butoxy)acetate: A solution of (S)-methyl 2-(2-(3-bromophenyl)-7-iodo-5-methylpyrazolo[1,5-a]pyrimidin-6-yl)-2-(tert-butoxy)acetate (0.160 g, 0.287 mmol) and 4-allyl-8-fluoro-6-(4,4,5,5-tetramethyl-1,3,2-dioxaborolan-2-yl)-3,4-dihydro-2H-benzo[b][1,4]oxazine (0.108 g, 0.287 mmol) in DMF (3 mL) was treated with 2.0 M aq. Na$_2$CO$_3$ (0.358 mL, 0.717 mmol), sparged with N$_2$ for 10 min, treated with Pd(Ph$_3$P)$_4$ (0.033 g, 0.029 mmol), sparged for 5 min, then sealed and heated (90° C.) for 9.5 h then allowed to cool to room temperature, stirring for 16 h. The reaction was diluted with EtOAc (20 mL) and washed with 1:1 water/brine (2×10 mL). The organic layer was dried (Na$_2$SO$_4$), filtered and concentrated, and the residue was purified by biotage column chromatography (4 g SiO$_2$, 0%-70%, 22 CV, EtOAc in hexanes) to afford the desired product (0.102 g, 0.104 mmol, 36.3% yield) as a yellow oil. LCMS (M+H)=625.3.

Intermediate 50

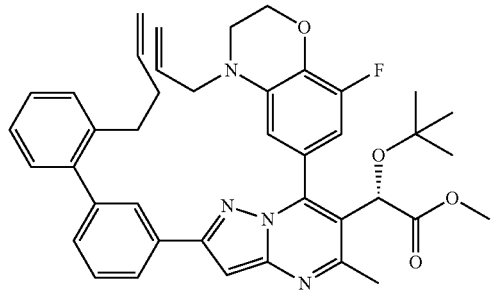

(S)-Methyl 2-(7-(4-allyl-8-fluoro-3,4-dihydro-2H-benzo[b][1,4]oxazin-6-yl)-2-(2'-(but-3-en-1-yl)-[1,1'-biphenyl]-3-yl)-5-methylpyrazolo[1,5-d]pyrimidin-6-yl)-2-(tert-butoxy)acetate: A solution of (S)-methyl 2-(7-(4-allyl-8-fluoro-3,4-dihydro-2H-benzo[b][1,4]oxazin-6-yl)-2-(3-bromophenyl)-5-methylpyrazolo[1,5-a]pyrimidin-6-yl)-2-(tert-butoxy)acetate (0.102 g, 0.164 mmol), (2-(but-3-en-1-yl)phenyl)boronic acid (0.058 g, 0.327 mmol) and 2.0 N $Na_2CO_3$ (0.204 mL, 0.409 mmol) in DMF (4.0 mL) was sparged with $N_2$ for 15 min, then treated with $Pd(Ph_3P)_4$ (0.013 g, 0.011 mmol), sparged for 5 min, and then heated (90° C.) for 3 h. The reaction was diluted with EtOAc (20 mL) and washed with 1:1 water/brine (2×10 mL). The organic layer was dried ($Na_2SO_4$), filtered, and concentrated and the residue was purified by biotage column chromatography (4 g $SiO_2$, 0% (6 CV), 0%-50% (15 CV), EtOAc in hexanes) to afford the desired product as an amber oil. LCMS (M+H)=675.4.

Intermediate 52

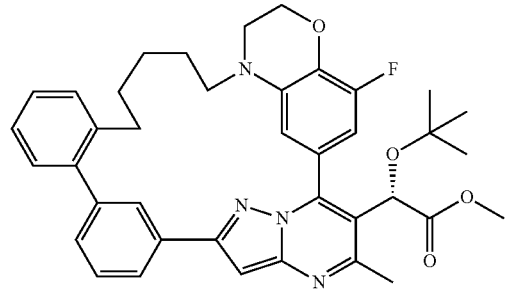

Methyl (2S)-2-(tert-butaxy)-2-{31-fluoro-4-methyl-29-oxa-5,7,8,26-tetraazaheptacyclo[24.6.2.$1^{6,9}.1^{10,14}.0^{2,7}.0^{15,20}.0^{30,34}$]hexatriaconta-1(32),2,4,6(36),8,10(35), 11, 13, 15(20),16,18,30,33-tridecaen-3-yl}acetate: A solution of methyl (2S)-2-(tert-butoxy)-2-[31-fluoro-4-methyl-29-oxa-5,7,8,26-tetraazaheptacyclo[24.6.2.$1^{6,9}.1^{10,14}.0^{2,7}.0^{15,20}.0^{30,34}$]hexatriaconta-1(32),2,4,6(36),8,10(35),11,13,15(20),16,18,23,30,33-tetradecaen-3-yl]acetate (0.063 g, 0.097 mmol) in MeOH (5 mL) was treated with 10 wt % Pd/C (0.002 g, 0.019 mmol) and the sealed flask was evacuated and flushed with hydrogen gas three times, then allowed to stir for 16 h. The reaction was cooled, then filtered (0.45 μm syringe tip filter) and concentrated and the residue was used immediately in the following step. LCMS (M+H)=649.4.

Intermediate 51

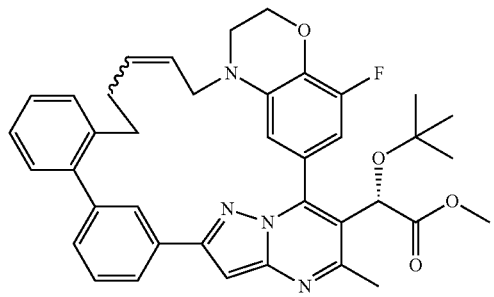

Methyl (2S)-2-(tert-butoxy)-2-[(31-fluoro-4-methyl-29-oxa-5,7,8,26-tetraazaheptacyclo[24.6.2.$1^{6,9}.1^{10,14}.0^{2,7}.0^{15,20}.0^{30,34}$]hexatriaconta-1(32),2,4,6(36),8,10(35),11,13,15(20), 16,18,23,30,33-tetradecaen-3-yl]acetate: A solution of (S)-methyl 2-(7-(4-allyl-8-fluoro-3,4-dihydro-2H-benzo[b][1,4]oxazin-6-yl)-2-(2'-(but-3-en-1-yl)-[1,1'-biphenyl]-3-yl)-5-methylpyrazolo[1,5-a]pyrimidin-6-yl)-2-(tert-butoxy)acetate (0.112 g, 0.166 mmol) in DCE (20 mL) was heated (70° C. oil bath) and then treated with Hoveyda-Grubbs Cat. 2nd Gen. (7.30 mg, 0.012 mmol). The reaction was stirred for 2 h, additional catalyst (7.30 mg, 0.012 mmol) was added and the reaction was stirred for 16 h. The solvent was removed and the residue was purified by biotage chromatography (4 g column, 0% (6 CV), 0%-60% (15 CV); EtOAc in hexanes) to afford the desired product (0.062 g, 0.090 mmol, 54.5% yield) as a light brown film. LC/MS (M+H)=647.5.

EXAMPLE 16

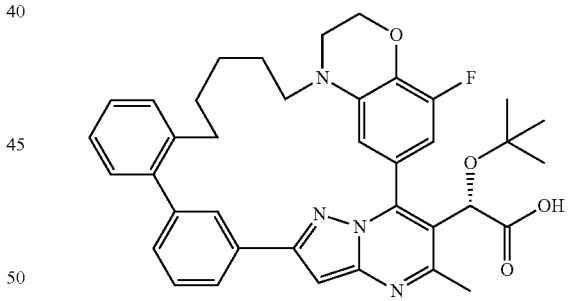

(2S)-2-(tert-Butoxy)-2-{31-fluoro-4-methyl-29-oxa-5,7,8,26-tetraazaheptacyclo[24.6.2.$1^{6,9}.1^{10,14}.0^{2,7}.0^{15,20}.0^{30,34}$]hexatriaconta-1(32),2,4,6(36),8,10(35), 11, 13, 15(20),16,18,30,33-tridecaen-3-yl}acetic acid: A solution of methyl (2S)-2-(tert-butoxy)-2-{31-fluoro-4-methyl-29-oxa-5,7,8,26-tetraazaheptacyclo[24.6.2.$1^{6,9}.1^{10,14}.0^{2,7}.0^{15,20}.0^{30,34}$]hexatriaconta-1(32),2,4,6(36),8,10(35),11,13,15(20),16,18,30,33-tridecaen-3-yl}acetate (0.063 g, 0.097 mmol) in MeOH (2 mL) was treated with NaOH (0.24 mL, 0.48 mmol) and the reaction was heated (70° C. oil bath) for 2.5 hrs. The reaction was cooled and then purified by prep-HPLC to afford the desired product (0.0278 g, 0.044 mmol, 45.2% yield). LCMS (M+H)=635.5.

Intermediate 53

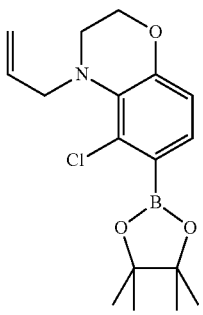

4-Allyl-5-chloro-6-(4,4,5,5-tetramethyl-1,3,2-dioxaborolan-2-yl)-3,4-dihydro-2H-benzo[b][1,4]oxazine: A solution of 5-chloro-6-(4,4,5,5-tetramethyl-1,3,2-dioxaborolan-2-yl)-3,4-dihydro-2H-benzo[b][1,4]oxazine (0.504 g, 1.426 mmol, Ref. WO20100130034) and K₂CO₃ (0.504 g, 3.65 mmol) in dry DMF (5 mL) was sparged with N₂ for 5 min, then treated with allyl bromide (0.8 mL, 9.17 mmol). The reaction tube was sealed and then heated (70° C.) for 22 h, then cooled and diluted with water (50 mL) and extracted into EtOAc (50 mL). The organic layer was washed with water, brine, then dried (Na₂SO₄), filtered, concentrated, and purified by biotage chromatography (4 g SiO₂, 0% (3 CV), 0-40% (15 CV), 40% (2 CV); EtOAc in hexanes) to afford the desired product (0.403 g, 1.201 mmol, 84% yield) as a clear viscous oil. ¹H NMR (500 MHz, CDCl₃) δ 7.30 (d, J=8.2 Hz, 1H), 6.79 (d, J=8.2 Hz, 1H), 6.15-6.02 (m, 1H), 5.31 (dd, J=17.2, 1.4 Hz, 1H), 5.28-5.21 (m, 1H), 4.18-4.13 (m, 2H), 3.59 (d, J=6.0 Hz, 2H), 3.14-3.07 (m, 2H), 1.36 (s, 12H). LCMS (M+H)=336.9.

Intermediate 54

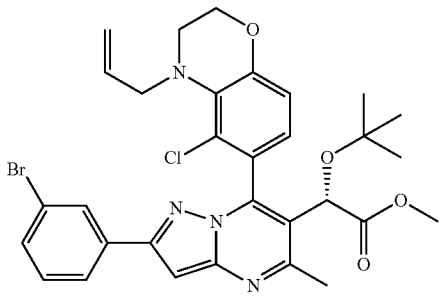

(2S)-Methyl 2-(7-(4-allyl-5-chloro-3,4-dihydro-2H-benzo[b][1,4]oxazin-6-yl)-2-(3-bromophenyl)-5-methylpyrazolo[1,5-a]pyrimidin-6-yl)-2-(tert-butoxy)acetate: A solution of (S)-methyl 2-(2-(3-bromophenyl)-7-iodo-5-methylpyrazolo[1,5-a]pyrimidin-6-yl)-2-(tert-butoxy)acetate (0.160 g, 0.287 mmol) and 4-allyl-5-chloro-6-(4,4,5,5-tetramethyl-1,3,2-dioxaborolan-2-yl)-3,4-dihydro-2H-benzo[b][1,4]oxazine (0.096 g, 0.287 mmol) in DMF (3 mL) was treated with 2.0 M aq. Na₂CO₃ (0.358 mL, 0.717 mmol), sparged with N₂ for 10 min, treated with Pd(Ph₃P)₄ (0.033 g, 0.029 mmol), sparged for 5 min, then sealed and heated (90° C.) for 16 h. The reaction was cooled, diluted with EtOAc (20 mL) and washed with 1:1 water/brine (2×10 mL). The organic layer was dried (Na₂SO₄), filtered, and concentrated. The residue was purified by biotage column chromatography (4 g Isco SiO₂, 0% (5 CV), 0%-80% (15 CV), EtOAc/hexanes) to afford semi-purified product (0.122 g, 0.143 mmol, 49.9% yield) as a clear oil. ¹H NMR (500 MHz, CDCl₃) δ 7.98 (t, J=1.7 Hz, 1H), 7.76 (dt, J=7.8, 1.2 Hz, 1H), 7.44 (ddd, J=8.0, 2.0, 1.1 Hz, 1H), 7.24 (t, J=7.9 Hz, 1H), 6.99-7.03 (m, 1H), 6.93-6.97 (m, 1H), 6.85 (s, 1H), 5.99-6.10 (m, 1H), 5.36 (dd, J=17.2, 1.6 Hz, 1H), 5.26 (dd, J=10.2, 1.5 Hz, 1H), 5.05 (s, 1H), 4.23-4.32 (m, 2H), 3.69 (dd, J=12.1, 6.0 Hz, 2H), 3.65 (s, 3H), 3.17-3.29 (m, 2H), 2.84 (s, 3H), 1.17 (s, 9H). LCMS (M+H)=641.2.

Intermediate 55

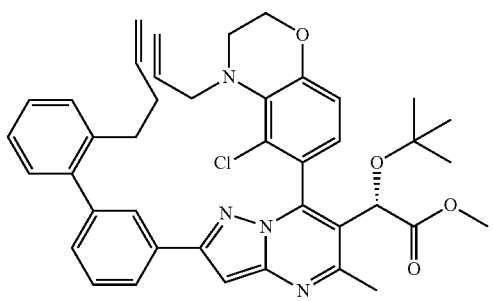

(2S)-Methyl 2-(7-(4-allyl-5-chloro-3,4-dihydro-2H-benzo[b][1,4]oxazin-6-yl)-2-(2'-(but-3-en-1-yl)-[1,1'-biphenyl]-3-yl)-5-methylpyrazolo[1,5-a]pyrimidin-6-yl)-2-(tert-butoxy)acetate: A solution of (2S)-methyl 2-(7-(4-allyl-5-chloro-3,4-dihydro-2H-benzo[b][1,4]oxazin-6-yl)-2-(3-bromophenyl)-5-methylpyrazolo[1,5-a]pyrimidin-6-yl)-2-(tert-butoxy)acetate (0.092 g, 0.143 mmol), (2-(but-3-en-1-yl)phenyl)boronic acid (0.050 g, 0.286 mmol) and 2.0 M aq. Na₂CO₃ (0.179 mL, 0.358 mmol) in DMF (4 mL) was sparged with nitrogen for 10 min, treated with Pd(Ph₃P)₄ (0.012 g, 10.01 μmol), sparged for 5 min, then heated (90° C.) for 5 h. The reaction was cooled, then diluted with EtOAc (20 mL) and washed with water (10 mL) and brine (10 mL). The organic layer was dried (Na₂SO₄), filtered, and concentrated and the residue was purified by biotage (Isco 4 g SiO₂, 0% (5 CV), 0-60% (20 CV), 60% (5 CV), EtOAc in hexanes) to afford the desired product (0.099 g, 0.143 mmol, 100% yield). LCMS (M+H)=691.4.

Intermediate 56

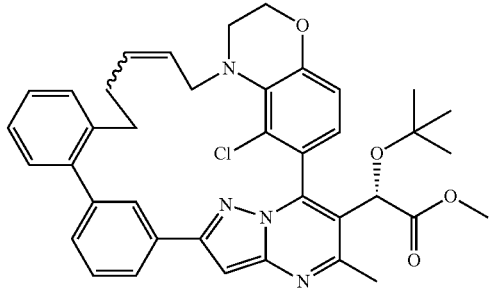

Methyl (2S)-2-(tert-butoxy)-2-[33-chloro-4-methyl-29-oxa-5,7,8,26-tetraazaheptacyclo[24.6.2.1⁶,⁹1¹⁰,¹⁴.0²,⁷.0¹⁵,²⁰.0³⁰,³⁴]hexatriaconta-1(32),2,4,6(36),8,10(35),11,13,15(20), 16,18,23,30,33-tetradecaen-3-yl]acetate: A solution of (2S)-methyl 2-(7-(4-allyl-5-chloro-3,4-dihydro-2H-benzo[b][1,4]oxazin-6-yl)-2-(2'-(but-3-en-1-yl)-[1,1'-biphenyl]-3-yl)-5-methylpyrazolo[1,5-a]pyrimidin-6-yl)-2-(tert-butoxy)acetate (0.099 g, 0.143 mmol) in DCE was heated (70° C.) and then treated with Hoveyda-Grubbs Catalyst 2nd Generation (6.30 mg, 10.03 µmol). The reaction was stirred for 2 h, additional Hoveyda-Grubbs Catalyst 2nd Generation (7.30 mg, 0.012 mmol) was added, and the reaction was stirred for 2 h and then cooled. The reaction was concentrated and the residue was purified by biotage (Isco 4 g SiO2, 0% (5 CV), 0-60% (15 CV), EtOAc in hexanes) to afford the desired product (0.069 g, 0.104 mmol, 73% yield). $^1$H NMR (500 MHz, CDC$_3$) δ 7.99 (t, J=1.6 Hz, 1H), 7.79 (dt, J=7.9, 1.3 Hz, 1H), 7.52 (t, J=7.7 Hz, 1H), 7.29-7.32 (m, 2H), 7.21-7.28 (m, 3H), 6.96 (s, 1H), 6.91 (s, 2H), 5.57-5.62 (m, 2H), 5.09 (s, 1H), 4.61-4.70 (m, 1H), 4.28-4.38 (m, 2H), 3.64 (s, 3H), 3.52-3.61 (m, 1H), 3.43-3.49 (m, 1H), 3.33 (dd, J=15.1, 5.2 Hz, 1H), 2.85 (s, 3H), 2.60-2.66 (m, 2H), 2.36 (td, J=8.0, 5.1 Hz, 2H), 1.21 (s, 9H). LCMS (M+H)=663.4.

Intermediate 57

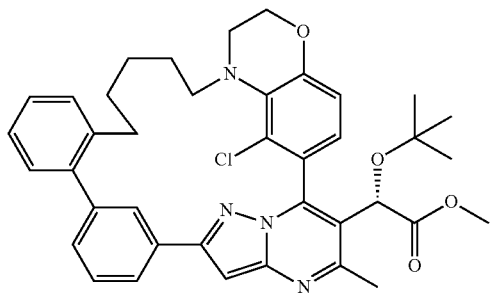

Methyl (2S)-2-(tert-butoxy)-2-{33-chloro-4-methyl-29-oxa-5,7,8,26-tetraazaheptacyclo[24.6.2.1$^{6,9}$.1$^{10,14}$.0$^{2,7}$.0$^{15,20}$.0$^{30,34}$]hexatriaconta-1(32),2,4,6(36),8,10(35), 11,13,15(20),16,18,30,33-tridecaen-3-yl}acetate: A solution of methyl (2S)-2-(tert-butoxy)-2-[33-chloro-4-methyl-29-oxa-5,7,8,26-tetraazaheptacyclo[24.6.2.1$^{6,9}$.1$^{10,14}$.0$^{2,7}$.0$^{15,20}$.0$^{30,34}$]hexatriaconta-1(32),2,4,6(36),8,10(35), 11,13,15(20),16,18,23,30,33-tetradecaen-3-yl]acetate (0.051 g, 0.077 mmol) in MeOH (3 mL) was evacuated and back-filled with hydrogen gas (balloon) three times, allowed to stir for 2 h, then filtered (0.45 µm syringe tip filter). The filtrate was used directly in the following step. LCMS (M+H)=667.4.

EXAMPLE 17

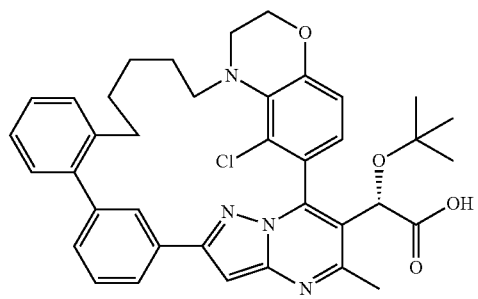 [SMILES: Cc1nc2cc3nn2c(c1[C@H](OC(C)(C)C)C(=O)O)-c1ccc2c(c1Cl)N(CCCCCc1ccccc1-c1cccc-3c1)CCO2]

(2S)-2-(tert-Butoxy)-2-{33-chloro-4-methyl-29-oxa-5,7,8,26-tetraazaheptacyclo[24.6.2.1$^{6,9}$.1$^{10,14}$.0$^{2,7}$.0$^{15,20}$.0$^{30,34}$]hexatriaconta-1(32),2,4,6(36),8,10(35), 11,13,15(20),16,18,30,33-tridecaen-3-yl}acetic acid: A solution of methyl (2S)-2-(tert-butoxy)-2-{33-chloro-4-methyl-29-oxa-5,7,8,26-tetraazaheptacyclo[24.6.2.1$^{6,9}$1$^{10,14}$.0$^{2,7}$.0$^{15,20}$.0$^{30,34}$] hexatriaconta-1(32),2,4,6(36),8,10(35),11,13,15(20),16,18, 30,33-tridecaen-3-yl}acetate (0.051 g, 0.077 mmol) in MeOH (2.0 ml) was treated with 1.0 N aq. NaOH (0.385 ml, 0.385 mmol) and the mixture was heated (70° C.) for 1 h. The mixture was purified by prep-HPLC to afford the desired product (0.0023 g, 3.4 µmol, 4.5% yield). $^1$H NMR (500 MHz, DMSO-d$_6$) δ 8.01-7.92 (m, 1H), 7.82 (br. s., 1H), 7.52 (t, J=7.5 Hz, 1H), 7.28 (d, J=6.1 Hz, 1H), 7.25-7.14 (m, 5H), 7.10 (d, J=7.0 Hz, 1H), 6.98 (d, J=7.6 Hz, 1H), 6.88 (d, J=7.9 Hz, 1H), 5.09 (br. s., 1H), 4.18 (d, J=11.0 Hz, 1H), 4.11-4.00 (m, 1H), 3.05-2.94 (m, 1H), 2.89 (s, 3H), 2.74 (d, J=5.8 Hz, 4H), 2.25 (br. s., 1H), 1.67 (br. s., 1H), 1.48 (br. s., 4H), 1.34 (br. s., 1H), 1.09 (br. s., 9H). LCMS (M+H)=651.5.

Intermediate 58

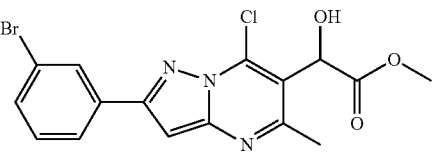

Methyl 2-(2-(3-bromophenyl)-7-chloro-5-methylpyrazolo[1,5-d]pyrimidin-6-yl)-2-hydroxyacetate: To a stirred solution of 0.91M KHMDS/THF (95 mL, 95 mmol) in THF (50 mL) at −78° C. was added dropwise a solution of methyl 24243-bromophenyl)-7-chloro-5-methylpyrazolo[1,5-a]pyrimidin-6-yl)acetate (25 g, 63.3 mmol) in THF (300 mL). After 1 h, 3-phenyl-2-(phenylsulfonyl)-1,2-oxaziridine (24.8 g, 95 mmol) in THF (100 mL) was added over the course of 10 min. This red reaction mixture was stirred at −78° C. for 2 h. Then, the resulting orange solution was quenched with sat. aq. NH$_4$Cl (400 mL), diluted with EtOAc (400 mL), and partitioned with a sep. funnel. The organic phase was washed with water and brine. The organic phase was dried (Na$_2$SO$_4$), filtered, and concentrated to give a light brown solid. Trituration with hexanes followed by trituration with ether (5×50 mL) gave 21 g of a yellow solid: methyl 2-(2-(3-bromophenyl)-7-chloro-5-methylpyrazolo[1,5-a]pyrimidin-6-yl)-2-hydroxyacetate (as a 1:1 complex with benzenesulfonamide). $^1$H NMR (400 MHz, CDCl$_3$) δ 8.20 (t, J=1.8 Hz, 1H), 7.95 (dq, J=7.8, 0.8 Hz, 1H), 7.57 (ddd, J=8.0, 2.0, 1.0 Hz, 1H), 7.37 (t, J=7.9 Hz, 1H), 6.95 (s, 1H), 5.79 (s, 1H), 3.87 (s, 3H), 3.59 (d, J=1.8 Hz, 1H), 2.65 (s, 3H). LCMS (M+H)=410 and 412.

Intermediate 59

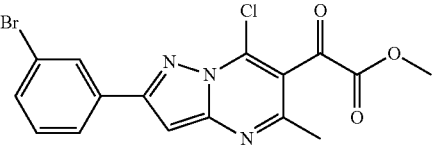

Methyl 2-(2-(3-bromophenyl)-7-chloro-5-methylpyrazolo[1,5-d]pyrimidin-6-yl)-2-oxoacetate: To a stirred inseparable mixture of methyl 2-(2-(3-bromophenyl)-7-chloro-5-methylpyrazolo[1,5-a]pyrimidin-6-yl)-2-hydroxyacetate (12.9 g, 31.4 mmol) and benzenesulfonamide (2.96 g, 18.85 mmol) in CH$_2$Cl$_2$ (700 mL) was added Dess-Martin Periodinane (13.3 g, 31.4 mmol). Stir for 60 min at rt at which time the reaction appeared complete by TLC (1:1 hexane/EtOAc). The reaction was placed in the refrigerator for 2 h and then filtered through a medium fritted glass funnel The brown homogeneous solution was treated with 140 mL of sat.aq. Na$_2$CO$_3$ and stirred rapidly for 30 min. The organic phase was separated and washed with additional sat.aq. Na$_2$CO$_3$ in a separatory funnel. The organic phase was dried (Na$_2$SO$_4$) and filtered through celite. The filtrate was then filtered through 170 g of silica gel with the aid of another 1 L of CH$_2$Cl$_2$. The light yellow filtrate was concentrated in vacuo to give 9.5 g of a yellow solid which after further drying gave 8.43 g (66%) of methyl 2-(2-(3-bromophenyl)-7-chloro-5-methylpyrazolo[1,5-a]pyrimidin-6-yl)-2-oxoacetate as a light yellow solid. $^1$H NMR (400 MHz, CDCl$_3$) δ 8.21 (t, J=1.6 Hz, 1H), 7.96 (d, J=7.8 Hz, 1H), 7.60 (dt, J=8.0, 0.9 Hz, 1H), 7.39 (t, J=7.9 Hz, 1H), 7.02 (s, 1H), 4.03 (s, 3H), 2.65 (s, 3H). LCMS (M+H)=408 and 410.

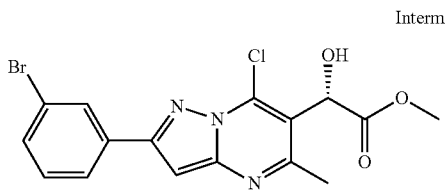

Intermediate 60

(S)-Methyl 2-(2-(3-bromophenyl)-7-chloro-5-methylpyrazolo[1,5-a]pyrimidin-6-yl)-2-hydroxyacetate: To a stirred solution of methyl 2-(2-(3-bromophenyl)-7-chloro-5-methylpyrazolo[1,5-a]pyrimidin-6-yl)-2-oxoacetate (14 g, 34.3 mmol) in anhydrous toluene (400 mL) was added 1.1M (R)-1-methyl-3,3-diphenylhexahydropyrrolo[1,2-c][1,3,2]oxazaborole/toluene (12.5 mL, 13.7 mmol). The mixture was cooled to −35° C. and then a 4.17M solution of catechoborane/toluene (11.7 mL, 48 mmol) was added over the course of 10 min. After 30 min, the reaction mixture was slowly warmed to −15° C. and stirred for additional 2 h. At this point the reaction mixture was diluted with EtOAc (300 mL) and treated with sat.aq. Na$_2$CO$_3$ (50 mL). The mixture was stirred vigorously for 10 min. The organic phase was separated and washed with sat. aq. Na$_2$CO$_3$ (5×100 mL), 0.1N HCl (1×100 mL), and brine. The organic phase was dried (Na$_2$SO$_4$), filtered, and concentrated. The residue was triturated with ether to obtain 12 g (77%) of the desired (S)-methyl 2-(2-(3-bromophenyl)-7-chloro-5-methylpyrazolo[1,5-a]pyrimidin-6-yl)-2-hydroxyacetate as a colorless oil. $^1$H NMR (400 MHz, CDCl$_3$) δ 8.20 (t, J=1.8 Hz, 1H), 7.95 (dq, J=7.8, 0.8 Hz, 1H), 7.57 (ddd, J=8.0, 2.0, 1.0 Hz, 1H), 7.37 (t, J=7.9 Hz, 1H), 6.95 (s, 1H), 5.79 (s, 1H), 3.87 (s, 3H), 3.59 (d, J=1.8 Hz, 1H), 2.65 (s, 3H). LCMS (M+H)=410 and 412.

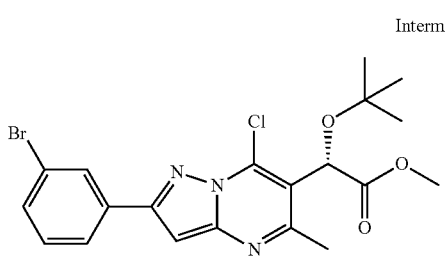

Intermediate 61

(S)-Methyl 2-(2-(3-bromophenyl)-7-chloro-5-methylpyrazolo[1,5-a]pyrimidin-6-yl)-2-(tert-butoxy)acetate: A mixture of (S)-methyl 2-(2-(3-bromophenyl)-7-chloro-5-methylpyrazolo[1,5-a]pyrimidin-6-yl)-2-hydroxyacetate (7.81 g, 19.02 mmol), t-butylacetate (160 mL) in DCM (330 mL) was added perchloric acid (3.43 mL, 57.1 mmol) and the mixture was stirred at rt for 3 h. It was then quenched with sat.aq.NaHCO$_3$ (adjusted to pH=7-8 by the addition of solid NaHCO$_3$). This mixture was diluted with EtOAc and the organic phase was washed with water. The organic phase was dried (MgSO$_4$), filtered, and concentrated in vacuo to obtain ~7 g of crude product as an oil. Filtration through 70 g of silica gel eluting with CH$_2$Cl$_2$ gave (S)-methyl 2-(2-(3-bromophenyl)-7-chloro-5-methylpyrazolo[1,5-a]pyrimidin-6-yl)-2-(tert-butoxy)acetate (5.71 g, 12.23 mmol, 64.3% yield). $^1$H NMR (400 MHz, CDCl$_3$) δ 8.20 (t, J=1.6 Hz, 1H), 7.95 (dt, J=7.8, 1.1 Hz, 1H), 7.63-7.53 (m, 1H), 7.37 (t, J=7.9 Hz, 1H), 6.94 (s, 1H), 5.69 (s, 1H), 3.76 (s, 3H), 2.70 (s, 3H), 1.30 (s, 9H). LCMS (M+H)=466 and 468.

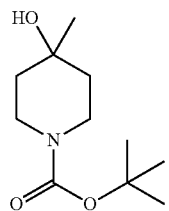

Intermediate 62 tert-Butyl 4-hydroxy-4-methylpiperidine-1-carboxylate: Under an N$_2$ atmosphere, a 3N MeMgBr/ether (1.67 mL, 5.02 mmol) was added dropwise to a cooled (−25° C.) solution of tert-butyl 4-hydroxy-4-methylpiperidine-1-carboxylate (4 g, 20.08 mmol) in ether (20 mL). The reaction mixture was allowed to warm to rt and was stirred for 2 h. It was then cooled to 0° C. and quenched by the addition of sat. NH$_4$Cl. Another 20 mL of ether was added and the mixture was partitioned in a separatory funnel The organic phase was set aside and the aqueous phase was extracted with another 20 mL of ether. The combined ether extracts were dried over MgSO$_4$, filtered and evaporated to obtain an oil, which was then purified by biotage, eluting with 0-50% EtOAc/hexane to obtain tert-butyl 4-hydroxy-4-methylpiperidine-1-carboxylate (4.30 g, 18.0 mmol, 90% yield) as a colorless oil. $^1$H NMR (500 MHz, CDCl$_3$) δ 3.84-3.65 (m, 2H), 3.34-3.18 (m, 2H), 2.59-2.39 (m, 1H), 1.61-1.53 (m, 4H), 1.50-1.45 (m, 9H), 1.32-1.27 (m, 3H).

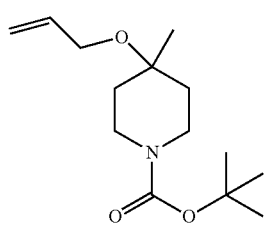

Intermediate 63 tert-Butyl 4-(allyloxy)-4-methylpiperidine-1-carboxylate: To a mixture of tert-butyl 4-hydroxy-4-methylpiperidine-1-carboxylate (4.30 g, 20.0 mmol) in DMF (50 mL) at 0° C. was added NaH (60 wt %) (1.60 g, 39.9 mmol). The mixture was then stirred at rt for 2 h. At this time allyl bromide (8.64 mL, 100 mmol) was added slowly over the course of 5 min. The reaction mixture was stirred at rt for 3 h. It was then cooled to 0° C. and quenched with sat. NH$_4$Cl. The reaction mixture was extracted with ether. The organic phase was dried over MgSO$_4$, filtered and concentrated to obtain a colorless oil, which was then purified by biotage, eluting with 0-25% EtOAc/hexane to isolate 3.1 g (61%) of tert-butyl 4-(allyloxy)-4-methylpiperidine-1-carboxylate as a colorless oil. $^1$H NMR (500 MHz, CDCl$_3$) δ 6.02-5.90 (m, 1H), 5.32 (dd, J=17.2, 1.7 Hz, 1H), 5.16 (dd, J=10.4, 1.4 Hz, 1H), 3.94-3.88 (m, 2H), 3.73 (br. s., 2H), 3.19 (br. s., 2H), 1.78 (d, J=13.1 Hz, 2H), 1.53-1.42 (m, 11H), 1.21 (s, 3H).

Intermediate 64

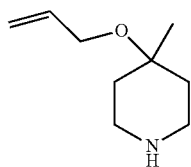

4-(Allyloxy)-4-methylpiperidine hydrochloride: A mixture of tert-butyl 4-(allyloxy)-4-methylpiperidine-1-carboxylate (3.10 g, 12.1 mmol) and 4N HCl/dioxane (15 mL, 60.0 mmol) was stirred at rt for 3 h. It was then concentrated in vacuum to obtain 2.2 g (95%) of 4-(allyloxy)-4-methylpiperidine hydrochloride as a light brown solid. $^1$H NMR (500 MHz, METHANOL-d$_4$) δ 6.02-5.92 (m, 1H), 5.33 (dd, J=17.2, 1.7 Hz, 1H), 5.15 (dd, J=10.6, 1.7 Hz, 1H), 3.96 (dt, J=5.1, 1.6 Hz, 2H), 3.23-3.18 (m, 4H), 2.06 (dd, J=15.3, 2.5 Hz, 2H), 1.77-1.69 (m, 2H), 1.31-1.28 (s, 3H).

Intermediate 65

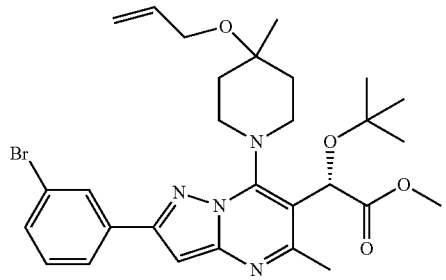

(S)-Methyl 2-(7-(4-(allyloxy)-4-methylpiperidin-1-yl)-2-(3-bromophenyl)-5-methylpyrazolo[1,5-a]pyrimidin-6-yl)-2-(tert-butoxy)acetate: (S)-methyl 2-(2-(3-bromophenyl)-7-chloro-5-methylpyrazolo[1,5-a]pyrimidin-6-yl)-2-(tert-butoxy)acetate (10.9 g, 23.3 mmol) was dissolved in DMF (100 mL). After flushing with N$_2$, 4-(allyloxy)-4-methylpiperidine.HCl (7.34 g, 35.0 mmol) and Hunig's Base (12.22 mL, 70.0 mmol) were added to the reaction mixture. After stirring for 18 h at rt, the reaction was heated at 50° C. for 3 h to complete the reaction. The reaction mixture was concentrated in vacuo at 50° C. to remove most of the DMF. The residue was partitioned between EtOAc and 0.01N HCl. The organic phase was washed with water and brine. Then, the organic phase was dried (MgSO$_4$), filtered, and concentrated in vacuo. The residue was dissolved in about 600 mL of hot hexanes and cooled for 18 h in the freezer to give a crystalline solid. Filtration gave 6.5 g of (S)-methyl 2-(7-(4-(allyloxy)-4-methylppiperidin-1-yl)-2-(3-bromophenyl)-5-methylpyrazolo[1,5-a]pyrimidin-6-yl)-2-(tert-butoxy)acetate.

The filtrate was purified by Biotage (10-50% EtOAc) to give another 5.71 g of (S)-methyl 2-(7-(4-(allyloxy)-4-methylpiperidin-1-yl)-2-(3-bromophenyl)-5-methylpyrazolo[1,5-a]pyrimidin-6-yl)-2-(tert-butoxy)acetate. The combined yield of the desired product was 12.21 g (89%). $^1$H NMR (400 MHz, METHANOL-d$_4$) δ 8.23 (t, J=1.8 Hz, 1H), 8.01 (dt, J=7.8, 1.3 Hz, 1H), 7.60-7.55 (m, 1H), 7.43-7.37 (m, 1H), 6.90 (s, 1H), 6.18-5.95 (m, 2H), 5.48 (d, J=17.3 Hz, 1H), 5.25 (d, J=10.0 Hz, 1H), 4.11-4.06 (m, 2H), 3.77 (s, 3H), 2.59 (s, 3H), 2.14-1.95 (m, 3H), 1.82-1.71 (m, 1H), 1.37 (s, 3H), 1.28 (s, 9H). LCMS (M+H)=585 and 587.

Intermediate 66

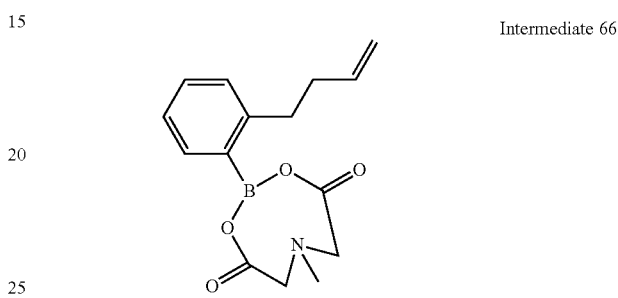

2-(2-(But-3-en-1-yl)phenyl)-6-methyl-1,3,6,2-dioxazaborocane-4,8-dione: The boronic acid was synthesized according to the general procedure described by Kuznetsov, N.Yu.; Russ.Chem.Bull., Int.Ed., 2005, 54(3), 678-683. 1-Bromo-2-(but-3-en-1-yl)benzene (953 mg, 4.51 mmol) was dissolved in dry THF (5 mL), placed under an N$_2$ atmosphere and cooled to −90° C. A 1.7M pentane solution of t-BuLi (5.31 mL, 9.02 mmol) was added over the course of 5 min. This light yellow solution was stirred for 15 min at which time trimethyl borate (716 µL, 6.41 mmol) was added all at once. This mixture was stirred and allowed to warm to 0° C. Once at this temperature for 30 min, TMS-Cl (710 µL, 5.55 mmol) was added and the reaction was allowed to warm to rt. The reaction mixture was concentrated in vacuo to give ~800 mg of crude product which was estimated to contain 396 mg of the desired boronate product 2-(but-3-en-1-yl)phenyl)boronic acid. Conversion of the crude boronate to the MIDA boronate was performed as described by Gillis, E.P.; and Burke, M.D. J. Am. Chem. Soc. 2008, 130, 14084-14085. 2-(But-3-en-1-yl)phenyl)boronic acid (396 mg, 2.25 mmol) was dissolved in 4 mL of toluene. This was added to a round bottom flask containing a solution of 2,2'-(methylazanediyl) diacetic acid in 2 mL of DMSO. The flask was fitted with a Dean-Stark trap filled with toluene. The reaction mixture was heated at reflux with azeotropic removal of water for 3 h. The cooled reaction mixture was concentrated in vacuo to remove toluene. The residue was subjected to a stream of N$_2$ for 18 h to blow off residual DMSO. The resulting brown oil was purified by Biotage chromatography (Et$_2$O/MeCN 0-60% gradient) to give 2-(2-(but-3-en-1-yl)phenyl)-6-methyl-1,3,6,2-dioxazaborocane-4,8-dione (446 mg, 1.55 mmol, 69.0% yield) as a yellow oil. $^1$H NMR (400 MHz, CDCl$_3$) δ 7.46-7.40 (m, 1H), 7.40-7.33 (m, 1H), 7.28-7.21 (m, 2H), 5.93 (ddt, J=17.1, 10.3, 6.7 Hz, 1H), 5.11 (dq, J=17.1, 1.7 Hz, 1H), 5.04-4.98 (m, 1H), 4.04-3.96 (m, 2H), 3.85-3.78 (m, 2H), 2.77-2.69 (m, 2H), 2.62 (s, 3H), 2.46-2.37 (m, 2H). LCMS (M−H)=286.

Intermediate 67

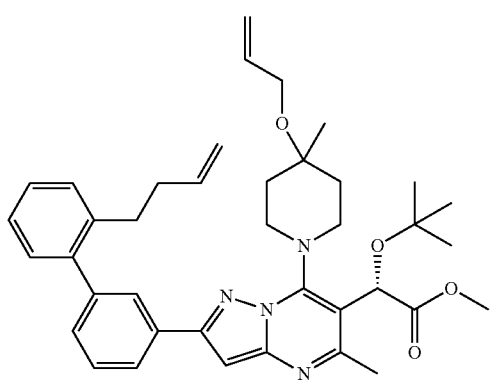

(S)-Methyl 2-(7-(4-(allyloxy)-4-methylpiperidin-1-yl)-2-(2'-(but-3-en-1-yl)-[1,1'-biphenyl]-3-yl)-5-methylpyrazolo[1,5-d]pyrimidin-6-yl)-2-(tert-butoxy)acetate: To a solution of (S)-methyl 2-(7-(4-(allyloxy)-4-methylpiperidin-1-yl)-2-(3-bromophenyl)-5-methylpyrazolo[1,5-a]pyrimidin-6-yl)-2-(tert-butoxy)acetate (250 mg, 0.427 mmol) in DMF (5 mL) was added 2-(2-(but-3-en-1-yl)phenyl)-6-methyl-1,3,6,2-dioxazaborocane-4,8-dione (147 mg, 0.512 mmol), 2M sodium carbonate (0.427 mL, 0.854 mmol), and tetrakis(triphenylphosphine)palladium(0)(35 mg, 0.030 mmol). This reaction mixture was flushed with $N_2$ and heated at 90° C. for 24 h. Upon completion of the reaction, the reaction mixture was partitioned between EtOAc and water. The organic phase was washed with water (3×), dried ($MgSO_4$), filtered, and concentrated in vacuo to give the crude product as a brown oil. This was purified by Biotage chromatography (0-40% EtOAc/hexanes) to give 233 mg (86% yield) of (S)-methyl 2-(7-(4-(allyloxy)-4-methylpiperidin-1-yl)-2-(2'-(but-3-en-1-yl)-[1,1'-biphenyl]-3-yl)-5-methylpyrazolo[1,5-a]pyrimidin-6-yl)-2-(tert-butoxy)acetate as a colorless oil. LCMS (M+H).=637.

Intermediate 68

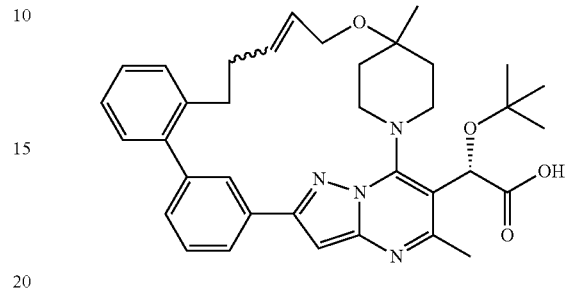

Methyl (2S)-2-(tert-butoxy)-2-[(23Z)-4,27-dimethyl-26-oxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18,23-undecaen-3-yl]acetate: (S)-Methyl 2-(7-(4-(allyloxy)-4-methylpiperidin-1-yl)-2-(2'-(but-3-en-1-yl)-[1,1'-biphenyl]-3-yl)-5-methylpyrazolo[1,5-a]pyrimidin-6-yl)-2-(tert-butoxy)acetate (116 mg, 0.182 mmol) was dissolved in DCE (150 mL). The solution was heated to 75° C. in an oil bath under an $N_2$ atmosphere. Once the reaction flask had reached 75° C. the Hoveyda-Grubbs Catalyst 2nd generation (11.45 mg, 0.018 mmol) was added. The yellow reaction mixture turned green. Stirring at 85° C. was continued for 2 h at which time the reaction appeared complete by TLC (4:1 hexane/EtOAc) and HPLC (~4:1 mixture of E/Z isomers). The cooled reaction mixture was concentrated in vacuo and purified by Biotage chromatography (0-50% EtOAc/hexanes) to give 84 mg of the desired product as a colorless oil. LCMS (M+H).=609.

EXAMPLE 18

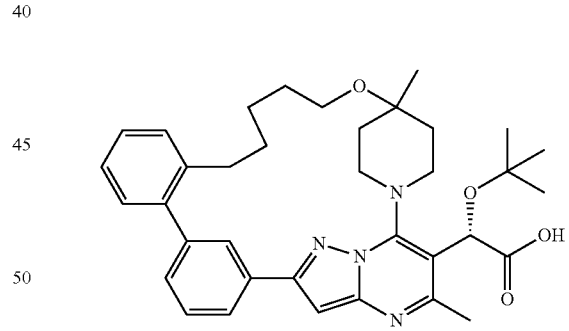

(2S)-2-(tert-Butoxy)-2-[4,27-dimethyl-26-oxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18,23-undecaen-3-yl] acetic acid: The intermediate 68 (82 mg, 0.135 mmol) was dissolved in MeOH (6 mL) and treated with 0.4 mL of 1N NaOH. After stirring at rt for 18 h, the reaction mixture was heated at 60° C. for 3 h. To drive the hydrolysis to completion another 0.4 mL of 1N NaOH was added and the reaction mixture was heated at 75° C. for 3 h. The mixture was concentrated in vacuo to remove methanol and the residue was partitioned between 0.1N HCl and EtOAc. The organic phase was dried ($Na_2SO_4$), filtered, and concentrated in vacuo to give 65 mg (77% yield, 95% purity) of the desired product as an off-white solid. Two olefin isomers are present in a 78:22 E/Z ratio or roughly 4:1 E/Z, respectively. LCMS (M+H).=595.

EXAMPLE 19

(2S)-2-(tert-Butoxy)-2-{4,27-dimethyl-26-oxa-1,5,7,8-tetraazahexacyclo[25.2.2.1$^{6,9}$.1$^{10,14}$. 0$^{2,7}$. 0$^{15,20}$]-tritriaconta-2,4,6(33),8,10(32),11,13,15(20),16,18-decaen-3-yl}acetic acid: The example 18 (15 mg, 0.025 mmol) was dissolved in MeOH (2 mL), and the solution was flushed briefly with $N_2$. 10% Pd/C (2.68 mg, 0.025 mmol) was added, and the reaction mixture was stirred under a hydrogen balloon for 1.5 h. It was then filtered through celite and purified by prep-HPLC to isolate 12 mg of 90% pure product as a white solid. It was purified further by biotage chromatography (4 g) eluting with 0-10% MeOH/DCM to isolate 7 mg (44% yield, 95% purity) of the desired product as a white solid. $^1$H NMR (500 MHz, METHANOL-d4) δ: 8.11 (s, 1H), 7.86 (d, J=6.8 Hz, 1H), 7.56 (t, J=7.6 Hz, 1H), 7.44 (d, J=7.9 Hz, 1H), 7.36

(t, J=7.6 Hz, 1H), 7.27 (d, J=7.6 Hz, 1H), 7.23 (t, J=7.4 Hz, 1H), 7.19-7.14 (m, 1H), 6.94 (s, 1H), 5.95-5.87 (m, 1H), 4.63-4.53 (m, 1H), 3.96-3.86 (m, 1H), 3.54-3.47 (m, 1H), 3.40 (br. s., 2H), 3.03 (d, J=10.4 Hz, 1H), 2.79-2.71 (m, 1H), 2.68 (s, 3H), 2.65-2.57 (m, 1H), 2.13 (d, J=12.8 Hz, 1H), 1.94 (br. s., 1H), 1.88 (m, 2H), 1.79 (br. s., 1H), 1.66 (m, 3H), 1.60-1.51 (m, 2H), 1.28 (m, 12H). LCMS (M+H)=597.

Intermediate 69

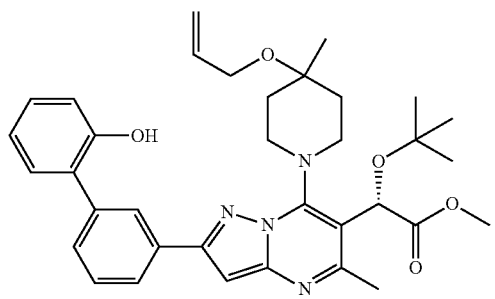

(S)-Methyl 2-(7-(4-(allyloxy)-4-methylpiperidin-1-yl)-2-(2'-hydroxy-[1,1'-biphenyl]-3-yl)-5-methylpyrazolo[1,5-d]pyrimidin-6-yl)-2-(tert-butoxy)acetate: To a 25 ml microwave tube was added intermediate 65, 2-(4,4,5,5-tetramethyl-1,3,2-dioxaborolan-2-yl)phenol (1.128 g, 5.12 mmol) and 2.0 M aqueous potassium carbonate (3.42 mL, 6.83 mmol) in 1,4-Dioxane (12.00 ml) and Water (3 ml). The reaction was sparged with nitrogen for 10 minutes, treated with (Ph₃P)₄Pd (0.395 g, 0.342 mmol), then sparged with N₂ for 1 min. The reaction tube was sealed and then heated at 90° C. in a microwave tube for 1 h. The reaction was concentrated, then diluted with water (15 mL) and extracted wtih EtOAc. The EtOAc layer was washed with brine, then dried (Na₂SO₄), filtered, and concentrated under reduced pressure. The residue was purified by biotage (0%-40% EtOAc in hexanes) to isolate 1.98 g (97%) of the desired product as an off-white foam. ¹H NMR at 60° C. (500 MHz, CD₃OD) δ 8.23 (t, J=1.5 Hz, 1H), 7.97 (dt, J=7.7, 1.4 Hz, 1H), 7.59 (dt, J=7.9, 1.3 Hz, 1H), 7.51-7.47 (m, 1H), 7.36-7.31 (m, 1H), 7.23-7.17 (m, 1H), 6.99-6.92 (m, 2H), 6.85 (s, 1H), 6.06-5.91 (m, 2H), 5.34 (dq, J=17.2, 1.8 Hz, 1H), 5.04 (dd, J=10.4, 1.5 Hz, 1H), 4.08-4.01 (m, 2H), 3.77 (s, 3H), 4.50-3.00 (m, 4H), 2.59 (s, 3H), 2.14-1.91 (m, 3H), 1.82-1.72 (m, 1H), 1.35 (s, 3H), 1.28 (s, 9H). LCMS (M+1)=599.43.

Intermediate 70

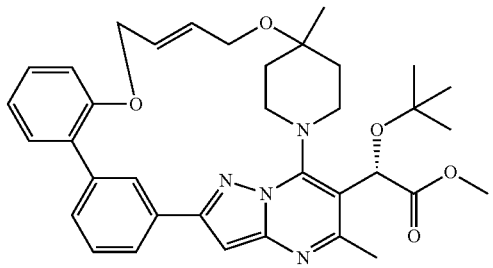

(S)-Methyl 2-(7-(4-(allyloxy)-4-methylpiperidin-1-yl)-2-(2'-(allyloxy)-[1,1'-biphenyl]-3-yl)-5-methylpyrazolo[1,5-d]pyrimidin-6-yl)-2-(tert-butoxy)acetate: To a mixture of intermediate 69 (80 mg, 0.134 mmol), prop-2-en-1-ol (23.28 mg, 0.401 mmol), triphenylphosphine (105 mg, 0.401 mmol) in THF (2 mL) was added DIAD (0.078 mL, 0.401 mmol) and stirred at rt for 16 h. It was then concentrated and purified by biotage, eluting with 20% EtOAc/hexane to isolate 80 mg oil. It was then purified by prep HPLC to isolate 50 mg (58.6%) of the desired product as an off-white solid. ¹H NMR (500 MHz, CD₃OD) δ 8.23 (t, J=1.5 Hz, 1H), 7.98 (dt, J=7.7, 1.4 Hz, 1H), 7.58-7.52 (m, 1H), 7.51-7.46 (m, 1H), 7.39 (dd, J=7.6, 1.8 Hz, 1H), 7.36-7.30 (m, 1H), 7.13-7.04 (m, 2H), 6.85 (s, 1H), 6.05-5.92 (m, 3H), 5.33 (dquin, J=17.2, 2.0 Hz, 2H), 5.14 (dq, J=10.7, 1.6 Hz, 1H), 5.01 (d, J=10.5 Hz, 1H), 4.57 (dt, J=4.9, 1.7 Hz, 3H), 4.30-3.30 (m, 3H), 4.05-4.00 (m, 2H), 3.77 (s, 3H), 2.59 (s, 3H), 2.08-1.92 (m, 3H), 1.80-1.72 (m, 1H), 1.34 (s, 3H), 1.28 (s, 9H). LCMS (M+1)=639.7.

Intermediate 71

Methyl (2S)-2-(tert-butoxy)-2-[(23E)-4,27-dimethyl-21,26-dioxa-1,5,7,8-tetraazahexacyclo[25.2.2.1⁶,⁹.1¹⁰,¹⁴.0²,⁷.0¹⁵,²⁰]tritriaconta-2,4,6(33),8,10(32),11,13,15(20),16,18,23-undecaen-3-yl]acetate: A mixture of intermediate 70 (50 mg, 0.078 mmol), Hoveyda-Grubbs catalyst 2nd generation (9.81 mg, 0.016 mmol) in DCE (60 mL) was refluxed for 2 h. It was then concentrated and purified by biotage, eluting with 20% EtOAc/hexane to isolate 48 mg (100%) of the desired product as an off-white solid. ¹H NMR (400 MHz, CDCl₃) δ 8.54 (t, J=1.5 Hz, 1H), 7.72 (dt, J=7.7, 1.4 Hz, 1H), 7.54 (t, J=7.7 Hz, 1H), 7.45 (dt, J=7.6, 1.5 Hz, 1H), 7.38 (dd, J=7.4, 1.6 Hz, 2H), 7.08-7.00 (m, 2H), 6.82 (s, 1H), 6.37-6.28 (m, 1H), 6.14-6.03 (m, 2H), 4.72 (d, J=4.3 Hz, 2H), 4.64 (t, J=11.4 Hz, 1H), 4.06-3.96 (m, 3H), 3.74 (s, 3H), 3.14 (d, J=13.3 Hz, 1H), 2.72 (d, J=11.5 Hz, 1H), 2.64 (s, 3H), 2.02 (d, J=14.3 Hz, 1H), 1.96-1.89 (m, 1H), 1.84 (dd, J=12.3, 4.5 Hz, 1H), 1.67-1.61 (m, 1H), 1.32 (s, 3H), 1.29-1.25 (m, 9H). LCMS (M+1)=611.6.

EXAMPLE 20

(2S)-2-(tert-Butoxy)-2-[(23E)-4,27-dimethyl-21,26-dioxa-1,5,7,8-tetraazahexacyclo[25.2.2.1⁶,⁹.1¹⁰,¹⁴.0²,⁷.0¹⁵,²⁰]tritriaconta-2,4,6(33),8,10(32),11,13,15(20),16,18,23-undecaen-3-yl]acetic acid: A mixture of intermediate 71 (48 mg, 0.079 mmol), 1 N NaOH (0.393 mL, 0.393 mmol) in MeOH (2 mL) was heated at refluxed for 3 h. It was then purified by prep HPLC (NH₄OAc/CH₃CN) (35%-65% B) to isolate 30 mg (71%, 95% pure) of the desired product as a white solid. ¹H NMR (500 MHz, CDCl₃) δ 8.54 (s, 1H), 7.72 (d, J=7.7 Hz, 1H), 7.54 (t, J=7.6 Hz, 1H), 7.46 (d, J=7.7 Hz, 1H), 7.38 (dd, J=7.5, 1.7 Hz, 1H), 7.36-7.31 (m, 1H), 7.08-7.00 (m, 2H), 6.84 (s, 1H), 6.31 (dt, J=15.6, 5.5 Hz, 1H), 6.13-6.06 (m, 1H), 6.02 (br. s., 1H), 4.76-4.65 (m, 3H), 4.09-3.96 (m, 3H), 3.37 (d, J=10.9 Hz, 1H), 2.75 (d, J=11.7 Hz, 1H), 2.64 (s, 3H), 2.07-2.01 (m, 1H), 1.95 (d, J=13.7 Hz, 1H), 1.77 (td, J=13.2, 4.6 Hz, 1H), 1.61 (td, J=13.3, 4.4 Hz, 1H), 1.35-1.29 (m, 12H). LCMS (M+1)=597.39.

EXAMPLE 21

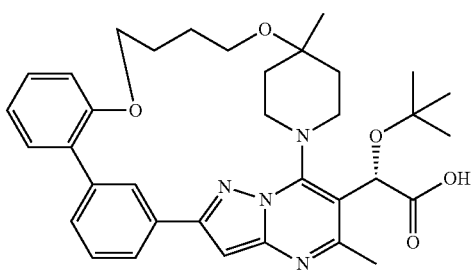 [SMILES: Cc1nc2cc3nn2c(c1[C@H](OC(C)(C)C)C(=O)O)N1CCC(C)(CC1)OCCCCOc1ccccc1-c1cccc-3c1]

(2S)-2-(tert-Butoxy)-2-{4,27-dimethyl-21,26-dioxa-1,5,7,8-tetraazahexacyclo[25.2.2.1⁶,⁹.1¹⁰,¹⁴.0²,⁷.0¹⁵,²⁰]-tritriaconta-2,4,6(33),8,10(32),11,13,15(20),16,18-decaen-3-yl}acetic acid: A mixture of example 20 (30 mg, 0.050 mmol), 10% Pd/C (5.35 mg, 5.03 μmol) in MeOH was stirred under a H₂ balloon for 3 h. It was then filtered and concentrated to obtain 28 mg (93%) of the desired product as a white solid. ¹H NMR (500 MHz, CDCl₃) δ 8.51 (br. s., 1H), 7.70 (d, J=7.1 Hz, 1H), 7.54 (t, J=7.6 Hz, 1H), 7.47 (d, J=7.3 Hz, 1H), 7.40 (d, J=6.6 Hz, 1H), 7.34 (t, J=7.2 Hz, 1H), 7.04 (d, J=7.1 Hz, 2H), 6.81 (s, 1H), 6.01 (br. s., 1H), 4.59 (t, J=11.9 Hz, 1H), 4.13 (br. s., 2H), 3.91 (t, J=11.5 Hz, 1H), 3.53 (d, J=3.5 Hz, 1H), 3.42 (d, J=4.9 Hz, 2H), 2.84 (d, J=9.9 Hz, 1H), 2.63 (br. s., 3H), 2.36 (br. s., 1H), 2.16 (br. s., 1H), 2.10-2.02 (m, 1H), 1.93 (d, J=12.5 Hz, 1H), 1.80 (d, J=9.0 Hz, 2H), 1.70-1.54 (m, 2H), 1.36-1.20 (m, 12H). LCMS (M+1)=599.38.

Intermediate 72

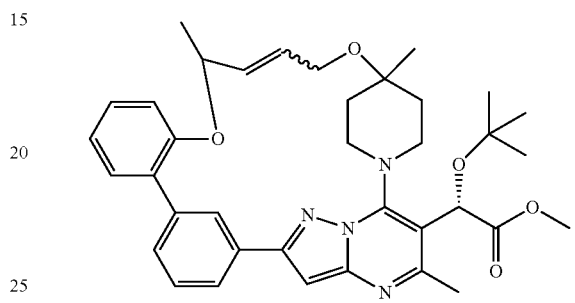

(2S)-Methyl 2-(7-(4-(allyloxy)-4-methylpiperidin-1-yl)-2-(2'-(but-3-en-2-yloxy)[1,1'-biphenyl]-3-yl)-5-methylpyrazolo[1,5-a]pyrimidin-6-yl)-2-(tert-butoxy)acetate: Intermediate 72 was prepared using intermediate 69 and but-3-en-2-ol by following the procedure to prepare intermediate 70. ¹H NMR 60° C. (500 MHz, CD3OD) δ 8.25-8.21 (m, 1H), 7.98 (d, J=7.6 Hz, 1H), 7.57-7.53 (m, 1H), 7.51-7.46 (m, 1H), 7.38 (dd, J=7.5, 1.7 Hz, 1H), 7.32-7.27 (m, 1H), 7.09 (d, J=8.1 Hz, 1H), 7.05 (td, J=7.5, 1.1 Hz, 1H), 6.85 (s, 1H), 6.02-5.92 (m, 2H), 5.91-5.82 (m, 1H), 5.33 (dd, J=17.2, 1.6 Hz, 1H), 5.17 (ddt, J=17.3, 2.7, 1.4 Hz, 1H), 5.07 (dq, J=10.6, 1.5 Hz, 1H), 5.01 (d, J=10.1 Hz, 1H), 4.78 (quin, J=6.3 Hz, 1H), 4.40-3.00 (m, 4H), 4.05-4.01 (m, 2H), 3.77 (s, 3H), 2.59 (s, 3H), 2.10-1.92 (m, 3H), 1.81-1.72 (m, 1H), 1.35 (s, 3H), 1.31 (dd, J=6.3, 2.1 Hz, 3H), 1.28 (s, 9H). LCMS (M+1)=653.58.

Intermediate 73

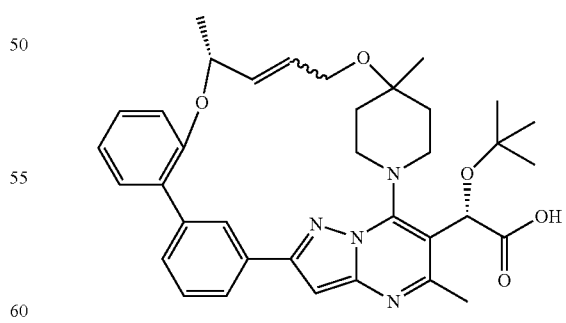

Methyl (2S)-2-(tert-butoxy)-2-[4,22,27-trimethyl-21,26-dioxa-1,5,7,8-tetraazahexacyclo[25.2.2.1⁶,⁹.1¹⁰,¹⁴.0²,⁷.0¹⁵,²⁰]tritriaconta-2,4,6(33),8,10(32),11,13,15(20),16,18,23-undecaen-3-yl]acetate: A mixture of intermediate 72 (50 mg, 0.077 mmol), Hoveyda-Grubbs catalyst 2nd generation (9.60 mg, 0.015 mmol) in DCE (60 mL) was refluxed for 2 h. It was then concentrated and purified by prep HPLC to isolate 47 mg (98%) of the desired product as an off-white solid. NMR: 1:1 mixture of two isomers. LCMS (M+1)=625.54.

EXAMPLE 22 AND 23

A mixture of intermediate 73 (47 mg, 0.075 mmol), NaOH (0.393 mL, 0.393 mmol) in MeOH (2 mL) was heated at refluxed for 3 h. It was then purified by prep-HPLC(NH₄OAc/CH₃CN) to afford two compounds.

EXAMPLE 22

(2S)-2-(tert-Butoxy)-2-[(22R)-4,22,27-trimethyl-21,26-dioxa-1,5,7,8-tetraazahexacyclo[25.2.2.1⁶,⁹.1¹⁰,¹⁴.0²,⁷.0¹⁵,²⁰]tritriaconta-2,4,6(33),8,10(32),11,13,15(20),16,18,23-undecaen-3-yl]acetic acid: The first eluting compound, white solid (18 mg, 37%). ¹H NMR (500 MHz, CDCl₃) δ 8.69 (s, 1H), 7.73 (d, J=7.7 Hz, 1H), 7.53 (t, J=7.6

Hz, 1H), 7.46 (d, J=7.7 Hz, 1H), 7.38 (dd, J=7.4, 1.6 Hz, 1H), 7.30-7.26 (m, 1H), 7.02 (t, J=7.5 Hz, 1H), 6.94 (d, J=8.4 Hz, 1H), 6.85 (s, 1H), 6.13-6.05 (m, 1H), 6.03-5.94 (m, 2H), 5.02-4.95 (m, 1H), 4.65 (t, J=11.8 Hz, 1H), 4.14-3.99 (m, 3H), 3.22 (d, J=10.4 Hz, 1H), 2.70 (d, J=10.9 Hz, 1H), 2.66 (s, 3H), 2.02 (br. s., 1H), 1.89 (d, J=12.3 Hz, 1H), 1.75 (td, J=13.1, 4.7 Hz, 1H), 1.63 (td, J=13.2, 3.8 Hz, 1H), 1.36-1.26 (m, 15H). LCMS (M+H)=611.4.

EXAMPLE 23

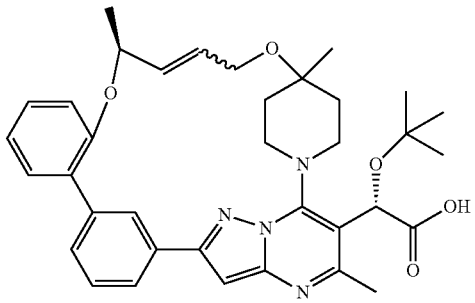 [SMILES: Cc1nc2cc3nn2c(c1[C@H](OC(C)(C)C)C(=O)O)N1CCC(C)(CC1)OCC=C[C@H](C)Oc1ccccc1-c1cccc-3c1]

(2S)-2-(tert-Butoxy)-2-[(22S)-4,22,27-trimethyl-21,26-dioxa-1,5,7,8-tetraazahexacyclo[25.2.2. 1$^{6,9}$.1$^{10,14}$.0$^{2,7}$.0$^{15,20}$]tritriaconta-2,4,6(33),8,10(32),11,13,15(20),16,18,23-undecaen-3-yl]acetic acid: The second compound, white solid (15 mg, 31%). $^1$H NMR (500 MHz, CDCl$_3$) δ 8.68 (s, 1H), 7.78 (d, J=7.7 Hz, 1H), 7.53 (t, J=7.6 Hz, 1H), 7.42 (d, J=7.6 Hz, 1H), 7.35 (dd, J=7.4, 1.6 Hz, 1H), 7.32-7.29 (m, 1H), 7.05-6.99 (m, 2H), 6.92 (s, 1H), 6.28 (dd, J=15.6, 7.1 Hz, 1H), 6.06 (br. s., 1H), 5.97 (dt, J=15.6, 3.7 Hz, 1H), 5.09 (quin, J=6.4 Hz, 1H), 4.83 (t, J=12.1 Hz, 1H), 4.07-3.92 (m, 3H), 3.38 (d, J=10.7 Hz, 1H), 2.75 (d, J=11.7 Hz, 1H), 2.63 (s, 3H), 1.98 (t, J=14.2 Hz, 2H), 1.75-1.59 (m, 2H), 1.38-1.26 (m, 15H). LCMS (M+H)=611.4.

EXAMPLE 24

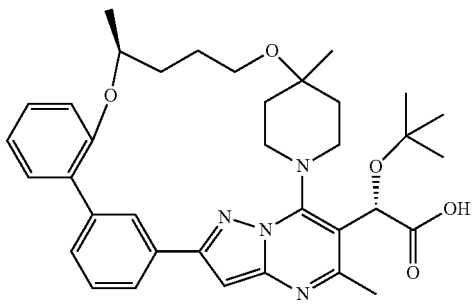 [SMILES: Cc1nc2cc3nn2c(c1[C@H](OC(C)(C)C)C(=O)O)N1CCC(C)(CC1)OCCC[C@H](C)Oc1ccccc1-c1cccc-3c1]

(2S)-2-(tert-Butoxy)-2-[(22S)-4,22,27-trimethyl-21,26-dioxa-1,5,7,8-tetraazahexacyclo[25.2.2. 1$^{6,9}$.1$^{10,14}$.0$^{2,7}$.0$^{15,20}$]tritriaconta-2,4,6(33),8,10(32),11,13,15(20),16,18-decaen-3-yl]acetic acid: Example 24 was prepared using example 23 by following the procedure to prepare example 21. $^1$H NMR (500 MHz, CDCl$_3$) δ 8.33 (br. s., 1H), 7.66 (d, J=7.4 Hz, 1H), 7.52 (d, J=6.9 Hz, 1H), 7.43 (d, J=6.8 Hz, 1H), 7.35-7.31 (m, 2H), 7.00 (br. s., 2H), 6.81-6.68 (m, 1H), 5.95 (br. s., 1H), 4.49 (d, J=19.4 Hz, 2H), 3.93 (br. s., 1H), 3.49 (br. s., 1H), 3.36 (br. s., 2H), 2.68 (br. s., 1H), 2.60 (br. s., 3H), 2.36 (br. s., 2H), 2.03 (d, J=13.1 Hz, 2H), 1.92-1.71 (m, 2H), 1.69-1.52 (m, 2H), 1.39-1.09 (m, 15H). LCMS (M+H)=613.4.

EXAMPLE 25

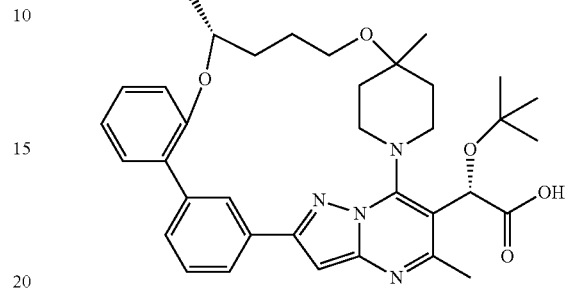

(2S)-2-(tert-Butoxy)-2-[(22R)-4,22,27-trimethyl-21,26-dioxa-1,5,7,8-tetraazahexacyclo[25.2.2. 1$^{6,9}$.1$^{10,14}$.0$^{2,7}$.0$^{15,20}$]tritriaconta-2,4,6(33),8,10(32),11,13,15(20),16,18-decaen-3-yl]acetic acid: Example 25 was prepared using example 22 by following the procedure to prepare example 21. $^1$H NMR (500 MHz, CDCl$_3$) δ 8.58 (br. s., 1H), 7.71 (d, J=5.4 Hz, 1H), 7.46 (br. s., 1H), 7.41-7.30 (m, 3H), 7.11-6.95 (m, 2H), 6.83 (br. s., 1H), 5.85 (br. s., 1H), 4.66 (br. s., 1H), 4.52 (br. s., 1H), 3.72 (br. s., 1H), 3.61 (br. s., 1H), 3.39 (d, J=15.4 Hz, 2H), 2.81 (d, J=7.9 Hz, 1H), 2.55 (br. s., 3H), 2.28-1.65 (m, 8H), 1.27-1.03 (m, 15H). LCMS (M+H)=613.44.

Intermediate 74

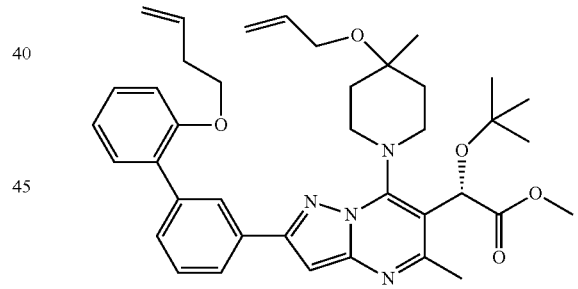

(S)-Methyl 2-(7-(4-(allyloxy)-4-methylpiperidin-1-yl)-2-(2'-(but-3-en-1-yloxy)-[1,1'-biphenyl]-3-yl)-5-methylpyrazolo[1,5-a]pyrimidin-6-yl)-2-(tert-butoxy)acetate: Intermediate 74 was prepared using intermediate 69 and 3-buten-1-ol by following the procedure to prepare intermediate 70. $^1$H NMR (500 MHz, CDCl$_3$) δ 8.16 (t, J=1.5 Hz, 1H), 8.04 (d, J=7.7 Hz, 1H), 7.60 (d, J=7.7 Hz, 1H), 7.52-7.47 (m, 1H), 7.44 (dd, J=7.6, 1.7 Hz, 1H), 7.35 (td, J=7.8, 1.7 Hz, 1H), 7.11-7.06 (m, 1H), 7.03 (d, J=8.4 Hz, 1H), 6.84 (s, 1H), 6.08-5.93 (m, 2H), 5.85 (ddt, J=17.1, 10.3, 6.8 Hz, 1H), 5.42 (dd, J=17.2, 1.7 Hz, 1H), 5.18-5.02 (m, 3H), 4.50-2.50 (m, 4H), 4.06 (t, J=6.6 Hz, 2H), 4.02 (d, J=4.7 Hz, 2H), 3.76 (s, 3H), 2.63 (s, 3H), 2.54-2.47 (m, 2H), 2.08-1.92 (m, 2H), 1.74 (br. s., 1H), 1.38 (br. s., 3H), 1.27 (s, 9H). LCMS (M+1)=653.7.

Intermediate 75

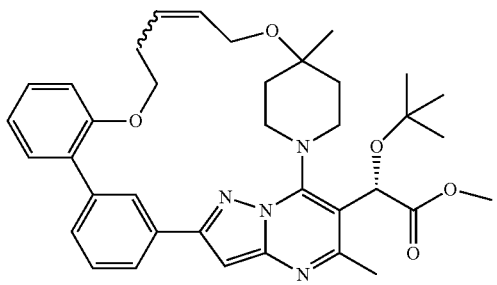

Intermediate 75 was prepared usinh intermediate 74 by following the procedure to prepare intermediate 71. The product was a mixture of two isomers (trans/cis), the ratio is 1:4. LCMS (M+1)=625.35.

EXAMPLE 26

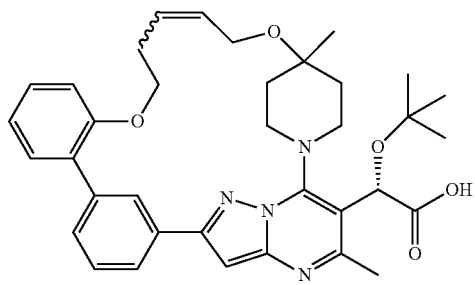 [SMILES: Cc1nc2cc3nn2c(c1[C@H](OC(C)(C)C)C(=O)O)N1CCC(C)(CC1)OCC=CCCOc1ccccc1-c1cccc-3c1]

(2S)-2-(tert-Butoxy)-2-[4,28-dimethyl-21,27-dioxa-1,5, 7,8-tetraazahexacyclo[26.2.2.1$^{6,9}$.1$^{10,14}$.0$^{2,7}$.0$^{15,20}$]tetratria-conta-2,4,6(34),8,10(33),11,13,15(20),16,18,24-undecaen-3-yl]acetic acid: Example 26 was prepared using intermediate 75 by following the procedure to prepare example 20. $^1$H NMR (500 MHz, CDCl$_3$) δ 8.55 (s, 1H), 7.78 (d, J=7.7 Hz, 1H), 7.53 (t, J=7.7 Hz, 1H), 7.40 (d, J=7.9 Hz, 1H), 7.38-7.32 (m, 2H), 7.07-7.01 (m, 2H), 6.89 (s, 1H), 6.22 (d, J=6.1 Hz, 1H), 5.98 (br. s., 1H), 4.72 (t, J=11.7 Hz, 1H), 4.58 (dt, J=8.5, 6.0 Hz, 1H), 4.20 (dt, J=9.4, 6.4 Hz, 1H), 4.06-3.98 (m, 1H), 3.81 (t, J=12.0 Hz, 1H), 3.51 (d, J=8.7 Hz, 1H), 2.96 (d, J=12.8 Hz, 1H), 2.76 (dq, J=14.7, 7.4 Hz, 1H), 2.63-2.58 (m, 4H), 2.20-1.65 (m, 6H), 1.39 (s, 3H), 1.33-1.29 (m, 9H). LCMS (M+H)=611.6.

EXAMPLE 27

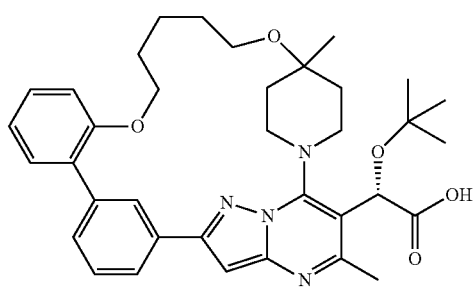 [SMILES: Cc1nc2cc3nn2c(c1[C@H](OC(C)(C)C)C(=O)O)N1CCC(C)(CC1)OCCCCCOc1ccccc1-c1cccc-3c1]

(2S)-2-(tert-Butoxy)-2-{4,28-dimethyl-21,27-dioxa-1,5, 7,8-tetraazahexacyclo[26.2.2.1$^{6,9}$.1$^{10,14}$.0$^{2,7}$.0$^{15,20}$]tetratria-conta-2,4,6(34),8,10(33),11,13,15(20),16,18-decaen-3-yl}acetic acid: Example 27 was prepared using example 26 by following the procedure to prepare example 21. $^1$H NMR (400 MHz, CDCl$_3$) δ 8.61 (s, 1H), 7.81 (d, J=7.8 Hz, 1H), 7.60-7.46 (m, 1H), 7.41-7.32 (m, 3H), 7.13-7.00 (m, 2H), 6.92 (s, 1H), 5.98 (s, 1H), 4.74-4.63 (m, 1H), 4.34-4.25 (m, 1H), 3.98-3.90 (m, 1H), 3.82-3.73 (m, 1H), 3.57-3.49 (m, 2H), 3.43-3.34 (m, 1H), 2.97 (d, J=12.5 Hz, 1H), 2.60 (s, 3H), 2.2-1.95 (m, 4H), 1.72-1.49 (m, 6H), 1.30 (s, 9H), 1.27 (s, 3H). LCMS (M+H)=613.4.

Intermediate 76

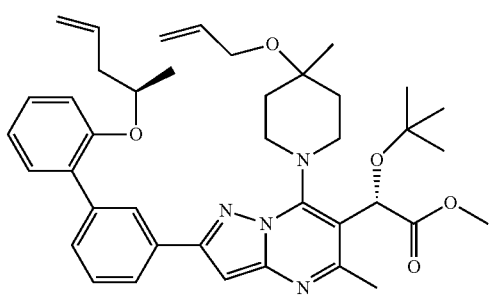

(S)-Methyl 2-(7-(4-(allyloxy)-4-methylpiperidin-1-yl)-5-methyl-2-(2'-((R)-pent-4-en-2-yloxy)-[1,1'-biphenyl]-3-yl)-pyrazolo[1,5-a]pyrimidin-6-yl)-2-(tert-butoxy)acetate: To a mixture of intermediate 69 (50 mg, 0.084 mmol), (S)-pent-4-en-2-ol (21.58 mg, 0.251 mmol), triphenylphosphine (65.7 mg, 0.251 mmol) in THF (2 mL) was added DIAD (0.049 mL, 0.251 mmol) stirred at rt for 48 h. It was then concentrated and purified by prep HPLC to isolate 40 mg (72%) of intermediate 76 as a white solid. $^1$H NMR (500 MHz, CDCl$_3$) δ 8.16 (t, J=1.6 Hz, 1H), 8.05 (d, J=7.3 Hz, 1H), 7.59 (d, J=7.7 Hz, 1H), 7.54-7.46 (m, 1H), 7.44 (dd, J=7.6, 1.7 Hz, 1H), 7.36-7.31 (m, 1H), 7.12-7.00 (m, 2H), 6.85 (s, 1H), 6.11-5.89 (m, 2H), 5.78 (ddt, J=17.1, 10.1, 7.1 Hz, 1H), 5.42 (dd, J=17.1, 1.5 Hz, 1H), 5.13 (d, J=9.6 Hz, 1H), 5.08-4.97 (m, 2H), 4.50-2.50 (m, 4H), 4.42 (sxt, J=6.0 Hz, 1H), 4.03 (d, J=4.7 Hz, 2H), 3.76 (s, 3H), 2.63 (s, 3H), 2.45 (qd, J=6.9, 5.5 Hz, 1H), 2.30 (dt, J=14.0, 6.9 Hz, 1H), 2.10-1.93 (m, 2H), 1.74 (br. s., 1H), 1.60 (m, 1 H), 1.38 (br. s., 3H), 1.27 (s, 9H), 1.26 (s, 3H). LCMS (M+1)=667.44.

Intermediate 77

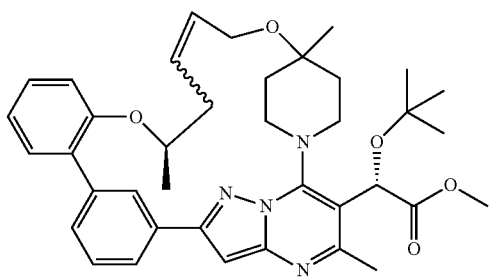

Methyl (2S)-2-(tert-butoxy)-2-[(22R)-4,22,28-trimethyl-21,27-dioxa-1,5,7,8-tetraazahexacyclo[26.2.2.1⁶,⁹.1¹⁰,¹⁴.0²,⁷.0¹⁵,²⁰]tetratriaconta-2,4,6(34),8,10(33),11,13,15(20),16,18,24-undecaen-3-yl]acetate: A mixture of intermediate 76 (38 mg, 0.057 mmol), Hoveyda-Grubbs catalyst 2nd generation (7.14 mg, 0.011 mmol) in DCE (40 mL) was refluxed for 2 h. It was then concentrated and purified by biotage, eluting with 20% EtOAc/hexane to isolate 35 mg (100%) of the desired product as light green solid. It's a mixture of cis/trans isomers. LCMS (M+1)=639.42.

Intermediate 78

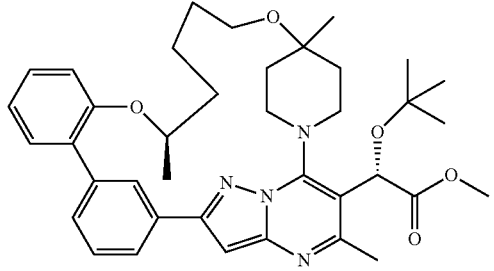

Methyl (2S)-2-(tert-butoxy)-2-[(22R)-4,22,28-trimethyl-21,27-dioxa-1,5,7,8-tetraazahexacyclo[26.2.2.1⁶,⁹.1¹⁰,¹⁴.0²,⁷.0¹⁵,²⁰]tetratriaconta-2,4,6(34), 8, 10(33), 11, 13, 15 (20),16,18-decaen-3-yl]acetate: A mixture of intermediate 77 (34 mg, 0.053 mmol), 10% Pd/C (5.66 mg, 5.32 μmol) in MeOH (2 mL) was stirred under a H₂ balloon for 2 h. It was then concentrated to obtain 30 mg (88%) of the desired product as a light green solid. LCMS (M+1)=641.6.

EXAMPLE 28

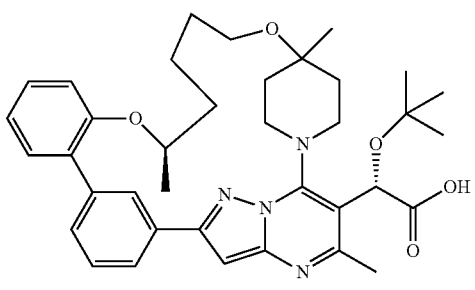 [SMILES: Cc1nc2cc3nn2c(c1[C@H](OC(C)(C)C)C(=O)O)N1CCC(C)(CC1)OCCCC[C@@H](C)Oc1ccccc1-c1cccc-3c1]

(2S)-2-(tert-Butoxy)-2-[(22R)-4,22,28-trimethyl-21,27-dioxa-1,5,7,8-tetraazahexacyclo[26.2.2.1⁶,⁹.1¹⁰,¹⁴.0²,⁷.0¹⁵,²⁰]tetratriaconta-2,4,6(34),8,10(33), 11, 13, 15 (20),16,18-decaen-3-yl]acetic acid: A mixture of intermediate 78 (35 mg, 0.055 mmol), 1N NaOH (273 μl, 0.273 mmol) in MeOH (2 mL) was refluxed for 3 h. It was then filtered and purified by prep HPLC to isolate 20 mg (56%) of the desired product as a white solid. ¹H NMR (500 MHz, CDCl₃) δ 8.28 (t, J=1.5 Hz, 1H), 7.74 (dt, J=7.8, 1.4 Hz, 1H), 7.54-7.49 (m, 1H), 7.39 (dt, J=7.8, 1.4 Hz, 1H), 7.35-7.28 (m, 2H), 7.07-7.02 (m, 2H), 6.85 (s, 1H), 5.97 (br. s., 1H), 4.51 (t, J=11.3 Hz, 1H), 4.37-4.29 (m, 1H), 3.98 (t, J=11.1 Hz, 1H), 3.47-3.35 (m, 2H), 3.20 (d, J=11.3 Hz, 1H), 2.84 (d, J=11.8 Hz, 1H), 2.65 (s, 3H), 2.15-1.51 (m, 10H), 1.32 (s, 9H), 1.25 (s, 3H), 1.15 (d, J=6.1 Hz, 3H). LCMS (M+H)=627.6.

Intermediate 79

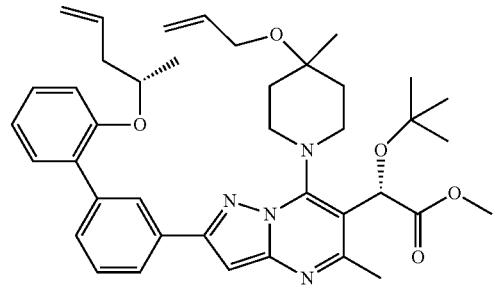

(S)-Methyl 2-(7-(4-(allyloxy)-4-methylpiperidin-1-yl)-5-methyl-2-(2'-((S)-pent-4-en-2-yloxy)-[1,1'-biphenyl]-3-yl)pyrazolo[1,5-a]pyrimidin-6-yl)-2-(tert-butoxy)acetate: To a mixture of intermediate 69 (50 mg, 0.084 mmol), (R)-pent-4-en-2-ol (21.58 mg, 0.251 mmol), triphenylphosphine (65.7 mg, 0.251 mmol) in THF (2 mL) was added DIAD (0.049 mL, 0.251 mmol) stirred at rt for 48 h. It was then concentraterd and purified by prep HPLC 55 mg (99%) of the desired product as a white solid. ¹H NMR (500 MHz, CDCl₃) δ 8.16 (t, J=1.6 Hz, 1H), 8.04 (d, J=7.3 Hz, 1H), 7.59 (d, J=7.7 Hz, 1H), 7.52-7.46 (m, 1H), 7.44 (dd, J=7.6, 1.7 Hz, 1H), 7.37-7.31 (m, 1H), 7.13-7.00 (m, 2H), 6.87-6.82 (m, 1H), 6.10-5.89 (m, 2H), 5.78 (ddt, J=17.2, 10.2, 7.1 Hz, 1H), 5.42 (dd, J=17.2, 1.6 Hz, 1H), 5.22-5.09 (m, 1H), 5.09-4.95 (m, 2H), 4.50-2.50 (m, 4H), 4.42 (sxt, J=6.0 Hz, 1H), 4.03 (d, J=4.9 Hz, 2H), 3.76 (s, 3H), 2.64 (s, 3H), 2.45 (qd, J=7.0, 5.6 Hz, 1H), 2.30 (dt, J=14.0, 6.9 Hz, 1H), 2.09-1.94 (m, 2H), 1.74 (br. s., 1H), 1.60 (m, 1 H), 1.38 (br. s., 3H), 1.30-1.25 (m, 12H). LCMS (M+1)=667.44.

Intermediate 80

Methyl (2S)-2-(tert-butoxy)-2-[(22S)-4,22,28-trimethyl-21,27-dioxa-1,5,7,8-tetraazahexacyclo[26.2.2.1⁶,⁹.1¹⁰,¹⁴.0²,⁷.0¹⁵,²⁰]tetratriaconta-2,4,6(34),8,10(33),11,13,15(20),16,18,24-undecaen-3-yl]acetate: A mixture of intermediate 79 (60 mg, 0.090 mmol), Hoveyda-Grubbs catalyst 2nd generation (11.28 mg, 0.018 mmol) in DCE (60 mL) was refluxed for 2 h. It was then concentrated and purified by biotage, eluting with 20% EtOAc/hexane to isolate 40 mg (70%) of the desired product as a light green solid. It's a mixture of cis/trans isomers, the ratio is 1:4. LCMS (M+1)=639.37.

Intermediate 81

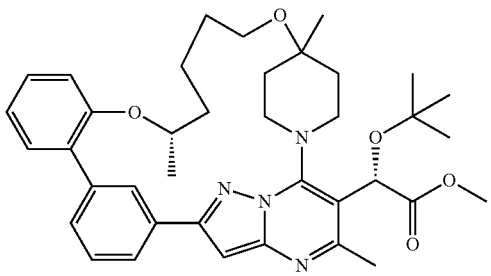

Methyl (2S)-2-(tert-butoxy)-2-[(22S)-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34), 8, 10(33), 11, 13, 15(20),16,18-decaen-3-yl]acetate: Intermediate 81 was prepared using intermediate 80 by following the procedure to prepare intermediate 78. $^1$H NMR (500 MHz, CDCl$_3$) δ 8.68-8.55 (m, 1H), 7.86-7.77 (m, 1H), 7.54-7.48 (m, 1H), 7.39-7.33 (m, 3H), 7.05-7.00 (m, 2H), 6.91 (s, 1H), 5.91 (s, 1H), 4.68-4.57 (m, 2H), 3.84-3.75 (m, 4H), 3.56-3.49 (m, 1 H), 3.43-3.35 (m, 1H), 3.25 (d, J=9.8 Hz, 1H), 2.90 (d, J=10.6 Hz, 1H), 2.61 (s, 3H), 2.09-1.95 (m, 3H), 1.92-1.81 (m, 1H), 1.81-1.70 (m, 3H), 1.70-1.50 (m, 3H), 1.28-1.23 (m, 12H), 1.19 (d, J=6.1 Hz, 3H). LCMS (M+1)=641.7.

EXAMPLE 29

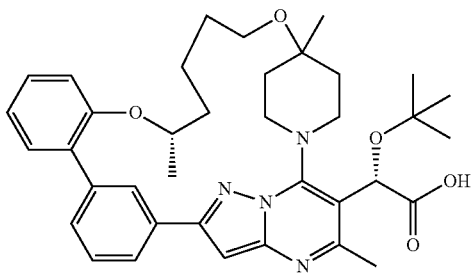 [SMILES: Cc1nc2cc3nn2c(c1[C@H](OC(C)(C)C)C(=O)O)N1CCC(C)(CC1)OCCCC[C@H](C)Oc1ccccc1-c1cccc-3c1]

(2S)-2-(tert-Butoxy)-2-[(22S)-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33), 11, 13, 15 (20),16,18-decaen-3-yl]acetic acid: Example 29 was prepared using intermediate 81 by following the procedure to prepare example 28. $^1$H NMR (500 MHz, CDCl$_3$) δ 8.64 (s, 1H), 7.81 (dt, J=7.8, 1.4 Hz, 1H), 7.55-7.48 (m, 1H), 7.40-7.32 (m, 3H), 7.05-6.99 (m, 2H), 6.93 (s, 1H), 5.97 (br. s., 1H), 4.73-4.64 (m, 1H), 4.64-4.57 (m, 1H), 3.82 (t, J=11.7 Hz, 1H), 3.56-3.48 (m., 2H), 3.39 (td, J=7.8, 3.2 Hz, 1H), 2.95 (d, J=12.8 Hz, 1H), 2.60 (s, 3H), 2.15-1.50 (m, 10H), 1.30 (s, 9H), 1.26 (s, 3H), 1.19 (d, J=6.0 Hz, 3H). LCMS (M+1)=627.6.

Intermediate 82

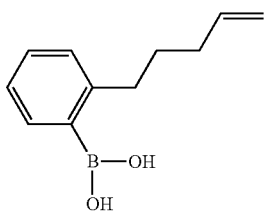

(2-(Pent-4-en-1-yl)phenyl)boronic acid: This compound was prepared according to the procedure described by Watson, I.D.G.; Ritter, S.; Toste, F.D. *J. Am. Chem. Soc.* 2009, 131, 2056-2057. 1-Bromo-2-(pent-4-en-1-yl)benzene (480 mg, 2.132 mmol) was dissolved in a mixture of toluene (8 mL) and THF (2 mL). Then triisopropyl borate (0.490 mL, 2.132 mmol) was added. While under N$_2$ atmosphere, the reaction mixture was cooled to −78° C. Using a manual syringe, n-butyllithium (0.853 mL, 2.132 mmol)(2.5 M in hexanes) was added dropwise over the course of 30 min. The resulting nearly colorless solution was stirred at −78° C. for 60 min and then at −20° C. for 15 min. The reaction was quenched with 10 mL of 2 N HCl and allowed to stir to warm to rt. The aqueous layer was extracted with ether. The organic phase was dried (Na$_2$SO$_4$), filtered, and concentrated in vacuo. Biotage purification eluting with 5-50% EtOAc/hexanes gave the desired product (65 mg, 0.342 mmol, 16.04% yield) as an off-white solid. $^1$H NMR (500 MHz, CDCl$_3$) δ 8.27-8.18 (m, 1H), 7.51 (td, J=7.5, 1.4 Hz, 1H), 7.36-7.31 (m, 2H), 5.90-5.80 (m, 1H), 5.04-4.91 (m, 2H), 3.26-3.18 (m, 2H), 2.18 (q, J=6.9 Hz, 2H), 1.83 (dt, J=15.3, 7.7 Hz, 2H).

Intermediate 83

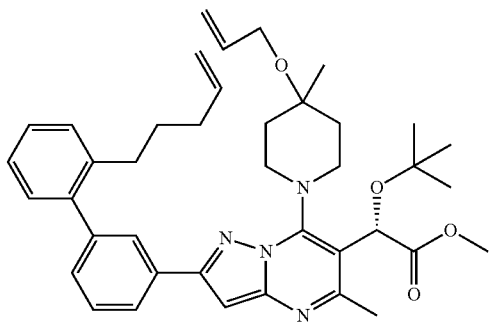

(S)-Methyl 2-(7-(4-(allyloxy)-4-methylpiperidin-1-yl)-5-methyl-2-(2'-(pent-4-en-1-yl)-[1,1'-biphenyl]-3-yl)pyrazolo[1,5-a]pyrimidin-6-yl)-2-(tert-butoxy)acetate: Intermediate 65 (159 mg, 0.272 mmol) was dissolved in DMF (5 mL). While flushing solution with N$_2$, add intermediate 82 (62 mg, 0.326 mmol), sodium carbonate (0.272 mL, 0.544 mmol), and (Ph$_3$P)$_4$Pd (21.99 mg, 0.019 mmol). This reaction mixture was flushed with N$_2$ and heated at 90° C. for 18 h. Upon completion of the reaction, the reaction mixture was partitioned between EtOAc and water. The organic phase was washed with water (3×), dried (MgSO$_4$), filtered, and concentrated in vacuo to give the crude product as a brown oil. This was purified by Biotage chromatography (0-50% EtOAc/hexanes) to gave 121 mg (68%) of the desired product as a colorless oil. LCMS (M+1)=651.45.

Intermediate 84

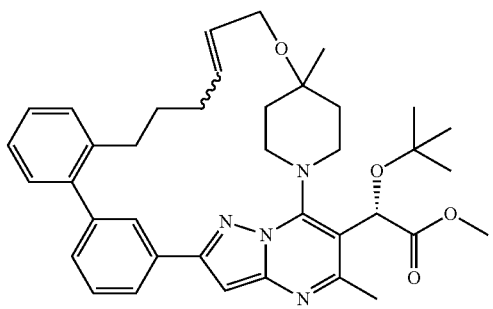

Methyl (2S)-2-(tert-butoxy)-2-[(24E)-4,28-dimethyl-27-oxa-1,5,7,8-tetraazahexacyclo[26.2.2.1⁶,⁹1¹⁰,¹⁴.0²,⁷.0¹⁵,²⁰]tetratriaconta 2,4, 6(34), 8, 10(33), 11,13, 15 (20),16,18,24-undecaen-3-yl]acetat: Intermediate 84 was prepared using intermediate 83 by following the procedure to prepare intermediate 68. It's a mixture of cis/trans products. LCMS (M+1)=623.36.

Intermediate 85

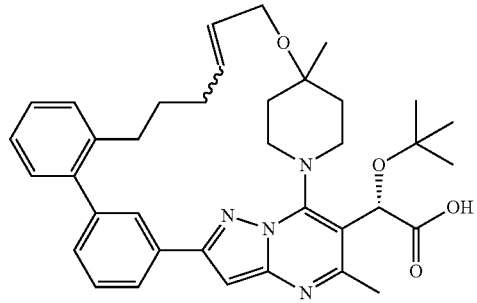

(2S)-2-(tert-Butoxy)-2-{4,28-dimethyl-27-oxa-1,5,7,8-tetraazahexacyclo[26.2.2.1⁶,⁹.1¹⁰,¹⁴.0²,⁷.0¹⁵,²⁰]tetratriaconta-2,4, 6(34), 8, 10(33), 11, 13, 15 (20),16,18,24-undecaen-3-yl}acetic acid: Intermediate 85 was prepared using intermediate 84 by following the procedure to prepare example 18. LCMS (M+1)=609.35.

EXAMPLE 30

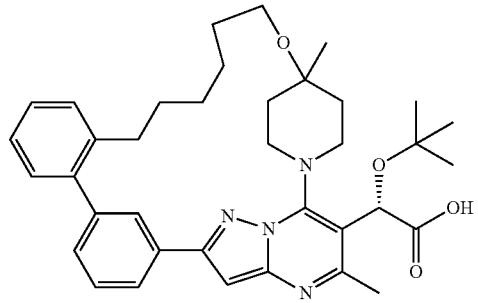 [SMILES: Cc1nc2cc3nn2c(c1[C@H](OC(C)(C)C)C(=O)O)N1CCC(C)(CC1)OCCCCCCc1ccccc1-c1cccc-3c1]

(2S)-2-(tert-Butoxy)-2-{4,28-dimethyl-27-oxa-1,5,7,8-tetraazahexacyclo[26.2.2.1⁶,⁹.1¹⁰,¹⁴.0²,⁷.0¹⁵,²⁰]tetratriaconta-2,4,6(34),8,10(33), 11, 13, 15(20),16,18-decaen-3-yl}acetic acid: Example 30 was prepared using intermediate 85 by following the procedure to prepare example 19. ¹H NMR (500 MHz, CDCl₃) δ 8.16-8.06 (m, 1H), 7.76 (d, J=7.7 Hz, 1H), 7.53-7.48 (m, 1H), 7.35-7.30 (m, 3H), 7.28-7.25 (m, 1H), 7.24-7.20 (m, 1H), 6.87 (s, 1H), 6.04-5.91 (m, 1H), 4.55 (t, J=11.7 Hz, 1H), 3.79 (t, J=11.7 Hz, 1H), 3.44-3.34 (m, 2H), 3.28-3.20 (m, 1H), 2.89 (d, J=12.1 Hz, 1H), 2.82 (dt, J=13.9, 6.8 Hz, 1H), 2.62 (s, 3H), 2.60-2.54 (m, 1H), 1.98 (t, J=11.7 Hz, 2H), 1.72-1.47 (m, 7H), 1.33-1.27 (m, 11H), 1.24 (s, 3H). LCMS (M+H)=611.46.

Intermediate 86

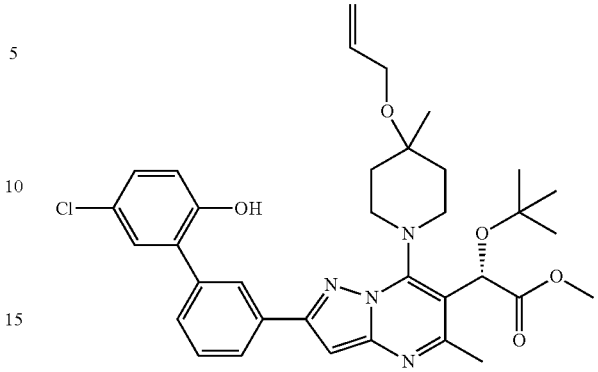

(S)-Methyl 2-(7-(4-(allyloxy)-4-methylpiperidin-1-yl)-2-(5'-chloro-2'-hydroxy-[1,1'-biphenyl]-3-yl)-5-methylpyrazolo[1,5-a]pyrimidin-6-yl)-2-(tert-butoxy)acetate: Intermediate 86 was prepared using intermediate 65 and 5-chloro-2-hydroxyphenylboronic acid following the procedure to prepare intermediate 69. ¹H NMR (500 MHz, CDCl₃) δ 8.10 (s, 1H), 8.05 (d, J=7.6 Hz, 1H), 7.57 (t, J=7.6 Hz, 1H), 7.46 (d, J=7.6 Hz, 1H), 7.33 (d, J=2.7 Hz, 1H), 7.25 (dd, J=8.7, 2.5 Hz, 1H), 6.98 (d, J=8.7 Hz, 1H), 6.86-6.82 (m, 1H), 6.11-5.80 (m, 3H), 5.41 (dq, J=17.2, 1.7 Hz, 1H), 5.18-5.03 (m, 1H), 5.00-2.50 (m, 4H), 4.02 (d, J=4.9 Hz, 2H), 3.76 (s, 3H), 2.61 (s, 3H), 2.06-1.92 (m, 3H), 1.73 (br. s., 1H), 1.43-1.33 (m, 3H), 1.27 (s, 9H). LCMS (M+1)=633.34.

Intermediate 87

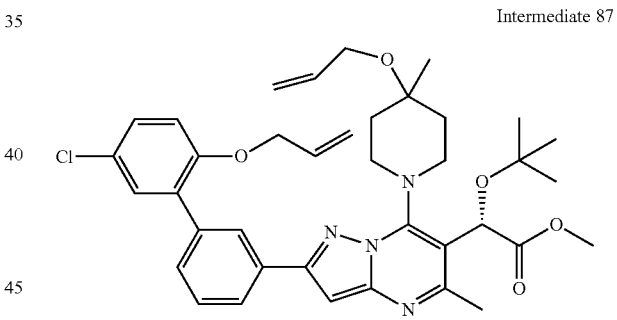

(S)-Methyl 2-(7-(4-(allyloxy)-4-methylpiperidin-1-yl)-2-(2'-(allyloxy)-5'-chloro-[1,1'-biphenyl]-3-yl)-5-methylpyrazolo[1,5-a]pyrimidin-6-yl)-2-(tert-butoxy)acetate: Intermediate 86 (205 mg, 0.296 mmol) was dissolved in DMF (3 mL). Solid potassium carbonate (82 mg, 0.593 mmol) was added and the mixture was heated to 90° C. for 1 h. The reaction was then cooled to rt and treated with 3-bromoprop-1-ene (0.051 mL, 0.593 mmol) and allowed to stir at rt for 18 h. The reaction was partitioned between EtOAc and water. The organic phase was washed with water, dried (Na₂SO₄), filtered, and concentrated in vacuo to give 192 mg (83% yield) of the desired product as a yellow oil. ¹H NMR (500 MHz, CDCl₃) δ 8.17 (s, 1H), 8.05 (d, J=6.3 Hz, 1H), 7.66-7.47 (m, 2H), 7.47-7.35 (m, 1H), 7.32-7.27 (m, 1H), 6.98-6.91 (m, 1H), 6.85 (s, 1H), 6.10-5.91 (m, 3H), 5.46-5.33 (m, 2H), 5.21 (dq, J=10.6, 1.4 Hz, 1H), 5.16-5.06 (m, 1H), 5.00-2.50 (m, 4H), 4.56 (dt, J=4.8, 1.6 Hz, 2H), 4.03 (d, J=4.7 Hz, 2H), 3.76 (s, 3H), 2.63 (s, 3H), 2.06-1.95 (m, 2H), 1.75-1.70 (m, 2H), 1.39 (br. s., 3H), 1.29-1.24 (m, 9H). LCMS (M+1)=674.24.

Intermediate 88

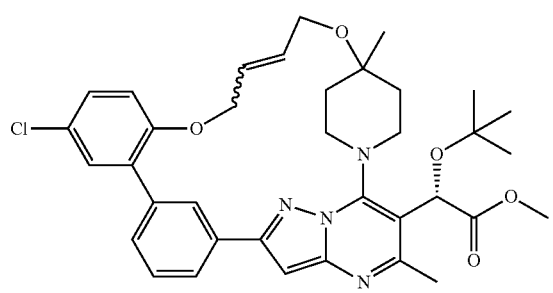

Methyl (2S)-2-(tert-butoxy)-2-[17-chloro-4,27-dimethyl-21,26-dioxa-1,5,7,8-tetraazahexacyclo [25.2.2.1$^{6,9}$.1$^{10,14}$.0$^{2,7}$.0$^{15,20}$]tritriaconta-2,4,6(33),8,10 (32),11,13,15(20),16,18,23-undecaen-3-yl]acetate: Intermediate 88 was prepared using intermediate 87 by following the procedure to prepare intermediate 71. $^{1}$H NMR (500 MHz, CDCl$_3$) δ 8.50 (t, J=1.6 Hz, 1H), 7.75 (dt, J=7.8, 1.4 Hz, 1H), 7.58-7.52 (m, 1H), 7.44-7.40 (m, 1H), 7.35 (d, J=2.7 Hz, 1H), 7.27 (dd, J=8.7, 2.7 Hz, 1H), 6.93 (d, J=8.8 Hz, 1H), 6.83 (s, 1H), 6.34-6.26 (m, 1H), 6.10-6.03 (m, 2H), 4.71-4.67 (m, 2H), 4.64 (td, J=12.5, 2.4 Hz, 1H), 4.08-3.96 (m, 3H), 3.74 (s, 3H), 3.14 (dt, J=11.4, 2.1 Hz, 1H), 2.76-2.70 (m, 1H), 2.65 (s, 3H), 2.02 (dd, J=13.9, 2.2 Hz, 1H), 1.95-1.89 (m, 1H), 1.82 (td, J=13.0, 4.7 Hz, 1H), 1.63 (td, J=13.4, 4.4 Hz, 1H), 1.32 (s, 3H), 1.28 (s, 9H). LCMS (M+1)=645.20.

EXAMPLE 31

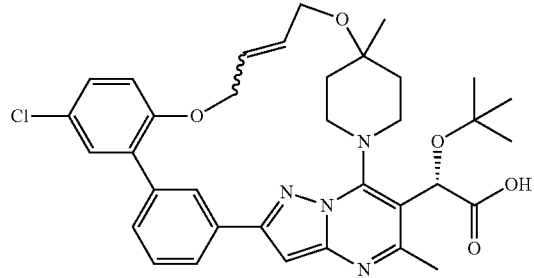 [SMILES: Cc1nc2cc3nn2c(c1[C@H](OC(C)(C)C)C(=O)O)N1CCC(C)(CC1)OCC=CCOc1ccc(Cl)cc1-c1cccc-3c1]

(2S)-2-(tert-Butoxy)-2-[17-chloro-4,2,7-dimethyl-21,26-dioxa-1,5,7,8-tetraazahexacyclo[25.2.2. 1$^{6,9}$.1$^{10,14}$.0$^{2,7}$.0$^{15,20}$]tritriaconta-2,4,6(33),8,10(32),11,13, 15(20),16,18,23-undecaen-3-yl]acetic acid: Example 31 was prepared using intermediate 88 by following the procedure to prepare example 20. $^{1}$H NMR (500 MHz, CDCl$_3$) δ 8.50 (t, J=1.6 Hz, 1H), 7.74 (dt, J=7.8, 1.4 Hz, 1H), 7.55 (t, J=7.7 Hz, 1H), 7.43 (dt, J=7.9, 1.3 Hz, 1H), 7.35 (d, J=2.7 Hz, 1H), 7.28-7.25 (m, 1H), 6.94 (d, J=9.0 Hz, 1H), 6.85 (s, 1H), 6.34-6.25 (m, 1H), 6.12-5.99 (m, 2H), 4.69 (d, J=5.0 Hz, 3H), 4.08-3.97 (m, 3H), 3.37 (d, J=11.3 Hz, 1H), 2.75 (d, J=12.5 Hz, 1H), 2.64 (s, 3H), 2.04 (d, J=10.4 Hz, 1H), 1.96 (dd, J=13.6, 2.3 Hz, 1H), 1.76 (td, J=13.2, 4.9 Hz, 1H), 1.65 (m, 1H), 1.35-1.30 (m, 12H). LCMS (M+H)=631.6.

EXAMPLE 32

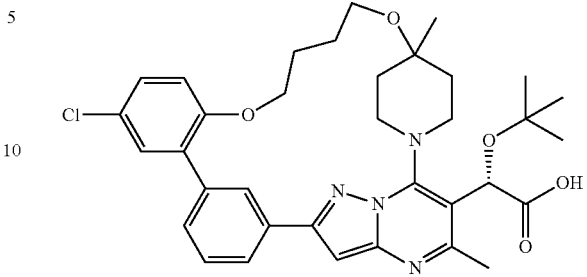

(2S)-2-(tert-Butoxy)-2-{17-chloro-4,27-dimethyl-21,26-dioxa-1,5,7,8-tetraazahexacyclo[25.2.2. 1$^{6,9}$.1$^{10,14}$.0$^{2,7}$.0$^{15,20}$]tritriaconta-2,4,6(33),8,10(32),11,13, 15(20),16,18-decaen-3-yl}acetic acid: Example 32 was prepared using example 31 by following the procedure to prepare example 21. $^{1}$H NMR (500 MHz, CDCl$_3$) δ 8.46 (s, 1H), 7.72 (d, J=7.7 Hz, 1H), 7.55 (t, J=7.6 Hz, 1H), 7.45 (d, J=7.9 Hz, 1H), 7.38 (d, J=2.5 Hz, 1H), 7.28-7.23 (m, 1H), 6.96 (d, J=8.8 Hz, 1H), 6.82 (s, 1H), 6.01 (br. s., 1H), 4.58 (br. s., 1H), 4.18-4.03 (m, 2H), 3.91 (br. s., 1H), 3.53 (d, J=3.5 Hz, 1H), 3.42 (br. s., 2H), 2.86 (br. s., 1H), 2.63 (s, 3H), 2.35 (d, J=3.5 Hz, 2H), 2.23-1.55 (m, 6H), 1.38-1.20 (m, 12H). LCMS (M+H)=633.6.

Intermediate 89

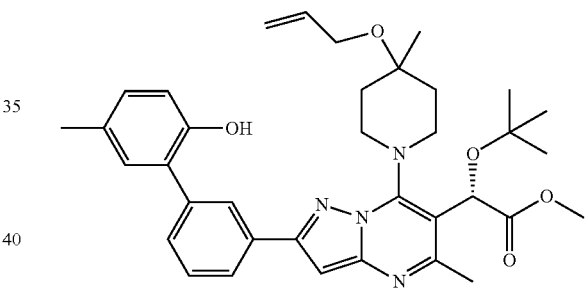

(S)-Methyl 2-(7-(4-(allyloxy)-4-methylpiperidin-1-yl)-2-(2'-hydroxy-5'-methyl-[1,1'-biphenyl]-3-yl)-5-methylpyrazolo[1,5-d]pyrimidin-6-yl)-2-(tert-butoxy)acetate: A solution of ((S)-methyl 2-(7-(4-(allyloxy)-4-methylpiperidin-1-yl)-2-(3-bromophenyl)-5-methylpyrazolo[1,5-a]pyrimidin-6-yl)-2-(tert-butoxy)acetate (0.375 g, 0.640 mmol), 2-hydroxy-5-methylphenylboronic acid (0.195 g, 1.281 mmol) and 2.0 M aq. Na$_2$CO$_3$ (0.961 ml, 1.921 mmol) in DMF (5 mL) was sparged with nitrogen for 10 min, treated with Pd(Ph$_3$P)$_4$ (0.052 g, 0.045 mmol), then sparged for 5 min. The reaction was stirred with heating (85° C.) for 7 h, then cooled, diluted with water (50 mL) and extracted into Et$_2$O (2×50 mL). The combined extracts were dried (MgSO$_4$), filtered, and concentrated, and the residue was purified by biotage (40 g SiO$_2$, 0% (3 CV), 0-60% (15 CV), 60% (2 CV), EtOAc in hexanes) to afford the desired product (0.303 g, 0.494 mmol, 77% yield), as a pale yellow glassy solid. $^{1}$H NMR (500 MHz, CDCl$_3$) δ: 8.08 (s, 1H), 8.04 (d, J=7.9 Hz, 1H), 7.57 (t, J=7.6 Hz, 1H), 7.50-7.43 (m, 1H), 7.14 (d, J=1.9 Hz, 1H), 7.10 (dd, J=8.4, 2.0 Hz, 1H), 6.92 (d, J=8.2 Hz, 1H), 6.83 (s, 1H), 6.05-5.94 (m, 1H), 5.39 (dd, J=17.2, 1.6 Hz, 1H), 5.21-5.13 (m, 1H), 5.13-5.03 (m, 1H), 4.00 (d, J=4.7 Hz, 2H), 3.74 (s, 3H), 2.61 (s, 3H), 2.35 (s, 3H), 2.06 (s, 4H), 2.04-1.93 (m, 2H), 1.72 (br. s., 1H), 1.36 (br. s., 2H), 1.28 (s, 1H), 1.27 (s, 2H), 1.25 (s, 9H). LCMS (M+H)=613.5.

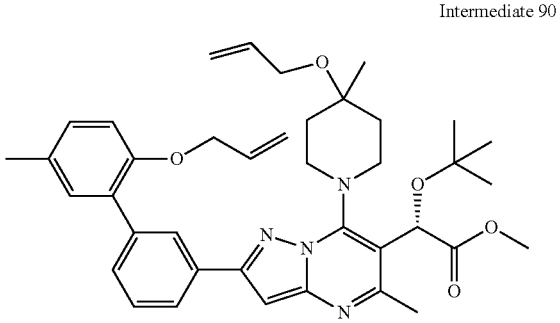

Intermediate 90

(S)-Methyl 2-(7-(4-(allyloxy)-4-methylpiperidin-1-yl)-2-(2'-(allyloxy)-5'-methyl-[1,1'-biphenyl]-3-yl)-5-methylpyrazolo[1,5-a]pyrimidin-6-yl)-2-(tert-butoxy)acetate: Intermediate 90 was prepared using intermediate 89 by following the procedure to prepare intermediate 87. $^1$H NMR (500 MHz, CDCl$_3$) δ 8.34-8.12 (m, 1H), 8.03 (d, J=5.2 Hz, 1H), 7.59 (d, J=7.4 Hz, 1H), 7.55-7.46 (m, 1H), 7.25 (d, J=1.7 Hz, 1H), 7.14 (dd, J=8.3, 2.0 Hz, 1H), 6.93 (d, J=8.4 Hz, 1H), 6.84 (s, 1H), 6.14-5.85 (m, 3H), 5.50-5.33 (m, 2H), 5.24-5.07 (m, 2H), 4.58-4.51 (m, 2H), 4.50-2.50 (m, 4H), 4.02 (d, J=4.7 Hz, 2H), 3.76 (s, 3H), 2.62 (s, 3H), 2.38 (s, 3H), 2.06-1.92 (m, 2H), 1.75 (br. s., 1H), 1.59 (m, 1H), 1.39 (br. s., 3H), 1.31-1.20 (s, 9H). LCMS (M+1)=653.7.

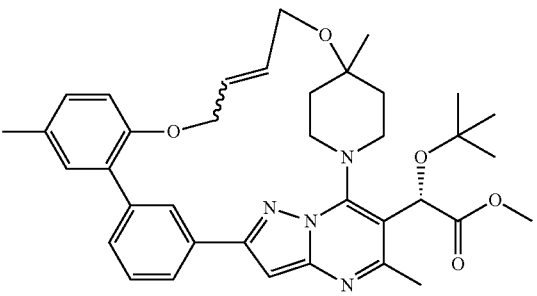

Intermediate 91

Methyl (2S)-2-(tert-butoxy)-2-[4,17,27-trimethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18,23-undecaen-3-yl]acetate: Intermediate 91 was prepared using intermediate 90 by following the procedure to prepare intermediate 71. $^1$H NMR (400 MHz, CDCl$_3$) δ 8.52 (t, J=1.5 Hz, 1H), 7.78-7.67 (m, 1H), 7.59-7.50 (m, 1H), 7.49-7.40 (m, 1H), 7.18 (d, J=2.0 Hz, 1H), 7.12 (d, J=8.3 Hz, 1H), 6.91 (d, J=8.5 Hz, 1H), 6.82 (s, 1H), 6.39-6.24 (m, 1H), 6.18-6.00 (m, 2H), 4.77-4.58 (m, 3H), 4.10-3.95 (m, 3H), 3.74 (s, 3H), 3.14 (d, J=11.5 Hz, 1H), 2.71 (d, J=11.8 Hz, 1H), 2.64 (s, 3H), 2.36 (s, 3H), 2.02 (d, J=11.5 Hz, 1H), 1.97-1.89 (m, 1H), 1.89-1.76 (m, 1H), 1.65 (s, 1H), 1.32 (s, 3H), 1.27 (s, 9H). LCMS (M+1)=625.22.

EXAMPLE 33 AND 34

Saponification of intermediate 91 by following the procedure to prepare example 20 provided examples 33 and 34.

EXAMPLE 33

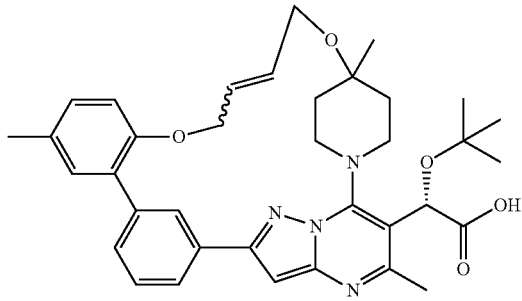 [SMILES: Cc1ccc2c(c1)-c1cccc(c1)-c1cc3nc(C)c([C@H](OC(C)(C)C)C(=O)O)c(n3n1)N1CCC(C)(CC1)OCC=CCO2]

(2S)-2-(tert-Butoxy)-2-[4,17,27-trimethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18,23-undecaen-3-yl]acetic acid: $^1$H NMR (500 MHz, CDCl$_3$) δ 8.52 (s, 1H), 7.71 (d, J=7.7 Hz, 1H), 7.53 (t, J=7.6 Hz, 1H), 7.48-7.43 (m, 1H), 7.18 (d, J=1.9 Hz, 1H), 7.12 (dd, J=8.3, 1.8 Hz, 1H), 6.91 (d, J=8.5 Hz, 1H), 6.84 (s, 1H), 6.31 (dt, J=15.5, 5.4 Hz, 1H), 6.12-6.00 (m, 2H), 4.77-4.64 (m, 3H), 4.08-3.96 (m, 3H), 3.36 (d, J=10.2 Hz, 1H), 2.74 (d, J=12.1 Hz, 1H), 2.64 (s, 3H), 2.36 (s, 3H), 1.95 (d, J=14.8 Hz, 1H), 1.91-1.72 (m, 2H), 1.66-1.55 (m, 1H), 1.34-1.26 (m, 12H). LCMS (M+H)=611.23.

EXAMPLE 34

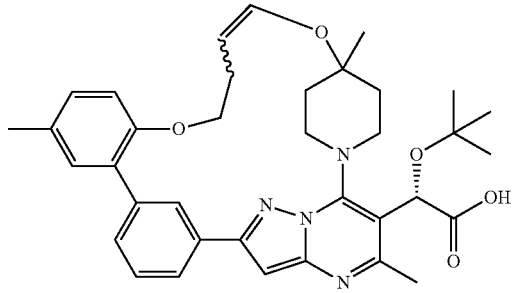 [SMILES: Cc1ccc2c(c1)-c1cccc(c1)-c1cc3nc(C)c([C@H](OC(C)(C)C)C(=O)O)c(n3n1)N1CCC(C)(CC1)OC=CCCO2]

(2S)-2-(tert-Butoxy)-2-[4,17,27-trimethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18,24-undecaen-3-yl]acetic acid: $^1$H NMR (500 MHz, C$_6$D$_6$) δ 9.26 (s, 1H), 7.62 (d, J=7.9 Hz, 1H), 7.42 (d, J=7.6 Hz, 1H), 7.28 (t, J=7.6 Hz, 1H), 7.21 (d, J=1.7 Hz, 1H), 7.05 (s, 1H), 6.93 (dd, J=8.3, 1.7 Hz, 1H), 6.73 (d, J=8.4 Hz, 1H), 6.05 (d, J=5.7 Hz, 1H), 6.00 (br. s., 1H), 5.04 (t, J=11.6 Hz, 1H), 4.47 (q, J=7.0 Hz, 1H), 4.05 (ddd, J=12.4, 7.8, 5.1 Hz, 1H), 4.00-3.92 (m, 1H), 3.77 (t, J=11.0 Hz, 1H), 3.59-3.41 (m, 2H), 2.80 (br. s., 3H), 2.63 (d, J=10.7 Hz, 1H), 2.51 (dq, J=11.9, 6.1 Hz, 1H), 2.18 (s, 3H), 1.78-1.47 (m, 4H), 1.05 (s, 3H), 0.98 (br. s., 9H). LCMS (M+H)=611.23.

EXAMPLE 35

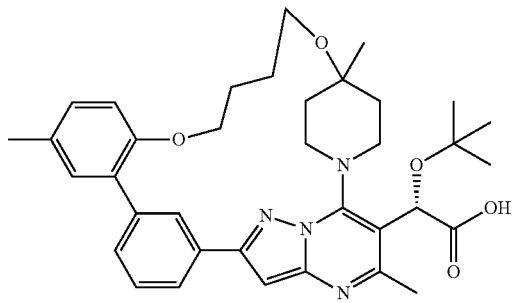 [SMILES: Cc1ccc2c(c1)-c1cccc(c1)-c1cc3nc(C)c([C@H](OC(C)(C)C)C(=O)O)c(n3n1)N1CCC(C)(CC1)OCCCCO2]

(2S)-2-(tert-Butoxy)-2-{4,17,27-trimethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18-decaen-3-yl}acetic acid: Example 35 was prepared using example 33 by following the procedure to prepare example 21. $^1$H NMR (500 MHz, CDCl$_3$) δ 8.49 (s, 1H), 7.69 (d, J=8.0 Hz, 1H), 7.56-7.45 (m, 2H), 7.21 (s, 1H), 7.13 (d, J=6.5 Hz, 1H), 6.94 (d, J=8.4 Hz, 1H), 6.82 (s, 1H), 6.02 (br. s., 1H), 4.60 (t, J=11.8 Hz, 1H), 4.10 (t, J=8.2 Hz, 2H), 3.92 (t, J=11.5 Hz, 1H), 3.57-3.53 (m, 1H), 3.43 (d, J=4.1 Hz, 2H), 2.83 (d, J=11.2 Hz, 1H), 2.63 (s, 3H), 2.36 (s, 3H), 2.18-1.96 (m, 8H), 1.36-1.22 (m, 12H). LCMS (M+H)=613.35.

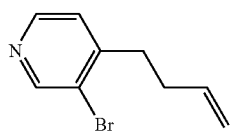

Intermediate 92

3-Bromo-4-(but-3-en-1-yl)pyridine: This compound was prepared according to Zhang, Z; Dwoskin, L. and Crooks, P. *Tetrahedron Lett.* 2011, 52, 2667-2669.

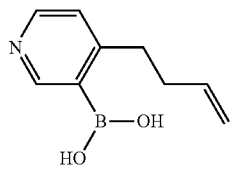

Intermediate 93 (60)

(4-(But-3-en-1-yl)pyridin-3-yl)boronic acid: A stirred solution of intermediate 92 (200 mg, 0.943 mmol) and triisopropyl borate (0.282 mL, 1.226 mmol) in toluene (4 mL) and THF (1 mL) cooled to −78° C. To this mixture was added 2.5M BuLi (0.490 mL, 1.226 mmol) over the course of 15 min. During this time period, the reaction color changed from yellow to orange. The reaction was stirred at −78° C. for 2 h then warmed to 0° C. for 15 min, the solution became pale yellow again. To this was added 2N HCl (5 mL) and stirred at rt for 10 min. The solution became a slurry (pH was found to be ~3). It was then diluted with ether and the organic layer was discarded. The aqueous layer was adjusted pH=7 by using 1N NaOH, a white ppt was formed. It was then extracted with EtOAc. The organic layer was dried over MgSO$_4$, filtered and concentrated to obtain 150 mg oil, which triturated with 2 mL of CH$_3$CN and a white solid was formed was dried to obtain the desired product (150 mg, 0.847 mmol, 90% yield) as a white solid. LCMS (M+1)=178.1.

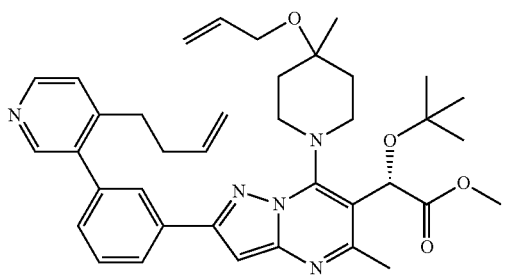

Intermediate 94

(S)-Methyl 2-(7-(4-(allyloxy)-4-methylpiperidin-1-yl)-2-(3-(4-(but-3-en-1-yl)pyridin-3-yl)phenyl)-5-methylpyrazolo[1,5-a]pyrimidin-6-yl)-2-(tert-butoxy)acetate: To a microwave tube was added intermediate 65 (200 mg, 0.342 mmol), intermediate 93 (121 mg, 0.683 mmol), and 2M aqueous sodium carbonate (0.342 mL, 0.683 mmol) in DMF (2 mL), was sparged with nitrogen for 1 minutes, treated (Ph$_3$P)$_4$Pd (39.5 mg, 0.034 mmol), and then sparged with N$_2$ for 1 min. The reaction tube was sealed and heated at 95° C. in a microwave tube for 1 h. The reaction was then concentrated, diluted with water (15 mL) and extracted wtih EtOAc. The EtOAc layer was washed with brine, then dried (Na$_2$SO$_4$), filtered, and concentrated under reduced pressure. The residue was then purified by biotage, eluting with 30% acetone/hexane to isolate 220 mg (100%) of the desired product as a white solid. $^1$H NMR (400 MHz, CDCl$_3$) δ 8.55 (d, J=5.1 Hz, 1H), 8.53 (d, J=0.5 Hz, 1H), 8.09 (d, J=7.8 Hz, 1H), 7.94 (t, J=1.6 Hz, 1H), 7.59-7.53 (m, 1H), 7.36-7.31 (m, 1H), 7.27 (d, J=5.1 Hz, 1H), 6.84 (s, 1H), 6.03-5.91 (m, 2H), 5.72 (ddt, J=16.9, 10.2, 6.6 Hz, 1H), 5.42-5.35 (m, 1H), 5.12-5.00 (m, 1H), 4.98-4.91 (m, 2H), 4.50-2.50 (m, 4 H), 4.00 (d, J=4.9 Hz, 2H), 3.76 (s, 3H), 2.80-2.74 (m, 2H), 2.63 (s, 3H), 2.31 (td, J=7.8, 6.6 Hz, 2H), 2.06-1.86 (m, 3H), 1.71 (d, J=13.2 Hz, 1H), 1.35 (s, 3H), 1.27 (s, 9H). LCMS (M+1)=638.4.

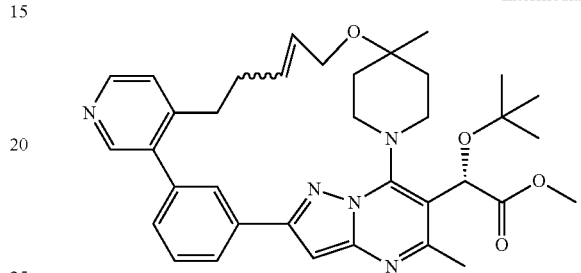

Intermediate 95

Methyl (2S)-2-(tert-butoxy)-2-[(23E)-4,27-dimethyl-26-oxa-1,5,7,8,17-pentaazahexacyclo[25.2.2.1$^{6,9}$.1$^{10,14}$.0$^{2,7}$.0$^{15,20}$]tritriaconta-2,4, 6(33), 8, 10(32), 11,13, 15 (20),16,18,23-undecaen-3-yl]acetate: A mixture of intermediate 94 (190 mg, 0.298 mmol), (1,3-dimesitylimidazolidin-2-ylidene)(2-isopropoxybenzylidene)ruthenium(VI) chloride (18.67 mg, 0.030 mmol), tosic acid (56.7 mg, 0.298 mmol) in DCE (150 mL) was heated at reflux for 2 h. It was then concentrated, the residue was added 10 mL sat. NaHCO$_3$, extracted with EtOAc. The organic layer was dried over MgSO$_4$, filtered and concentrated to obtain 200 mg yellow oil, which was then purified by biotage, eluted with 30% acetone/hexane to isolate 150 mg (83%) of the desired product as a white solid and mixture of cis/trans isomers. LCMS (M+1)=610.3.

EXAMPLE 36 AND 37

A mixture of intermediate 95 (100 mg, 0.164 mmol), sodium hydroxide (0.820 mL, 0.820 mmol) in MeOH (2 mL) was refluxed for 3 h. It was then concentrated and adjusted pH=6 using 1N HCl. It was then extracted with EtOAc. The organic layer was dried over MgSO$_4$, filtered and concentrated to obtain 100 mg white solid. 20 mg of this mixture was purified by prep HPLC to afford example 36 and 37.

EXAMPLE 36

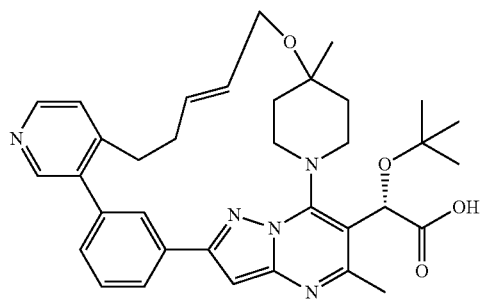 [SMILES: Cc1nc2cc3nn2c(c1[C@H](OC(C)(C)C)C(=O)O)N1CCC(C)(CC1)OC/C=C/CCc1ccncc1-c1cccc-3c1]

(2S)-2-(tert-Butoxy)-2-[(23E)-4,27-dimethyl-26-oxa-1,5, 7,8,17-pentaazahexacyclo[25.2.2.1$^{6,9}$.1$^{10,14}$.0$^{2,7}$.0$^{15,20}$]tritriaconta-2,4,6(33),8,10(32),11,13,15(20),16,18,23-undecaen-3-yl]acetic acid: Major isomer (19 mg) and as white solid. $^1$H NMR (500 MHz, DMSO-d$_6$) δ 8.52 (br. s., 1H), 8.33 (d, J=2.4 Hz, 1H), 7.98-7.90 (m, 2H), 7.66-7.56 (m, 1H), 7.47 (br. s., 1H), 7.33 (d, J=7.6 Hz, 1H), 6.99 (d, J=2.1 Hz, 1H), 5.74 (br. s., 1H), 5.68 (br. s., 1H), 5.57 (d, J=14.0 Hz, 1H), 4.53 (t, J=11.9 Hz, 1H), 3.78 (br. s., 2H), 3.70 (t, J=10.8 Hz, 1H), 3.32 (br. s., 1H), 2.83 (d, J=11.9 Hz, 1H), 2.68 (br. s., 1H), 2.60 (d, J=9.8 Hz, 2H), 2.54 (s, 3H), 2.44-2.38 (m, 1H), 1.95 (br. s., 1H), 1.75 (d, J=12.5 Hz, 1H), 1.67 (d, J=11.9 Hz, 1H), 1.56-1.43 (m, 1H), 1.16 (d, J=2.4 Hz, 12H). LCMS (M+H)=596.39.

EXAMPLE 37

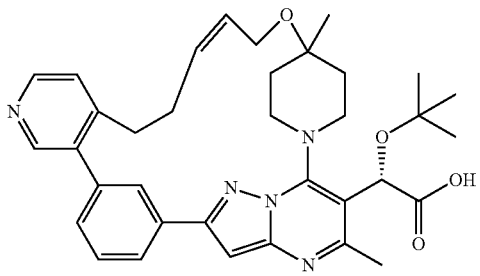 [SMILES: Cc1nc2cc3nn2c(c1[C@H](OC(C)(C)C)C(=O)O)N1CCC(C)(CC1)OC/C=C\CCc1ccncc1-c1cccc-3c1]

(2S)-2-(tert-Butoxy)-2-[(23Z)-4,27-dimethyl-26-oxa-1,5, 7,8,17-pentaazahexacyclo[25.2.2.1$^{6,9}$.1$^{10,14}$.0$^{2,7}$.0$^{15,20}$]tritriaconta-2,4,6(33),8,10(32), 11, 13, 15(20),16,18,23-undecaen-3-yl]acetic acid: Minor isomer (1 mg). $^1$H NMR (400 MHz, MeOH-d$_4$) δ 8.54-8.31 (m, 2H), 8.23 (s, 1H), 7.92 (d, J=7.8 Hz, 1H), 7.62 (t, J=7.7 Hz, 1H), 7.47 (d, J=4.8 Hz, 1H), 7.34 (d, J=7.5 Hz, 1H), 6.91-6.86 (m, 1H), 5.91-5.79 (m, 2H), 5.78-5.68 (m, 1H), 4.64-4.51 (m, 1H), 4.15-4.04 (m, 1H), 3.90-3.78 (m, 2H), 3.53-3.42 (m, 1H), 2.97-2.85 (m, 2H), 2.80-2.68 (m, 3H), 2.66 (s, 3H), 2.15 (d, J=12.5 Hz, 1H), 1.89-1.74 (m, 2H), 1.66 (td, J=13.1, 4.4 Hz, 1H), 1.31-1.18 (m, 12H). LCMS (M+H)=596.35.

EXAMPLE 38

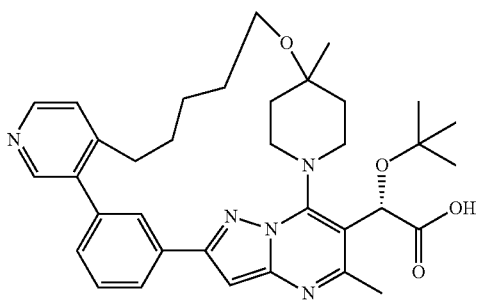 [SMILES: Cc1nc2cc3nn2c(c1[C@H](OC(C)(C)C)C(=O)O)N1CCC(C)(CC1)OCCCCCc1ccncc1-c1cccc-3c1]

(2S)-2-(tert-Butoxy)-2-{4,27-dimethyl-26-oxa-1,5,7,8, 17-pentaazahexacyclo[25.2.2.1$^{6,9}$.1$^{10,14}$.0$^{2,7}$.0$^{15,20}$]tritriaconta-2,4,6(33),8,10(32), 11, 13, 15 (20),16,18-decaen-3-yl}acetic acid: A mixture of examples 36 and 37 (60 mg, 0.101 mmol), tosic acid (19.16 mg, 0.101 mmol), Pd/C (10.72 mg, 10.07 μmol) in MeOH (2 mL) was stirred under a H$_2$ balloon for 2 h. It was then filtered and purified by prep HPLC(CH$_3$CN/TFA system). The fractions were collected, adjusted pH=6 using 1 N NaOH and concentrated. The residue was extracted with EtOAc. The organic layer was dried over MgSO$_4$, filtered and concentrated to obtain 26.5 mg (42%) of the desired product as a white solid. $^1$H NMR (400 MHz, CDCl$_3$) δ 8.55 (d, J=5.4 Hz, 1H), 8.45 (s, 1H), 8.12 (s, 1H), 7.83 (d, J=7.8 Hz, 1H), 7.56 (t, J=7.7 Hz, 1H), 7.37 (d, J=5.4 Hz, 1H), 7.26 (s, 1 H), 6.89 (s, 1H), 6.00 (s, 1H), 4.55 (t, J=11.4 Hz, 1H), 3.91-3.83 (m, 1H), 3.47-3.41 (m, 1H), 3.34 (d, J=9.0 Hz, 2H), 2.89-2.76 (m, 2H), 2.73-2.65 (m, 1H), 2.64 (s, 3H), 1.88 (m, 3H), 1.79-1.48 (m, 7H), 1.30 (s, 9H), 1.25 (s, 3H). LCMS (M+H)=598.5.

Intermediate 96

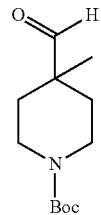

tert-Butyl 4-formyl-4-methylpiperidine-1-carboxylate: To a solution of tert-butyl 4-formylpiperidine-1-carboxylate (4.5 g, 21.10 mmol) in CH$_2$Cl$_2$ (50 mL) at 0° C. was added t-BuOK (3.08 g, 27.4 mmol) followed by MeI (3.96 mL, 63.3 mmol) at 0° C. The resulting mixture was stirred 30 min, and then warmed to room temp and stirred for 1.5 h. The reaction mixture was then poured into brine and the mixture was extracted with dichloromethane, dried (Na$_2$SO$_4$), filtered and concentrated. The residue was then purified by Biotage (0-20% EtOAc/hexane) to afford tert-butyl 4-formyl-4-methylpiperidine-1-carboxylate (1.8 g, 7.92 mmol, 37.5% yield) as colorless oil. $^1$H NMR (500 MHz, CDCl$_3$) δ 9.48 (s, 1H), 3.71-3.66 (m, 2H), 3.19-3.05 (m, 2H), 1.93 (dt, J=13.7, 4.1 Hz, 2H), 1.47 (s, 9H), 1.46-1.37 (m, 2H), 1.10 (s, 3H). LCMS (M+H)=228.1.

Intermediate 97

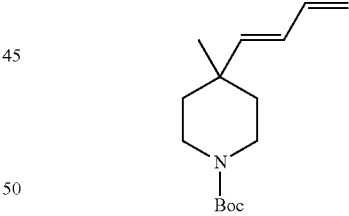

((E)-tert-butyl 4-(buta-1,3-dien-1-yl)-4-methylpiperidine-1-carboxylate: To a solution of diethyl allylphosphonate (2.82 g, 15.84 mmol) in THF (50 mL) at −78° C. was added added 1.6 M MeLi (9.90 mL, 15.84 mmol) and the resulting mixture was stirred for 30 min. Then, HMPT (9.68 mL, 52.8 mmol) followed by (E)-tert-butyl 4-(buta-1,3-dien-1-yl)-4-methylpiperidine-1-carboxylate (1.8 g, 7.16 mmol, 54.3% yield) in THF (10 mL) was added and the mixture was stirred at −78° C. for 1 h and then allowed to warm to room temp. After 16 h, the mixture was quenched with sat.NH$_4$Cl solution and extracted with ether (2×100 mL). The combined organic extracts were dried (Na$_2$SO$_4$), filtered and concentrated. The residue was purified via Biotage (0-20% EtOAc/hexane; 80 g column) to afford ((E)-tert-butyl 4-(buta-1,3-dien-1-yl)-4-methylpiperidine-1-carboxylate (1.8 g, 7.16 mmol, 54.3% yield) as colorless oil. ¹H NMR (500 MHz, CDCl₃) δ 6.42-6.27 (m, 1H), 6.05 (dd, J=15.8, 10.2 Hz, 1H), 5.68 (d, J=15.8 Hz, 1H), 5.21-5.09 (m, 1H), 5.08-4.91 (m, 1H), 3.61-3.44 (m, 2H), 3.37-3.15 (m, 2H), 1.61 (dd, J=9.5, 2.8 Hz, 2H), 1.47 (s, 9H), 1.45-1.37 (m, 2H), 1.07 (s, 3H).

Intermediate 98

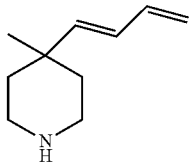

(E)-4-(Buta-1,3-dien-1-yl)-4-methylpiperidine.HCl: A mixture of (E)-tert-butyl 4-(buta-1,3-dien-1-yl)-4-methylpiperidine-1-carboxylate (1.8 g, 7.16 mmol) and 4M HCl/dioxane (8.95 ml, 35.8 mmol) was stirred at room temp for 3 h. Mixture was then concentrated and the solids were triturated with ether/hexane, filtered and dried under high vac to afford (E)-4-(buta-1,3-dien-1-yl)-4-methylpiperidine.HCl (1.2 g, 6.39 mmol, 89% yield) as off-white solid. ¹H NMR (500 MHz, DMSO-d₆) δ 6.35 (dt, J=16.9, 10.2 Hz, 1H), 6.12 (dd, J=15.7, 10.3 Hz, 1H), 5.78-5.73 (m, 1H), 5.21 (d, J=17.0 Hz, 1H), 5.06 (d, J=10.1 Hz, 1H), 3.14-3.00 (m, 2H), 2.97-2.79 (m, 2H), 1.83-1.69 (m, 2H), 1.64-1.53 (m, 2H), 1.06 (s, 3H). LCMS (M+H)=152.1.

Intermediate 99

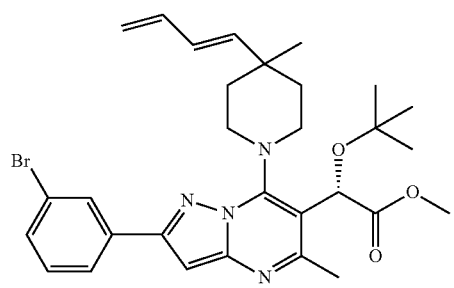

(S,E)-Methyl 2-(2-(3-bromophenyl)-7-(4-(buta-1,3-dien-1-yl)-4-methylpiperidin-1-yl)-5-methylpyrazolo[1,5-a]pyrimidin-6-yl)-2-(tert-butoxy)acetate: Intermediate 61 (207 mg, 0.444 mmol) was dissolved in DMF (3 mL) and treated with (E)-4-(buta-1,3-dien-1-yl)-4-methylpiperidine.HCl (100 mg, 0.533 mmol) followed by Hunig's Base (0.233 mL, 1.332 mmol). The light brown homogeneous reaction mixture was allowed to stir at rt for 18 h. Concentrated at 50° C. and partition between 50 mL of EtOAc and 5 mL 0.1 N HCl. The organic phase was washed with water (5 mL) and dry over Na₂SO₄, filtered and concentrated in vacuo to give a yellow oil. It was then purified by biotage, eluting with 20% EtOAc/hexane to isolate 219 mg (81%) of the desired product as a white solid. ¹H NMR (500 MHz, CDCl₃) δ 8.14 (s, 1H), 8.03-7.87 (m, 1H), 7.53 (dd, J=8.0, 0.9 Hz, 1H), 7.34 (t, J=7.9 Hz, 1H), 6.81 (s, 1H), 6.49 (br. s., 1H), 6.27-6.14 (m, 1H), 6.07 (s, 1H), 6.01-5.84 (m, 1H), 5.25 (d, J=17.0 Hz, 1H), 5.12 (d, J=9.9 Hz, 1H), 5.00-2.50 (m, 4H), 3.75 (s, 3H), 2.64 (s, 3H), 1.93 (d, J=9.3 Hz, 1H), 1.87-1.73 (m, 2H), 1.67 (br. s., 1H), 1.34-1.21 (m, 12H). LCMS (M+1)=581.11.

Intermediate 100

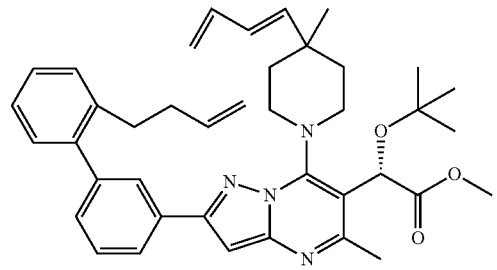

Methyl (2S)-2-(2-{3-[2-(but-3-en-1-Aphenyl]phenyl}-7-{4-[(1E)-buta-1,3-dien-1-yl]-4-methylpiperidin-1-yl}-5-methylpyrazolo[1,5-a]pyrimidin-6-yl)-2-(tert-butoxy)acetate A mixture of intermediate 26 (56.8 mg, 0.258 mmol), intermediate 99 (100 mg, 0.172 mmol), 2.0 M aqueous K₂CO₃ (0.172 mL, 0.344 mmol) in dioxane (1.6 mL), water (0.4 mL) was sparged with nitrogen for 5 minute, treated with (Ph₃P)₄Pd (19.87 mg, 0.017 mmol), then sparged under N₂ for 1 min. The reaction tube was sealed and then heated at 90° C. in a microwave tube for 1 h. The reaction was concentrated, then diluted with water (5 mL) and extracted wtih EtOAc. The EtOAc layer was washed with brine, then dried (Na₂SO₄), filtered, and concentrated under reduced pressure. The residue was purified by biotage (0%-20% EtOAc in hexanes) to isolate 75 mg (69%) of the desired product as an off-white foam. ¹H NMR (500 MHz, CDCl₃) δ 8.06-8.02 (m, 1H), 7.94 (s, 1H), 7.55-7.48 (m, 1H), 7.38-7.30 (m, 5H), 6.84 (s, 1H), 6.43-6.31 (m, 1H), 6.16 (dd, J=15.8, 10.0 Hz, 1H), 6.07 (s, 1H), 5.88 (d, J=15.6 Hz, 1H), 5.74 (ddt, J=17.0, 10.3, 6.7 Hz, 1H), 5.19 (d, J=17.3 Hz, 1H), 5.04 (d, J=10.1 Hz, 1H), 5.00-2.00 (m, 4 H), 4.97-4.86 (m, 2H), 3.75 (s, 3H), 2.79-2.73 (m, 2H), 2.63 (s, 3H), 2.33-2.26 (m, 2H), 1.95-1.85 (m, 1H), 1.85-1.62 (m, 3H), 1.29-1.25 (m, 12H). LCMS (M+1)=633.4.

INTERMEDIATE 101 AND 102

A mixture of intermediate 100 (75 mg, 0.119 mmol), Hoveyda-Grubbs catalyst 2nd generation (14.85 mg, 0.024 mmol) in DCE (75 mL) was heated at 70° C. for 2 h. It was then concentrated and purified by biotage, eluting with 20% EtOAc/hexane to afford two compounds.

Intermediate 101

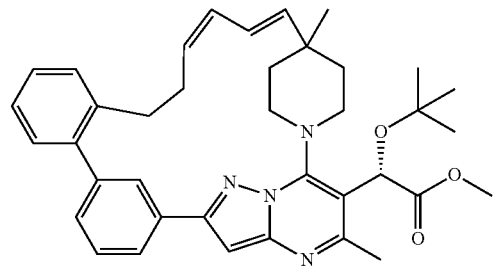

Methyl (2S)-2-(tert-butoxy)-2-[(23Z,25E)-4,27-dimethyl-1,5,7,8-tetraazahexacyclo[25.2.2.1$^{6,9}$.1$^{10,14}$.0$^{2,7}$.0$^{15,20}$]tritriaconta-2,4,6(33),8,10(32), 11, 13, 15(20),16,18,23,25-dodecaen-3-yl]acetate: Isolate 20 mg (25%, 90% pure) as a white solid. ¹H NMR (500 MHz, CDCl₃) δ 7.90 (s, 1H), 7.71 (d, J=7.7 Hz, 1H), 7.52 (t, J=7.6 Hz, 1H), 7.46-7.41 (m, 1H), 7.41-7.36 (m, 1H), 7.28-7.22 (m, 2H), 7.20-7.14 (m, 1H), 6.75 (s, 1H), 6.49 (dd, J=15.8, 10.8 Hz, 1H), 6.02 (t, J=10.7 Hz, 1H), 5.97 (s, 1H), 5.51 (td, J=9.6, 4.7 Hz, 1H), 5.45 (d, J=15.8 Hz, 1H), 4.91-4.77 (m, 1H), 3.77 (s, 3H), 3.54-3.43 (m, 1H), 3.19 (d, J=12.3 Hz, 1H), 2.98-2.82 (m, 3H), 2.77-2.66 (m, 1H), 2.61 (s, 3H), 2.52 (br. s., 1H), 2.23-2.13 (m, 1H), 1.87-1.76 (m, 1H), 1.71 (td, J=13.3, 4.9 Hz, 1H), 1.63 (d, J=14.0 Hz, 1H), 1.29-1.23 (m, 12H). LCMS (M+1)=605.29.

Intermediate 102

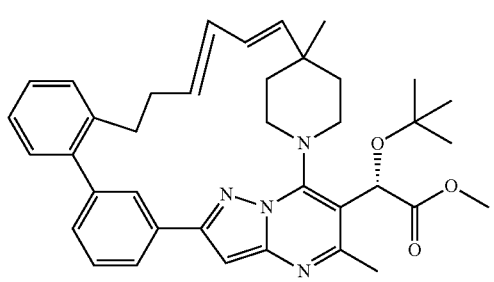

Methyl (2S)-2-(tert-butoxy)-2-[(23E,25E)-4,27-dimethyl-1,5,7,8-tetraazahexacyclo[25.2.2.1$^{6,9}$.1$^{10,14}$.0$^{2,7}$.0$^{15,20}$]tritriaconta-2,4,6(33),8,10(32), 11, 13, 15(20),16,18,23,25-dodecaen-3-yl]acetate: Isolate 62 mg (78%, 90% pure) as a white solid. $^1$H NMR (500 MHz, CDCl$_3$) δ 7.83 (s, 1H), 7.75-7.66 (m, 1H), 7.47-7.42 (m, 2H), 7.41-7.37 (m, 1H), 7.25-7.19 (m, 2H), 7.13 (d, J=7.4 Hz, 1H), 6.78 (s, 1H), 6.26 (s, 1H), 6.03 (dd, J=15.8, 9.9 Hz, 2H), 5.74 (br. s., 1H), 5.45 (d, J=16.4 Hz, 1H), 5.39-5.33 (m, 1H), 3.71 (s, 3H), 2.91-2.80 (m, 2H), 2.65 (s, 3H), 2.62 (d, J=8.0 Hz, 2H), 2.54-2.40 (m, 3H), 1.82 (d, J=12.8 Hz, 1H), 1.76-1.64 (m, 3H), 1.31-1.26 (m, 12H). LCMS (M+1)=605.29.

EXAMPLE 39

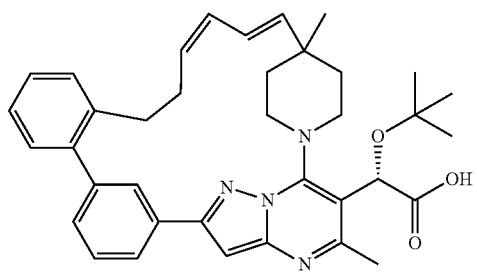 [SMILES: Cc1nc2cc3nn2c(c1[C@H](OC(C)(C)C)C(=O)O)N1CCC(C)(/C=C/C=C\CCc2ccccc2-c2cccc-3c2)CC1]

(2S)-2-(tert-Butoxy)-2-[(23Z,25E)-4,27-dimethyl-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13, 15(20), 16,18,23,25-dodecaen-3-yl]acetic acid: A mixture of intermediate 101 (20 mg, 0.033 mmol), NaOH (0.165 mL, 0.165 mmol) in MeOH (2 mL) was refluxed for 3 h. It was then filtered and purified by prep HPLC to isolate 10.8 mg (53%) of the desired product as a white solid. $^1$H NMR (400 MHz, CDCl$_3$) δ 7.90 (s, 1H), 7.70 (d, J=7.8 Hz, 1H), 7.52 (t, J=7.5 Hz, 1H), 7.46-7.40 (m, 1H), 7.37 (td, J=7.5, 1.4 Hz, 1H), 7.30-7.23 (m, 2H), 7.16 (dd, J=7.5, 1.3 Hz, 1H), 6.75 (s, 1H), 6.47 (dd, J=15.9, 10.7 Hz, 1H), 6.06-5.94 (m, 2H), 5.50 (td, J=9.7, 4.6 Hz, 1H), 5.43 (d, J=16.1 Hz, 1H), 4.88 (t, J=11.8 Hz, 1H), 3.46 (d, J=7.3 Hz, 2H), 2.96-2.81 (m, 3H), 2.75-2.63 (m, 1H), 2.58 (s, 3H), 2.52 (d, J=15.6 Hz, 1H), 2.20 (d, J=13.6 Hz, 1H), 1.83-1.57 (m, 3H), 1.29 (s, 9H), 1.12 (s, 3H). LCMS (M+H)=591.4.

EXAMPLE 40

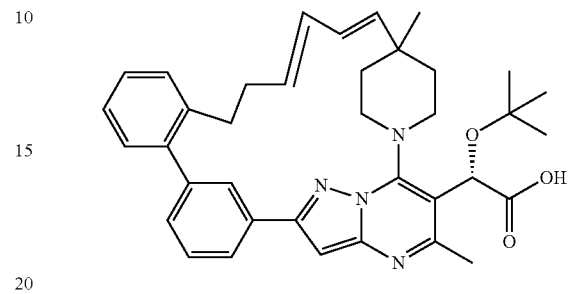

(2S)-2-(tert-Butoxy)-2-[(23E,25E)-4,27-dimethyl-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13, 15(20), 16,18,23,25-dodecaen-3-yl]acetic acid: Example 40 was prepared using intermediate 102 by following the procedure to prepare example 39. $^1$H NMR (400 MHz, CDCl$_3$) δ 7.81 (s, 1H), 7.68 (d, J=7.8 Hz, 1H), 7.52-7.35 (m, 3H), 7.26-7.16 (m, 2H), 7.12 (d, J=7.5 Hz, 1H), 6.89-6.69 (m, 1H), 6.01 (dd, J=16.1, 10.0 Hz, 2H), 5.74 (br. s., 1H), 5.49-5.23 (m, 2H), 4.85 (br. s., 1H), 4.06-3.00 (m, 2H), 3.07 (d, J=10.8 Hz, 1H), 2.87-2.56 (m, 5H), 2.57-2.34 (m, 2H), 1.93-1.77 (m, 1H), 1.75-1.60 (m, 3H), 1.34-1.20 (s, 9H), 1.05 (s, 3H). LCMS (M+H)=591.4.

EXAMPLE 41

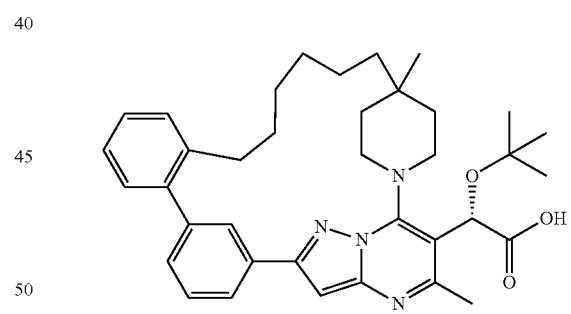

(2S)-2-(tert-Butoxy)-2-{4,27-dimethyl-1,5,7,8-tetraazahexacyclo[25.2.2.1$^{6,9}$.1$^{10,14}$.0$^{2,7}$.0$^{15,20}$]tritriaconta-2,4,6 (33),8,10(32), 11,13,15(20),16,18-decaen-3-yl}acetic acid: A mixture of example 40 (32 mg, 0.054 mmol), Pd/C (5.76 mg, 5.42 µmol) in MeOH (5 mL), DCM (0.5 mL) was stirred under a H$_2$ balloon for 48 h. It was then purified by prep HPLC to isolate 2.2 mg (6.5%) of the desired product as a white solid. $^1$H NMR (400 MHz, CDCl$_3$) δ 7.91 (s, 1H), 7.73 (d, J=7.8 Hz, 1H), 7.49 (t, J=7.7 Hz, 1H), 7.42-7.34 (m, 2H), 7.26-7.19 (m, 2H), 7.17-7.12 (m, 1H), 6.82 (s, 1H), 5.99 (br. s., 1H), 4.53 (t, J=11.3 Hz, 1H), 3.87 (t, J=11.2 Hz, 1H), 3.19 (d, J=9.8 Hz, 1H), 2.76-2.58 (m, 5H), 2.08 (br. s., 1H), 1.84-1.46 (m, 7H), 1.39-1.17 (m, 19H). LCMS (M+H)=595.4.

Intermediate 103

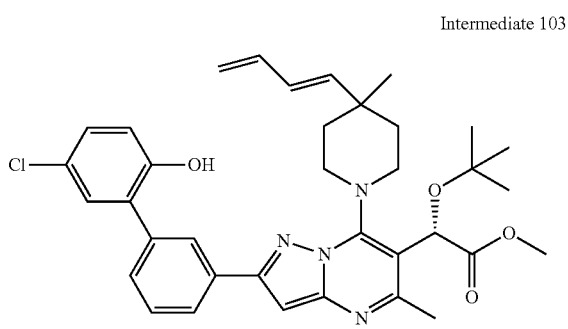 [SMILES: C=C/C=C/C1(C)CCN(c2c([C@H](OC(C)(C)C)C(=O)OC)c(C)nc3cc(-c4cccc(-c5cc(Cl)ccc5O)c4)nn23)CC1]

(S,E)-Methyl 2-(7-(4-(buta-1,3-dien-1-yl)-4-methylpiperidin-1-yl)-2-(5'-chloro-2'-hydroxy-[1,1'-biphenyl]-3-yl)-5-methylpyrazolo[1,5-a]pyrimidin-6-yl)-2-(tert-butoxy)acetate: To a microwave tube was added (S,E)-methyl 2-(2-(3-bromophenyl)-7-(4-(buta-1,3-dien-1-yl)-4-methylpiperidin-1-yl)-5-methylpyrazolo[1,5-a]pyrimidin-6-yl)-2-(tert-butoxy)acetate (100 mg, 0.172 mmol), (5-chloro-2-hydroxyphenyl)boronic acid (44.5 mg, 0.258 mmol), and 2.0 M aqueous $K_2CO_3$ (0.086 mL, 0.172 mmol) in dioxane (2 mL) and water (0.5 mL). The reaction was sparged with nitrogen for 1 minutes, treated $Pd(PPh_3)_4$ (19.87 mg, 0.017 mmol) then sparged for 1 min. The reaction tube was sealed and then heated at 90° C. in a microwave tube for 1 h. LCMS analysis showed 40% completion. Additional 10 mg of $Pd(PPh_3)_4$ added and heated at 90° C. for another 2 h. The reaction was concentrated, diluted with water (15 mL) and extracted wtih EtOAc. The EtOAc layer was washed with brine, then dried ($Na_2SO_4$), filtered, and concentrated under reduced pressure. The residue was purified by biotage (0%-40% EtOAc in hexanes) to isolate 80 mg (74%) of the product as off-white foam. $^1$H NMR (500 MHz, CDCl$_3$) δ 8.09 (br. s., 1H), 8.06 (d, J=7.9 Hz, 1H), 7.60 (t, J=7.5 Hz, 1H), 7.50-7.45 (m, 1H), 7.34 (d, J=2.5 Hz, 1H), 6.99 (d, J=8.7 Hz, 1H), 6.85 (s, 1H), 6.39 (dt, J=16.9, 10.2 Hz, 1H), 6.17 (dd, J=15.4, 10.4 Hz, 1H), 6.07 (s, 1H), 5.88 (d, J=15.3 Hz, 1H), 5.33 (br. s., 1H), 5.19 (d, J=17.2 Hz, 1H), 5.04 (d, J=9.6 Hz, 1H), 4.50-2.50 (m, 4 H), 3.75 (s, 3H), 2.64 (s, 3H), 1.93 (d, J=12.9 Hz, 1H), 1.87-1.73 (m, 2H), 1.67 (br. s., 1H), 1.29-1.24 (m, 12H). LCMS (M+1)=629.08.

Intermediate 104

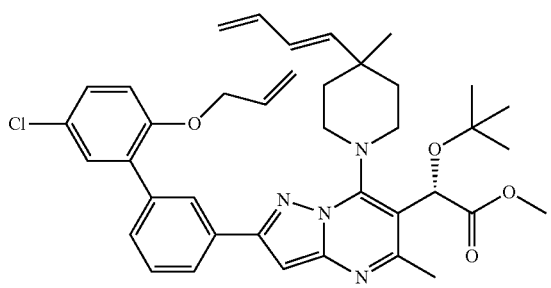

(S,E)-Methyl 2-(2-(2'-(allyloxy)-5'-chloro-[1,1'-biphenyl]-3-yl)-7-(4-(buta-1,3-dien-1-yl)-4-methylpiperidin-1-yl)-5-methylpyrazolo[1,5-a]pyrimidin-6-yl)-2-(tert-butoxy)acetate: .(S,E)-Methyl 2-(7-(4-(buta-1,3-dien-1-yl)-4-methylpiperidin-1-yl)-2-(5'-chloro-2'-hydroxy-[1,1'-biphenyl]-3-yl)-5-methylpyrazolo[1,5-a]pyrimidin-6-yl)-2-(tert-butoxy)acetate (90 mg, 0.143 mmol) was dissolved in DMF (3 mL). Solid K2CO3 (39.5 mg, 0.286 mmol) was added and the mixture was heated to 90° C. for 1 h. The reaction was then cooled to rt and treated with 3-bromoprop-1-ene (0.024 mL, 0.286 mmol) and allowed to stir at rt for 18 h. The reaction was partitioned between EtOAc and water. The organic phase was washed with water, dried ($Na_2SO_4$), filtered, and concentrated in vacuo to yield (S,E)-methyl 2-(2-(2'-(allyloxy)-5'-chloro-[1,1'-biphenyl]-3-yl)-7-(4-(buta-1,3-dien-1-yl)-4-methylpiperidin-1-yl)-5-methylpyrazolo[1,5-a]pyrimidin-6-yl)-2-(tert-butoxy)acetate (90 mg, 0.134 mmol, 94% yield) as a white solid. $^1$H NMR (400 MHz, CDCl$_3$) δ 8.18 (br. s., 1H), 8.07-8.00 (m, 1H), 7.60-7.48 (m, 2H), 7.42 (d, J=2.7 Hz, 1H), 7.31 (d, J=2.7 Hz, 1H), 6.95 (d, J=8.8 Hz, 1H), 6.85 (s, 1H), 6.39 (dt, J=17.0, 10.1 Hz, 1H), 6.16 (dd, J=15.5, 10.1 Hz, 1H), 6.08 (s, 1H), 5.98 (ddt, J=17.3, 10.6, 4.8 Hz, 1H), 5.88 (d, J=15.7 Hz, 1H), 5.40-5.33 (m, 1H), 5.25-5.15 (m, 2H), 5.03 (d, J=10.0 Hz, 1H), 5.00-2.50 (m, 4 H), 4.56 (dt, J=4.8, 1.6 Hz, 2H), 3.74 (s, 3H), 2.64 (s, 3H), 1.97-1.63 (m, 4H), 1.32-1.23 (m, 12H). LCMS (M+1)=669.3.

Intermediate 105

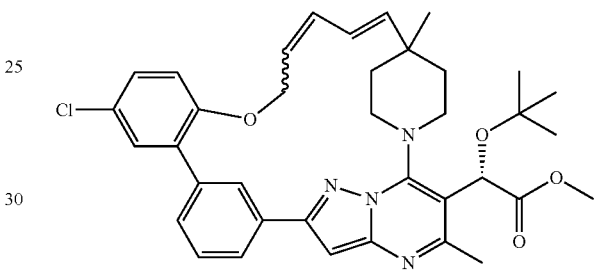

Methyl (2S)-2-(tert-butoxy)-2-[(23Z,25E)-17-chloro-4,27-dimethyl-21-oxa-1,5,7,8-tetraazahexacyclo[25.2.2.1$^{6,9}$.1$^{10,14}$.0$^{2,7}$.0$^{15,20}$]tritriaconta-2,4, 6(33), 8, 10(32), 11, 13, 15(20),16,18,23,25-dodecaen-3-yl]acetate: Intermediate 105 was prepared using intermediate 104 by following the procedure to prepare intermediate 101. It's a 5:3 mixture of trans/cis isomers. LCMS (M+1)=641.3.

EXAMPLES 42 AND 43

A mixture of intermediate 105 (80 mg, 0.078 mmol), NaOH (0.390 mL, 0.390 mmol) in MeOH (2 mL)/THF (1 mL) was heated at reflux for 2 h. It was then concentrated, adjusted pH=5 using 1 N HCl. It was then extracted with EtOAc, dried over MgSO$_4$, filtered and concentrated to obtain 63 mg (76%) white solid. 20 mg of it was purified by prep HPLC to afford two compounds.

EXAMPLE 42

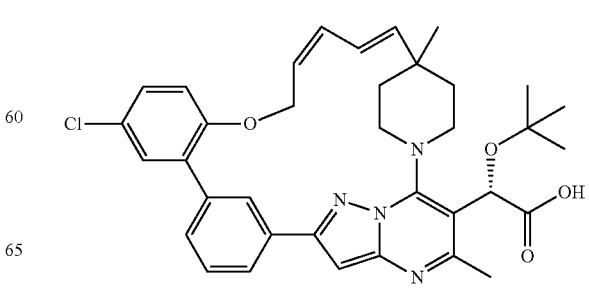

(2S)-2-(tert-Butoxy)-2-[(23Z,25E)-17-chloro-4,27-dimethyl-21-oxa-1,5,7,8-tetraazahexacyclo[25.2.2.1$^{6,9}$.1$^{10,14}$.0$^{2,7}$.0$^{15,20}$]tritriaconta-2,4,6(33),8,10(32), 11, 13, 15(20),16,18,23,25-dodecaen-3-yl]acetic acid: Isolated 4.1 mg as a white solid. $^1$H NMR (500 MHz, DMSO-d$_6$) δ 7.84 (d, J=7.6 Hz, 1H), 7.79 (br. s., 1H), 7.54 (t, J=7.3 Hz, 1H), 7.40 (d, J=8.9 Hz, 1H), 7.35-7.25 (m, 2H), 7.14 (br. s., 1H), 6.99 (s, 1H), 6.29-6.18 (m, 1H), 6.18-6.07 (m, 2H), 6.00 (br. s., 1H), 5.65 (d, J=14.0 Hz, 1H), 4.84 (d, J=14.3 Hz, 1H), 4.70 (d, J=15.3 Hz, 1H), 4.53 (t, J=11.6 Hz, 1H), 3.96-3.84 (m, 1H), 2.96 (d, J=9.8 Hz, 1H), 2.61 (d, J=10.1 Hz, 1H), 2.55 (s, 3H), 1.77-1.54 (m, 4H), 1.21 (s, 9H), 1.09 (br. s., 3H). LCMS (M+H)=627.8.

EXAMPLE 43

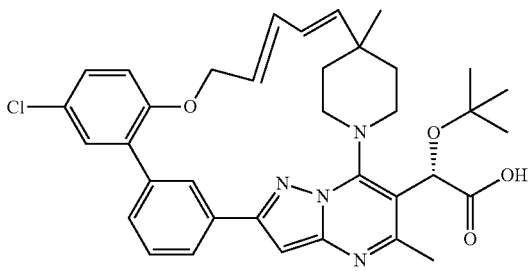 [SMILES: Cc1nc2cc3nn2c(c1[C@H](OC(C)(C)C)C(=O)O)N1CCC(C)(/C=C/C=C/COc2ccc(Cl)cc2-c2cccc-3c2)CC1]

(2S)-2-(tert-Butoxy)-2-[(23E,25E)-17-chloro-4,27-dimethyl-21-oxa-1,5,7,8-tetraazahexacyclo[25.2.2.1$^{6,9}$.1$^{10,14}$.0$^{2,7}$.0$^{15,20}$]tritriaconta-2,4,6(33),8,10(32), 11, 13, 15(20),16,18,23,25-dodecaen-3-yl]acetic acid: Isolated 1.1 mg. $^1$H NMR (500 MHz, DMSO-d$_6$) δ 8.11 (s, 1H), 7.81 (d, J=7.6 Hz, 1H), 7.57 (t, J=7.5 Hz, 1H), 7.45-7.28 (m, 3H), 7.25 (d, J=2.4 Hz, 1H), 6.89 (s, 1H), 6.74 (dd, J=15.6, 11.3 Hz, 1H), 6.37 (t, J=10.7 Hz, 1H), 5.90-5.78 (m, 1H), 5.72 (d, J=15.6 Hz, 1H), 5.67 (br. s., 1H), 5.01 (t, J=11.3 Hz, 1H), 4.71 (t, J=12.5 Hz, 1H), 4.61 (dd, J=11.4, 5.3 Hz, 1H), 2.83 (d, J=13.1 Hz, 1H), 2.50 (m, 5 H), 2.30 (d, J=11.9 Hz, 1H), 1.83-1.55 (m, 3H), 1.18 (s, 9H), 1.10 (s, 3H). LCMS (M+H)=627.4.

EXAMPLE 44 AND 45

A mixture of examples 42 and 43 (40 mg, 0.040 mmol), Pd/C (4.24 mg, 3.99 μmol) in MeOH (5 mL) was hydrogenated using Parr shaker at 60 psi for 6 h. It was then filtered and purified by prep HPLC(CH$_3$CN/NH$_4$OAc) to afford two compounds.

EXAMPLE 44

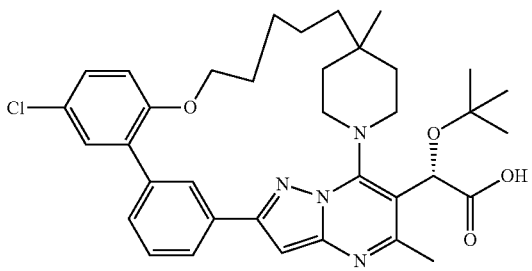 [SMILES: Cc1nc2cc3nn2c(c1[C@H](OC(C)(C)C)C(=O)O)N1CCC(C)(CCCCCOc2ccc(Cl)cc2-c2cccc-3c2)CC1]

(2S)-2-(tert-Butoxy)-2-{17-chloro-4,27-dimethyl-21-oxa-1,5,7,8-tetraazahexacyclo[25.2.2.1$^{6,9}$.1$^{10,14}$.0$^{2,7}$.0$^{15,20}$]tritriaconta-2,4, 6(33), 8, 10(32), 11, 13, 15 (20),16,18-decaen-3-yl}acetic acid: Isolated 12 mg (43%, 90% pure) as a white solid. $^1$H NMR (400 MHz, CDCl$_3$) δ 8.28 (s, 1H), 7.74 (d, J=7.6 Hz, 1H), 7.55 (t, J=7.6 Hz, 1H), 7.43-7.37 (m, 1H), 7.33-7.28 (m, 2H), 6.99 (d, J=9.0 Hz, 1H), 6.82 (s, 1H), 6.01 (br. s., 1H), 4.58 (t, J=12.0 Hz, 1H), 4.13-4.05 (m, 2H), 3.86 (t, J=11.4 Hz, 1H), 3.41 (d, J=12.7 Hz, 1H), 2.84 (d, J=12.5 Hz, 1H), 2.63 (s, 3H), 2.11-1.41 (m, 12H), 1.35-1.29 (m, 12H). LCMS (M+H)=631.3.

EXAMPLE 45

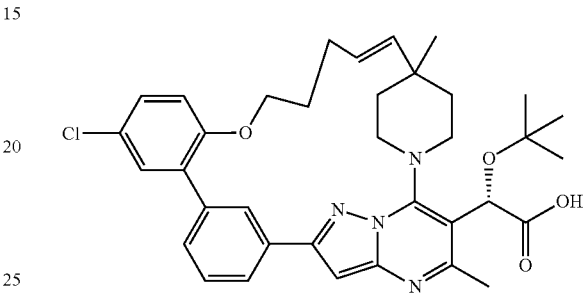

(2S)-2-(tert-Butoxy)-2-[(25E)-17-chloro-4,27-dimethyl-21-oxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18,25-undecaen-3-yl]acetic acid: Isolated 2 mg (7%, 90% pure) as a white solid. $^1$H NMR (400 MHz, C$_6$D$_6$) δ 8.65 (s, 1H), 7.50 (dt, J=6.8, 1.8 Hz, 1H), 7.39-7.33 (m, 2H), 7.20-7.10 (m, 2H), 6.95 (s, 1H), 6.93 (s, 1H), 6.60 (d, J=8.8 Hz, 1H), 6.02 (br. s., 1H), 5.49-5.39 (m, 1H), 5.39-5.28 (m, 1H), 4.66-4.51 (m, 1H), 3.85-3.68 (m, 3H), 3.49 (d, J=11.0 Hz, 1H), 2.68 (s, 3H), 2.07-1.84 (m, 2H), 1.77-1.26 (m, 7H), 1.03 (s, 3H), 0.88 (s, 9H). LCMS (M+H)=629.3.

Intermediate 106

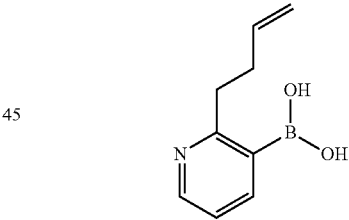

(2-(But-3-en-1-yl)pyridin-3-yl)boronic acid: To a stirring solution of 3-bromo-2-(but-3-en-1-yl)pyridine (Ref. Zhang, Z; Dwoskin, L. and Crooks, P. Tetrahedron Lett. 2011, 52, 2667-2669, 550 mg, 2.59 mmol) and triisopropyl borate (0.775 mL, 3.37 mmol) in toluene (4 mL) and THF (1 mL) cooled to −78° C. was added 2.5 M n-BuLi (1.349 mL, 3.37 mmol) over the course of 15 min. During this time period, the reaction color changed from yellow to orange. The reaction was stirred at −78° C. for 2 h then warmed to 0° C. for 15 min. It was then quenched with 2 N HCl (5 mL) and stirred for 10 min. The solution became a slurry (pH was found to be 3). It was then diluted with ether, the ether layer was discarded. The aqueous layer was adjusted pH=7-8. A white cloud was formed. It was then extracted with EtOAc, the organic layer was dried over MgSO$_4$, filtered and concentrated to obtain 450 mg (98%) of the desired product as a white foam. LCMS (M+1)=178.1.

Intermediate 107

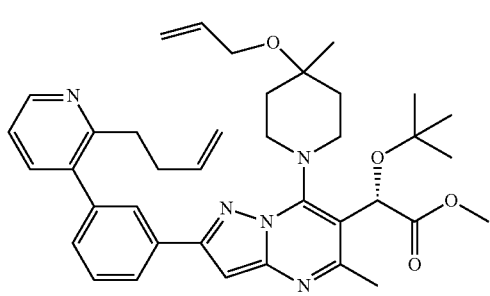

(S)-Methyl 2-(7-(4-(allyloxy)-4-methylpiperidin-1-yl)-2-(3-(2-(but-3-en-1-yl)pyridin-3-yl)phenyl)-5-methylpyrazolo[1,5-a]pyrimidin-6-yl)-2-(tert-butoxy)acetate: Intermediate 107 was prepared using intermediates 65 and 106 by following the procedure to prepare intermediate 94. $^1$H NMR (400 MHz, CDCl$_3$) δ 8.68-8.59 (m, 1H), 8.07 (d, J=7.8 Hz, 1H), 7.99-7.90 (m, 1H), 7.61 (dd, J=7.6, 1.7 Hz, 1H), 7.54 (t, J=7.7 Hz, 1H), 7.33 (d, J=7.8 Hz, 1H), 7.24 (dd, J=7.6, 4.9 Hz, 1H), 6.84 (s, 1H), 6.04-5.89 (m, 2H), 5.78 (ddt, J=17.0, 10.2, 6.7 Hz, 1H), 5.38 (dd, J=17.1, 1.7 Hz, 1H), 5.05 (br. s., 1H), 4.99-4.91 (m, 1H), 4.91-4.86 (m, 1H), 4.50-2.50 (m, 4 H), 3.99 (d, J=4.6 Hz, 2H), 3.75 (s, 3H), 2.93 (dd, J=9.0, 6.8 Hz, 2H), 2.62 (s, 3H), 2.52-2.45 (m, 2H), 2.08-1.68 (m, 4H), 1.35 (s, 3H), 1.26 (s, 9H). LCMS (M+1)=638.4.

Intermediate 108

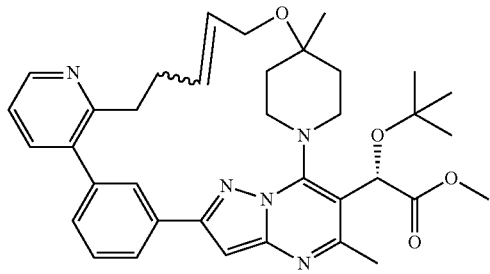

Methyl (2S)-2-(tert-butoxy)-2-[(23E)-4,27-dimethyl-26-oxa-1,5,7,8,19-pentaazahexacyclo[25.2.2.1$^{6,9}$.1$^{10,14}$.0$^{2,7}$.0$^{15,20}$]tritriaconta-2,4,6(33),8,10(32),11,13,15 (20),16,18,23-undecaen-3-yl]acetate: Intermediate 108 was prepared using intermediate 107 by following the procedure to prepare intermediate 95. LCMS (M+1)=610.3.

Intermediate 109

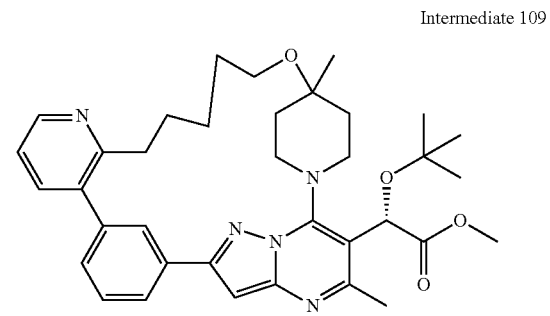 [SMILES: COC(=O)[C@@H](OC(C)(C)C)c1c(C)nc2cc3nn2c1N1CCC(C)(CC1)OCCCCCc1ncccc1-c1cccc-3c1]

Methyl (2S)-2-(tert-butoxy)-2-{4,27-dimethyl-26-oxa-1,5,7,8,19-pentaazahexacyclo[25.2.2.1$^{6,9}$.1$^{10,14}$.0$^{2,7}$.0$^{15,20}$]tritriaconta-2,4,6(33),8,10(32), 11,13,15 (20),16,18-decaen-3-yl}acetate: A mixture of intermediate 108 (32 mg, 0.052 mmol), Pd/C (5.58 mg, 5.25 μmol) in MeOH (2 mL) was stirred under a H$_2$ balloon for 2 h. It was then filtered and concentrated to obtain 30 mg (93%) of the desired product as an off-white solid. $^1$H NMR (400 MHz, CDCl$_3$) δ 8.64 (dd, J=4.6, 1.7 Hz, 1H), 8.15 (s, 1H), 7.82 (d, J=8.1 Hz, 1H), 7.57-7.50 (m, 2H), 7.26-7.17 (m, 2H), 6.86 (s, 1H), 6.03 (s, 1H), 4.59-4.47 (m, 1H), 3.89 (t, J=11.0 Hz, 1H), 3.74 (s, 3H), 3.43 (d, J=5.4 Hz, 1H), 3.40-3.33 (m, 1H), 3.09 (d, J=11.0 Hz, 1H), 2.97 (ddd, J=14.4, 9.1, 5.6 Hz, 1H), 2.87-2.73 (m, 2H), 2.64 (s, 3H), 2.25-2.11 (m, 1H), 2.01 (d, J=15.2 Hz, 1H), 1.89 (d, J=11.5 Hz, 2H), 1.77 (td, J=13.0, 4.8 Hz, 1H), 1.75-1.53 (m, 5 H), 1.27-1.24 (m, 12H). LCMS (M+1)=612.3.

EXAMPLE 46

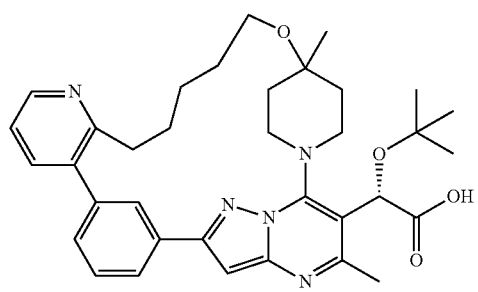 [SMILES: Cc1nc2cc3nn2c(c1[C@H](OC(C)(C)C)C(=O)O)N1CCC(C)(CC1)OCCCCCc1ncccc1-c1cccc-3c1]

(2S)-2-(tert-Butoxy)-2-{4,27-dimethyl-26-oxa-1,5,7,8,19-pentaazahexacyclo[25.2.2.1$^{6,9}$.1$^{10,14}$.0$^{2,7}$.0$^{15,20}$]tritriaconta-2,4,6(33),8,10(32),11,13,15(20),16,18-decaen-3-yl}acetic acid: A mixture of intermediate 109 (30 mg, 0.049 mmol), NaOH (0.245 mL, 0.245 mmol) in MeOH (2 mL) was refluxed for 3 h. It was then filtered and purified by prep HPLC (NH$_4$OAc/CH$_3$CN) to isolate 25 mg (81%) of the desired product as a white solid. $^1$H NMR (400 MHz, CDCl$_3$) δ 8.68 (br. s., 1H), 8.15 (br. s., 1H), 7.81 (d, J=7.6 Hz, 1H), 7.54 (br. s., 2H), 7.23 (d, J=6.4 Hz, 2H), 6.88 (s, 1H), 6.02 (br. s., 1H), 4.57 (t, J=12.7 Hz, 1H), 3.96-3.83 (m, 1H), 3.49-3.30 (m, 3H), 3.02-2.72 (m, 3H), 2.64 (s, 3H), 2.23-1.85 (m, 4H), 1.80-1.51 (m, 6H), 1.38-1.20 (m, 12H). LCMS (M+H)=598.5.

Intermediate 110

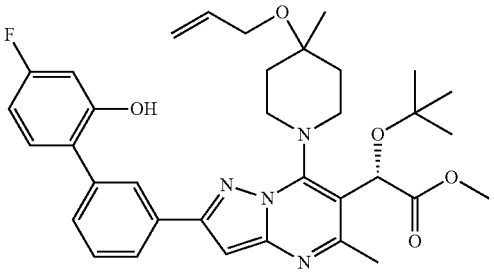

(S)Methyl 2-(7-(4-(allyloxy)-4-methylpiperidin-1-yl)-2-(4'-fluoro-2'-hydroxy-[1,1'-biphenyl]-3-yl)-5-methylpyrazolo[1,5-a]pyrimidin-6-yl)-2-(tert-butoxy)acetate: Intermediate 110 (73) was prepared using intermediate 65 and 4-fluoro-2-hydroxyphenylboronic acid by following the procedure to prepare intermediate 69 (31). LCMS (M+1)=617.3.

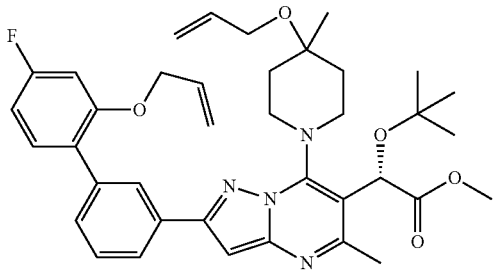

(S)-Methyl 2-(2-(2'-(allyloxy)-4'-fluoro-[1,1'-biphenyl]-3-yl)-7-(4-(allyloxy)-4-methylpiperidin-1-yl)-5-methylpyrazolo[1,5-a]pyrimidin-6-yl)-2-(tert-butoxy)acetate: Intermediate 111 was prepared using intermediate 110 by following the procedure to prepare intermediate 87. $^1$H NMR (400 MHz, CDCl$_3$) δ 8.09-7.94 (m, 2H), 7.59-7.46 (m, 2H), 7.42-7.35 (m, 1H), 6.84 (s, 1H), 6.82-6.73 (m, 2H), 6.07-5.93 (m, 3H), 5.46-5.34 (m, 2H), 5.23 (dq, J=10.6, 1.5 Hz, 1H), 5.12 (d, J=10.0 Hz, 1H), 5.00-2.50 (m, 4 H), 4.57 (dt, J=4.8, 1.6 Hz, 2H), 4.02 (d, J=5.1 Hz, 2H), 3.75 (s, 3H), 2.63 (s, 3H), 2.09-1.90 (m, 3H), 1.74 (br. s., 1H), 1.37 (s, 3H), 1.25 (s, 9H). LCMS (M+1)=657.4.

Intermediate 112

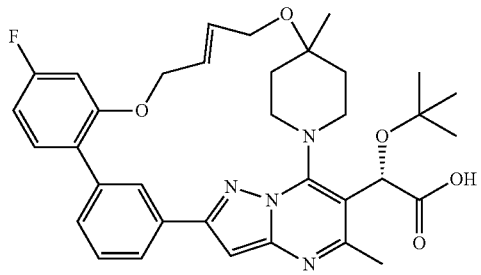

Methyl (2S)-2-(tert-butoxy)-2-[(23Z)-18-fluoro-4,27-dimethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18,23-undecaen-3-yl]acetate: Intermediate 112 was prepared using intermediate 111 by following the procedure to prepare intermediate 71. It's a mixture of trans/cis isomers. LCMS (M+1)=629.3.

EXAMPLE 47 AND 48

Saponification of intermediate 112 by following the procedure to prepare example 20 afforded two compounds.

EXAMPLE 47

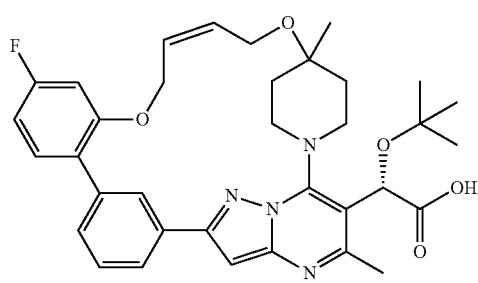 [SMILES: Cc1nc2cc3nn2c(c1[C@H](OC(C)(C)C)C(=O)O)N1CCC(C)(CC1)OC/C=C\COc1cc(F)ccc1-c1cccc-3c1]

(2S)-2-(tert-Butoxy)-2-[(23Z)-18-fluoro-4,2,7-dimethyl-21,26-dioxa-1,5,7,8-tetraazahexacyclo [25.2.2.1$^{6,9}$.1$^{10,14}$.0$^{2,7}$.0$^{15,20}$]tritriaconta-2,4,6(33),8,10(32),11,13,15(20),16,18,23-undecaen-3-yl]acetic acid: $^1$H NMR (400 MHz, CDCl$_3$) δ 8.70 (s, 1H), 7.75 (d, J=7.5 Hz, 1H), 7.51 (t, J=7.7 Hz, 1H), 7.44-7.32 (m, 2H), 6.88 (s, 1H), 6.80-6.69 (m, 2H), 6.31 (br. s., 1H), 5.97 (br. s., 1H), 4.90 (t, J=12.2 Hz, 1H), 4.71-4.58 (m, 1H), 4.11-3.95 (m, 2H), 3.67 (br. s., 1H), 3.48-3.26 (m, 2H), 2.83 (d, J=12.5 Hz, 1H), 2.60 (br. s., 3H), 2.43 (br. s., 1H), 2.04-1.85 (m, 2H) 1.74 (d, J=9.3 Hz, 2H), 1.40 (br. s., 3H), 1.26 (br. s., 9H). LCMS (M+H)=615.4.

EXAMPLE 48

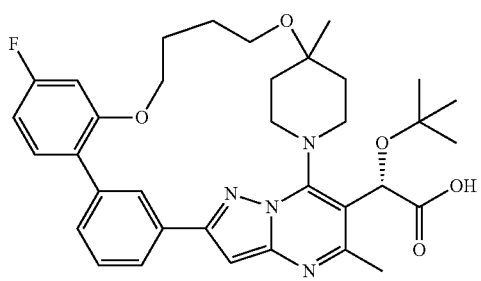 [SMILES: Cc1nc2cc3nn2c(c1[C@H](OC(C)(C)C)C(=O)O)N1CCC(C)(CC1)OCCCCOc1cc(F)ccc1-c1cccc-3c1]

(2S)-2-(tert-Butoxy)-2-[(23E)-18-fluoro-4,2,7-dimethyl-21,26-dioxa-1,5,7,8-tetraazahexacyclo [25.2.2.1$^{6,9}$.1$^{10,14}$.0$^{2,7}$.0$^{15,20}$]tritriaconta-2,4,6(33),8,10(32),11,13,15(20),16,18,23-undecaen-3-yl]acetic acid: $^1$H NMR (400 MHz, CDCl$_3$) δ 8.48 (t, J=1.6 Hz, 1H), 7.72 (dt, J=7.8, 1.4 Hz, 1H), 7.56-7.50 (m, 1H), 7.40 (dt, J=7.8, 1.4 Hz, 1H), 7.34-7.29 (m, 1H), 6.84 (s, 1H), 6.76-6.71 (m, 2H), 6.35-6.23 (m, 1H), 6.08 (dt, J=15.7, 4.2 Hz, 1H), 6.02 (br. s., 1H), 4.76-4.62 (m, 3H), 4.10-3.93 (m, 3H), 3.36 (d, J=11.5 Hz, 1H), 2.75 (d, J=12.0 Hz, 1H), 2.64 (s, 3H), 2.08-2.00 (m, 1H), 1.95 (dd, J=13.7, 2.0 Hz, 1H), 1.77 (td, J=13.1, 4.6 Hz, 1H), 1.62 (td, J=13.4, 4.3 Hz, 1H), 1.34-1.28 (m, 12H). LCMS (M+H)=615.4.

EXAMPLE 49

(2S)-2-(tert-Butoxy)-2-{18-fluoro-4,27-dimethyl-21,26-dioxa-1,5,7,8-tetraazahexacyclo[25.2.2. 1$^{6,9}$.1$^{10,14}$.0$^{2,7}$.0$^{15,20}$]tritriaconta-2,4,6(33),8,10(32),11,13,15(20),16,18-decaen-3-yl}acetic acid: Example 49 was prepared using mixture of examples 47 and 48 following the procedure to prepare example 21. $^1$H NMR (400 MHz, CDCl$_3$) δ 8.43 (t, J=1.5 Hz, 1H), 7.68 (dt, J=7.9, 1.3 Hz, 1H), 7.56-7.49 (m, 1H), 7.41 (dt, J=7.8, 1.5 Hz, 1H), 7.33 (dd, J=8.0, 7.0 Hz, 1H), 6.80 (s, 1H), 6.78-6.70 (m, 2H), 6.00 (s, 1H), 4.62-4.52 (m, 1H), 4.13-4.05 (m, 2H), 3.90 (dd, J=12.2, 10.2 Hz, 1H), 3.57-3.49 (m, 1H), 3.41 (td, J=8.5, 3.3 Hz, 2H), 2.83 (d, J=12.3 Hz, 1H), 2.62 (s, 3H), 2.35 (ddt, J=16.3, 10.9, 5.6 Hz, 1H), 2.20-2.11 (m, 1H), 2.09-2.04 (m, 1 H), 1.93 (dd, J=13.6, 2.0 Hz, 1H), 1.85-1.73 (m, 2H), 1.70-1.53 (m, 2H), 1.30 (s, 9H), 1.26 (s, 3H). LCMS (M+H)=617.4.

Intermediate 113

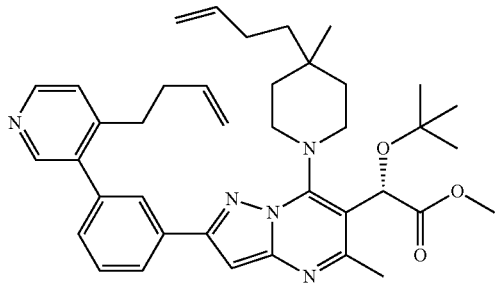

(S)-Methyl 2-(7-(4-(but-3-en-1-yl)-4-methylpiperidin-1-yl)-2-(3-(4-(but-3-en-1-yl)pyridin-3-yl)phenyl)-5-methylpyrazolo[1,5-a]pyrimidin-6-yl)-2-(tert-butoxy)acetate: Intermediate 113 was prepared using intermediate 65 and intermediate 93 by following the procedure to prepare intermediate 94. $^1$H NMR (400 MHz, CDCl$_3$) δ 8.58-8.53 (m, 2H), 8.07 (d, J=7.8 Hz, 1H), 7.96 (t, J=1.5 Hz, 1H), 7.57 (t, J=7.7 Hz, 1H), 7.35 (dt, J=7.8, 1.3 Hz, 1H), 7.28-7.26 (m, 1H), 6.84 (s, 1H), 6.07 (s, 1H), 5.94-5.79 (m, 1H), 5.72 (ddt, J=16.9, 10.3, 6.7 Hz, 1H), 5.06 (d, J=15.7 Hz, 1H), 5.00-2.50 (m, 4 H), 4.99-4.91 (m, 3H), 3.75 (s, 3H), 2.81-2.75 (m, 2H), 2.63 (s, 3H), 2.32 (td, J=7.8, 6.5 Hz, 2H), 2.10 (br. s., 2H), 1.81-1.69 (m, 1H), 1.62 (t, J=5.5 Hz, 2H), 1.57-1.49 (m, 2H), 1.28 (s, 10H), 1.14 (br. s., 3H). LCMS (M+1)=636.4.

Intermediate 114

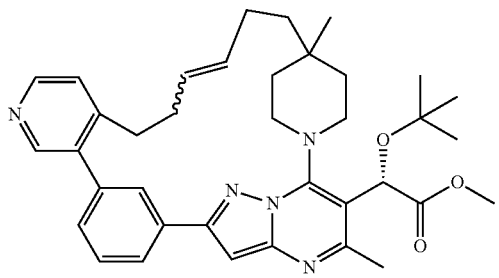

Methyl (2S)-2-(tert-butoxy)-2-[(23E)-4,27-dimethyl-1,5,7,8,17-pentaazahexacyclo[25.2.2.1$^{6,9}$.1$^{10,14}$.0$^{2,7}$.0$^{15,20}$]tritriaconta-2,4,6(33),8,10(32),11,13,15(20),16,18,23-undecaen-3-yl]acetate: Intermediate 114 was prepared using intermediate 113 by following the procedure to prepare intermediate 95. It's a mixture of cis/trans isomers. LCMS (M+1)=608.3.

EXAMPLE 50 (39) AND 51 (40)

Hydrolysis of intermediate 114 by following the procedure to prepare example 20 provided two compounds.

EXAMPLE 50

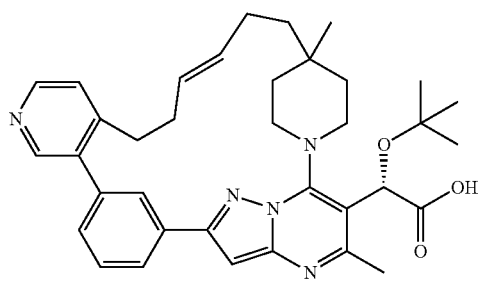 [SMILES: Cc1nc2cc3nn2c(c1[C@H](OC(C)(C)C)C(=O)O)N1CCC(C)(CC/C=C/CCc2ccncc2-c2cccc-3c2)CC1]

(2S)-2-(tert-Butoxy)-2-[(23E)-4,27-dimethyl-1,5,7,8,17-pentaazahexacyclo[25.2.2.1$^{6,9}$.1$^{10,14}$.0$^{2,7}$.0$^{15,20}$]tritriaconta-2,4,6(33),8,10(32),11,13,15(20),16,18,23-undecaen-3-yl]acetic acid: $^1$H NMR (500 MHz, CDCl$_3$) δ 8.57 (d, J=5.4 Hz, 1H), 8.33 (s, 1H), 7.95 (s, 1H), 7.78 (d, J=7.7 Hz, 1H), 7.51 (t, J=7.6 Hz, 1H), 7.35 (d, J=5.4 Hz, 1H), 7.22 (d, J=7.7 Hz, 1H), 6.81 (s, 1H), 6.02 (br. s., 1H), 5.30-5.20 (m, 1H), 5.19-5.11 (m, 1H), 4.68-4.55 (m, 1H), 4.04 (br. s., 1H), 3.10 (d, J=12.6 Hz, 1H), 2.85-2.74 (m, 2H), 2.67 (s, 3H), 2.64 (d, J=3.6 Hz, 1H), 2.52-2.36 (m, 2H), 1.85-1.75 (m, 2H), 1.70 (br. s., 1H), 1.64-1.53 (m, 2H), 1.53-1.39 (m, 3H), 1.30 (s, 9H), 0.93 (s, 3H). LCMS (M+H)=594.45.

EXAMPLE 51

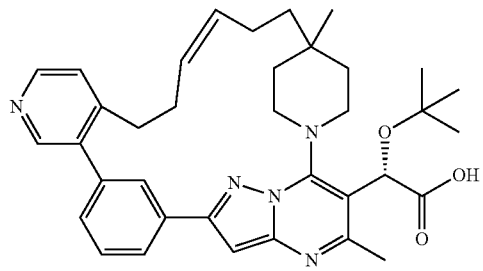 [SMILES: Cc1nc2cc3nn2c(c1[C@H](OC(C)(C)C)C(=O)O)N1CCC(C)(CC/C=C\CCc2ccncc2-c2cccc-3c2)CC1]

(2S)-2-(tert-Butoxy)-2-[(23Z)-4,27-dimethyl-1,5,7,8,17-pentaazahexacyclo[25.2.2.1$^{6,9}$.1$^{10,14}$.0$^{2,7}$.0$^{15,20}$]tritriaconta-2,4,6(33),8,10(32),11,13,15(20),16,18,23-undecaen-3-yl]acetic acid: $^1$H NMR (500 MHz, CDCl$_3$) δ 8.53 (d, J=5.0 Hz, 1H), 8.45 (s, 1 H), 8.12 (s, 1H), 7.83 (d, J=7.9 Hz, 1H), 7.57 (t, J=7.6 Hz, 1H), 7.32-7.30 (m, 2H), 6.84 (s, 1H), 5.89 (br. s., 1H), 5.63-5.50 (m, 2H), 4.40 (t, J=11.0 Hz, 1H), 3.79 (t, J=11.0 Hz, 1H), 3.50-3.41 (m, 1H), 2.84 (dt, J=13.8, 7.0 Hz, 1H), 2.72-2.65 (m, 2H), 2.61 (s, 3H), 2.59-2.53 (m, 3H), 2.11-1.97 (m, 2H), 1.87 (d, J=7.9 Hz, 2H), 1.58 (d, J=10.1 Hz, 1H), 1.50 (d, J=13.2 Hz, 1H), 1.42 (t, J=10.6 Hz, 1H), 1.28 (s, 9H), 1.03 (s, 3H). LCMS (M+H)=594.5.

EXAMPLE 52

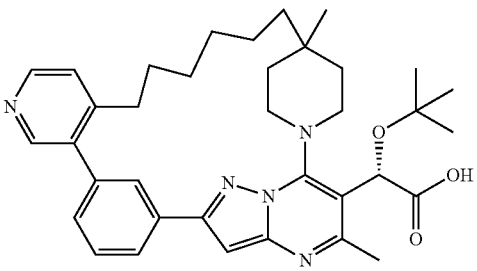 [SMILES: Cc1nc2cc3nn2c(c1[C@H](OC(C)(C)C)C(=O)O)N1CCC(C)(CCCCCCc2ccncc2-c2cccc-3c2)CC1]

(2S)-2-(tert-Butoxy)-2-{4,27-dimethyl-1,5,7,8,17-pentaazahexacyclo[25.2.2.1$^{6,9}$.1$^{10,14}$.0$^{2,7}$.0$^{15,20}$]tritriaconta-2,4,6(33),8,10(32),11,13,15(20),16,18-decaen-3-yl}acetic acid: Example 52 was prepared using mixture of examples 50 and 51 by following the procedure to prepare example 21. $^1$H NMR (400 MHz, CDCl$_3$) δ 8.79-8.22 (m, 1H), 7.92 (s, 1H), 7.79 (d, J=7.6 Hz, 1H), 7.60-7.49 (m, 1H), 7.44-7.31 (m, 1 H), 7.23 (d, J=7.3 Hz, 1H), 6.82 (s, 1H), 6.02 (br. s., 1H), 4.50 (t, J=11.0 Hz, 1H), 3.90 (br. s., 1H), 3.18 (br. s., 1H), 2.77-2.61 (m, 6H), 1.82-1.43 (m, 7H), 1.41-1.13 (m, 17H), 0.96 (s, 3H). LCMS (M+H)=596.5.

Intermediate 115

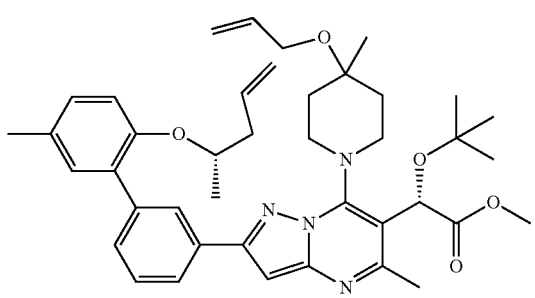

(S)-Methyl 2-(7-(4-(allyloxy)-4-methylpiperidin-1-yl)-5-methyl-2-(5'-methyl-2'-((S)-pent-4-en-2-yloxy)-[1,1'-biphenyl]-3-yl)pyrazolo[1,5-a]pyrimidin-6-yl)-2-(tert-butoxy)acetate: A mixture of intermediate 89 (600 mg, 0.979 mmol), (R)-pent-4-en-2-ol (253 mg, 2.94 mmol), triphenylphosphine (514 mg, 1.958 mmol), DEAD (0.310 mL, 1.958 mmol) in THF (5 ml) was stirred at rt for 2 days. It was then diluted with EtOAc. The organic was washed with water, dried over MgSO$_4$, filtered, concentrated and purified by biotage, eluting with 20% EtOAc/hexane to isolate 500 mg of the desired product as an oil. $^1$H NMR (400 MHz, CDCl$_3$) δ 8.15 (s, 1H), 8.04 (d, J=6.8 Hz, 1H), 7.58 (d, J=7.8 Hz, 1H), 7.51-7.45 (m, 1H), 7.25 (d, J=1.7 Hz, 1H), 7.13 (dd, J=8.1, 1.7 Hz, 1H), 6.94 (d, J=8.3 Hz, 1H), 6.85 (s, 1H), 6.12-5.91 (m, 2H), 5.77 (ddt, J=17.1, 10.1, 7.1 Hz, 1H), 5.43 (d, J=17.1 Hz, 1H), 5.14 (d, J=10.8 Hz, 1H), 5.07-4.98 (m, 2H), 5.00-2.50 (m, 4H), 4.33 (sxt, J=6.1 Hz, 1H), 4.03 (d, J=4.9 Hz, 2H), 3.75 (s, 3H), 2.62 (s, 3H), 2.46-2.36 (m, 4H), 2.27 (dt, J=13.9, 6.9 Hz, 1H), 2.07-1.85 (m, 3H), 1.74 (br. s., 1H), 1.39 (s, 3H), 1.27 (s, 9H), 1.24-1.20 (m, 3H). LCMS (M+1)=681.4.

Intermediate 116

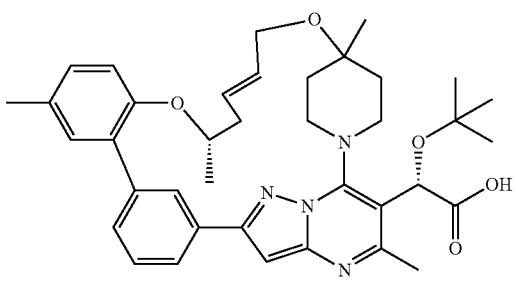 [SMILES: Cc1ccc2c(c1)-c1cccc(c1)-c1cc3nc(C)c([C@H](OC(C)(C)C)C(=O)O)c(n3n1)N1CCC(C)(CC1)OC/C=C/C[C@H](C)O2]

Methyl (2S)-2-(tert-butoxy)-2-[(22S)-4,17,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetate: A mixture of intermediate 115 (600 mg, 0.881 mmol), (1,3-dimesitylimidazolidin-2-ylidene)(2-isopropoxybenzylidene)ruthenium (VI) chloride (55.2 mg, 0.088 mmol), copper(I) iodide (168 mg, 0.881 mmol) in DCE (750 mL) was refluxed for 1 h. It was then concentrated to obtain 600 mg dark green solid. LCMS (M+1)=653.5. The product is a mixture of cis/trans product. This material was used in the next step without purification.

EXAMPLES 53 (42) And 54 (43)

A mixture of intermediate 116 (40 mg, 0.061 mmol), NaOH (0.613 mL, 0.613 mmol) in MeOH (2 mL) was refluxed for 3 h. It was then filtered and purify by prep HPLC to two compounds.

EXAMPLE 53

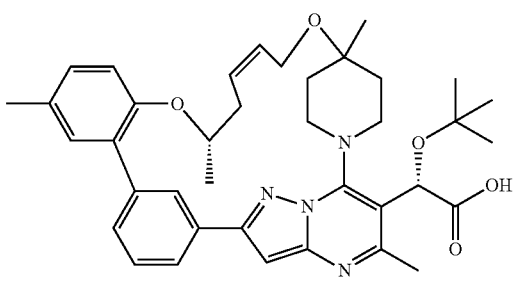 [SMILES: Cc1ccc2c(c1)-c1cccc(c1)-c1cc3nc(C)c([C@H](OC(C)(C)C)C(=O)O)c(n3n1)N1CCC(C)(CC1)OC/C=C\C[C@H](C)O2]

(2S)-2-(tert-Butoxy)-2-[(22S,$^{24}$E)-4,17,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetic acid: Isolate 17.6 mg (44%) as a white solid. $^1$H NMR (500 MHz, DMSO-d$_6$) δ 8.43 (s, 1H), 8.01-7.87 (m, 1H), 7.52 (t, J=7.6 Hz, 1H), 7.31 (d, J=7.3 Hz, 1H), 7.17-6.97 (m, 4H), 6.28 (br. s., 1H), 5.78-5.55 (m, 2H), 4.86-4.66 (m, 1H), 4.51 (br. s., 1H), 4.02-3.91 (m, 1H), 3.92-3.82 (m, 1H), 3.70-3.10 (m, 3H), 2.50 (s, 3H), 2.35-2.23 (m, 4H), 2.22-2.07 (m, 1H), 2.02 (d, J=14.0 Hz, 1H), 1.86 (d, J=11.0 Hz, 1H), 1.70-1.50 (m, 2H), 1.21 (s, 3H), 1.16 (s, 9H), 1.02 (d, J=5.8 Hz, 3H). LCMS (M+1)=639.5.

EXAMPLE 54

(2S)-2-(tert-Butoxy)-2-[(22S,24Z)-4,17,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetic acid: Isolate 1.8 mg (4.5%) as a white solid. $^1$H NMR (500 MHz, DMSO-d$_6$) δ 8.58 (s, 1H), 7.86 (d, J=7.9 Hz, 1H), 7.52 (t, J=7.8 Hz, 1H), 7.40 (d, J=7.6 Hz, 1H), 7.21 (s, 1H), 7.18-7.12 (m, 1H), 7.12-7.07 (m, 1H), 7.01 (s, 1H), 5.79-5.62 (m, 2H), 5.46 (s, 1H), 4.64-4.55 (m, 1H), 4.26 (t, J=11.9 Hz, 1H), 4.02-3.96 (m, 1H), 3.78 (dd, J=9.9, 5.0 Hz, 1H), 3.70-3.20 (m, 2H), 3.07 (d, J=11.6 Hz, 1H), 2.86 (br. s., 1H), 2.60-2.53 (m, 1H), 2.51 (s, 3 H), 2.30 (s, 3H), 2.07 (d, J=12.5 Hz, 1H), 1.86-1.73 (m, 2H), 1.59-1.47 (m, 1H), 1.21 (s, 3H), 1.19 (d, J=5.8 Hz, 3H), 1.14 (s, 9H). LCMS (M+1)=639.5.

Intermediate 117

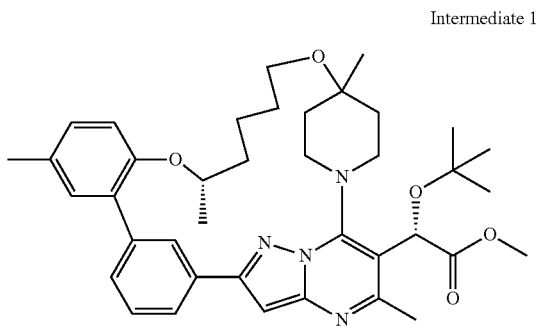

Methyl (2S)-2-(tert-butoxy)-2-[(22S)-4,17,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10 (33), 11, 13, 15 (20),16,18-decaen-3-yl]acetate: To a crude mixture of intermediate 116 (700 mg, 1.072 mmol), in MeOH (30 mL) was added NaBH$_4$ (203 mg, 5.36 mmol) five times in 1 h. After 1 h, it was quenched with water, extracted with EtOAc. The organic was dried over MgSO$_4$, filtered and concentrated to obtain 800 mg white solid. It was then purified by biotage, eluting with 20% EtOAc/hexane to isolate 480 mg (68%) of the desired product as a white solid. $^1$H NMR (400 MHz, CDCl$_3$) δ 8.60 (s, 1H), 7.80 (d, J=7.8 Hz, 1H), 7.50 (t, J=7.7 Hz, 1H), 7.35 (d, J=7.6 Hz, 1H), 7.17 (s, 1H), 7.13 (d, J=8.3 Hz, 1H), 6.95-6.88 (m, 2H), 5.90 (s, 1H), 4.67-4.51 (m, 2H), 3.84-3.78 (m, 1H), 3.77 (s, 3H), 3.49 (d, J=7.6 Hz, 1H), 3.42-3.34 (m, 1H), 3.25 (d, J=13.4 Hz, 1H), 2.89 (d, J=11.5 Hz, 1H), 2.60 (s, 3H), 2.36 (s, 3H), 2.09-1.67 (m, 8H), 1.64-1.54 (m, 2H), 1.26 (s, 3H), 1.24 (s, 9H), 1.17 (d, J=5.9 Hz, 3H). LCMS (M+1)=655.3.

EXAMPLE 55

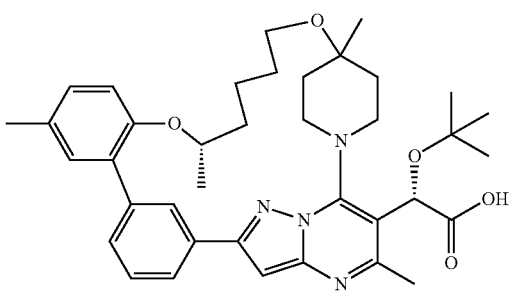 [SMILES: Cc1ccc2c(c1)-c1cccc(c1)-c1cc3nc(C)c([C@H](OC(C)(C)C)C(=O)O)c(n3n1)N1CCC(C)(CC1)OCCCC[C@H](C)O2]

(2S)-2-(tert-Butoxy)-2-[(22S)-4,17,22,28-tetramethyl-21,27-dioxa-1,5,7,8-tetraazahexacyclo[26.2.2. 1$^{6,9}$.1$^{10,14}$.0$^{2,7}$.0$^{15,20}$]tetratriaconta-2,4,6(34), 8, 10(33), 11, 13, 15 (20),16,18-decaen-3-yl]acetic acid: Example 55 was prepared using intermediate 117 by following the procedure to prepare example 28. $^1$H NMR (400 MHz, CDCl$_3$) δ 8.63 (s, 1H), 7.79 (d, J=7.6 Hz, 1H), 7.50 (t, J=7.7 Hz, 1H), 7.37 (d, J=7.6 Hz, 1H), 7.18 (d, J=2.0 Hz, 1H), 7.16-7.10 (m, 1H), 6.95-6.88 (m, 2H), 5.97 (br. s., 1H), 4.67 (t, J=11.7 Hz, 1H), 4.61-4.48 (m, 1H), 3.82 (t, J=11.6 Hz, 1H), 3.61-3.44 (m, 2H), 3.42-3.33 (m, 1H), 2.95 (d, J=12.0 Hz, 1H), 2.59 (s, 3H), 2.36 (s, 3H), 2.09-1.96 (m, 3H), 1.92-1.63 (m, 7H), 1.29 (s, 9H), 1.26 (s, 3H), 1.17 (d, J=6.1 Hz, 3H). LCMS (M+1)=641.3.

Intermediate 118

3-Bromo-4-(but-3-en-2-yloxy)pyridine: A mixture of 3-bromopyridin-4-ol (0.6 g, 3.45 mmol), but-3-en-2-ol (0.746 g, 10.35 mmol), triphenylphosphine (2.71 g, 10.35 mmol), DIAD (2.011 mL, 10.35 mmol) in THF (1 mL) was stirred at rt for 16 h. It was then diluted with EtOac, washed with water. The organic layer was dried over MgSO$_4$, filtered and concentrated to obtain 1 g oil, which was then purified by biotage, eluting with 30% acetone/hexane to isolate 750 mg (95%) of the desired product as an oil. $^1$H NMR (400 MHz, CDCl$_3$) δ 8.60 (s, 1H), 8.34 (d, J=5.6 Hz, 1H), 6.83-6.80 (m, 1H), 5.98-5.87 (m, 1H), 5.40-5.25 (m, 2H), 5.00-4.92 (m, 1H), 1.55 (d, J=6.4 Hz, 3H). LCMS (M+1)=229.9.

Intermediate 119

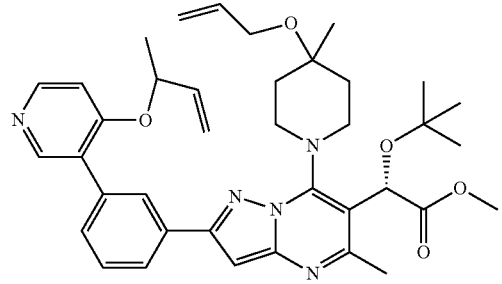

(2S)-Methyl 2-(7-(4-(allylaxy)-4-methylpiperidin-1-yl)-2-(3-(4-(but-3-en-2-yloxy)pyridin-3-Aphenyl)-5-methylpyrazolo[1,5-a]pyrimidin-6-yl)-2-(tert-butoxy)acetate: To a microwave tube was added intermediate 65 (100 mg, 0.171 mmol), (4-(but-3-en-2-yloxy)pyridin-3-yl)boronic acid (49.4 mg, 0.256 mmol) (prepared using intermediate 118 following the proceduce to prepare intermediate 93 and 2.0 M aqueous sodium carbonate (0.171 mL, 0.342 mmol) in DMF (2 mL), was sparged with nitrogen for 1 minutes, treated with (Ph$_3$)$_4$Pd (19.74 mg, 0.017 mmol), then sparged with N$_2$ for 1 min. The reaction tube was sealed and then heated at 95° C. in a microwave tube for 1 h. The reaction was then concentrated, diluted with water (15 mL) and extracted wtih EtOAc. The EtOAc layer was washed with brine, dried (Na$_2$SO$_4$), filtered, and concentrated under reduced pressure. The residue was purified by biotage, eluting with 30% acetone/hexane to isolate 80 mg (72%) of the desired product as a white solid. LCMS (M+1)=654.4.

INTERMEDIATE 120 AND 121

A mixture of intermediate 119 (100 mg, 0.153 mmol), (1,3-dimesitylimidazolidin-2-ylidene)(2-isopropoxybenzylidene)ruthenium(VI) chloride (9.58 mg, 0.015 mmol), tosic acid (29.1 mg, 0.153 mmol) in DCE (100 mL) was heated at reflux for 2 h. It was then concentrated, and purified by prep HPLC to afford two compounds.

Intermediate 120

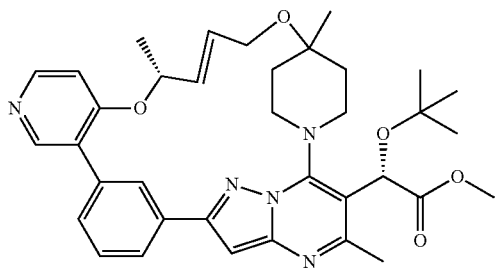

Methyl (2S)-2-(tert-butoxy)-2-[(22R,23E)-4,22,27-trimethyl-21,26-dioxa-1,5,7,8,17-pentaazahexacyclo[25.2.2.1$^{6,9}$.0$^{10,14}$.0$^{2,7}$.0$^{15,20}$]-tritriaconta-2,4,6(33),8,10(32),11,13,15(20),16,18,23-undecaen-3-yl]acetate: Isolate 5.9 mg (6%) as a white solid. $^1$H NMR (400 MHz, CDCl$_3$) δ 8.24 (t, J=1.6 Hz, 1H), 8.23-8.20 (m, 1H), 7.85 (d, J=2.4 Hz, 1H), 7.78 (dt, J=7.8, 1.3 Hz, 1H), 7.52 (t, J=7.7 Hz, 1H), 7.41 (dd, J=7.6, 2.4 Hz, 1H), 6.88 (s, 1H), 6.60 (d, J=7.3 Hz, 1H), 6.24-6.17 (m, 1H), 6.13-6.01 (m, 2H), 4.72-4.58 (m, 2H), 4.13-4.07 (m, 2H), 3.83 (t, J=11.1 Hz, 1H), 3.75 (s, 3H), 3.07 (d, J=11.2 Hz, 1H), 2.76 (d, J=11.7 Hz, 1H), 2.66 (s, 3H), 2.07-1.98 (m, 3H), 1.89-1.66 (m, 3H), 1.62 (d, J=6.6 Hz, 3H), 1.34 (s, 3H), 1.28 (s, 9H). LCMS (M+1)=626.3.

Intermediate 121

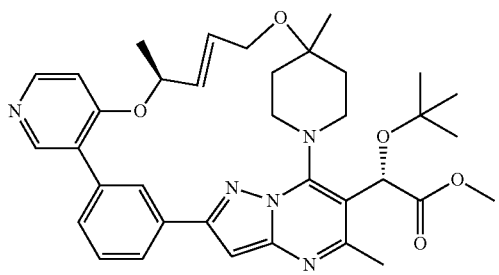

Methyl (2S)-2-(tert-butoxy)-2-[(22S,23E)-4,22,27-trimethyl-21,26-dioxa-1,5,7,8,17-pentaazahexacyclo[25.2.2.1$^{6,9}$.1$^{10,14}$.0$^{2,7}$.0$^{15,20}$]tritriaconta-2,4,6(33),8,10(32),11,13,15(20),16,18,23-undecaen-3-yl]acetate: Isolate 5 mg (5%) as a white solid. $^1$H NMR (400 MHz, CDCl$_3$) δ 8.24-8.19 (m, 1H), 8.11 (t, J=1.6 Hz, 1H), 7.87 (d, J=2.7 Hz, 1H), 7.75 (d, J=8.1 Hz, 1H), 7.56-7.50 (m, 1H), 7.41 (dd, J=7.5, 2.6 Hz, 1H), 6.84 (s, 1H), 6.56 (d, J=7.6 Hz, 1H), 6.18-6.02 (m, 3H), 4.62 (t, J=6.4 Hz, 1H), 4.54-4.45 (m, 1H), 4.09 (d, J=2.7 Hz, 2H), 4.02 (t, J=10.9 Hz, 1H), 3.72 (s, 3H), 3.02 (d, J=10.8 Hz, 1H), 2.72 (br. s., 1H), 2.67 (s, 3H), 2.02 (d, J=13.9 Hz, 2H), 1.88-1.72 (m, 2H), 1.63 (d, J=6.8 Hz, 3H), 1.35 (s, 3H), 1.29 (s, 9H). LCMS (M+1)=626.4.

EXAMPLE 56

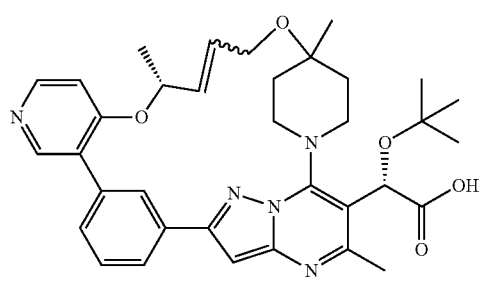 [SMILES: Cc1nc2cc3nn2c(c1[C@H](OC(C)(C)C)C(=O)O)N1CCC(C)(CC1)OCC=C[C@@H](C)Oc1ccncc1-c1cccc-3c1]

(2S)-2-(tert-Butoxy)-2-[(22R)-4,22,27-trimethyl-21,26-dioxa-1,5,7,8,17-pentaazahexacyclo[25.2.2.1$^{6,9}$.1$^{10,14}$.0$^{2,7}$.0$^{15,20}$]tritriaconta-2,4,6(33),8,10(32), 11, 13, 15 (20),16,18,23-undecaen-3-yl]acetic acid: Example 56 was prepared using intermediate 120 by following the procedure to prepare example 20. LCMS (M+H)=612.4.

EXAMPLE 57

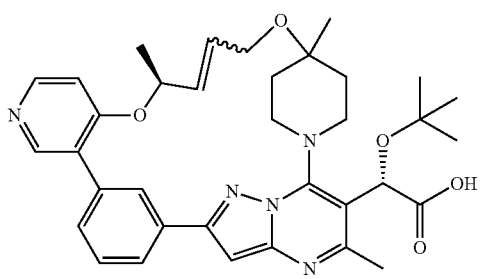 [SMILES: Cc1nc2cc3nn2c(c1[C@H](OC(C)(C)C)C(=O)O)N1CCC(C)(CC1)OCC=C[C@H](C)Oc1ccncc1-c1cccc-3c1]

(2S)-2-(tert-Butoxy)-2-[(22S)-4,22,27-trimethyl-21,26-dioxa-1,5,7,8,17-pentaazahexacyclo[25.2.2.1$^{6,9}$.1$^{10,14}$.0$^{2,7}$.0$^{15,20}$]tritriaconta-2,4,6(33),8,10(32), 11, 13, 15(20),16,18,23-undecaen-3-yl]acetic acid: Example 57 was prepared using intermediate 121 by following the procedure to prepare example 20. LCMS (M+H)=612.3.

Intermediate 122

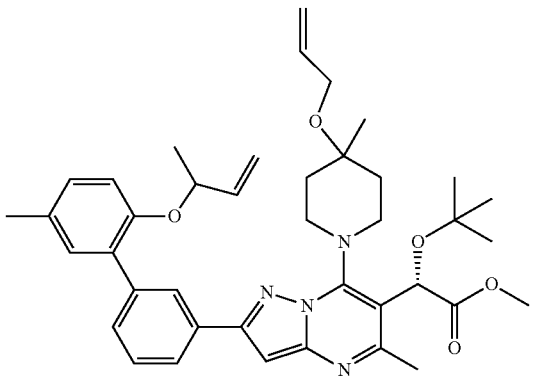

(2S)-Methyl 2-(7-(4-(allyloxy)-4-methylpiperidin-1 yl)-2-(2'-(but-3-en-2-yloxy)-5'-methyl-[1,1'-biphenyl]-3-yl)-5-methylpyrazolo[1,5-a]pyrimidin-6-yl)-2-(tert-butoxy)acetate: Intermediate 122 was prepared using intermediate 89 and but-3-en-2-ol by following the procedure to prepare intermediate 70. LCMS (M+1)=667.5.

Intermediate 123

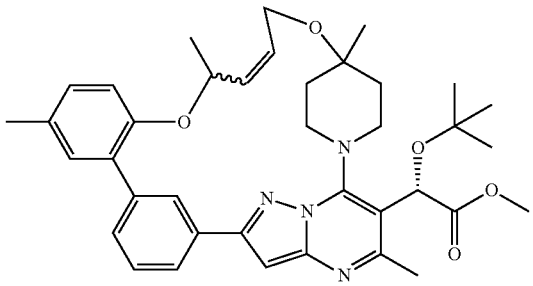

Methyl (2S)-2-(tert-butoxy)-2-[4,17,22,27-tetramethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18,23-undecaen-3-yl]acetate: Intermediate 123 was prepared by using intermediate 122 by following the procedure to prepare intermediate 71. LCMS (M+1)=639.2.

EXAMPLE 58 AND 59

A mixture of intermediate 123 (116 mg, 0.182 mmol), NaOH (0.908 mL, 0.908 mmol) in MeOH (2 mL) was refluxed for 2 h. It was then filtered and purified by prep HPLC to afford two products.

EXAMPLE 58

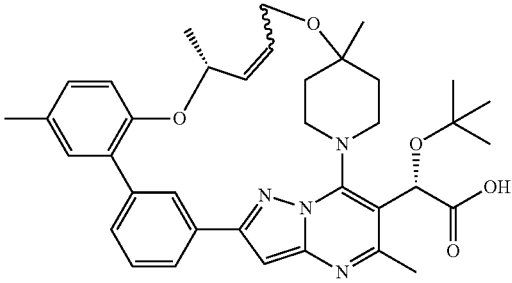 [SMILES: Cc1ccc2c(c1)-c1cccc(c1)-c1cc3nc(C)c([C@H](OC(C)(C)C)C(=O)O)c(n3n1)N1CCC(C)(CC1)OCC=C[C@@H](C)O2]

(2S)-2-(tert-Butoxy)-2-[(22R)-4,17,22,2,7-tetramethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18,23-undecaen-3-yl]acetic acid: Obtained 11.8 mg (10%) as a white solid. $^1$H NMR (400 MHz, CDCl$_3$) δ 8.64 (s, 1H), 7.70 (dt, J=7.7, 1.3 Hz, 1H), 7.55-7.48 (m, 1H), 7.47-7.41 (m, 1H), 7.17 (d, J=2.0 Hz, 1H), 7.07 (dd, J=8.3, 1.8 Hz, 1H), 6.86-6.77 (m, 2H), 6.10-5.92 (m, 3H), 5.02-4.86 (m, 1H), 4.63 (t, J=11.4 Hz, 1H), 4.16-3.93 (m, 3H), 3.26-3.13 (m, 1H), 2.73-2.60 (m, 4H), 2.34 (s, 3H), 2.08-1.96 (m, 1H), 1.92-1.82 (m, 1H), 1.74 (td, J=13.1, 4.6 Hz, 1H), 1.62 (td, J=13.4, 4.4 Hz, 1H), 1.30 (s, 9H), 1.28 (s, 3H), 1.26 (d, J=6.3 Hz, 3H). LCMS (M+1)=625.5.

EXAMPLE 59

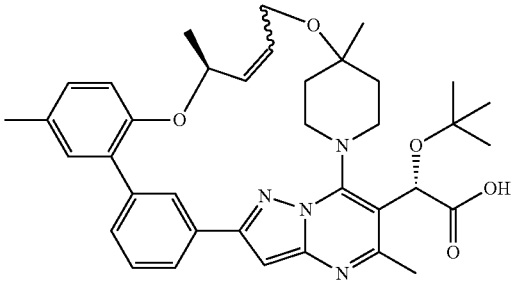 [SMILES: Cc1ccc2c(c1)-c1cccc(c1)-c1cc3nc(C)c([C@H](OC(C)(C)C)C(=O)O)c(n3n1)N1CCC(C)(CC1)OCC=C[C@H](C)O2]

(2S)-2-(tert-Butoxy)-2-[(22S)-4,17,22,27-tetramethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18,23-undecaen-3-yl]acetic acid: Obtained 10.3 mg (8.6%) as a white solid. $^1$H NMR (400 MHz, CDCl$_3$) δ 8.64 (s, 1H), 7.78-7.73 (m, 1H), 7.50 (t, J=7.7 Hz, 1H), 7.42-7.38 (m, 1H), 7.14 (d, J=2.0 Hz, 1H), 7.08 (dd, J=8.4, 1.9 Hz, 1H), 6.94-6.88 (m, 2H), 6.26 (dd, J=15.6, 7.3 Hz, 1H), 6.03 (br. s., 1H), 5.94 (dt, J=15.6, 3.7 Hz, 1H), 5.03 (quin, J=6.5 Hz, 1H), 4.82 (t, J=11.7 Hz, 1H), 4.05-3.89 (m, 3H), 3.36 (d, J=11.0 Hz, 1H), 2.73 (d, J=11.8 Hz, 1H), 2.62 (s, 3H), 2.34 (s, 3H), 1.95 (t, J=13.7 Hz, 2H), 1.75-1.55 (m, 2H), 1.32-1.23 (m, 15H). LCMS (M+H)=625.5.

EXAMPLE 60

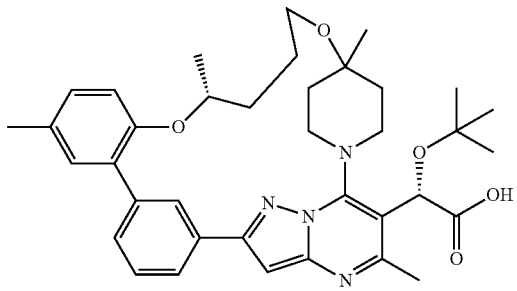 [SMILES: Cc1ccc2c(c1)-c1cccc(c1)-c1cc3nc(C)c([C@H](OC(C)(C)C)C(=O)O)c(n3n1)N1CCC(C)(CC1)OCCC[C@@H](C)O2]

(2S)-2-(tert-Butoxy)-2-[(22R)-4,17,22,2,7-tetramethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18-decaen-3-yl]acetic acid: Example 60 was prepared using example 58 by following the procedure to prepare example 21. $^1$H NMR (500 MHz, DMSO-d$_6$) δ 8.23 (s, 1H), 7.74 (d, J=7.6 Hz, 1H), 7.55 (t, J=7.6 Hz, 1H), 7.41 (d, J=7.9 Hz, 1H), 7.17-7.06 (m, 2H), 7.01 (d, J=8.2 Hz, 1H), 6.89 (s, 1H), 5.86 (s, 1H), 4.62-4.46 (m, 1H), 4.28 (t, J=12.2 Hz, 1H), 3.77 (d, J=7.0 Hz, 2H), 3.12 (d, J=11.3 Hz, 2H), 2.65 (d, J=10.7 Hz, 1H), 2.55 (s, 3H), 2.27 (s, 3H), 2.18 (br. s., 1H), 2.02 (d, J=12.8 Hz, 1H), 1.83-1.68 (m, 4H), 1.63-1.51 (m, 2H), 1.21 (s, 3H), 1.20 (s, 9H), 1.15 (d, J=5.8 Hz, 3H). LCMS (M+H)=627.5.

EXAMPLE 61

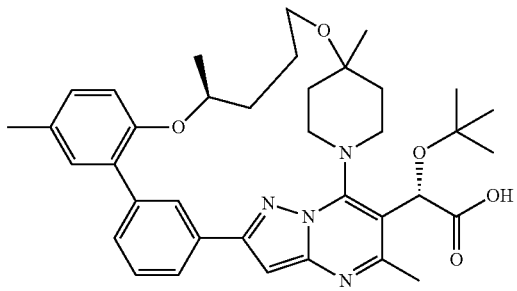 [SMILES: Cc1ccc2c(c1)-c1cccc(c1)-c1cc3nc(C)c([C@H](OC(C)(C)C)C(=O)O)c(n3n1)N1CCC(C)(CC1)OCCC[C@H](C)O2]

(2S)-2-(tert-Butoxy)-2-[(22S)-4,17,22,27-tetramethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18-decaen-3-yl]acetic acid: Example 61 was prepared using example 59 by following the procedure to prepare example 21. $^1$H NMR (500 MHz, DMSO-d$_6$) δ 8.47 (s, 1H), 7.87 (d, J=7.6 Hz, 1H), 7.52 (t, J=7.5 Hz, 1H), 7.36 (d, J=8.2 Hz, 1H), 7.17-7.06 (m, 3H), 7.03 (s, 1H), 5.65 (br. s., 1H), 4.61-4.43 (m, 2H), 3.60-3.20 (m, 7H), 2.70 (br. s., 1H), 2.56 (s, 3H), 2.28 (s, 3H), 2.12 (br. s., 1H), 1.96-1.46 (m, 7H), 1.19 (s, 3H), 1.15 (s, 9H). LCMS (M+H)=627.5.

Intermediate 124

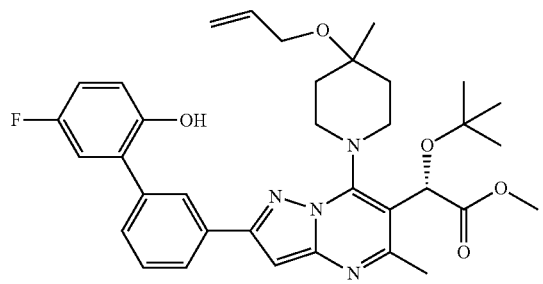

(S)-Methyl 2-(7-(4-(allyloxy)-4-methylpiperidin-1-A-2-(5'-fluoro-2'-hydroxy-[1,1'-biphenyl]-3-yl)-5-methylpyrazolo[1,5-a]pyrimidin-6-yl)-2-(tert-butoxy)acetate: Intermediate 124 was prepared by using intermediate 65 and 5-fluoro-2-hydroxyphenylboronic acid by following the procedure to prepare intermediate 69. $^1$H NMR (400 MHz, CDCl$_3$) δ 8.11 (t, J=1.6 Hz, 1H), 8.06 (d, J=7.8 Hz, 1H), 7.60 (t, J=7.7 Hz, 1H), 7.48 (d, J=7.6 Hz, 1H), 7.07 (dd, J=8.9, 2.3 Hz, 1H), 7.02-6.95 (m, 2H), 6.85 (s, 1H), 6.11-5.88 (m, 2H), 5.40 (dd, J=17.1, 2.0 Hz, 1H), 5.33 (s, 1H), 5.11 (br. s., 1H), 5.00-2.50 (m, 4 H), 4.02 (d, J=5.1 Hz, 2H), 3.76 (s, 3H), 2.63 (s, 3H), 2.11-1.91 (m, 2H), 1.73 (br. s., 1H), 1.37 (br. s., 3H), 1.29-1.25 (s, 9H). LCMS (M+1)=617.2.

Intermediate 125

(S)-Methyl 2-(7-(4-(allyloxy)-4-methylpiperidin-1-yl)-2-(2'-(allyloxy)-5'-fluoro-[1,1'-biphenyl]-3-yl)-5-methylpyrazolo[1,5-a]pyrimidin-6-yl)-2-(tert-butoxy)acetate: Intermediate 125 was prepared using intermediate 124 by following the procedure to prepare intermediate 87. $^1$H NMR (400 MHz, CDCl$_3$) δ 8.18 (s, 1H), 8.05 (d, J=7.3 Hz, 1H), 7.61-7.56 (m, 1H), 7.54-7.48 (m, 1H), 7.17 (dd, J=9.0, 2.9 Hz, 1H), 7.07-6.99 (m, 1H), 6.99-6.94 (m, 1H), 6.84 (s, 1H), 6.11-5.89 (m, 3H), 5.46-5.35 (m, 2H), 5.20 (dq, J=10.6, 1.5 Hz, 1H), 5.17-5.01 (m, 1H), 5.00-2.50 (m, 4H), 4.53 (dt, J=4.8, 1.6 Hz, 2H), 4.02 (d, J=4.9 Hz, 2H), 3.76 (s, 3H), 2.63 (s, 3H), 2.06-1.91 (m, 3H), 1.74 (br. s., 1H), 1.38 (br. s., 3H), 1.28-1.22 (s, 9H). LCMS (M+1)=657.3.

Intermediate 126

Methyl (2S)-2-(tert-butoxy)-2-[17-fluoro-4,27-dimethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18,23-undecaen-3-yl]acetate: Intermediate 126 was prepared using intermediate 125 by following the procedure to prepare intermediate 71. LCMS (M+1)=629.3. It's a mixture of cis/trans isomers.

EXAMPLE 62

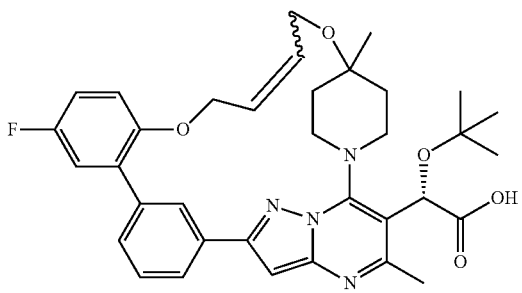 [SMILES: Cc1nc2cc3nn2c(c1[C@H](OC(C)(C)C)C(=O)O)N1CCC(C)(CC1)OCC=CCOc1ccc(F)cc1-c1cccc-3c1]

(2S)-2-(tert-Butoxy)-2-[(17-fluoro-4,2,7-dimethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32), 11, 13, 15(20),16,18,23-undecaen-3-yl]acetic acid: Example 62 was prepared using intermediate 126 by following the procedure to prepare example 20. $^1$H NMR (500 MHz, DMSO-d$_6$) δ 8.66 (s, 1H), 7.93 (d, J=7.9 Hz, 1H), 7.60-7.52 (m, 1H), 7.48 (d, J=7.6 Hz, 1H), 7.26 (dd, J=9.5, 2.4 Hz, 1H), 7.21-7.13 (m, 2H), 7.08 (s, 1H), 6.46 (d, J=5.8 Hz, 1H), 5.71 (s, 1H), 4.78-4.67 (m, 1H), 4.66-4.58 (m, 1H), 4.16-4.06 (m, 1H), 3.96-3.89 (m, 1H), 3.50-3.43 (m, 1H), 3.37 (br. s., 1H), 3.20-3.12 (m, 1H), 2.78 (br. s., 1H), 2.55 (s, 3H), 2.34 (td, J=12.1, 6.1 Hz, 1H), 1.89 (br. s., 1H), 1.85-1.79 (m, 1H), 1.75-1.67 (m, 1H), 1.38 (s, 3H), 1.18 (s, 9H). LCMS (M+H)=615.2.

Intermediate 127

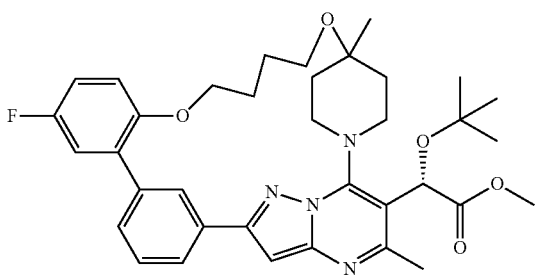

Methyl (2S)-2-(tert-butoxy)-2-{17-fluoro-4,27-dimethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15 (20),16,18-decaen-3-yl}acetate: Intermediate 127 was prepared using intermediate 126 by following the procedure to prepare intermediate 78. $^1$H NMR (400 MHz, CDCl$_3$) δ 8.50 (s, 1H), 7.72 (d, J=7.8 Hz, 1H), 7.62-7.51 (m, 1H), 7.44 (d, J=8.1 Hz, 1H), 7.14 (dd, J=9.3, 3.2 Hz, 1H), 7.07-6.91 (m, 2H), 6.85 (br. s., 1H), 5.98 (br. s., 1H), 4.55 (t, J=12.6 Hz, 1H), 4.16-4.02 (m, 2H), 3.99-3.86 (m, 1H), 3.82-3.71 (m, 3H), 3.59-3.50 (m, 1H), 3.43 (td, J=8.7, 3.2 Hz, 1H), 3.21 (s, 1H), 2.94-2.76 (m, 1H), 2.68 (s, 3H), 2.46-2.28 (m, 1H), 2.27-2.00 (m, 2H), 1.96-1.75 (m, 3H), 1.72-1.62 (m, 2H), 1.31 (s, 3H), 1.27 (s, 9H). LCMS (M+1)=631.3.

EXAMPLE 63

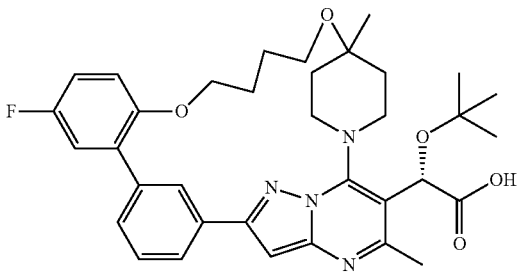 [SMILES: Cc1nc2cc3nn2c(c1[C@H](OC(C)(C)C)C(=O)O)N1CCC(C)(CC1)OCCCCOc1ccc(F)cc1-c1cccc-3c1]

(2S)-2-(tert-Butoxy)-2-{17-fluoro-4,27-dimethyl-21,26-dioxa-1,5,7,8-tetraazahexacyclo[25.2.2.1$^{6,9}$.1$^{10,14}$.0$^{2,7}$.0$^{15,20}$]tritriaconta-2,4,6(33),8,10(32),11,13,15(20),16,18-decaen-3-yl}acetic acid: Example 63 was prepared using intermediate 127 by following the procedure to prepare example 28. $^1$H NMR (500 MHz, DMSO-d$_6$) δ 8.41 (s, 1H), 7.82 (d, J=7.9 Hz, 1H), 7.57 (t, J=7.6 Hz, 1H), 7.48 (d, J=7.6 Hz, 1H), 7.22 (d, J=9.5 Hz, 1H), 7.17 (d, J=6.1 Hz, 2H), 6.95 (s, 1H), 5.73 (s, 1H), 4.40 (t, J=11.6 Hz, 1H), 4.12-4.05 (m, 2H), 3.70-3.63 (m, 1H), 3.46-3.42 (m, 1H), 3.37 (dd, J=9.0, 5.6 Hz, 1H), 3.31 (d, J=9.8 Hz, 1H), 2.74 (s, 1H), 2.54 (s, 3H), 2.15 (br. s., 1H), 2.01 (d, J=12.8 Hz, 2H), 1.80 (br. s., 2H), 1.67 (dd, J=8.9, 4.6 Hz, 1H), 1.61-1.47 (m, 2H), 1.21 (s, 3H), 1.17 (s, 9H). LCMS (M+H)=617.4.

Intermediate 128

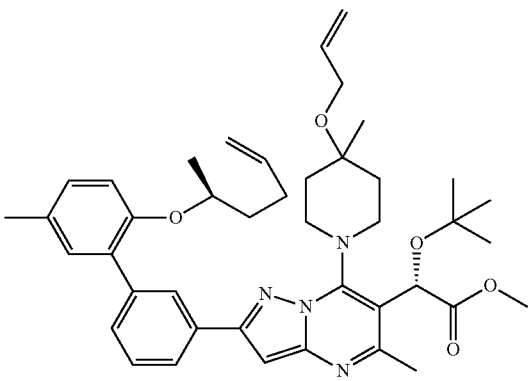

(S)-Methyl 2-(7-(4-(allyloxy)-4-methylpiperidin-1-yl)-2-(2'-((S)-hex-5-en-2-yloxy)-5'-methyl-[1,1'-biphenyl]-3-yl)-5-methylpyrazolo[1,5-a]pyrimidin-6-yl)-2-(tert-butoxy)acetate: Intermediate 128 was prepared using intermediate 89 and (R)-hex-5-en-2-ol by following the procedure to prepare intermediate 78. $^1$H NMR (500 MHz, CDCl$_3$) δ 8.14 (s, 1H), 8.03 (d, J=6.5 Hz, 1H), 7.57 (d, J=7.7 Hz, 1H), 7.53-7.44 (m, 1H), 7.24 (d, J=1.9 Hz, 1H), 7.13 (dd, J=8.3, 1.7 Hz, 1H), 6.93 (d, J=8.4 Hz, 1H), 6.84 (s, 1H), 6.03 (ddt, J=17.2, 10.4, 5.2 Hz, 2H), 5.77-5.69 (m, 1H), 5.42 (d, J=15.6 Hz, 1H), 5.14 (d, J=8.7 Hz, 1H), 5.05 (dd, J=17.3, 1.7 Hz, 1H), 5.00-2.50 (m, 4H), 4.94-4.85 (m, 1H), 4.31 (dq, J=12.1, 6.1 Hz, 1H), 4.03 (d, J=4.9 Hz, 2H), 3.76 (s, 3H), 2.63 (s, 3H), 2.38 (s, 3H), 2.17-1.94 (m, 5H), 1.76 (ddt, J=13.5, 8.5, 6.6 Hz, 1H), 1.43-1.37 (m, 3H), 1.33-1.25 (m, 11H), 1.25-1.20 (m, 3H). LCMS (M+1)=695.4.

Intermediate 129

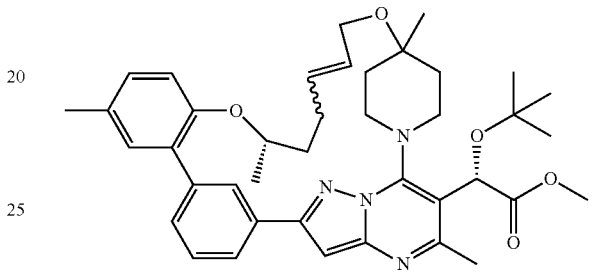

Methyl (2S)-2-(tert-butoxy)-2-[(22S)-4,17,22,29-tetramethyl-21,28-dioxa-1,5,7,8-tetraazahexacyclo[27.2.2.1$^{6,9}$.1$^{10,14}$.0$^{2,7}$.0$^{15,20}$]pentatriaconta-2,4,6(35),8,10(34), 11,13,15(20),16,18,25-undecaen-3-yl]acetate: Intermediate 129 was prepared using intermediate 128 by following the procedure to prepare intermediate 116. LCMS (M+1)=667.4. It's a mixture of cis/trans product.

EXAMPLE 64

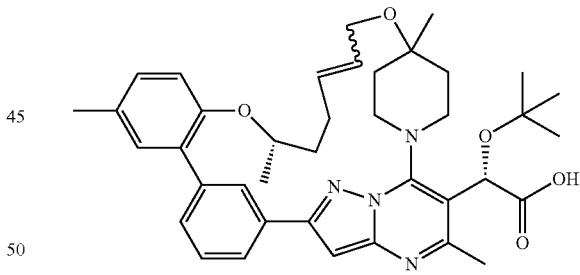

(2S)-2-(tert-Butoxy)-2-[(22S)-4,17,22,29-tetramethyl-21,28-dioxa-1,5,7,8-tetraazahexacyclo[27.2.2.1$^{6,9}$.1$^{10,14}$.0$^{2,7}$.0$^{15,20}$]pentatriaconta-2,4,6(35),8,10(34), 11, 13, 15(20),16,18,25-undecaen-3-yl]acetic acid: Example 64 was prepared using intermediate 129 by following the procedure to prepare example 20. $^1$H NMR (400 MHz, CDCl$_3$) δ 7.95 (t, J=1.5 Hz, 1H), 7.67 (dt, J=7.5, 1.4 Hz, 1H), 7.54-7.49 (m, 1H), 7.48-7.42 (m, 1H), 7.14-7.06 (m, 2H), 7.05-7.00 (m, 1H), 6.78 (s, 1H), 6.00 (br. s., 1H), 5.76-5.62 (m, 1H), 5.47 (dt, J=15.5, 5.5 Hz, 1H), 4.82 (t, J=11.4 Hz, 1H), 4.35-4.25 (m, 1H), 3.85-3.74 (m, 3H), 3.27 (d, J=11.0 Hz, 2H), 2.65 (s, 3H), 2.34 (s, 3H), 2.03-1.90 (m, 2H), 1.87-1.72 (m, 2H), 1.72-1.61 (m, 2H), 1.60-1.47 (m, 1H), 1.42-1.32 (m, 1H), 1.31-1.28 (m, 9H), 1.27-1.24 (m, 6H). LCMS (M+1)=653.3.

Intermediate 130

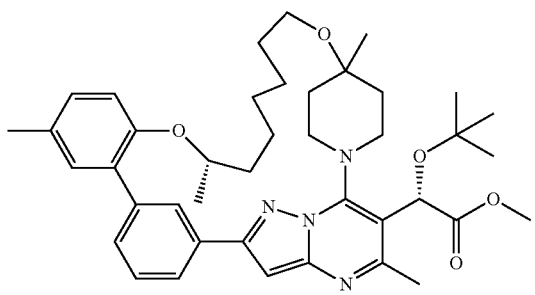

Methyl (2S)-2-(tert-butoxy)-2-[(22S)-4,17,22,29-tetramethyl-21,28-dioxa-1,5,7,8-tetraazahexacyclo [27.2.2.1$^{6,9}$.1$^{10,14}$.0$^{2,7}$.0$^{15,20}$]pentatriaconta-2,4,6(35),8,10 (34),11,13,15(20),16,18-decaen-3-yl]acetate: Intermediate 130 was prepared using intermediate 129 by following the procedure to prepare intermediate 117. $^1$H NMR (400 MHz, CDCl$_3$) δ 8.10-8.05 (m, 1H), 7.73-7.65 (m, 1H), 7.48-7.45 (m, 2H), 7.16-7.10 (m, 2H), 7.05-7.00 (m, 1H), 6.79 (s, 1H), 5.99 (s, 1 H), 4.70-4.60 (m, 1H), 4.28-4.19 (m, 1H), 3.83-3.70 (m, 4H), 3.41-3.32 (m, 1H), 3.31-3.22 (m, 1H), 3.10 (d, J=11.5 Hz, 1H), 2.96 (d, J=12.2 Hz, 1H), 2.62 (s, 3H), 2.36 (s, 3H), 2.02-1.90 (m, 2H), 1.76-1.14 (m, 10H), 1.26 (s, 9H), 1.24 (s, 3H), 1.12 (d, J=6.1 Hz, 3H). LCMS (M+1)=669.5.

EXAMPLE 65

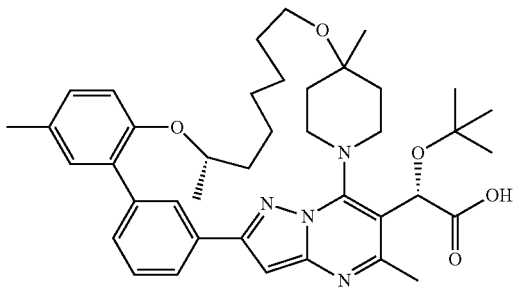 [SMILES: Cc1ccc2c(c1)-c1cccc(c1)-c1cc3nc(C)c([C@H](OC(C)(C)C)C(=O)O)c(n3n1)N1CCC(C)(CC1)OCCCCCC[C@H](C)O2]

(2S)-2-(tert-Butoxy)-2-[(22S)-4,17,22,29-tetra-methyl-21,28-dioxa-1,5,7,8-tetraazahexacyclo[27.2.2. 1$^{6,9}$.1$^{10,14}$.0$^{2,7}$.0$^{15,20}$]pentatriaconta-2,4, 6(35), 8, 10(34), 11, 13, 15 (20),16,18-decaen-3-yl]acetic acid: Example 65 was prepared using intermediate 130 by following the procedure to prepare example 28. $^1$H NMR (400 MHz, CDCl$_3$) δ 8.12 (s, 1H), 7.74-7.66 (m, 1H), 7.51-7.41 (m, 2H), 7.18-7.08 (m, 2H), 7.06-6.99 (m, 1H), 6.79 (s, 1H), 5.88 (s, 1H), 4.71-4.58 (m, 1H), 4.23 (sxt, J=5.9 Hz, 1H), 3.81-3.69 (m, 1H), 3.49-3.41 (m, 1H), 3.41-3.31 (m, 1H), 3.31-3.20 (m, 1H), 3.03 (d, J=12.0 Hz, 1H), 2.62 (s, 3H), 2.36 (s, 3H), 2.02-1.89 (m, 2H), 1.75-1.30 (m, 8H), 1.26 (s, 9H), 1.23 (s, 3H), 1.21-1.17 (m 2 H), 1.10 (d, J=6.1 Hz, 3H). LCMS (M+1)=655.4.

Intermediate 131

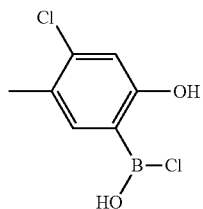

(4-Chloro-2-hydroxy-5-methylphenyl) boronic acid: A mixture of (4-chloro-2-methoxy-5-methylphenyl)boronic acid (100 mg, 0.499 mmol) in DCM (2 mL) was cooled to 0° C. and BBr$_3$ (0.142 mL, 1.497 mmol) was added. The mixture was then stirred at rt for 2 h. It was then poured into ice and extracted with EtOAc. The organic layer was dried over MgSO$_4$, filtered and concentrated to obtain 150 mg (97% yield, 60% pure) of the desired product as a brown solid. $^1$H NMR (400 MHz, CDCl$_3$) δ 7.59 (br. s., 1H), 7.11 (br. s., 1H), 4.30-4.11 (m, 1H), 4.01 (br. s., 1H), 2.37 (s, 3H).

Intermediate 132

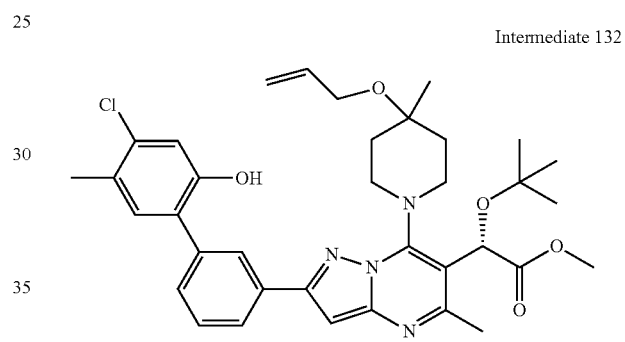

(S)-Methyl 2-(7-(4-(allyloxy)-4-methylpiperidin-1-yl)-2-(4'-chloro-2'-hydroxy-5'-methyl-[1,1'-biphenyl]-3-yl)-5-methylpyrazolo[1,5-a]pyrimidin-6-yl)-2-(tert-butoxy)acetate: Intermediate 132 was prepared using intermediates 65 and 131 by following the procedure to prepare intermediate 89. $^1$H NMR (400 MHz, CDCl$_3$) δ 8.11-7.99 (m, 2H), 7.58 (t, J=7.7 Hz, 1H), 7.48-7.37 (m, 2H), 7.19 (s, 1H), 7.07 (s, 1H), 6.85 (br. s., 1H), 6.13-5.86 (m, 2H), 5.40 (dd, J=17.2, 1.8 Hz, 1H), 5.50-2.50 (m, 4 H), 5.10 (br. s., 1H), 4.02 (d, J=5.1 Hz, 2H), 3.76 (s, 3H), 2.63 (s, 3H), 2.37 (s, 3H), 2.10-1.90 (m, 2H), 1.74 (br. s., 1H), 1.63-1.65 (m, 1H), 1.37 (br. s., 3H), 1.30-1.23 (s, 9H). LCMS (M+1)=647.4.

Intermediate 133

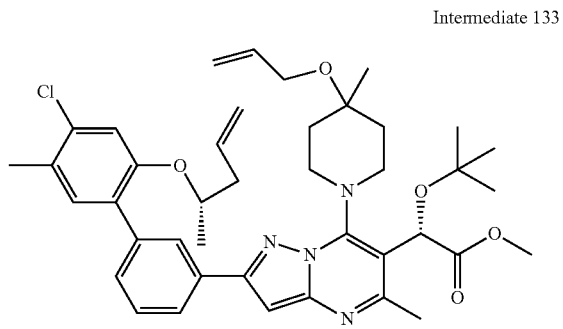

(S)-Methyl 2-(7-(4-(allyloxy)-4-methylpiperidin-1-yl)-2-(4'-chloro-5'-methyl-2'-((S)-pent-4-en-2-yloxy)-[1,1'-biphenyl]-3-yl)-5-methylpyrazolo[1,5-a]pyrimidin-6-yl)-2-(tert-butoxy)acetate: Intermediate 133 was prepared using intermediate 132 and (R)-pent-4-en-2-ol by following the procedure to prepare intermediate 115. $^1$H NMR (400 MHz, CDCl$_3$) δ 8.11 (s, 1H), 8.03 (d, J=6.6 Hz, 1H), 7.57-7.43 (m, 2H), 7.27 (s, 1H), 7.02 (s, 1H), 6.84 (s, 1H), 6.14-5.90 (m, 2H), 5.80-5.72 (m, 1H), 5.42 (d, J=17.1 Hz, 1H), 5.13 (d, J=10.5 Hz, 1H), 5.05 (d, J=7.6 Hz, 1H), 5.00-2.50 (m, 4H), 5.02 (s, 1H), 4.39-4.32 (m, 1H), 4.05-3.97 (m, 2H), 3.75 (s, 3H), 2.62 (s, 3H), 2.47-2.34 (m, 4H), 2.29 (dt, J=14.0, 6.8 Hz, 1H), 2.09-1.88 (m, 3H), 1.74 (br. s., 1H), 1.41-1.36 (m, 3H), 1.29-1.24 (m, 12H). LCMS (M+1)=715.4.

Intermediate 134

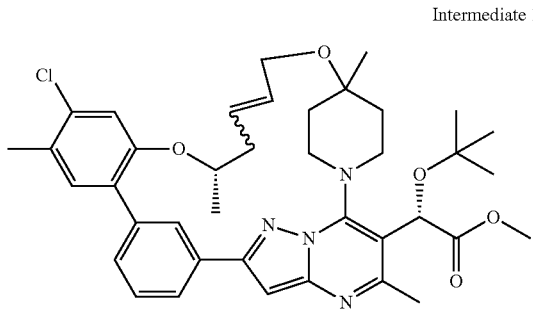

Methyl (2S)-2-(tert-butoxy)-2-[(22S)-18-chloro-4,17,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetate: Intermediate 134 was prepared using intermediate 133 by following the procedure to prepare intermediate 116. LCMS (M+1)=687.4. It's a mixture of cis/trans isomers.

EXAMPLE 66

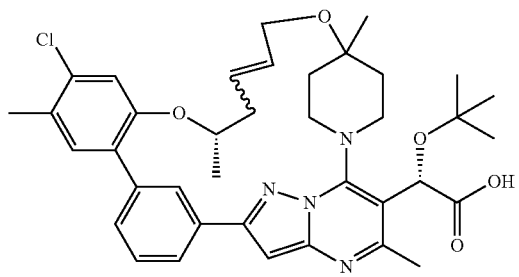 [SMILES: Cc1cc2c(cc1Cl)O[C@@H](C)CC=CCOC1(C)CCN(CC1)c1c([C@H](OC(C)(C)C)C(=O)O)c(C)nc3cc(nn13)-c1cccc-2c1]

(2S)-2-(tert-Butoxy)-2-[(22S)-18-chloro-4,17,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetic acid: Example 66 was prepared using intermediate 134 by following the procedure to prepare example 20. $^1$H NMR (500 MHz, DMSO-d$_6$) δ 8.39 (s, 1H), 7.96 (d, J=7.6 Hz, 1H), 7.53 (t, J=7.8 Hz, 1H), 7.31 (d, J=7.6 Hz, 1H), 7.26-7.17 (m, 2H), 7.11 (s, 1H), 6.25 (br. s., 1H), 5.75-5.62 (m, 2H), 4.75 (t, J=12.1 Hz, 1H), 4.58 (br. s., 1H), 4.03-3.84 (m, 2H), 3.56-3.49 (m, 1H), 3.40-2.50 (m, 1 H), 2.75 (d, J=9.5 Hz, 1H), 2.51 (br. s., 3H), 2.35-2.26 (m, 4H), 2.16 (br. s., 1H), 2.03 (d, J=13.7 Hz, 1H), 1.85 (d, J=12.5 Hz, 1H), 1.69-1.55 (m, 2H), 1.22 (s, 3H), 1.17 (s, 9H), 1.04 (d, J=5.8 Hz, 3H). LCMS (M+1)=673.3.

Intermediate 135

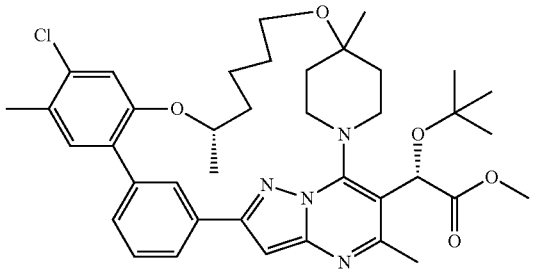

Methyl (2S)-2-(tert-butoxy)-2-[(22S)-18-chloro-4,17,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4, 6(34), 8,10(33), 11, 13, 15 (20),16,18-decaen-3-yl]acetate: Intermediate 135 was prepared using intermediate 134 by following the procedure to prepare intermediate 117. $^1$H NMR (400 MHz, CDCl$_3$) δ 8.55 (s, 1H), 7.81 (d, J=7.8 Hz, 1H), 7.49 (t, J=7.7 Hz, 1H), 7.31 (d, J=7.8 Hz, 1H), 7.19 (s, 1H), 7.00 (s, 1H), 6.90 (s, 1H), 5.90 (s, 1H), 4.63 (t, J=11.7 Hz, 1H), 4.58-4.48 (m, 1H), 3.83-3.72 (m, 4H), 3.55-3.48 (m, 1H), 3.39 (td, J=7.8, 2.9 Hz, 1H), 3.25 (d, J=11.7 Hz, 1H), 2.88 (d, J=12.0 Hz, 1H), 2.60 (s, 3H), 2.37 (s, 3H), 2.08-1.28 (m, 10H) 1.27 (s, 3H), 1.25 (s, 9H), 1.18 (d, J=5.9 Hz, 3H). LCMS (M+1)=689.4.

EXAMPLE 67

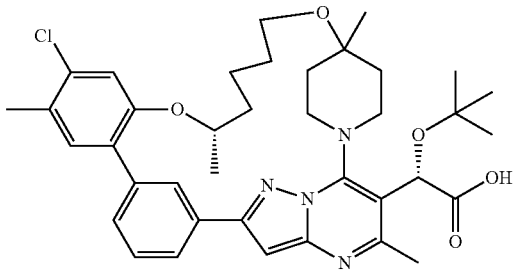 [SMILES: Cc1cc2c(cc1Cl)O[C@@H](C)CCCCOC1(C)CCN(CC1)c1c([C@H](OC(C)(C)C)C(=O)O)c(C)nc3cc(nn13)-c1cccc-2c1]

(2S)-2-(tert-butoxy)-2-[(22S)-18-chloro-4,17,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33), 11, 13, 15 (20),16,18-decaen-3-yl]acetic acid: Example 67 was prepared using intermediate 135 by following the procedure to prepare example 28. $^1$H NMR (500 MHz, DMSO-d$_6$) δ 8.45 (s, 1H), 7.94 (d, J=7.9 Hz, 1H), 7.52 (t, J=7.6 Hz, 1H), 7.33 (d, J=7.0 Hz, 1H), 7.27 (s, 1H), 7.23 (s, 1H), 7.10 (s, 1H), 5.66 (br. s., 1H), 4.68 (d, J=5.5 Hz, 1H), 4.48 (t, J=12.2 Hz, 1H), 3.75-3.00 (m, 4 H), 2.79 (d, J=10.7 Hz, 1H), 2.51 (br. s., 3H), 2.30 (s, 3H), 2.00-1.85 (m, 3H), 1.68 (br. s., 4H), 1.60-1.41 (m, 3H), 1.18 (s, 3H), 1.16 (s, 9H), 1.07 (d, J=5.8 Hz, 3H). LCMS (M+1)=675.3.

Intermediate 136

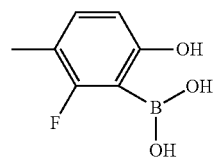

(2-Fluoro-6-hydroxy-3-methylphenyl)boronic acid: A mixture of (2-fluoro-6-methoxy-3-methylphenyl)boronic acid (200 mg, 1.087 mmol) was cooled to 0° C. and BBr$_3$ (0.308 mL, 3.26 mmol) was added. The mixture was then stirred at rt for 2 h. It was then poured into ice and extracted with EtOAc. The organic layer was dried over MgSO$_4$, filtered and concentrated to obtain 185 mg (95%) of the desired product as a white solid. $^1$H NMR (400 MHz, CDCl$_3$) δ 8.57 (s, 1H), 7.25-7.15 (m, 1H), 6.71-6.61 (m, 1H), 5.76-5.53 (m, 2H), 2.20 (d, J=2.0 Hz, 3H). LCMS (M+23)=193.

Intermediate 137

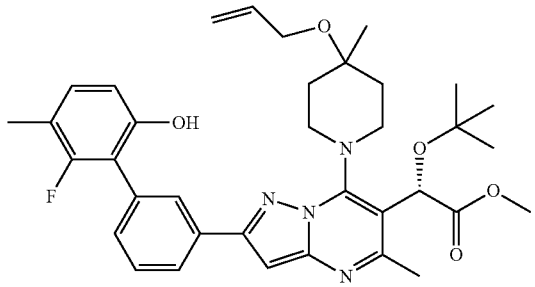

(S)-Methyl 2-(7-(4-(allyloxy)-4-methylpiperidin-1-yl)-2-(2'-fluoro-6'-hydroxy-3'-methyl-[1,1'-biphenyl]-3-yl)-5-methylpyrazolo[1,5-a]pyrimidin-6-yl)-2-(tert-butoxy)acetate: Intermediate 137 was prepared using intermediates 65 and 136 by following the procedure to prepare intermediate 89. $^1$H NMR (400 MHz, CDCl$_3$) δ 8.09 (d, J=7.3 Hz, 1H), 8.03 (s, 1H), 7.61 (t, J=7.7 Hz, 1H), 7.44 (d, J=7.6 Hz, 1H), 7.11 (t, J=8.4 Hz, 1H), 6.83 (s, 1H), 6.77 (d, J=8.3 Hz, 1H), 6.17-5.84 (m, 2H), 5.50-2.50 (m, 4 H), 5.40 (dd, J=17.1, 1.5 Hz, 1H), 5.27 (brs, 1 H), 5.12 (br. s., 1H), 4.01 (d, J=4.9 Hz, 2H), 3.76 (s, 3H), 2.62 (s, 3H), 2.28 (d, J=1.7 Hz, 3H), 2.07-1.92 (m, 2H), 1.75 (d, J=7.3 Hz, 1H), 1.59 (s, 1H), 1.36 (br. s., 3H), 1.27 (s, 9H). LCMS (M+1)=631.3.

Intermediate 138

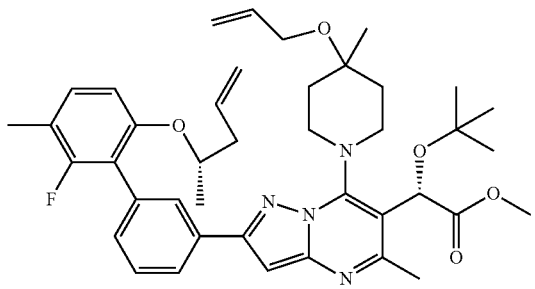

(S)-Methyl 2-(7-(4-(allyloxy)-4-methylpiperidin-1-yl)-2-(2'-fluoro-3'-methyl-6'-((S)-pent-4-en-2-yloxy)-[1,1'-biphenyl]-3-yl)-5-methylpyrazolo[1,5-a]pyrimidin-6-yl)-2-(tert-butoxy)acetate: Intermediate 138 was prepared using intermediate 137 and (R)-pent-4-en-2-ol by following the procedure to prepare intermediate 115. LCMS (M+1)=699.4. It's a mixture of cis/trans mixture.

Intermediate 139

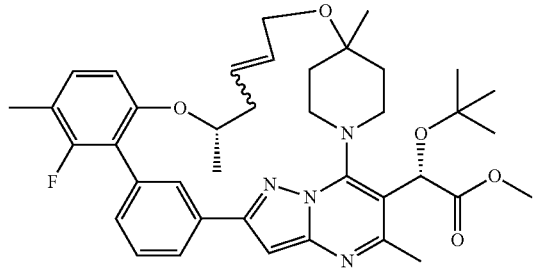

Methyl (2S)-2-(tert-butoxy)-2-[(22S)-16-fluoro-4,17,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10 (33), 11,13,15(20),16,18,24-undecaen-3-yl]acetate: Intermediate 139 was prepared using intermediate 138 by following the procedure to prepare intermediate 116. LCMS (M+1)=671.4. The product is a mixture of cis/trans product.

EXAMPLE 68 AND 69

Saponification of intermediate 139 by following the procedure to prepare example 20 afforded two compounds.

EXAMPLE 68

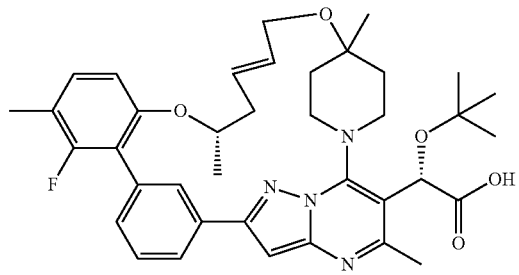 [SMILES: Cc1ccc2c(c1F)-c1cccc(c1)-c1cc3nc(C)c([C@H](OC(C)(C)C)C(=O)O)c(n3n1)N1CCC(C)(CC1)OC/C=C/C[C@H](C)O2]

(2S)-2-(tert-Butoxy)-2-[(22S,$^{24}$E)-16-fluoro-4,17,22,28-tetramethyl-21,27-dioxa-1,5,7,8-tetraazahexacyclo[26.2.2.1$^{6,9}$.1$^{10,14}$. 0$^{2,7}$.0$^{15,20}$]tetratriaconta-2,4,6(34),8,10 (33), 11, 13, 15 (20), 16,18,24-undecaen-3-yl]acetic acid: $^1$H NMR (500 MHz, DMSO-d$_6$) δ 8.17 (s, 1H), 7.95 (d, J=7.9 Hz, 1H), 7.52 (t, J=7.6 Hz, 1H), 7.32-7.17 (m, 2H), 7.08 (s, 1H), 6.93 (d, J=8.2 Hz, 1H), 6.20-6.04 (m, 1H), 5.74 (br. s., 1H), 5.64 (d, J=15.6 Hz, 1H), 4.76 (t, J=12.1 Hz, 1H), 4.52 (br. s., 1H), 3.97-3.80 (m, 2H), 3.54-3.47 (m, 1H), 3.40-3.20 (m, 1 H), 2.74 (d, J=10.1 Hz, 1H), 2.52 (br. s., 3H), 2.31-2.23 (m, 1H), 2.20 (s, 3H), 2.11 (br. s., 1H), 2.01 (d, J=13.7 Hz, 1H), 1.87 (d, J=12.2 Hz, 1H), 1.70-1.56 (m, 2H), 1.21 (s, 3H), 1.18 (s, 9H), 1.06 (d, J=5.8 Hz, 3H). LCMS (M+1)=657.4.

EXAMPLE 69

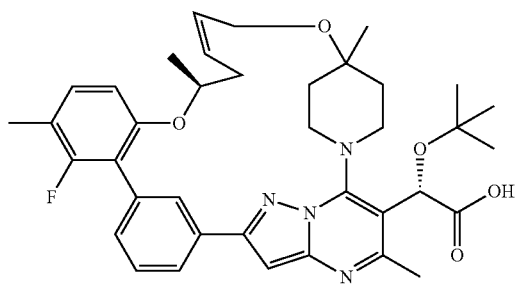 [SMILES: Cc1ccc2c(c1F)-c1cccc(c1)-c1cc3nc(C)c([C@H](OC(C)(C)C)C(=O)O)c(n3n1)N1CCC(C)(CC1)OC/C=C\C[C@H](C)O2]

(2S)-2-(tert-Butoxy)-2-[(22S,24Z)-16-fluoro-4,17,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetic acid: $^1$H NMR (500 MHz, DMSO-d$_6$) δ 8.22 (br. s., 1H), 7.89 (d, J=7.0 Hz, 1H), 7.52 (t, J=7.0 Hz, 1H), 7.35 (br. s., 1H), 7.22 (d, J=7.9 Hz, 1H), 7.05-6.92 (m, 2H), 5.78-5.59 (m, 2H), 5.53 (br. s., 1H), 4.59 (br. s., 1H), 4.27 (t, J=12.7 Hz, 1H), 3.96 (d, J=8.5 Hz, 1H), 3.79 (br. s., 1H), 3.74-3.15 (m, 2H), 3.04 (d, J=10.7 Hz, 1H), 2.82 (d, J=13.1 Hz, 1H), 2.52 (s, 3H), 2.46 (d, J=9.2 Hz, 1H), 2.21 (br. s., 3H), 2.06 (d, J=13.7 Hz, 1H), 1.79 (d, J=15.9 Hz, 2H), 1.54 (br. s., 1H), 1.21 (br. s., 3H), 1.15 (br. s., 12H). LCMS (M+1)=657.4.

EXAMPLE 70

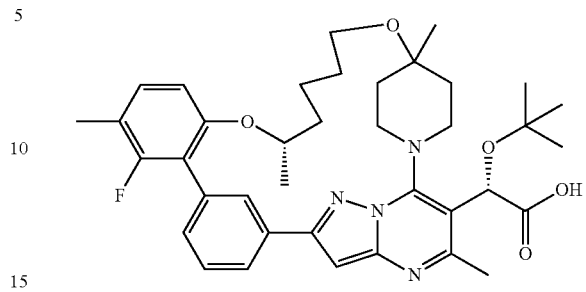

(2S)-2-(tert-Butoxy)-2-[(22S)-16-fluoro-4,17,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid: Example 70 was prepared using intermediate 140 by following the procedure to prepare example 20. $^1$H NMR (500 MHz, DMSO-d$_6$) δ 8.24 (s, 1H), 7.94 (d, J=7.3 Hz, 1H), 7.50 (t, J=7.9 Hz, 1H), 7.35-7.16 (m, 2H), 7.16-7.02 (m, 1H), 6.93 (d, J=8.5 Hz, 1H), 5.81-5.56 (m, 1H), 4.62 (br. s., 1H), 4.52 (t, J=11.7 Hz, 1H), 3.60-3.20 (m, 4H), 2.82-2.72 (m, 1H), 2.51 (br. s., 3H), 2.20 (s, 3H), 1.98-1.85 (m, 3H), 1.71-1.53 (m, 5H), 1.41 (br. s., 2H), 1.21-1.13 (m, 12H), 1.10-1.04 (m, 3H). LCMS (M+1)=659.6.

Intermediate 140

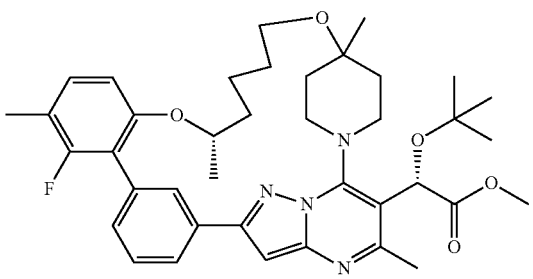

Methyl (2S)-2-(tert-butoxy)-2-[(22S)-16-fluoro-4,17,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate: Intermediate 140 was prepared using intermediate 139 by following the procedure to prepare intermediate 117. $^1$H NMR (400 MHz, CDCl$_3$) δ 8.35 (s, 1H), 7.89-7.77 (m, 1H), 7.58-7.44 (m, 1H), 7.34 (d, J=7.6 Hz, 1H), 7.11 (t, J=8.7 Hz, 1H), 6.73-6.66 (m, 1H), 5.94 (s, 1H), 4.65 (t, J=11.9 Hz, 1H), 4.59-4.44 (m, 1H), 3.83-3.72 (m, 4H), 3.48 (td, J=7.5, 3.3 Hz, 1H), 3.37 (td, J=7.7, 3.2 Hz, 1H), 3.20 (d, J=11.5 Hz, 1H), 2.85 (d, J=12.0 Hz, 1H), 2.61 (s, 3H), 2.27 (s, 3H), 2.03-1.89 (m, 3H), 1.83-1.70 (m, 3H), 1.66-1.43 (m, 5H), 1.41-1.29 (m, 3H), 1.25 (s, 9H), 1.19-1.12 (m, 3H). LCMS (M+1)=673.4.

Intermediate 141

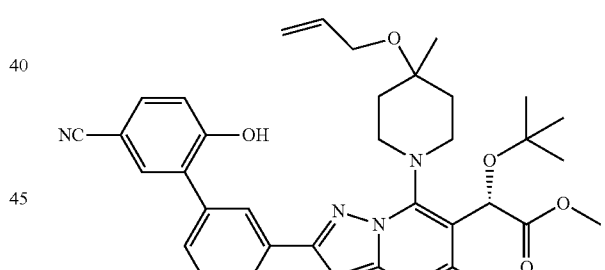

(S)-Methyl 2-(7-(4-(allyloxy)-4-methylpiperidin-1-yl)-2-(5'-cyano-2'-hydroxy-[1,1'-biphenyl]-3-yl)-5-methylpyrazolo[1,5-a]pyrimidin-6-yl)-2-(tert-butoxy)acetate: Intermediate 141 was prepared uaing intermediate 65 and 5-cyano-2-hydroxylphenylboronic acid by following the procedure to prepare intermediate 89. $^1$H NMR (400 MHz, CDCl$_3$) δ 8.13 (s, 1H), 8.08 (d, J=7.6 Hz, 1H), 7.66 (d, J=2.2 Hz, 1H), 7.63-7.56 (m, 2H), 7.44 (d, J=7.6 Hz, 1H), 7.11 (d, J=8.3 Hz, 1H), 6.85 (s, 1H), 6.23-5.74 (m, 2H), 5.41 (dd, J=17.1, 1.7 Hz, 1H), 5.10 (d, J=10.0 Hz, 1H), 5.00-2.50 (m, 4H), 4.02 (d, J=4.9 Hz, 2H), 3.77 (s, 3H), 2.61 (s, 3H), 2.10-1.94 (m, 2H), 1.74 (br. s., 1H), 1.60 (s, 1H), 1.37 (s, 3H), 1.26 (s, 9H). LCMS (M+1)=624.24.

Intermediate 142

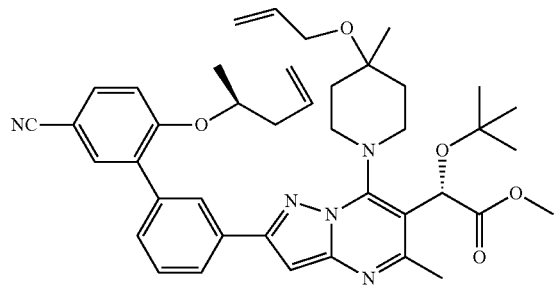

(S)-Methyl 2-(7-(4-(allyloxy)-4-methylpiperidin-1-yl)-2-(5'-cyano-2'-((S)-pent-4-en-2-yloxy)-[1,1'-biphenyl]-3-yl)-5-methylpyrazolo[1,5-a]pyrimidin-6-yl)-2-(tert-butoxy)acetate: Intermediate 142 was prepared using intermediate 141 and (R)-pent-4-en-2-ol by following the procedure to prepare intermediate 115. $^1$H NMR (400 MHz, CDCl$_3$) δ 8.15-8.03 (m, 2H), 7.70 (d, J=2.0 Hz, 1H), 7.64 (dd, J=8.6, 2.0 Hz, 1H), 7.53-7.47 (m, 2H), 7.06 (d, J=8.6 Hz, 1H), 6.84 (s, 1H), 6.09-5.90 (m, 2H), 5.82-5.71 (m, 1H), 5.41 (d, J=15.7 Hz, 1H), 5.07 (d, J=12.0 Hz, 3H), 5.00-2.50 (m, 4 H), 4.63-4.54 (m, 1H), 4.02 (d, J=4.9 Hz, 2H), 3.76 (s, 3H), 2.63 (s, 3H), 2.51-2.41 (m, 1H), 2.40-2.30 (m, 1H), 2.02 (d, J=10.5 Hz, 3H), 1.74 (br. s., 1H), 1.38 (br. s., 3H), 1.34 (d, J=6.1 Hz, 3H), 1.27 (s, 9H). LCMS (M+1)=692.4.

Intermediate 143

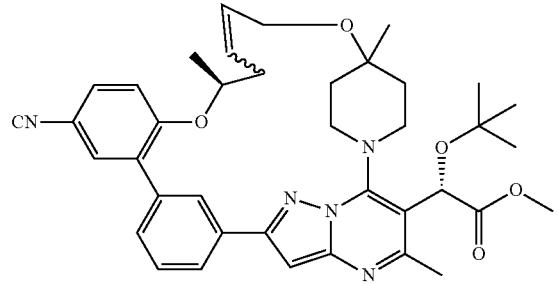

Methyl (2S)-2-(tert-butoxy)-2-[(22S)-17-isocyano-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13, 15 (20),16,18,24-undecaen-3-yl]acetate: Intermediate 142 was prepared using intermediate 142 following the procedure to prepare intermediate 116. LCMS (M+1)=664.4. The product is a mixture of cis/trans isomers.

EXAMPLES 71 AND 72

A mixture of intermediate 143 (12 mg, 0.018 mmol), NaOH (0.090 mL, 0.090 mmol) in MeOH (1 mL) heated at reflux for 3 h. Then the reaction mixture cooled, filtered and purified by prep HPLC to afford two compounds.

EXAMPLE 71

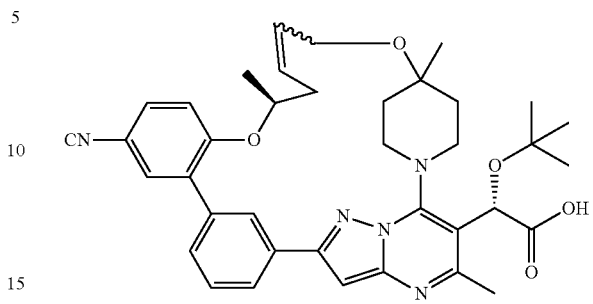

(2S)-2-(tert-Butoxy)-2-[(22S)-17-isocyano-4,22,28-trimethyl-21,27-dioxa-1,5,7,8-tetraazahexacyclo[26.2.2. 1$^{6,9}$.1$^{10,14}$.0$^{2,7}$.0$^{15,20}$]tetratriaconta-2,4,6(34),8,10(33),11, 13,15(20),16,18,24-undecaen-3-yl]acetic acid: Isolated 3.3 mg (27%) as a white solid. $^1$H NMR (500 MHz, DMSO-d$_6$) δ 8.42 (s, 1H), 8.01 (d, J=7.6 Hz, 1H), 7.83 (d, J=8.5 Hz, 1H), 7.73 (d, J=1.5 Hz, 1H), 7.57 (t, J=7.6 Hz, 1H), 7.43-7.33 (m, 2H), 7.08 (s, 1H), 6.26 (br. s., 1H), 5.70 (d, J=14.6 Hz, 1H), 5.52 (br. s., 1H), 4.81-4.69 (m, 2H), 4.02-3.93 (m, 1H), 3.91-3.84 (m, 1H), 3.59 (br. s., 1H), 3.51-3.42 (m, 1H), 2.77-2.69 (m, 1H), 2.52 (s, 3H), 2.42-2.32 (m, 1H), 2.23 (br. s., 1H), 2.00 (d, J=14.0 Hz, 1H), 1.85 (d, J=12.5 Hz, 1H), 1.68-1.52 (m, 2H), 1.21 (s, 3H), 1.15 (s, 9H), 1.10 (d, J=5.8 Hz, 3H). LCMS (M+1)=650.7.

EXAMPLE 72

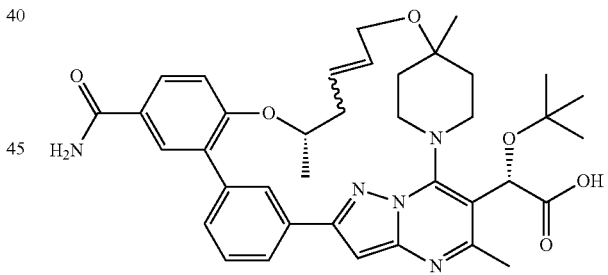

(2S)-2-(tert-Butoxy)-2-[(22S)-17-carbamoyl-4,22,27-trimethyl-21,26-dioxa-1,5,7,8-tetraazahexacyclo[25.2.2. 1$^{6,9}$.1$^{10,14}$.0$^{2,7}$.0$^{15,20}$]tritriaconta-2,4, 6(33), 8, 10(32), 11, 13, 15(20),16,18,23-undecaen-3-yl]acetic acid: Isolated 1.5 mg (12%) as a white solid. $^1$H NMR (500 MHz, DMSO-d6) δ 8.45 (s, 1H), 7.98 (d, J=7.9 Hz, 1H), 7.95-7.86 (m, 2H), 7.84 (s, 1H), 7.57 (t, J=7.5 Hz, 1H), 7.37 (d, J=7.6 Hz, 1H), 7.25 (d, J=8.5 Hz, 1H), 7.20 (br. s., 1H), 7.10 (s, 1H), 6.29 (br. s., 1H), 5.70 (d, J=15.6 Hz, 1H), 5.61 (br. s., 1H), 4.77 (t, J=11.7 Hz, 1H), 4.68 (br. s., 1H), 4.02-3.93 (m, 1H), 3.93-3.84 (m, 1H), 3.54-3.24 (m, 5H), 2.75 (br. s., 1H), 2.52 (br. s., 3H), 2.41-2.31 (m, 1H), 2.22 (br. s., 1H), 2.02 (d, J=13.7 Hz, 1H), 1.87 (d, J=13.1 Hz, 1H), 1.61 (d, J=12.8 Hz, 2H), 1.22 (s, 3H), 1.17 (s, 9H), 1.09 (d, J=5.5 Hz, 3H). LCMS (M+1)=668.6.

Intermediate 144

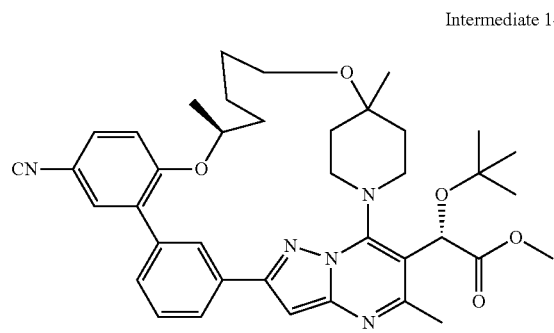

Methyl (2S)-2-(tert-butoxy)-2-[(22S)-17-isocyano-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4, 6(34), 8, 10(33), 11, 13, 15 (20),16,18-decaen-3-yl]acetate: A mixture of intermediate 143 (40 mg, 0.060 mmol), Pd/C (0.641 mg, 6.03 μmol) in MeOH (1 mL) was stirred at rt under a H$_2$ balloon for 3 h. It was then filtered. The filterate was concentrated and purified by biotage, eluting with 20% EtOAc/hexane to isolate 25 mg (62%) of the desired product as a white solid. $^1$H NMR (400 MHz, CDCl$_3$) δ 8.53 (s, 1H), 7.86 (d, J=8.1 Hz, 1H), 7.70-7.61 (m, 2H), 7.54 (t, J=7.7 Hz, 1H), 7.32 (m, 1 H), 7.05 (d, J=9.3 Hz, 1H), 6.92 (s, 1H), 5.90 (s, 1H), 4.74-4.58 (m, 2H), 3.87-3.70 (m, 4H), 3.59-3.49 (m, 1H), 3.47-3.36 (m, 1H), 3.26 (d, J=12.0 Hz, 1H), 2.99-2.85 (m, 1H), 2.61 (s, 3H), 2.08-1.93 (m, 3H), 1.93-1.69 (m, 5H), 1.70-1.63 (m, 2H), 1.29-1.21 (m, 15H). LCMS (M+1)=666.4.

EXAMPLE 73

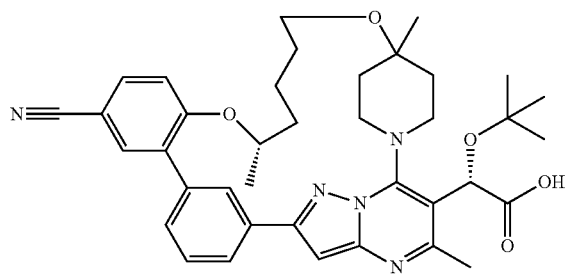 [SMILES: Cc1nc2cc3nn2c(c1[C@H](OC(C)(C)C)C(=O)O)N1CCC(C)(CC1)OCCCC[C@H](C)Oc1ccc(C#N)cc1-c1cccc-3c1]

(2S)-2-(tert-Butoxy)-2-[(22S)-17-cyano-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33), 11, 13, 15(20),16,18-decaen-3-yl]acetic acid: Example 73 was prepared using intermediate 144 by following the procedure to prepare example 28. $^1$H NMR (500 MHz, DMSO-d$_6$) δ 8.47 (br. s., 1H), 7.99 (d, J=7.3 Hz, 1H), 7.83 (d, J=8.9 Hz, 1H), 7.75 (br. s., 1H), 7.56 (t, J=7.8 Hz, 1H), 7.39 (d, J=8.5 Hz, 2H), 7.11 (s, 1H), 5.59 (br. s., 1H), 4.82 (d, J=4.9 Hz, 1H), 4.45 (t, J=11.6 Hz, 1H), 3.71-3.10 (m, 4H), 2.80 (d, J=10.7 Hz, 1H), 2.51 (br. s., 3H), 2.00-1.81 (m, 3H), 1.80-1.60 (m, 4H), 1.52 (d, J=15.0 Hz, 3H), 1.21-1.07 (m, 15H). LCMS (M+1)=652.6.

Intermediate 145

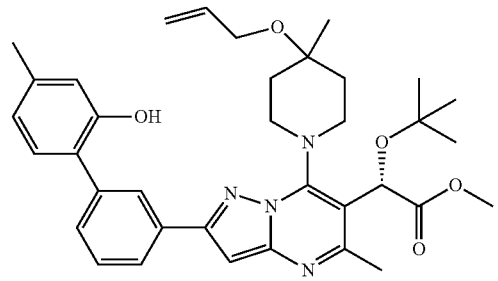

(S)-Methyl 2-(7-(4-(allyloxy)-4-methylpiperidin-1-yl)-2-(2'-hydroxy-4'-methyl-[1,1'-biphenyl]-3-yl)-5-methylpyrazolo[1,5-a]pyrimidin-6-yl)-2-(tert-butoxy)acetate: Intermediate 145 was prepared using intermediate 65 and 5-methyl-2-(4,4,5,5-tetramethyl-1,3,2-dioxaborolan-2-yl)phenol by following the procedure to prepare intermediate 89. $^1$H NMR (400 MHz, CDCl$_3$) δ 8.09 (s, 1H), 8.04 (d, J=7.3 Hz, 1H), 7.61-7.54 (m, 1H), 7.53-7.46 (m, 1H), 7.25-7.18 (m, 1H), 6.89-6.81 (m, 3H), 6.19-5.80 (m, 2H), 5.41 (dd, J=17.1, 1.7 Hz, 1H), 5.37-5.30 (m, 1H), 5.12 (d, J=9.8 Hz, 1H), 5.00-2.50 (m, 4H), 4.11-3.93 (m, 2H), 3.76 (s, 3H), 2.62 (s, 3H), 2.40 (s, 3H), 2.10-1.95 (m, 3H), 1.73 (br. s., 1H), 1.37 (d, J=2.2 Hz, 3H), 1.26 (s, 9H). LCMS (M+1)=613.3.

Intermediate 146

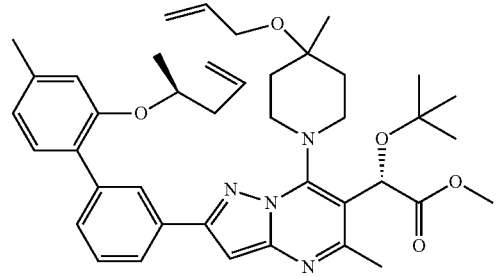

(S)-methyl 2-(7-(4-(allyloxy)-4-methylpiperidin-1-yl)-5-methyl-2-(4'-methyl-2'-((S)-pent-4-en-2-yloxy)-[1,1'-biphenyl]-3-yl)pyrazolo[1,5-a]pyrimidin-6-yl)-2-(tert-butoxy)acetate: Intermediate 146 was prepared using intermediate 145 and (R)-pent-4-en-2-ol by following the procedure to prepare intermediate 115. LCMS (M+1)=681.5.

Intermediate 147

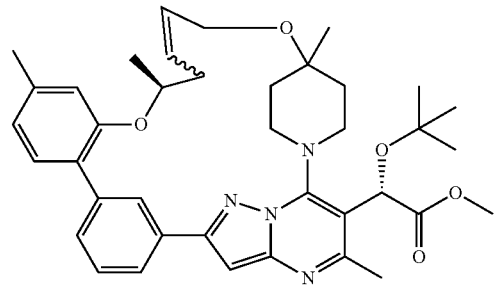

Methyl (2S)-2-(tert-butoxy)-2-[(22S)-4,18,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetate: Intermediate 147 was prepared using intermediate 146 by following the procedure to prepare intermediate 116. LCMS (M+1)=653.4. The product is a mixture of cis/trans isomers.

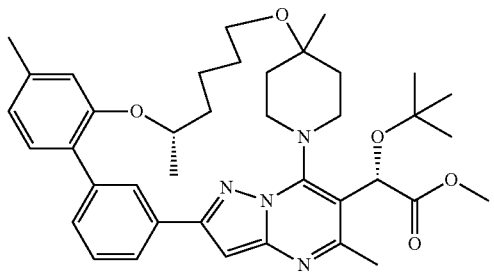

Intermediate 148

Methyl (2S)-2-(tert-butoxy)-2-[(22S)-4,18,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33), 11, 13, 15(20), 16,18-decaen-3-yl]acetate: Intermediate 148 was prepared using 147 by following the procedure to prepare intermediate 117. $^1$H NMR (400 MHz, CDCl$_3$) δ 8.59 (s, 1H), 7.79 (d, J=7.8 Hz, 1H), 7.49 (t, J=7.7 Hz, 1H), 7.33 (d, J=7.8 Hz, 2H), 7.24 (d, J=8.1 Hz, 1H), 6.90 (s, 1H), 6.83 (s, 1H), 5.90 (s, 1H), 4.67-4.54 (m, 2H), 3.85-3.72 (m, 4H), 3.57-3.46 (m, 1H), 3.44-3.35 (m, 1H), 3.25 (d, J=12.2 Hz, 1H), 2.89 (d, J=12.2 Hz, 1H), 2.60 (s, 3H), 2.43 (s, 3H), 2.05-1.50 (m, 10H), 1.27 (s, 3H), 1.25 (s, 9H), 1.18 (d, J=6.1 Hz, 3H). LCMS (M+1)=655.3.

EXAMPLE 74

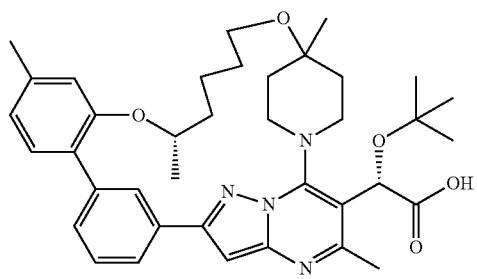 [SMILES: Cc1ccc2c(c1)O[C@@H](C)CCCCOC1(C)CCN(CC1)c1c([C@H](OC(C)(C)C)C(=O)O)c(C)nc3cc(nn13)-c1cccc-2c1]

(2S)-2-(tert-Butoxy)-2-[(22S)-4,18,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid: Example 74 was prepared using intermediate 148 by following the procedure to prepare example 28. $^1$H NMR (500 MHz, DMSO-d$_6$) δ 8.49 (s, 1H), 7.90 (d, J=7.3 Hz, 1H), 7.50 (t, J=7.8 Hz, 1H), 7.29 (d, J=7.6 Hz, 1H), 7.17 (d, J=7.3 Hz, 1H), 7.07 (s, 1H), 6.99 (s, 1H), 6.81 (d, J=7.6 Hz, 1H), 5.59 (br. s., 1H), 4.67 (d, J=6.4 Hz, 1H), 4.50 (t, J=13.1 Hz, 1H), 3.60-3.20 (m, 4H), 2.80 (d, J=10.1 Hz, 1H), 2.51 (br. s., 3H), 2.37 (s, 3H), 2.05-1.84 (m, 3H), 1.77-1.64 (m, 4H), 1.60-1.41 (m, 3H), 1.18 (s, 3H), 1.16 (s, 9H), 1.09 (d, J=5.5 Hz, 3H). LCMS (M+1)=641.4.

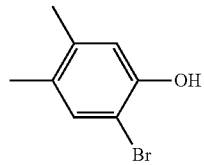

Intermediate 149

2-Bromo-4,5-dimethylphenol: A mixture of 3,4-dimethylphenol (2 g, 16.37 mmol) in DCM (10 mL) at −78° C. was added bromine (0.843 mL, 16.37 mmol) dropwise and the reaction was stirred for 1 h at this temperature. Sat. sodium sulfite solution was added and it was then stirred 5 min at rt and then extracted with EtOAc. The organic layer was dried over MgSO$_4$, filtered and concentrated to obtain 2 g oil. It was then purified with 5% EtOAc/hexane to isolate 800 mg (24%) of the desired product as a white solid. $^1$H NMR (400 MHz, CDCl$_3$) δ 7.22 (s, 1H), 6.84 (s, 1H), 5.33-5.23 (m, 1H), 2.20 (s, 3H), 2.19 (s, 3H).

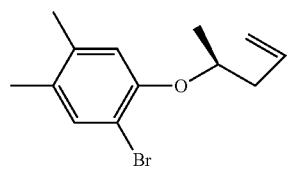

Intermediate 150

(S)-1-Bromo-4,5-dimethyl-2-(pent-4-en-2-yloxy)benzene: A mixture of intermediate 149 (200 mg, 0.995 mmol), (R)-pent-4-en-2-ol (171 mg, 1.989 mmol), triphenylphosphine (522 mg, 1.989 mmol), (Z)-diethyl diazene-1,2-dicarboxylate (346 mg, 1.989 mmol) in THF (5 ml) was stirred at rt for 2 h. It was then diluted with EtOAc, washed with water, dried over MgSO$_4$. The organic layer was filtered, concentrated and purified by biotage, eluting with 3% EtOAc/hexane to isolate 220 mg (82%) of the desired product as an oil. $^1$H NMR (400 MHz, CDCl$_3$) δ 7.31 (s, 1H), 6.74 (s, 1H), 5.93 (ddt, J=17.2, 10.1, 7.0 Hz, 1H), 5.20-5.07 (m, 2H), 4.39 (sxt, J=6.1 Hz, 1H), 2.55 (qd, J=7.0, 5.6 Hz, 1H), 2.46-2.35 (m, 1H), 2.22 (s, 3H), 2.19 (s, 3H), 1.35 (d, J=6.1 Hz, 3H).

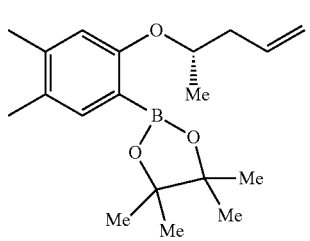

Intermediate 151

(S)-2-(4,5-Dimethyl-2-(pent-4-en-2-yloxy)phenyl)-4,4,5,5-tetramethyl-1,3,2-dioxaborolane: To a mixture of intermediate 150 (120 mg, 0.446 mmol) in THF (2 mL) was added 2.5M n-BuLi (0.214 mL, 0.535 mmol) at −78° C. It was then stirred at this temperature for 1 h, then added 2-isopropoxy-4,4,5,5-tetramethyl-1,3,2-dioxaborolane (100 mg, 0.535 mmol) and stirred at −78° C. for 30 min, then warmed to rt and stirred at rt for 3 h. It was then quenched with water, extracted with EtOAc. The organic was dried over MgSO$_4$, filtered and concentrated to obtain 0.108 g (45%) of the desired product as an oil. $^1$H NMR (500 MHz, CDCl$_3$) δ 7.42 (s, 1H), 6.72 (s, 1H), 6.03-5.96 (m, 1H), 5.14-5.06 (m, 2H), 4.35-4.30 (m, 1H), 2.55-2.49 (m, 1H), 2.44-2.36 (m, 1H), 2.25 (s, 3H), 2.21 (s, 3H), 1.37-1.35 (m, 12H), 1.30-1.29 (m, 3H).

Intermediate 152

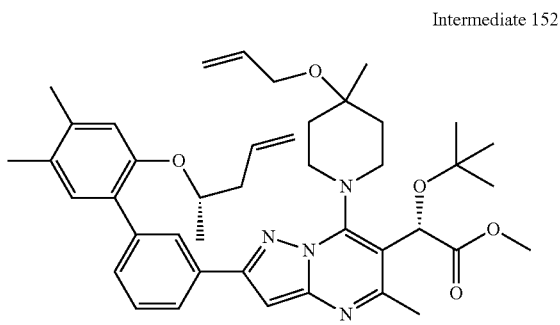

(S)-Methyl 2-(7-(4-(allyloxy)-4-methylpiperidin-1-yl)-2-(4',5'-ditnethyl-2'-((S)-pent-4-en-2-yloxy)-[1,1'-biphenyl]-3-yl)-5-methylpyrazolo[1,5-a]pyrimidin-6-yl)-2-(tert-butoxy)acetate: A mixture of intermediate 65 (50 mg, 0.085 mmol), intermediate 151 (108 mg, 0.171 mmol), Na$_2$CO$_3$ (0.107 mL, 0.213 mmol) in DMF (1.5 mL) was vacuum, back-filled with N$_2$ for 3 times. It was then added (Ph$_3$P)$_4$Pd (9.87 mg, 8.54 μmol) and heated at 95° C. in a mcrowave tube for 1 h. It was then diluted with EtOAc, washed with water. The organic was dried over MgSO$_4$, filtered and concentrated to obtain 150 mg oil, which was then purified by biotage, eluting with 25% acetone/hexane to isolate 80 mg (94%) of the desired product as a white solid. LCMS (M+1)=695.5.

Intermediate 153

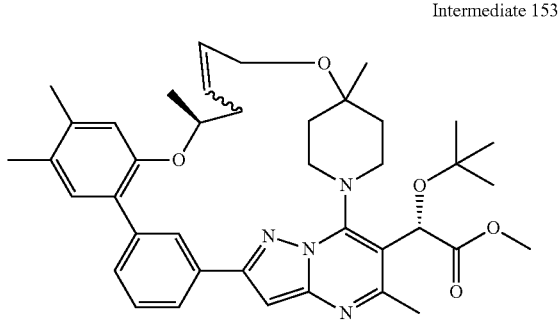

Methyl (2S)-2-(tert-butoxy)-2-[(22S)-4,17,18,22,28-pentamethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetate: Intermediate 153 was prepared using intermediate 152 by following the procedure to prepare intermediate 116. LCMS (M+1)=667.4. The product is a mixture of cis/trans isomers.

EXAMPLE 75

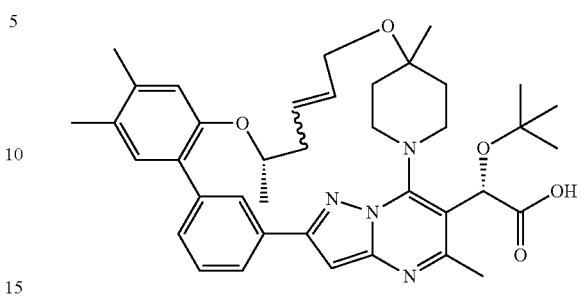

(2S)-2-(tert-Butoxy)-2-[(22S)-4,17,18,22,28-pentamethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33), 11, 13, 15 (20),16,18,24-undecaen-3-yl]acetic acid: Example 75 was prepared using intermediate 153 by following the procedure to prepare example 20. $^1$H NMR (500 MHz, DMSO-d$_6$) δ 8.42 (s, 1H), 7.91 (d, J=7.9 Hz, 1H), 7.50 (t, J=7.6 Hz, 1H), 7.29 (d, J=7.6 Hz, 1H), 7.10 (s, 1H), 7.02 (s, 1H), 6.96 (s, 1H), 6.29 (br. s., 1H), 5.80-5.60 (m, 2H), 4.85-4.66 (m, 1H), 4.54 (br. s., 1H), 4.06-3.82 (m, 2H), 3.57-3.48 (m, 1H), 3.40-3.25 (m, 1 H), 2.75 (d, J=10.7 Hz, 1H), 2.52 (br. s., 3H), 2.35-2.22 (m, 4H), 2.22-2.12 (m, 4H), 2.03 (d, J=13.4 Hz, 1H), 1.85 (d, J=11.6 Hz, 1H), 1.70-1.56 (m, 2H), 1.22 (s, 3H), 1.17 (s, 9H), 1.03 (d, J=5.8 Hz, 3H). LCMS (M+1)=653.4.

Intermediate 154

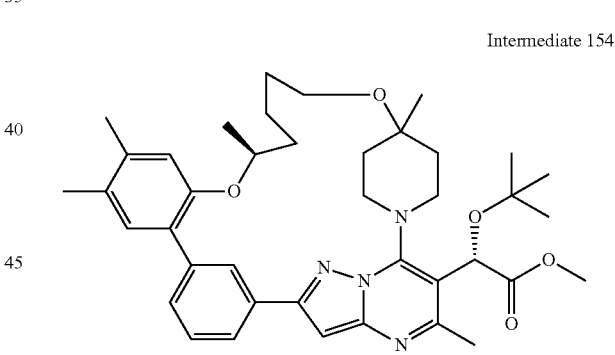

Methyl (2S)-2-(tert-butoxy)-2-[(22S)-4,17,18,22,28-pentamethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33), 11,13,15(20), 16,18-decaen-3-yl]acetate: Intermediate 154 was prepared using intermediate 153 by following the procedure to prepare intermediate 117. $^1$H NMR (400 MHz, CDCl$_3$) δ 8.59 (s, 1H), 7.78 (d, J=7.8 Hz, 1H), 7.55-7.43 (m, 1H), 7.35 (d, J=7.6 Hz, 1H), 7.12 (s, 1H), 6.90 (s, 1H), 6.82 (s, 1H), 5.90 (s, 1H), 4.68-4.50 (m, 2H), 3.85-3.72 (m, 4H), 3.50 (d, J=7.1 Hz, 1H), 3.43-3.35 (m, 1H), 3.25 (d, J=12.0 Hz, 1H), 2.88 (d, J=11.0 Hz, 1H), 2.60 (s, 3H), 2.34 (s, 3H), 2.27 (s, 3H), 2.09-1.94 (m, 3H), 1.89-1.66 (m, 4H), 1.65-1.50 (m, 3 H), 1.27-1.23 (m, 12H), 1.17 (d, J=6.1 Hz, 3H). LCMS (M+1)=669.5.

EXAMPLE 76

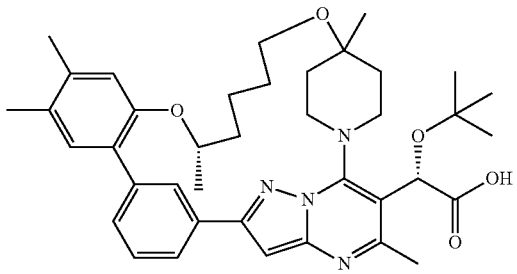 [SMILES: Cc1cc2c(cc1C)-c1cccc(c1)-c1cc3nc(C)c([C@H](OC(C)(C)C)C(=O)O)c(n3n1)N1CCC(C)(CC1)OCCCC[C@H](C)O2]

(2S)-2-(tert-Butoxy)-2-[(22S)-4,17,18,22,28-pentamethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid: Example 76 was prepared using intermediate 154 by following the procedure to prepare example 28. $^1$H NMR (500 MHz, DMSO-d$_6$) δ 8.49 (s, 1H), 7.90 (d, J=7.3 Hz, 1H), 7.50 (t, J=7.8 Hz, 1H), 7.29 (d, J=7.6 Hz, 1H), 7.17 (d, J=7.3 Hz, 1H), 7.07 (s, 1H), 6.99 (s, 1H), 6.81 (d, J=7.6 Hz, 1H), 5.59 (br. s., 1H), 4.67 (d, J=6.4 Hz, 1H), 4.50 (t, J=13.1 Hz, 1H), 3.60-3.20 (m, 4H), 2.80 (d, J=10.1 Hz, 1H), 2.51 (br. s., 3H), 2.37 (s, 3H), 2.05-1.84 (m, 3H), 1.77-1.64 (m, 4H), 1.60-1.41 (m, 3H), 1.18 (s, 3H), 1.16 (s, 9H), 1.09 (d, J=5.5 Hz, 3H). LCMS (M+1)=641.4.

Intermediate 155

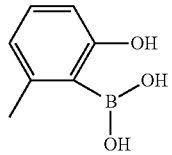

(2-Hydroxy-6-methylphenyl)boronic acid: Intermediate 155 was prepared using (2-methoxy-6-methylphenyl)boranediol by following the procedure to prepare intermediate 136. $^1$H NMR (400 MHz, DMSO-d$_6$) δ 9.11 (br. s., 1H), 7.44-7.25 (m, 1H), 6.94-6.81 (m, 1H), 6.78 (d, J=8.1 Hz, 1H), 2.51 (s, 3H).

Intermediate 156

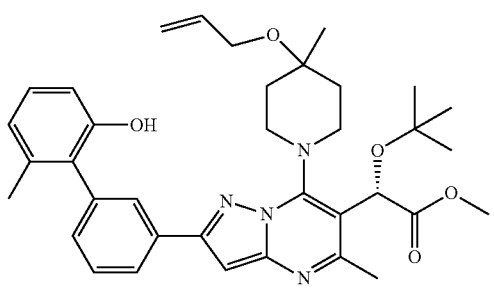

(S)-Methyl 2-(7-(4-(allyloxy)-4-methylpiperidin-1 yl)-2-(2'-hydroxy-6'-methyl-[1,1'-biphenyl]-3-yl)-5-methylpyrazolo[1,5-a]pyrimidin-6-yl)-2-(tert-butoxy)acetate: Intermediate 156 was prepared using intermediates 65 and 155 by following the procedure to prepare intermediate 89. $^1$H NMR (400 MHz, CDCl$_3$) δ 8.12 (d, J=6.8 Hz, 1H), 7.91 (s, 1H), 7.61 (t, J=7.5 Hz, 1H), 7.33 (d, J=7.3 Hz, 1H), 7.22 (t, J=7.8 Hz, 1H), 6.91 (d, J=8.6 Hz, 2H), 6.83 (s, 1H), 6.07-5.90 (m, 2H), 5.40 (d, J=17.9 Hz, 1H), 5.09 (br. s., 1H), 5.00-2.50 (m, 4H), 4.88 (s, 1H), 4.00 (d, J=4.4 Hz, 2H), 3.75 (s, 3H), 2.63 (s, 3H), 2.15 (s, 3H), 2.06-1.92 (m, 2H), 1.73 (br. s., 1H), 1.62-1.57 (m, 1 H), 1.36 (br. s., 3H), 1.26 (s, 9H). LCMS (M+1)=613.3.

Intermediate 157

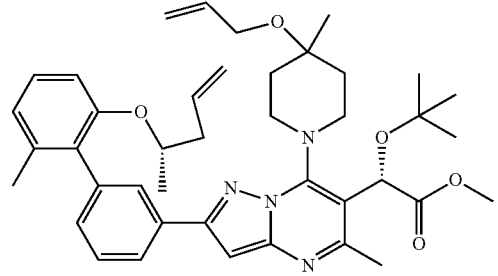

(S)-Methyl 2-(7-(4-(allyloxy)-4-methylpiperidin-1-yl)-5-methyl-2-(2'-methyl-6'-((S)-pent-4-en-2-yloxy)-[1,1'-biphenyl]-3-yl)-pyrazolo[1,5-d]pyrimidin-6-yl)-2-(tert-butoxy) acetate: Intermediate 157 was prepared intermediate 156 and (R)-pent-4-en-2-ol by following the procedure to prepare intermediate 115. LCMS (M+1)=681.5.

Intermediate 158

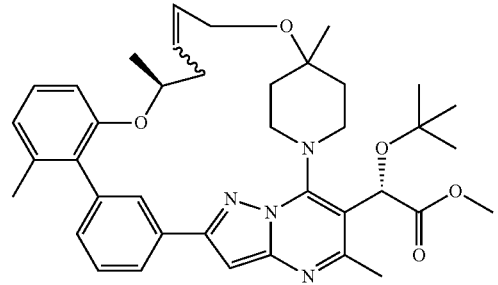

Methyl (2S)-2-(tert-butoxy)-2-[(22S)-4,16,22,28-tetramethyl-21,27-dioxa-1,5,7,8-tetraazahexacyclo[26.2.2.1$^{6,9}$.1$^{10,14}$.0$^{2,7}$. 0$^{15,20}$]tetratriaconta-2,4,6(34),8,10(33),11,13,15(20),16,18,24-undecaen-3-yl]acetate: Intermediate 158 was prepared using intermediate 157 by following the procedure to prepare intermediate 116. LCMS (M+1)=653.5. The product is a mixture of cis/trans isomers.

Intermediate 159

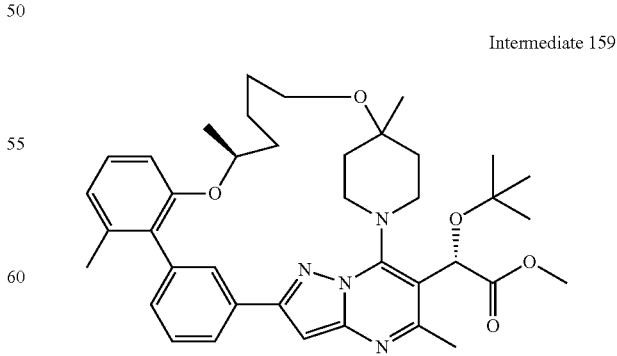

Methyl (2S)-2-(tert-butoxy)-2-[(22S)-4,16,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4, 6(34), 8, 10(33), 11, 13, 15(20),16,18-decaen-3-yl]acetate: Intermediate 159 was prepared using intermediate 158 by following the procedure to prepare intermediate 117. $^1$H NMR (400 MHz, CDCl$_3$) δ 8.14 (s, 1H), 7.76 (d, J=7.6 Hz, 1H), 7.49 (t, J=7.6 Hz, 1H), 7.24 (t, J=7.8 Hz, 1H), 7.16 (d, J=7.6 Hz, 1H), 6.92-6.79 (m, 3H), 6.00 (s, 1H), 4.70 (t, J=11.7 Hz, 1H), 4.50 (br. s., 1H), 3.81-3.66 (m, 4H), 3.45 (d, J=6.6 Hz, 1H), 3.36 (d, J=4.4 Hz, 1H), 3.13 (d, J=11.2 Hz, 1H), 2.87-2.77 (m, 1H), 2.61 (s, 3H), 2.10 (s, 3 H), 2.03-1.84 (m, 3H), 1.79-1.44 (m, 7H), 1.26 (s, 12H), 1.17 (d, J=5.9 Hz, 3H). LCMS (M+1)=655.5.

EXAMPLE 77

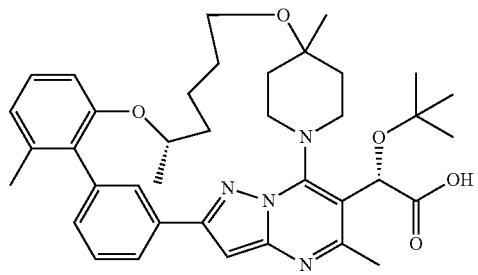 [SMILES: Cc1cccc2c1-c1cccc(c1)-c1cc3nc(C)c([C@H](OC(C)(C)C)C(=O)O)c(n3n1)N1CCC(C)(CC1)OCCCC[C@H](C)O2]

(2S)-2-(tert-Butoxy)-2-[(22S)-4,16,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33), 11, 13, 15(20),16,18-decaen-3-yl]acetic acid: Example 77 was prepared using intermediate 159 by following the procedure to prepare example 28. $^1$H NMR (500 MHz, DMSO-d$_6$) δ 8.14-8.00 (m, 1H), 7.88 (d, J=7.6 Hz, 1H), 7.50 (t, J=7.6 Hz, 1H), 7.28-7.19 (m, 1H), 7.15 (d, J=7.3 Hz, 1H), 7.05 (s, 1H), 6.96 (d, J=8.5 Hz, 1H), 6.86 (d, J=7.6 Hz, 1H), 5.75 (br. s., 1H), 4.57 (br. s., 2H), 3.70-3.20 (m, 4H), 2.73 (d, J=11.3 Hz, 1H), 2.58-2.47 (m, 12H), 2.00 (s, 3H), 1.98-1.76 (m, 3H), 1.71-1.46 (m, 5H), 1.37 (br. s., 2H), 1.17 (s, 12H), 1.07 (d, J=5.5 Hz, 3H). LCMS (M+1)=641.4.

Intermediate 160

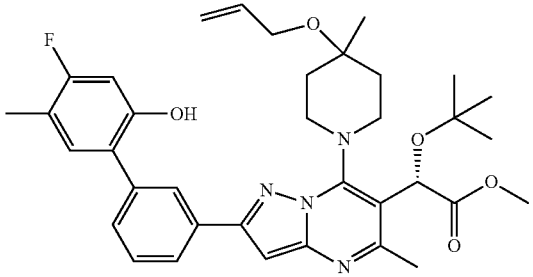

(S)-Methyl 2-(7-(4-(allyloxy)-4-methylpiperidin-1-yl)-2-(4'-fluoro-2'-hydroxy-5'-methyl-[1,1'-biphenyl]-3-yl)-5-methylpyrazolo[1,5-a]pyrimidin-6-yl)-2-(tert-butoxy)acetate: Intermediate 160 was prepared using intermediate 65 and (4-fluoro-2-hydroxy-5-methylphenyl)boronic acid by following the procedure to prepare intermediate 89. $^1$H NMR (400 MHz, CDCl$_3$) δ 8.17-7.99 (m, 2H), 7.60-7.52 (m, 1H), 7.44 (d, J=7.8 Hz, 1H), 7.13 (d, J=8.6 Hz, 1H), 6.84 (s, 1H), 6.74 (d, J=10.8 Hz, 1H), 6.12-5.86 (m, 2H), 5.72 (d, J=18.8 Hz, 1H), 5.41 (d, J=17.1 Hz, 1H), 5.11 (d, J=9.5 Hz, 1H), 5.00-2.50 (m, 4H), 4.02 (d, J=4.9 Hz, 2H), 3.76 (s, 3H), 2.62 (s, 3H), 2.27 (s, 3H), 2.09-1.94 (m, 2H), 1.75 (d, J=7.3 Hz, 1H), 1.58-1.47 (m, 1H), 1.37 (br. s., 3H), 1.27 (s, 9H). LCMS (M+1)=631.4.

Intermediate 161

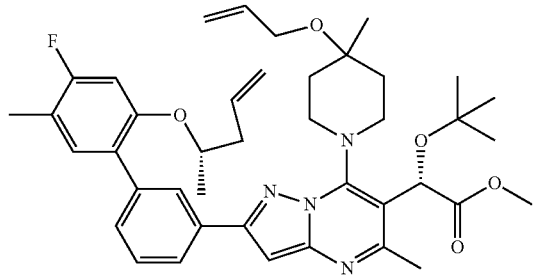

(S)-Methyl 2-(7-(4-(allyloxy)-4-methylpiperidin-1-yl)-2-(4'-fluoro-5'-methyl-2'-((S)-pent-4-en-2-yloxy)-[1,1'-biphenyl]-3-yl)-5-methylpyrazolo[1,5-a]pyrimidin-6-yl)-2-(tert-butoxy)acetate: Intermediate 161 was prepared using intermediate 161 and (R)-pent-4-en-2-ol by following the procedure to prepare intermediate 115. LCMS (M+1)=699.5.

Intermediate 162

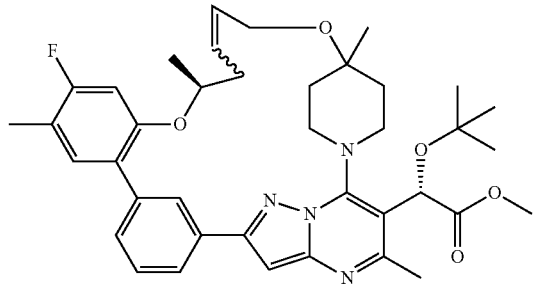

Methyl (2S)-2-(tert-butoxy)-2-[(22S)-18-fluoro-4,17,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20), 16,18,24-undecaen-3-yl]acetate: Intermediate 162 was prepared using intermediate 161 by following the procedure to prepare intermediate 116. LCMS (M+1)=671.4. The product is a mixture of cis/trans isomers.

EXAMPLE 78

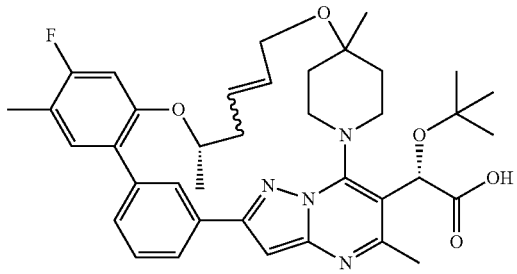 [SMILES: Cc1cc2c(cc1F)O[C@@H](C)CC=CCOC1(C)CCN(CC1)c1c([C@H](OC(C)(C)C)C(=O)O)c(C)nc3cc(nn13)-c1cccc-2c1]

(2S)-2-(tert-Butoxy)-2-[(22S)-18-fluoro-4,17,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11, 13,15(20), 16,18,24-undecaen-3-yl]acetic acid: Example 78 was prepared using intermediate 162 by following the procedure to prepare example 20. $^1$H NMR (500 MHz, DMSO-$d_6$) δ 8.39 (s, 1H), 7.95 (d, J=7.6 Hz, 1H), 7.56-7.47 (m, 1H), 7.30 (d, J=7.3 Hz, 1H), 7.17 (d, J=9.2 Hz, 1H), 7.11 (s, 1H), 7.05 (d, J=12.2 Hz, 1H), 6.26 (br. s., 1H), 5.77-5.64 (m, 2H), 4.76 (t, J=12.5 Hz, 1H), 4.54 (br. s., 1H), 4.01-3.93 (m, 1H), 3.91-3.84 (m, 1H), 3.56-3.50 (m, 1H), 3.50-3.25 (m, 1H), 2.79-2.71 (m, 1H), 2.52 (br. s., 3H), 2.36-2.26 (m, 1H), 2.25-2.14 (m, 4H), 2.03 (d, J=13.1 Hz, 1H), 1.86 (d, J=11.9 Hz, 1H), 1.63 (d, J=11.3 Hz, 2H), 1.22 (s, 3H), 1.17 (s, 9H), 1.05 (d, J=5.5 Hz, 3H). LCMS (M+1)=657.6.

Intermediate 163

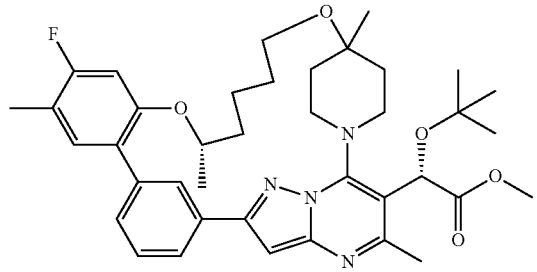

Methyl (2S)-2-(tert-butoxy)-2-[(22S)-18-fluoro-4,17,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate: Intermediate 163 was prepared using intermediate 162 by following the procedure to prepare intermediate 117. $^1$H NMR (400 MHz, CDCl$_3$) δ 8.55 (s, 1H), 7.80 (d, J=7.6 Hz, 1H), 7.49 (t, J=7.7 Hz, 1H), 7.31 (br. s., 1H), 7.14 (d, J=9.3 Hz, 1H), 6.90 (s, 1H), 6.71 (d, J=12.0 Hz, 1H), 5.90 (s, 1H), 4.63 (t, J=12.1 Hz, 1H), 4.48 (br. s., 1H), 3.82-3.74 (m, 4H), 3.51 (d, J=7.3 Hz, 1H), 3.40 (br. s., 1H), 3.25 (d, J=8.1 Hz, 1H), 2.89 (d, J=11.5 Hz, 1H), 2.60 (s, 3H), 2.27 (s, 3H), 2.05-1.94 (m, 3H), 1.82-1.69 (m, 5H), 1.66-1.51 (m, 2H), 1.27 (s, 3H), 1.25 (s, 9H), 1.19 (d, J=6.1 Hz, 3H). LCMS (M+1)=673.6.

EXAMPLE 79

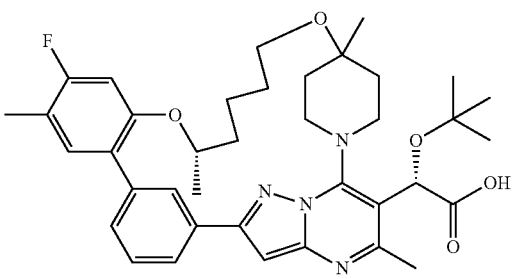 [SMILES: Cc1cc2c(cc1F)O[C@@H](C)CCCCOC1(C)CCN(CC1)c1c([C@H](OC(C)(C)C)C(=O)O)c(C)nc3cc(nn13)-c1cccc-2c1]

(2S)-2-(tert-Butoxy)-2-[(22S)-18-fluoro-4,17,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid: Example 79 was prepared using intermediate 163 by following the procedure to prepare example 28. $^1$H NMR (500 MHz, DMSO-$d_6$) δ 8.46 (s, 1H), 7.92 (d, J=7.9 Hz, 1H), 7.51 (t, J=7.6 Hz, 1H), 7.31 (d, J=7.6 Hz, 1H), 7.20 (d, J=9.2 Hz, 1H), 7.10 (s, 1H), 7.05 (d, J=12.2 Hz, 1H), 5.65 (br. s., 1H), 5.71-5.57 (m, 1H), 4.64 (d, J=5.5 Hz, 1H), 4.48 (t, J=12.4 Hz, 1H), 3.63-3.54 (m, 1H), 3.52-3.22 (m, 2H), 2.80 (d, J=11.3 Hz, 1H), 2.52 (s, 3H), 2.21 (s, 3H), 2.00-1.84 (m, 3H), 1.69 (br. s., 4H), 1.60-1.41 (m, 3H), 1.20-1.12 (m, 12H), 1.08 (d, J=5.8 Hz, 3H). LCMS (M+1)=659.5.

Intermediate 164

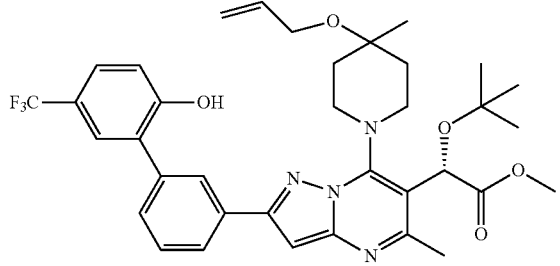

(S)-Methyl 2-(7-(4-(allyloxy)-4-methylpiperidin-1-yl)-2-(2'-hydroxy-5'-(trifluoromethyl)-[1,1'-biphenyl]-3-yl)-5-methylpyrazolo[1,5-a]pyrimidin-6-yl)-2-(tert-butoxy)acetate: A mixture of (2-hydroxy-5-(trifluoromethyl)phenyl)boronic acid (106 mg, 0.512 mmol), (S)-methyl 2-(7-(4-(allyloxy)-4-methylpiperidin-1-yl)-2-(3-bromophenyl)-5-methylpyrazolo[1,5-a]pyrimidin-6-yl)-2-(tert-butoxy)acetate (150 mg, 0.256 mmol), Na$_2$CO$_3$ (0.320 mL, 0.640 mmol) in DMF (1 mL) was evacuated and back-filled with N2 for 3 times. To this was added (Ph$_3$P)$_4$Pd (29.6 mg, 0.026 mmol) and heated at 95° C. in a mcrowave tube for 1 h. Then, cooled, diluted with EtOAc and washed with water. The organic was dried over MgSO$_4$, filtered and concentrated to obtain 150 mg oil, which was purified by biotage eluting with 50% EtOAc/hexane to isolate 89 mg (52%) of (S)-methyl 2-(7-(4-(allyloxy)-4-methylpiperidin-1-yl)-2-(2'-hydroxy-5'-(trifluoromethyl)-[1,1'-biphenyl]-3-yl)-5-methylpyrazolo[1,5-a]pyrimidin-6-yl)-2-(tert-butoxy)acetate as a white solid. $^1$H NMR (400 MHz, CDCl$_3$) δ 8.14 (s, 1H), 8.07 (d, J=7.8 Hz, 1H), 7.65-7.54 (m, 3H), 7.49 (d, J=7.6 Hz, 1H), 7.12 (d, J=8.3 Hz, 1H), 6.85 (s, 1H), 6.28 (br. s., 1H), 6.05-5.83 (m, 2H), 5.39 (d, J=17.4 Hz, 1H), 5.09 (br. s., 1H), 5.00-2.50 (m, 4H), 4.01 (d, J=4.4 Hz, 2H), 3.76 (s, 3H), 2.62 (s, 3H), 2.08-1.93 (m, 3H), 1.73 (br. s., 1H), 1.36 (s, 3H), 1.29-1.22 (m, 9H). LCMS (M+1)=667.6.

Intermediate 165

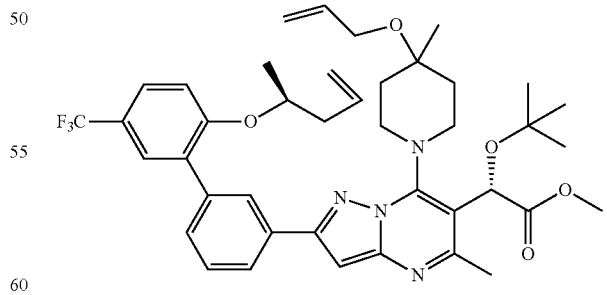

(S)-Methyl 2-(7-(4-(allyloxy)-4-methylpiperidin-1-yl)-5-methyl-2-(2'-((S)-pent-4-en-2-yloxy)-5'-(trifluoromethyl)-[1,1'-biphenyl]-3-yl)pyrazolo[1,5-a]pyrimidin-6-yl)-2-(tert-butoxy)acetate: A mixture of (S)-methyl 2-(7-(4-(allyloxy)-4-methylpiperidin-1-yl)-2-(2'-hydroxy-5'-(trifluoromethyl)-[1,1'-biphenyl]-3-yl)-5-methylpyrazolo[1,5-a]pyrimidin-6- yl)-2-(tert-butoxy)acetate (89 mg, 0.133 mmol), (R)-pent-4-en-2-ol (34.5 mg, 0.400 mmol), triphenylphosphine (105 mg, 0.400 mmol) and DEAD (69.7 mg, 0.400 mmol) in THF (2 mL) was stirred at rt for 3 h. It was then diluted with EtOAc and washed with water. The organic was dried over $MgSO_4$, filtered and concentrated to obtain 100 mg yellow oil, which was purified by biotage eluting with 30% EtOAc/hexane to isolate 74 mg (75%) of (S)-methyl 2-(7-(4-(allyloxy)-4-methylpiperidin-1-yl)-5-methyl-2-(2'-((S)-pent-4-en-2-yloxy)-5'-(trifluoromethyl)-[1,1'-biphenyl]-3-yl)pyrazolo[1,5-a]pyrimidin-6-yl)-2-(tert-butoxy)acetate as an oil. LCMS (M+1)=735.8.

Intermediate 166

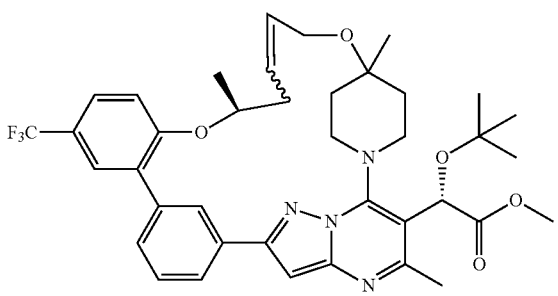

Methyl (2S)-2-(tert-butoxy)-2-[(22S)-4,22,28-trimethyl-17-(trifluoromethyl)-21,27-dioxa-1,5,7,8-tetraazahexacyclo [26.2.2.1$^{6,9}$.1$^{10,14}$.0$^{10,14}$.0$^{2,7}$0$^{15,20}$]tetratriaconta-2,4,6(34), 8,10(33),11,13,15(20),16,18,24-undecaen-3-yl]acetate: A mixture of (S)-methyl 2-(7-(4-(allyloxy)-4-methylpiperidin-1-yl)-5-methyl-2-(2'-((S)-pent-4-en-2-yloxy)-5'-(trifluoromethyl)-[1,1'-biphenyl]-3-yl)pyrazolo[1,5-a]pyrimidin-6-yl)-2-(tert-butoxy)acetate (74 mg, 0.101 mmol), (1,3-dimesitylimidazolidin-2-ylidene)(2-isopropoxybenzylidene)ruthenium(VI) chloride (6.31 mg, 10.07 µmol),copper(i) iodide (19.18 mg, 0.101 mmol) in ClCH$_2$CH$_2$Cl (80 mL) was refluxed for 3 h. It was then concentrated and purified by biotage eluting with 20% EtOac/hexane to isolate 50 mg (70%) of methyl (2S)-2-(tert-butoxy)-2-[(22S,24Z)-4,22,28-trimethyl-17-(trifluoromethyl)-21,27-dioxa-1,5,7,8-tetraazahexacyclo[26.2.2. 1$^{6,9}$,1$^{10,14}$.0$^{2,7}$.0$^{15,20}$]tetratriaconta-2,4,6(34),8,10(33),11, 13,15(20),16,18,24-undecaen-3-yl]acetate as an off-white solid. The product is a mixture of cis/trans product. LCMS (M+1)=707.3.

Intermediate 167

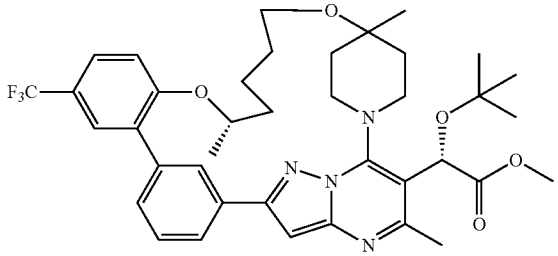

Methyl (2S)-2-(tert-butoxy)-2-[(22S)-4,22,28-trimethyl-17-(trifluoromethyl)-21,27-dioxa-1,5,7,8-tetraazahexacyclo [26.2.2.1$^{6,9}$.1$^{10,14}$.0$^{2,7}$.0$^{15,20}$]tetratriaconta-2,4,6(34),8,10 (33), 11, 13, 15 (20),16,18-decaen-3-yl]acetate: A mixture of methyl (2S)-2-(tert-butoxy)-2-[(22S,24Z)-4,22,28-trimethyl-17-(trifluoromethyl)-21,27-dioxa-1,5,7,8-tetraazahexacyclo[26.2.2.1$^{6,9}$.1$^{10,14}$.0$^{2,7}$.0$^{15,20}$]tetratriaconta-2,4,6 (34),8,10(33),11,13,15(20),16,18,24-undecaen-3-yl]acetate (50 mg, 0.071 mmol), 10% Pd/C (7.53 mg, 7.07 µmol) in MeOH (2 mL) was stirred under a H$_2$ balloon for 2 h. It was then filtered, concentrated and purified by biotage eluting with 20% EtOAc/hexane to isolate 38 mg of methyl (2S)-2-(tert-butoxy)-2-[(22S)-4,22,28-trimethyl-17-(trifluoromethyl)-21,27-dioxa-1,5,7,8-tetraazahexacyclo[26.2.2. 1$^{6,9}$.1$^{10,14}$.0$^{2,7}$.0$^{15,20}$]tetratriaconta-2,4,6(34),8,10(33),11, 13,15(20),16,18-decaen-3-yl]acetate as an off-white solid. LCMS (M+1)=709.3.

EXAMPLE 80

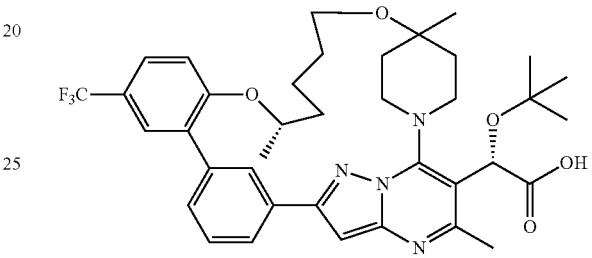

(2S)-2-(tert-Butoxy)-2-[(22S)-4,22,28-trimethyl-17-(trifluoromethyl)-21,27-dioxa-1,5,7,8-tetraazahexacyclo [26.2.2.1$^{6,9}$.1$^{10,14}$.0$^{2,7}$.0$^{15,20}$]tetratriaconta-2,4,6(34), 8, 10(33), 11, 13, 15 (20),16,18-decaen-3-yl]acetic acid: A mixture of methyl (2S)-2-(tert-butoxy)-2-[(22S)-4,22,28-trimethyl-17-(trifluoromethyl)-21,27-dioxa-1,5,7,8-tetraazahexacyclo[26.2.2.1$^{6,9}$. 1$^{10,14}$.0$^{2,7}$.0$^{15,20}$]tetratriaconta-2,4,6 (34),8,10(33),11,13,15(20),16,18-decaen-3-yl]acetate (38 mg, 0.054 mmol), NaOH (0.268 mL, 0.268 mmol) in MeOH (2 mL) was refluxed for 3 h. It was then filtered and purified by prep HPLC to isolate the desired product as a white solid. LCMS (M+1)=695.3.

Intermediate 168

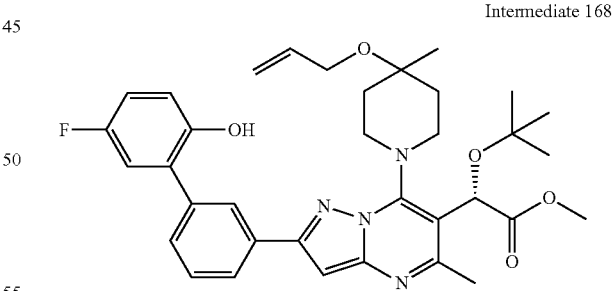

(S)-Methyl 2-(7-(4-(allyloxy)-4-methylpiperidin-1-yl)-2-(5'-fluoro-2'-hydroxy-[1,1'-biphenyl]-3-yl)-5-methylpyrazolo[1,5-a]pyrimidin-6-yl)-2-(tert-butoxy)acetate: To (S)-methyl 2-(7-(4-(allyloxy)-4-methylpiperidin-1-yl)-2-(3-bromophenyl)-5-methylpyrazolo[1,5-a]pyrimidin-6-yl)-2-(tert-butoxy)acetate (0.24 g, 0.41 mmol, 1 equiv), (5-fluoro-2-hydroxyphenyl)boronic acid (96 mg, 0.62 mmol, 1.5 equiv), and Pd(PPh$_3$)$_4$ (47 mg, 0.041 mmol, 0.1 equiv) was added DMF (4.1 mL that had been degassed by sparging with nitrogen for 10 min) Na$_2$CO$_3$ (0.41 mL of a 2 M aqueous solution, 0.82 mmol, 2 equiv) was added and the reaction was heated to 90° C. for 3 h. Upon cooling to ambient temperature, the reaction was diluted with EtOAc and washed with water. The EtOAc layer was dried (Na$_2$SO$_4$) and concentrated in vacuo. The crude product was purified by flash column chromatography (0-60% acetone in hexane) to provide the product as a yellow foam (0.19 g, 75%). $^1$H NMR (400 MHz, CDCl$_3$) δ 8.13-8.08 (m, 1H), 8.05-8.00 (m, 1H), 7.67-7.48 (m, 3H), 7.09-6.94 (m, 4H), 6.07-5.92 (m, 1H), 5.45-5.36 (m, 1H), 5.22-5.07 (m, 2H), 4.04-3.97 (m, 2H), 3.81-3.77 (m, 3H), 3.77-3.74 (m, 4H), 2.74-2.65 (m, 3H), 2.08-1.94 (m, 3H), 1.80-1.68 (m, 1H), 1.36 (s, 3H), 1.24 (s, 9H). LCMS (M+1)=617.35.

Intermediate 169

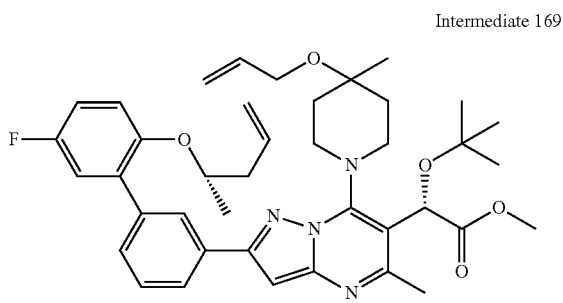 [SMILES: C=CCOC1(C)CCN(c2c([C@H](OC(C)(C)C)C(=O)OC)c(C)nc3cc(-c4cccc(-c5cc(F)ccc5O[C@@H](C)CC=C)c4)nn23)CC1]

(S)-Methyl 2-(7-(4-(allyloxy)-4-methylpiperidin-1-yl)-2-(5'-fluoro-2'-((S)-pent-4-en-2-yloxy)-[1,1'-biphenyl]-3-yl)-5-methylpyrazolo[1,5-a]pyrimidin-6-yl)-2-(tert-butoxy)acetate: To a solution of (S)-methyl 2-(7-(4-(allyloxy)-4-methylpiperidin-1-yl)-2-(5'-fluoro-2'-hydroxy-[1,1'-biphenyl]-3-yl)-5-methylpyrazolo[1,5-a]pyrimidin-6-yl)-2-(tert-butoxy)acetate (0.19 g, 0.31 mmol, 1 equiv), (R)-pent-4-en-2-ol (0.095 mL, 0.92 mmol, 3 equiv), and PPh$_3$ (0.16 g, 0.62 mmol, 2 equiv) in THF (1.54 mL) was added DEAD (0.098 mL, 0.62 mmol, 2 equiv). After stirring 2 h, dilute with ether and wash with water. The ether layer was dried (MgSO$_4$) and concentrated in vacuo. The crude product was purified by flash column chromatography (0-60% EtOAc in hexane) to provide the product as a white foam (0.17 g, 81%). $^1$H NMR (500 MHz, CDCl$_3$) [note: 4H of piperidine not observed and are likely very broad] δ 8.16 (s, 1H), 8.08-7.99 (m, 1H), 7.61-7.56 (m, 1H), 7.51 (d, J=7.6 Hz, 1H), 7.16 (dd, J=9.1, 2.8 Hz, 1H), 7.04-6.95 (m, 2H), 6.92-6.82 (m, 1H), 6.08-5.97 (m, 1H), 5.74 (s, 1H), 5.42 (d, J=17.3 Hz, 1H), 5.22-5.08 (m, 2H), 5.06-4.99 (m, 2H), 4.27 (d, J=6.0 Hz, 1H), 4.03 (d, J=4.7 Hz, 2H), 3.77 (s, 3H), 2.65 (br. s., 3H), 2.45-2.35 (m, 1H), 2.28 (s, 1H), 2.06-1.95 (m, 3H), 1.79-1.69 (m, 1H), 1.38 (br. s., 3H), 1.27 (s, 9H), 1.21 (d, J=6.0 Hz, 3H). LCMS (M+1)=685.4.

Intermediate 170

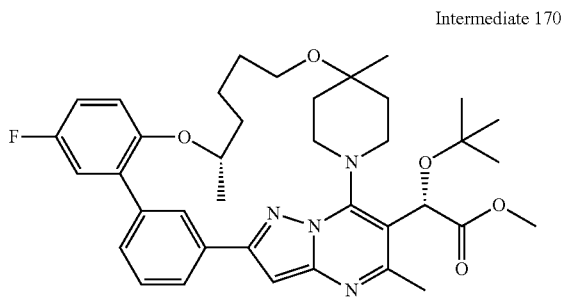 [SMILES: COC(=O)[C@@H](OC(C)(C)C)c1c(C)nc2cc3nn2c1N1CCC(C)(CC1)OCCCC[C@H](C)Oc1ccc(F)cc1-c1cccc-3c1]

Methyl (2S)-2-(tert-butoxy)-2-[(22S)-17-fluoro-4,22,28-trimethyl-21,27-dioxa-1,5,7,8-tetraazahexacyclo[26.2.2. 1$^{6,9}$.1$^{10,14}$.0$^{2,7}$.0$^{15,20}$]tetratriaconta-2,4,6(34),8,10(33),11, 13,15(20),16,18-decaen-3-yl]acetate: A solution of (S)-methyl 2-(7-(4-(allyloxy)-4-methylpiperidin-1-yl)-2-(5'-fluoro-2'-((S)-pent-4-en-2-yloxy)-[1,1'-biphenyl]-3-yl)-5-methylpyrazolo[1,5-a]pyrimidin-6-yl)-2-(tert-butoxy) acetate (0.17 g, 0.25 mmol, 1 equiv) in DCE (50 mL) was heated to 80° C. The Hoyveda Grubbs 2$^{nd}$ generation catalyst (31 mg, 0.05 mmol, 0.2 equiv) was added. The pale green brown solution was stirred for 1.5 h and then allowed to cool to ambient temperature. The reaction was concentrated in vacuo. The dark residue was then taken up in MeOH (5 mL) and NaBH$_4$ (13 mg, 0.35 mmol, 1.4 equiv) was added. After stirring 30 min, the reaction was diluted with EtOAc and washed with water. The EtOAc layer was dried (Na$_2$SO$_4$) and concentrated in vacuo. The crude product was purified by flash column chromatography (0-100% EtOAc in hexane) to provide the product as a colorless film (62 mg, 38%). $^1$H NMR (400 MHz, CDCl$_3$) δ 8.59 (s, 1H), 7.80 (s, 1H), 7.51 (s, 1H), 7.39-7.31 (m, 1H), 7.09 (s, 1H), 7.05-6.87 (m, 3H), 5.93-5.82 (m, 1H), 4.68-4.42 (m, 2H), 4.27-4.17 (m, 1H), 3.84-3.68 (m, J=3.5 Hz, 4H), 3.56-3.22 (m, 2H), 3.03-2.85 (m, 1H), 2.62 (br. s., 3H), 2.02-1.70 (m, J=12.8 Hz, 10H), 1.26-1.21 (m, 12H), 1.15 (d, J=6.0 Hz, 3H). LCMS (M+1)=659.45.

EXAMPLE 81

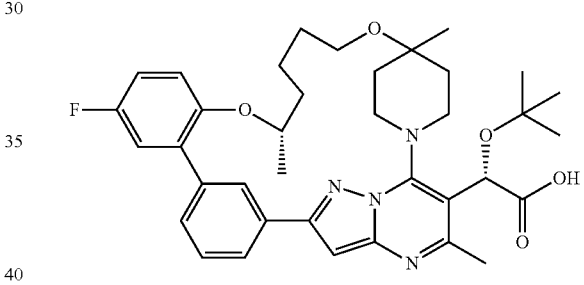

(2S)-2-(tert-Butoxy)-2-[(22S)-17-fluoro-4,22,28-trimethyl-21,27-dioxa-1,5,7,8-tetraazahexacyclo[26.2.2. 1$^{6,9}$.1$^{10,14}$.0$^{2,7}$.0$^{15,20}$]tetratriaconta-2,4,6(34),8,10(33),11, 13, 15(20),16,18-decaen-3-yl]acetic acid: To a solution of methyl (2S)-2-(tert-butoxy)-2-[(22S)-17-fluoro-4,22,28-trimethyl-21,27-dioxa-1,5,7,8-tetraazahexacyclo[26.2.2. 1$^{6,9}$1$^{10,14}$.0$^{2,7}$0$^{15,20}$]tetratriaconta-2,4,6(34),8,10(33),11,13, 15(20),16,18-decaen-3-yl]acetate (62 mg, 0.094 mmol, 1 equiv) in MeOH (0.85 mL) and water (0.09 mL) was added LiOHH$_2$O (79 mg, 1.88 mmol, 20 equiv). The reaction was heated to 60 oC for 1.5 h. Upon cooling to ambient temperature, DMF (1 mL) added to solubolize milky white opaque solution. The reaction was then filtered and purified via preparative LC/MS with the following conditions: Column. XBridge Phenyl, 19×mm, 5-1 μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min. Product (13.7 mg, 22%) isolated. $^1$H NMR (500 MHz, DMSO-d$_6$) δ 8.53 (s, 1H), 7.95 (d, J=7.3 Hz, 1H), 7.53 (t, J=7.8 Hz, 1H), 7.37 (d, J=7.9 Hz, 1H), 7.22-7.14 (m, 3H), 7.09 (s, 1H), 5.59 (br. s., 1H), 4.63 (d, J=6.1 Hz, 1H), 4.52-4.42 (m, 1H), 3.61-3.49 (m, 4H), 2.82 (d, J=11.3 Hz, 1H), 2.51 (br. s., 3H), 1.98-1.87 (m, 3H), 1.71 (br. s., 4H), 1.59-1.45 (m, 3H), 1.18 (s, 3H), 1.16 (s, 9H), 1.07 (d, J=5.8 Hz, 3H). LCMS (M+1)=645.4.

Intermediate 171

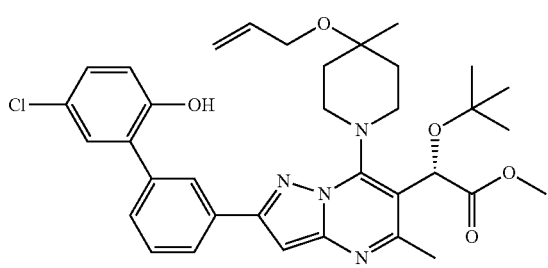

(S)-Methyl 2-(7-(4-(allyloxy)-4-methylpiperidin-1-yl)-2-(5'-chloro-2'-hydroxy-[1,1'-biphenyl]-3-yl)-5-methylpyrazolo[1,5-a]pyrimidin-6-yl)-2-(tert-butoxy)acetate: Prepared from (S)-methyl 2-(7-(4-(allyloxy)-4-methylpiperidin-1-yl)-2-(3-bromophenyl)-5-methylpyrazolo[1,5-a]pyrimidin-6-yl)-2-(tert-butoxy)acetate and (5-chloro-2-hydroxyphenyl) boronic acid using the same procedure as intermediate 168 in 69% yield. $^1$H NMR (400 MHz, CDCl$_3$) [note: 4H of piperidine not observed] δ8.08 (s, 1H), 8.04 (d, J=6.3 Hz, 1H), 7.58 (t, J=7.7 Hz, 1H), 7.46 (d, J=7.5 Hz, 1H), 7.32 (d, J=2.5 Hz, 1H), 7.27-7.23 (m, 1H), 6.97 (d, J=8.8 Hz, 1H), 6.85 (br. s., 1H), 5.98 (dd, J=11.2, 5.9 Hz, 1H), 5.93-5.83 (m, 1H), 5.64-5.57 (m, 1H), 5.40 (dd, J=17.1, 1.5 Hz, 1H), 5.16-5.07 (m, 1H), 4.01 (d, J=4.8 Hz, 2H), 3.76 (s, 3H), 2.62 (s, 3H), 2.09-1.90 (m, 3H), 1.78-1.68 (m, 1H), 1.36 (br. s., 3H), 1.25 (s, 9H). LCMS (M+1)=633.34.

Intermediate 172

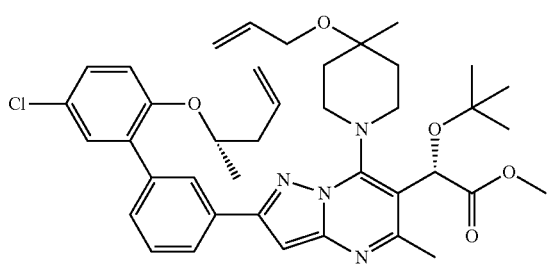

(S)-Methyl 2-(7-(4-(allyloxy)-4-methylpiperidin-1-yl)-2-(5'-chloro-2'4(S)-pent-4-en-2-yloxy)-[1,1'-biphenyl]-3-yl)-5-methylpyrazolo[1,5-a]pyrimidin-6-yl)-2-(tert-butoxy)acetate: Prepared from S)-methyl 2-(7-(4-(allyloxy)-4-methylpiperidin-1-yl)-2-(5'-chloro-2'-hydroxy-[1,1'-biphenyl]-3-yl)-5-methylpyrazolo[1,5-a]pyrimidin-6-yl)-2-(tert-butoxy)acetate using the same procedure as intermediate 169 in 94% yield. LCMS (M+1)=701.35.

Intermediate 172

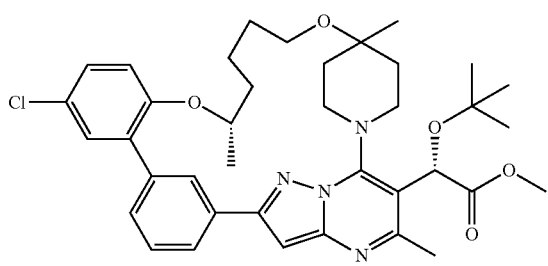

Methyl (2S)-2-(tert-butoxy)-2-[(22S)-17-chloro-4,22,28-trimethyl-21,27-dioxa-1,5,7,8-tetraazahexacyclo[26.2.2. 1$^{6,9}$.1$^{10,14}$.0$^{2,7}$.0$^{15,20}$]tetratriaconta-2,4,6(34),8,10(33),11, 13,15 (20),16,18-decaen-3-yl]acetate: Prepared from (S)-methyl 2-(7-(4-(allyloxy)-4-methylpiperidin-1-yl)-2-(5'-chloro-2'-((S)-pent-4-en-2-yloxy)-[1,1'-biphenyl]-3-yl)-5-methylpyrazolo[1,5-a]pyrimidin-6-yl)-2-(tert-butoxy) acetate using the same procedure as intermediate 170 in 47% yield. $^1$H NMR (400 MHz, CDCl$_3$) δ 8.62-8.51 (m, 1H), 7.85-7.80 (m, 1H), 7.55-7.48 (m, 1H), 7.36-7.31 (m, 2H), 7.27-7.25 (m, 1H), 6.95-6.88 (m, 2H), 5.90-5.78 (m, 1H), 4.66-4.51 (m, 2H), 4.26-4.17 (m, 2H), 3.77 (s, 3H), 3.55-3.21 (m, 3H), 2.66-2.59 (m, 3H), 2.02-1.59 (m, 10H), 1.32-1.21 (m, 15H). LCMS (M+1)=675.5.

EXAMPLE 82

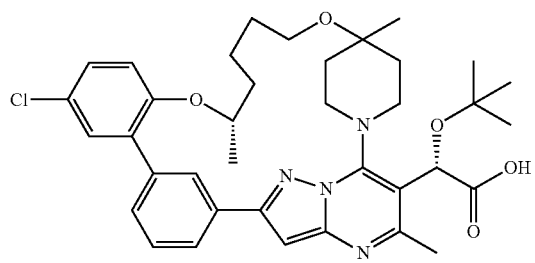 [SMILES: Cc1nc2cc3nn2c(c1[C@H](OC(C)(C)C)C(=O)O)N1CCC(C)(CC1)OCCCC[C@H](C)Oc1ccc(Cl)cc1-c1cccc-3c1]

(2S)-2-(tert-Butoxy)-2-[(22S)-17-chloro-4,22,28-trimethyl-21,27-dioxa-1,5,7,8-tetraazahexacyclo[26.2.2. 1$^{6,9}$.1$^{10,14}$.0$^{2,7}$.0$^{15,20}$]tetratriaconta-2,4,6(34),8,10(33), 11, 13, 15 (20),16,18-decaen-3-yl]acetic acid: Prepared from methyl (2S)-2-(tert-butoxy)-2-[(22S)-17-chloro-4,22,28-trimethyl-21,27-dioxa-1,5,7,8-tetraazahexacyclo[26.2.2. 1$^{6,9}$.1$^{10,14}$.0$^{2,7}$.0$^{15,20}$]tetratriaconta-2,4,6(34),8,10(33),11, 13,15(20),16,18-decaen-3-yl]acetate using the same procedure as example 81 in 47% yield. $^1$H NMR (500 MHz, DMSO-d$_6$) δ 8.47 (s, 1H), 7.95 (br. s., 1H), 7.57-7.49 (m, 1H), 7.35 (t, J=9.0 Hz, 2H), 7.30 (d, J=2.1 Hz, 1H), 7.19 (d, J=8.9 Hz, 1H), 7.09 (s, 1H), 5.63 (br. s., 1H), 4.67-4.60 (m, 1H), 4.50-4.41 (m, 1H), 3.91-3.87 (m, 1H), 3.39 (br. s., 3H), 2.81-2.76 (m, 1H), 2.50 (br. s., 3H), 1.99-1.24 (m, 10H), 1.15 (br. s., 3H), 1.14 (s, 9H), 1.06 (d, J=5.8 Hz, 3H). LCMS (M+1)= 661.4.

Intermediate 173

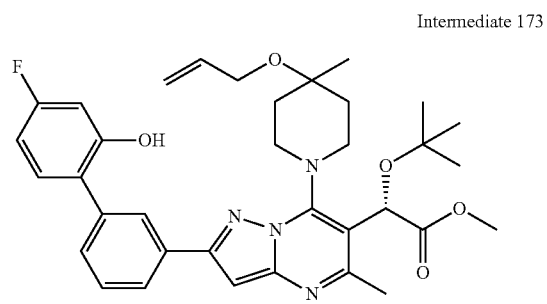 [SMILES: C=CCOC1(C)CCN(c2c([C@H](OC(C)(C)C)C(=O)OC)c(C)nc3cc(-c4cccc(-c5ccc(F)cc5O)c4)nn23)CC1]

(S)-Methyl 2-(7-(4-(allyloxy)-4-methylpiperidin-1-yl)-2-(4'-fluoro-2'-hydroxy-[1,1'-biphenyl]-3-yl)-5-methylpyrazolo[1,5-a]pyrimidin-6-yl)-2-(tert-butoxy)acetate: Prepared from (S)-methyl 2-(7-(4-(allyloxy)-4-methylpiperidin-1-yl)-2-(3-bromophenyl)-5-methylpyrazolo[1,5-a]pyrimidin-6-yl)-2-(tert-butoxy)acetate and (4-fluoro-2-hydroxyphenyl) boronic acid using the same procedure as intermediate 168 in 69% yield. $^1$H NMR (400 MHz, CDCl$_3$) δ 8.08 (s, 1H), 8.02 (d, J=7.5 Hz, 1H), 7.54 (t, J=7.7 Hz, 1H), 7.43 (d, J=7.8 Hz, 1H), 7.31-7.24 (m, 1H), 6.84 (s, 1H), 6.81-6.70 (m, 2H), 6.67-6.52 (m, 1H), 6.09-5.81 (m, 2H), 5.40 (dd, J=17.1, 1.8 Hz, 1H), 5.18-5.04 (m, 1H), 4.00 (d, J=5.0 Hz, 2H), 3.76 (s, 3H), 2.04-1.91 (m, 2H), 1.78-1.55 (m, 2H), 1.36 (s, 3H), 1.25 (s, 9H). LCMS (M+1)=617.35.

Intermediate 174

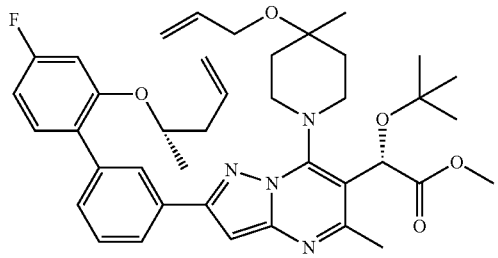

(S)-Methyl 2-(7-(4-(allyloxy)-4-methylpiperidin-1-yl)-2-(4'-fluoro-2'4(S)-pent-4-en-2-yloxy)-[1,1'-biphenyl]-3-yl)-5-methylpyrazolo[1,5-a]pyrimidin-6-yl)-2-(tert-butoxy)acetate: Prepared from (S)-methyl 2-(7-(4-(allyloxy)-4-methylpiperidin-1-yl)-2-(4'-fluoro-2'-hydroxy-[1,1'-biphenyl]-3-yl)-5-methylpyrazolo[1,5-a]pyrimidin-6-yl)-2-(tert-butoxy)acetate using the same procedure as intermediate 169 in 95% yield. $^1$H NMR (500 MHz, CDCl$_3$) [note: 4H of piperidine not observed and are likely very broad] δ 8.11-8.08 (m, 1H), 8.06-7.99 (m, 1H), 7.57-7.46 (m, 2H), 7.39-7.33 (m, 1H), 6.96-6.82 (m, 1H), 6.81-6.73 (m, 2H), 6.08-5.94 (m, 1H), 5.84-5.71 (m, 1H), 5.46-5.38 (m, 1H), 5.22-5.00 (m, 4H), 4.47-4.35 (m, 1H), 4.05-4.01 (m, 2H), 3.77 (d, J=2.0 Hz, 3H), 2.68-2.61 (m, 3H), 2.51-2.42 (m, 1H), 2.38-2.28 (m, 1H), 2.06-1.92 (m, 3H), 1.82-1.67 (m, 1H), 1.30 (s, 3H), 1.29 (d, J=1.1 Hz, 3H), 1.27-1.26 (m, 9H). LCMS (M+1)=685.4.

Intermediate 175

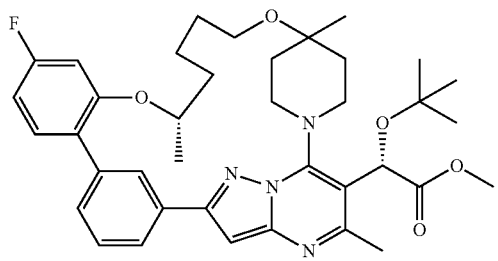

Methyl (2S)-2-(tert-butoxy)-2-[(22S)-18-fluoro-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33), 11, 13, 15(20),16,18-decaen-3-yl]acetate: Prepared from (S)-methyl 2-(7-(4-(allyloxy)-4-methylpiperidin-1-yl)-2-(4'-fluoro-2'-hydroxy-[1,1'-biphenyl]-3-yl)-5-methylpyrazolo[1,5-a]pyrimidin-6-yl)-2-(tert-butoxy)acetate using the same procedure as intermediate 170 in 21% yield. $^1$H NMR (400 MHz, CDCl$_3$) δ 8.55 (s, 1H), 7.80 (d, J=7.8 Hz, 1H), 7.49 (t, J=7.7 Hz, 1H), 7.31-7.25 (m, 2H), 6.96-6.88 (m, 1H), 6.78-6.68 (m, 2H), 5.95-5.82 (m, 1H), 4.63 (s, 1H), 4.53 (br. s., 1H), 3.83-3.73 (m, 4H), 3.52 (br. s., 1H), 3.39 (br. s., 1H), 3.32-3.19 (m, 1H), 2.97-2.82 (m, 1H), 2.61 (br. s., 3H), 2.04-1.53 (m, 10H), 1.27 (s, 3H), 1.24 (s, 9H), 1.20 (d, J=6.0 Hz, 3H). LCMS (M+1)=659.4.

EXAMPLE 83

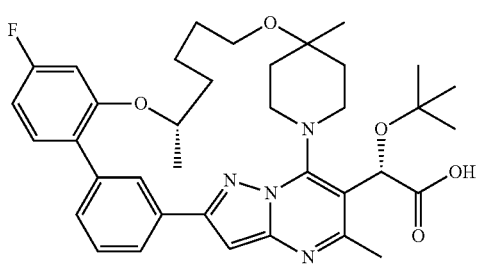 [SMILES: Cc1nc2cc3nn2c(c1[C@H](OC(C)(C)C)C(=O)O)N1CCC(C)(CC1)OCCCC[C@H](C)Oc1cc(F)ccc1-c1cccc-3c1]

(2S)-2-(tert-Butoxy)-2-[(22S)-18-fluoro-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4, 6(34), 8, 10(33), 11, 13, 15(20),16,18-decaen-3-yl]acetic acid: Prepared from methyl (2S)-2-(tert-butoxy)-2-[(22S)-18-fluoro-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate using the same procedure as example 81 in 47% yield. $^1$H NMR (500 MHz, DMSO-d$_6$) δ 8.47 (s, 1H), 7.92 (d, J=7.6 Hz, 1H), 7.51 (t, J=7.6 Hz, 1H), 7.37-7.26 (m, 2H), 7.11 (d, J=10.7 Hz, 1H), 7.05 (s, 1H), 6.83 (t, J=8.1 Hz, 1H), 5.50 (br. s., 1H), 4.70 (d, J=6.1 Hz, 1H), 4.47 (t, J=12.7 Hz, 1H), 3.68-3.52 (m, 3H), 2.88-2.78 (m, 2H), 2.55 (s, 3H), 1.91 (s, 3H), 1.77-1.63 (m, 4H), 1.58-1.44 (m, 3H), 1.18 (s, 3H), 1.14 (s, 9H), 1.10 (d, J=5.8 Hz, 3H). LCMS (M+1)=645.5.

Intermediate 176

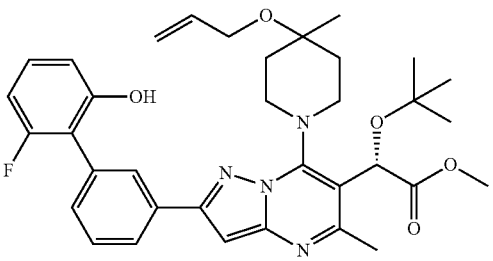

(S)-Methyl 2-(7-(4-(allyloxy)-4-methylpiperidin-1-yl)-2-(2'-fluoro-6'-hydroxy-[1,1'-biphenyl]-3-yl)-5-methylpyrazolo[1,5-a]pyrimidin-6-yl)-2-(tert-butoxy)acetate: Prepared from (S)-methyl 2-(7-(4-(allyloxy)-4-methylpiperidin-1-yl)-2-(3-bromophenyl)-5-methylpyrazolo[1,5-a]pyrimidin-6-yl)-2-(tert-butoxy)acetate and (2-fluoro-6-hydroxyphenyl)boronic acid using the same procedure as intermediate 168 in 75% yield. $^1$H NMR (400 MHz, CDCl$_3$) δ 8.19-7.99 (m, 2H), 7.61 (t, J=7.8 Hz, 1H), 7.46 (br. s., 1H), 7.25 (d, J=6.5 Hz, 1H), 6.92-6.74 (m, 3H), 6.13-5.78 (m, 2H), 5.59-5.47 (m, 1H), 5.39 (dd, J=17.2, 1.6 Hz, 1H), 5.20-4.99 (m, 1H), 4.00 (d, J=4.8 Hz, 2H), 3.76 (s, 3H), 2.72-2.54 (m, 3H), 2.05-1.87 (m, 3H), 1.79-1.64 (m, 3H), 1.35 (s, 3H), 1.25 (s, 9H). LCMS (M+1)=617.35.

Intermediate 177

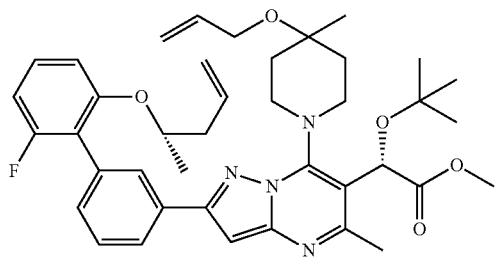

(S)-Methyl 2-(7-(4-(allyloxy)-4-methylpiperidin-1-yl)-2-(2'-fluoro-6'-((S)-pent-4-en-2-yloxy)-[1,1'-biphenyl]-3-yl)-5-methylpyrazolo[1,5-a]pyrimidin-6-yl)-2-(tert-butoxy)acetate: Prepared from (S)-methyl 2-(7-(4-(allyloxy)-4-methylpiperidin-1-yl)-2-(2'-fluoro-6'-hydroxy-[1,1'-biphenyl]-3-yl)-5-methylpyrazolo[1,5-a]pyrimidin-6-yl)-2-(tert-butoxy)acetate using the same procedure as intermediate 169 in 80% yield. $^1$H NMR (400 MHz, CDCl$_3$) [note: 4H of piperidine not observed and are likely very broad] δ 8.03 (s, 2H), 7.59-7.40 (m, 2H), 7.30-7.21 (m, 2H), 6.92-6.75 (m, 2H), 6.10-5.94 (m, 1H), 5.78-5.63 (m, 1H), 5.41 (d, J=16.8 Hz, 1H), 5.21-5.04 (m, 1H), 5.03-4.95 (m, 2H), 4.39 (d, J=6.0 Hz, 1H), 4.26-4.17 (m, 1H), 4.01 (d, J=4.5 Hz, 2H), 3.75 (s, 3H), 2.62 (br. s., 3H), 2.35 (s, 1H), 2.25 (d, J=6.5 Hz, 2H), 2.00 (br. s., 3H), 1.36 (br. s., 3H), 1.31-1.13 (m, 12H). LCMS (M+1)=685.45.

EXAMPLE 84

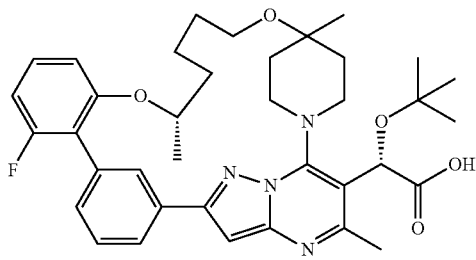 [SMILES: Cc1nc2cc3nn2c(c1[C@H](OC(C)(C)C)C(=O)O)N1CCC(C)(CC1)OCCCC[C@H](C)Oc1cccc(F)c1-c1cccc-3c1]

(2S)-2-(tert-Butoxy)-2-[(22S)-16-fluoro-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid: Prepared from (5)-methyl 2-(7-(4-(allyloxy)-4-methylpiperidin-1-yl)-2-(2'-fluoro-6'-((S)-pent-4-en-2-yloxy)-[1,1'-b iphenyl]-3-yl)-5-methylpyrazolo[1,5-a]pyrimidin-6-yl)-2-(tert-butoxy) acetate using the same procedures as intermediate 170 and example 81 in 12% yield. $^1$H NMR (500 MHz, DMSO-d$_6$) δ 8.26 (br. s., 1H), 7.95 (d, J=7.0 Hz, 1H), 7.51 (t, J=7.6 Hz, 1H), 7.37 (d, J=7.3 Hz, 1H), 7.28 (d, J=6.7 Hz, 1H), 7.08 (s, 1H), 7.04 (d, J=8.2 Hz, 1H), 6.87 (t, J=8.7 Hz, 1H), 5.63 (br. s., 1H), 4.66 (br. s., 1H), 4.52 (t, J=12.1 Hz, 1H), 3.58-3.49 (m, 1H), 3.41 (br. s., 2H), 3.31 (br. s., 1H), 2.77 (d, J=11.6 Hz, 1H), 2.51 (br. s., 3H), 1.94-1.84 (m, 4H), 1.64 (d, J=6.1 Hz, 5H), 1.56 (d, J=13.4 Hz, 1H), 1.43 (br. s., 3H), 1.15 (s, 9H), 1.08 (d, J=5.5 Hz, 3H). LCMS (M+1)=645.5.

Intermediate 178

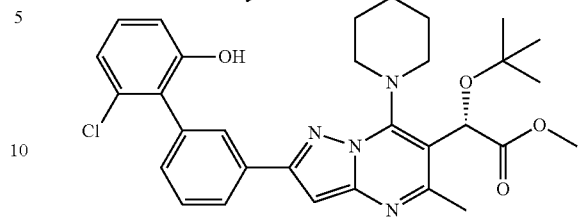

(S)-Methyl 2-(7-(4-(allyloxy)-4-methylpiperidin-1-yl)-2-(2'-chloro-6'-hydroxy-[1,1'-biphenyl]-3-yl)-5-methylpyrazolo[1,5-a]pyrimidin-6-yl)-2-(tert-butoxy)acetate: Prepared from (S)-methyl 2-(7-(4-(allyloxy)-4-methylpiperidin-1-yl)-2-(3-bromophenyl)-5-methylpyrazolo[1,5-a]pyrimidin-6-yl)-2-(tert-butoxy)acetate and (2-chloro-6-hydroxyphenyl)boronic acid using the same procedure as intermediate 168 in 81% yield. $^1$H NMR (400 MHz, CDCl$_3$) [note: 4H of piperidine and phenolic —OH not observed] δ 8.13-8.06 (m, 1H), 7.97 (s, 1H), 7.62 (t, J=7.8 Hz, 1H), 7.38 (d, J=7.5 Hz, 1H), 7.26-7.20 (m, 1H), 7.11 (d, J=8.0 Hz, 1H), 6.97 (d, J=8.3 Hz, 1H), 6.89-6.77 (m, 1H), 6.06-5.90 (m, 1H), 5.39 (dd, J=17.1, 1.5 Hz, 1H), 5.29-5.20 (m, 1H), 5.15-5.04 (m, 1H), 3.99 (d, J=4.8 Hz, 2H), 3.76 (s, 3H), 2.63 (br. s., 3H), 2.07-1.91 (m, 3H), 1.79-1.65 (m, 1H), 1.35 (s, 3H), 1.25 (s, 9H). LCMS (M+1)=633.3.

Intermediate 179

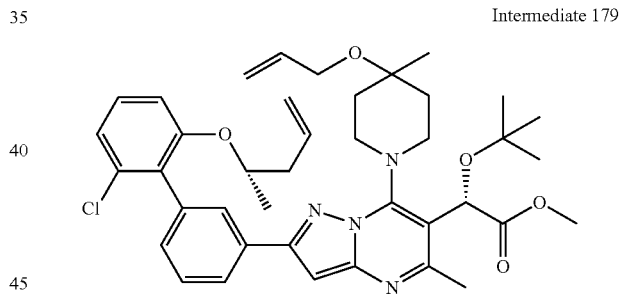

(S)-Methyl 2-(7-(4-(allyloxy)-4-methylpiperidin-1-yl)-2-(2'-chloro-6'-((S)-pent-4-en-2-yloxy)-[1,1'-biphenyl]-3-yl)-5-methylpyrazolo[1,5-a]pyrimidin-6-yl)-2-(tert-butoxy)acetate: Prepared from (S)-methyl 2-(7-(4-(allyloxy)-4-methylpiperidin-1-yl)-2-(2'-chloro-6'-hydroxy-[1,1'-biphenyl]-3-yl)-5-methylpyrazolo[1,5-a]pyrimidin-6-yl)-2-(tert-butoxy)acetate using the same procedure as intermediate 169 in 83% yield. $^1$H NMR (400 MHz, CDCl$_3$) [note: 2H of piperidine not observed and are likely very broad] δ 8.10-7.97 (m, 1H), 7.91 (s, 1H), 7.50 (t, J=7.7 Hz, 1H), 7.33 (d, J=7.3 Hz, 1H), 7.26-7.22 (m, 1H), 7.13 (d, J=8.0 Hz, 1H), 6.92 (d, J=8.3 Hz, 1H), 6.86-6.77 (m, 1H), 5.98 (dd, J=11.2, 5.9 Hz, 2H), 5.71-5.57 (m, 1H), 5.40 (d, J=16.6 Hz, 1H), 5.11 (br. s., 2H), 5.00-4.89 (m, 2H), 4.32 (d, J=6.0 Hz, 1H), 4.21 (br. s., 1H), 4.00 (d, J=5.0 Hz, 2H), 3.75 (s, 3H), 2.62 (br. s., 3H), 2.28 (d, J=6.8 Hz, 1H), 2.19 (d, J=6.8 Hz, 1H), 1.99 (br. s., 3H), 1.77-1.69 (m, 1H), 1.35 (br. s., 3H), 1.25 (s, 9H), 1.18 (d, J=6.0 Hz, 3H). LCMS (M+1)=701.35.

Intermediate 180

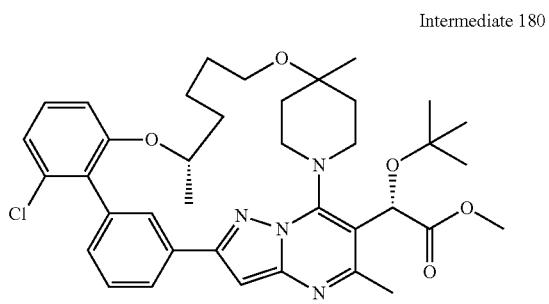 [SMILES: COC(=O)[C@@H](OC(C)(C)C)c1c(C)nc2cc3nn2c1N1CCC(C)(CC1)OCCCC[C@H](C)Oc1cccc(Cl)c1-c1cccc-3c1]

Methyl (2S)-2-(tert-butoxy)-2-[(22S)-16-chloro-4,22,28-trimethyl-21,27-dioxa-1,5,7,8-tetraazahexacyclo[26.2.2.1⁶,⁹.1¹⁰,¹⁴.0²,⁷.0¹⁵,²⁰]tetratriaconta-2,4,6(34),8,10(33), 11, 13, 15(20),16,18-decaen-3-yl]acetate: Prepared from (S)-methyl 2-(7-(4-(allyloxy)-4-methylpiperidin-1-yl)-2-(2'-chloro-6'-((S)-pent-4-en-2-yloxy)-[1,1'-biphenyl]-3-yl)-5-methylpyrazolo[1,5-a]pyrimidin-6-yl)-2-(tert-butoxy)acetate using the same procedure as intermediate 170 in 32% yield. ¹H NMR (400 MHz, CDCl₃) δ 8.14-8.09 (m, 1H), 7.83-7.77 (m, 1H), 7.56-7.49 (m, 1H), 7.24 (s, 2H), 7.09-7.04 (m, 1H), 6.92-6.84 (m, 2H), 6.25-6.11 (m, 1H), 6.05-5.94 (m, 1H), 5.68-5.56 (m, 1H), 4.54-4.40 (m, 1H), 4.20 (br. s., 2H), 3.94-3.84 (m, 2H), 3.77-3.70 (m, 5H), 2.64 (br. s., 3H), 2.40-2.16 (m, 2H), 2.04-1.63 (m, 4H), 1.32-1.23 (m, 12H), 1.16 (d, J=6.0 Hz, 3H). LCMS (M+1)=673.35.

EXAMPLE 85

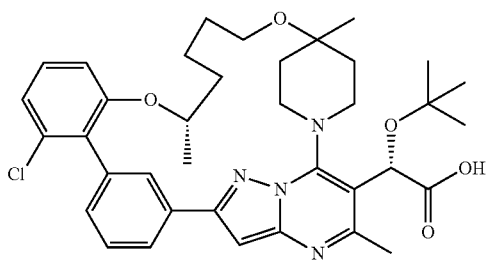 [SMILES: Cc1nc2cc3nn2c(c1[C@H](OC(C)(C)C)C(=O)O)N1CCC(C)(CC1)OCCCC[C@H](C)Oc1cccc(Cl)c1-c1cccc-3c1]

(2S)-2-(tert-Butoxy)-2-[(22S)-16-chloro-4,22,28-trimethyl-21,27-dioxa-1,5,7,8-tetraazahexacyclo[26.2.2.1⁶,⁹.1¹⁰,¹⁴.0²,⁷.0¹⁵,²⁰]tetratriaconta-2,4, 6(34), 8, 10(33), 11, 13, 15 (20),16,18-decaen-3-yl]acetic acid: Prepared from methyl (2S)-2-(tert-butoxy)-2-[(22S)-16-chloro-4,22,28-trimethyl-21,27-dioxa-1,5,7,8-tetraazahexacyclo[26.2.2.1⁶,⁹.1¹⁰,¹⁴.0²,⁷.0¹⁵,²⁰]tetratriaconta-2,4,6(34),8,10(33),11,13,15 (20),16,18-decaen-3-yl]acetate using the same procedures as example 81 in 32% yield. ¹H NMR (500 MHz, DMSO-d₆) δ 8.06 (br. s., 1H), 7.92 (d, J=7.6 Hz, 1H), 7.52 (t, J=7.8 Hz, 1H), 7.39-7.32 (m, 1H), 7.21 (d, J=7.6 Hz, 1H), 7.17 (d, J=8.5 Hz, 1H), 7.12 (d, J=7.9 Hz, 1H), 7.05 (s, 1H), 5.69 (br. s., 1H), 4.63 (br. s., 1H), 4.56 (t, J=13.1 Hz, 1H), 3.56-3.43 (m, J=11.9 Hz, 3H), 2.79-2.71 (m, 2H), 2.55 (s, 3H), 1.87-1.32 (m, 10H), 1.16 (s, 12H), 1.08 (d, J=5.8 Hz, 3H). LCMS (M+1)=661.5.

Intermediate 181

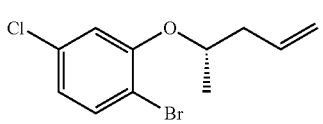

(S)-1-Bromo-4-chloro-2-(pent-4-en-2-yloxy)benzene: To a solution of 2-bromo-5-chlorophenol (0.40 g, 1.93 mmol, 1 equiv), (R)-pent-4-en-2-ol (0.397 mL, 3.86 mmol, 2 equiv), and PPh₃ (1.01 g, 3.86 mmol, 2 equiv) in THF (6.4 mL) was added DEAD (0.61 mL, 3.86 mmol, 2 equiv). After stirring 20 h, reaction diluted with ether and washed with 1 N NaOH. The ether layer was dried (MgSO₄) and concentrated in vacuo. The crude product was purified by flash column chromatography (0-10% EtOAc in hexane) to provide the product as a colorless oil (0.49 g, 92%). ¹H NMR (400 MHz, CDCl₃) δ 7.45 (d, J=8.3 Hz, 1H), 6.89 (d, J=2.3 Hz, 1H), 6.83 (dd, J=8.5, 2.3 Hz, 1H), 5.90 (ddt, J=17.1, 10.1, 7.2 Hz, 1H), 5.21-5.11 (m, 2H), 4.49-4.39 (m, 1H), 2.60-2.50 (m, 1H), 2.48-2.38 (m, 1H), 1.37 (d, J=6.3 Hz, 3H).

Intermediate 182

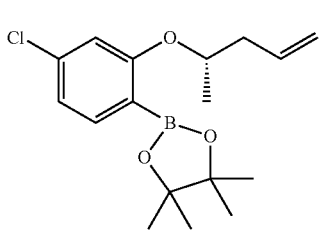

(S)-2-(4-Chloro-2-(pent-4-en-2-yloxy)phenyl)-4,4,5,5-tetramethyl-1,3,2-dioxaborolane: A solution of (S)-1-bromo-4-chloro-2-(pent-4-en-2-yloxy)benzene (0.49 g, 1.78 mmol, 1 equiv) in THF was cooled to −78° C. (IPA/CO₂). nBuLi (1.33 mL of a 1.6 M solution in hexane, 2.13 mmol, 1.2 equiv) was added. No color change observed. After stirring 30 min, 2-isopropoxy-4,4,5,5-tetramethyl-1,3,2-dioxaborolane (0.44 mL, 3.13 mmol, 1.2 equiv) was added and the reaction was allowed to warm to ambient temperature. Upon stirring for 3 h, the reaction was diluted with EtOAc and washed with water. The EtOAc layer was dried (Na₂SO₄) and concentrated in vacuo to provide the product as a tan oil (0.59 g, ~100%). ¹H NMR (400 MHz, CDCl₃) δ 7.55 (d, J=7.8 Hz, 1H), 6.93 (dd, J=8.0, 1.8 Hz, 1H), 6.87 (d, J=1.5 Hz, 1H), 6.04-5.89 (m, 1H), 5.20-5.04 (m, 2H), 4.38 (d, J=6.0 Hz, 1H), 2.56-2.35 (m, 2H), 1.35 (s, 12H), 1.27 (d, J=6.3 Hz, 3H).

Intermediate 183

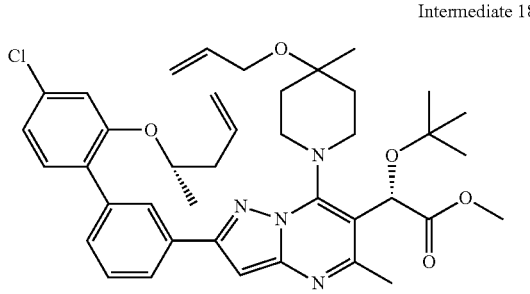

(S)-Methyl 2-(7-(4-(allyloxy)-4-methylpiperidin-1-yl)-2-(4'-chloro-2'4(S)-pent-4-en-2-yloxy)-[1,1'-biphenyl]-3-yl)-5-methylpyrazolo[1,5-a]pyrimidin-6-yl)-2-(tert-butoxy)acetate: Prepared from (S)-2-(4-chloro-2-(pent-4-en-2-yloxy)phenyl)-4,4,5,5-tetramethyl-1,3,2-dioxaborolane and (S)-methyl 2-(7-(4-(allyloxy)-4-methylpiperidin-1-yl)-2-(3-bromophenyl)-5-methylpyrazolo[1,5-a]pyrimidin-6-yl)-2-(tert-butoxy)acetate using the same procedure as intermediate 168 in 92% yield. $^1$H NMR (400 MHz, CDCl$_3$) [note: 4H of piperidine not observed] δ 8.09 (s, 1H), 8.05-7.98 (m, 1H), 7.57-7.44 (m, 2H), 7.34 (d, J=8.0 Hz, 2H), 7.08-7.02 (m, 1H), 7.00 (d, J=1.8 Hz, 1H), 6.06-5.69 (m, 3H), 5.46-5.35 (m, 1H), 5.18-5.10 (m, 1H), 5.09-5.04 (m, 1H), 5.03 (s, 1H), 4.47-4.36 (m, 1H), 4.01 (d, J=5.0 Hz, 2H), 3.76 (d, J=3.3 Hz, 3H), 2.66-2.61 (m, 3H), 2.49-2.39 (m, 1H), 2.36-2.25 (m, 1H), 2.00-1.91 (m, 2H), 1.84-1.63 (m, 2H), 1.36 (br. s., 3H), 1.28 (d, J=6.3 Hz, 3H), 1.25 (s, 9H). LCMS (M+1)=701.35.

Intermediate 184

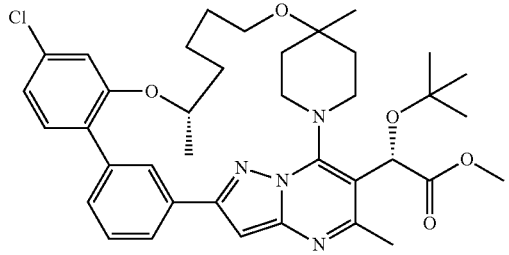

Methyl (2S)-2-(tert-butoxy)-2-[(22S)-18-chloro-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13, 15 (20),16,18-decaen-3-yl]acetate: Prepared from (S)-methyl 2-(7-(4-(allyloxy)-4-methylpiperidin-1-yl)-2-(4'-chloro-2'-((S)-pent-4-en-2-yloxy)-[1,1'-biphenyl]-3-yl)-5-methylpyrazolo[1,5-a]pyrimidin-6-yl)-2-(tert-butoxy)acetate using the same procedure as intermediate 170 in 57% yield. $^1$H NMR (400 MHz, CDCl$_3$) δ 8.55 (s, 1H), 7.81 (d, J=7.8 Hz, 1H), 7.56-7.46 (m, 1H), 7.31-7.25 (m, 3H), 7.03-6.97 (m, 2H), 5.84 (br. s., 1H), 4.68-4.52 (m, 2H), 3.83-3.74 (m, 4H), 3.51 (d, J=6.3 Hz, 1H), 3.41 (d, J=5.3 Hz, 1H), 3.29 (br. s., 1H), 2.92 (br. s., 1H), 2.63 (br. s., 3H), 2.01 (d, J=12.5 Hz, 3H), 1.88-1.69 (m, 4H), 1.66-1.59 (m, 3H), 1.27 (s, 3H), 1.24 (s, 9H), 1.19 (d, J=6.0 Hz, 3H). LCMS (M+1)=675.35.

EXAMPLE 86

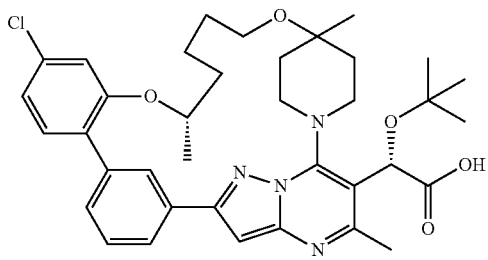 [SMILES: Cc1nc2cc3nn2c(c1[C@H](OC(C)(C)C)C(=O)O)N1CCC(C)(CC1)OCCCC[C@H](C)Oc1cc(Cl)ccc1-c1cccc-3c1]

(2S)-2-(tert-Butoxy)-2-[(22S)-18-chloro-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33), 11, 13, 15 (20),16,18-decaen-3-yl]acetic acid: Prepared from methyl (2S)-2-(tert-butoxy)-2-[(22S)-18-chloro-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11, 13,15 (20),16,18-decaen-3-yl]acetate using the same procedure as example 81 in 82% yield. $^1$H NMR (500 MHz, DMSO-d$_6$) δ 8.46 (br. s., 1H), 7.95 (d, J=7.6 Hz, 1H), 7.52 (t, J=7.6 Hz, 1H), 7.33-7.25 (m, 3H), 7.10 (s, 1H), 7.05 (d, J=8.2 Hz, 1H), 5.63 (br. s., 1H), 4.73 (br. s., 1H), 4.54-4.42 (m, 1H), 3.63-3.48 (m, J=11.3 Hz, 4H), 2.80 (d, J=9.8 Hz, 1H), 2.50 (s, 3H), 195-1.86 (m, 3H), 1.70 (br. s., 4H), 1.58-1.44 (m, 3H), 1.18 (br. s., 3H), 1.16 (s, 9H), 1.08 (d, J=5.5 Hz, 3H). LCMS (M+1)=661.5.

Intermediate 185

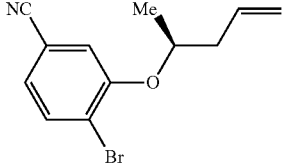

(S)-4-Bromo-3-(pent-4-en-2-yloxy)benzonitrile: To a solution of 4-bromo-3-fluorobenzonitrile (1.0 g, 5.00 mmol, 1 equiv) and (S)-pent-4-en-2-ol (0.52 g, 6.00 mmol, 1.2 equiv) in THF (25 mL) was added NaH (0.24 g of a 60% suspension in mineral oil, 6.00 mmol, 1.2 equiv). Slow gas evolution with considerable foaming observed. After 5 h, dilute with ether then wash with water and brine. The ether layer was dried (MgSO$_4$) and concentrated in vacuo. The crude product was purified by flash column chromatography (0-10% EtOAc in hexane) to provide the product as a colorless oil (0.94 g, 71%). $^1$H NMR (400 MHz, CDCl$_3$) δ 7.69-7.62 (m, 1H), 7.15-7.08 (m, 2H), 5.89 (ddt, J=17.1, 10.1, 7.2 Hz, 1H), 5.23-5.12 (m, 2H), 4.54-4.42 (m, 1H), 2.61-2.51 (m, 1H), 2.51-2.40 (m, 1H), 1.39 (d, J=6.0 Hz, 3H).

Intermediate 186

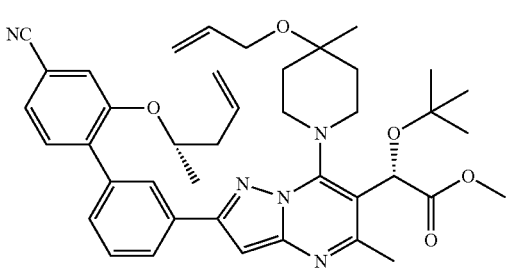

(S)-Methyl 2-(7-(4-(allyloxy)-4-methylpiperidin-1-yl)-2-(4'-cyano-2'-((S)-pent-4-en-2-yloxy)-[1,1'-biphenyl]-3-yl)-5-methylpyrazolo[1,5-a]pyrimidin-6-yl)-2-(tert-butoxy)acetate: To a solution of (S)-4-bromo-3-(pent-4-en-2-yloxy)benzonitrile (0.136 g, 0.51 mmol, 1.5 equiv) in THF (3.4 mL) was added Reike zinc (0.67 mL of a 10 g/100 mL slurry in THF, 1.03 mmol, 3 equiv). The reaction was then heated at 60° C. for 2 h. Upon cooling to ambient temperature, the zincate solution was filtered and added to a solution of (S)-methyl 2-(7-(4-(allyloxy)-4-methylpiperidin-1-yl)-2-(3-bromophenyl)-5-methylpyrazolo[1,5-a]pyrimidin-6-yl)-2-(tert-butoxy)acetate (0.20 g, 0.34 mmol, 1 equiv) in THF (1.7 mL). The reaction was then heated at 60° C. for 18 h. Upon cooling to ambient temperature, the reaction was diluted with EtOAc and washed with a saturated aqueous solution of NaHCO$_3$. The EtOAc layer was dried (Na$_2$SO$_4$) and concentrated in vacuo. The crude product was purified by flash column chromatography (0-100% EtOAc in hexane) to provide the product as a colorless oil (0.14 g, 59%). $^1$H NMR (400 MHz, CDCl₃) [note: 4H of piperidine not observed] δ 8.12 (s, 1H), 8.07 (d, J=6.8 Hz, 1H), 7.56-7.48 (m, 3H), 7.36 (dd, J=7.8, 1.3 Hz, 1H), 7.24 (s, 1H), 6.85 (br. s., 1H), 6.06-5.92 (m, J=11.2, 11.2, 5.0 Hz, 2H), 5.72 (s, 1H), 5.40 (dd, J=17.1, 1.5 Hz, 1H), 5.13-5.05 (m, J=3.5 Hz, 2H), 5.03 (s, 1H), 4.52-4.43 (m, J=5.8 Hz, 1H), 4.01 (d, J=4.5 Hz, 2H), 3.75 (s, 3H), 2.63 (s, 3H), 2.48-2.39 (m, 1H), 2.38-2.28 (m, J=7.5 Hz, 1H), 2.05-1.94 (m, 2H), 1.78-1.68 (m, 1H), 1.59 (br. s., 1H), 1.36 (br. s., 3H), 1.30 (d, J=6.0 Hz, 3H), 1.26 (s, 9H). LCMS (M+1)=692.35.

Intermediate 187

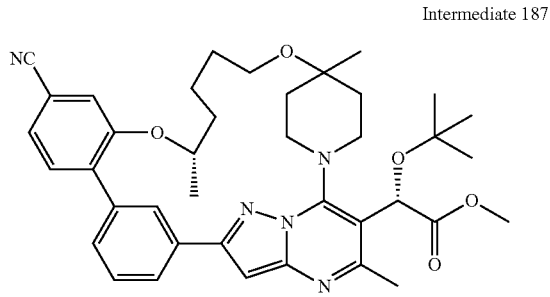 [SMILES: COC(=O)[C@@H](OC(C)(C)C)c1c(C)nc2cc3nn2c1N1CCC(C)(CC1)OCCCC[C@H](C)Oc1cc(C#N)ccc1-c1cccc-3c1]

Methyl (2S)-2-(tert-butoxy)-2-[(22S)-18-cyano-4,22,28-trimethyl-21,27-dioxa-1,5,7,8-tetraazahexacyclo[26.2.2.1⁶,⁹.1¹⁰,¹⁴.0²,⁷.0¹⁵,²⁰]tetratriaconta-2,4, 6(34), 8, 10(33), 11, 13, 15 (20),16,18-decaen-3-yl]acetate: Prepared from (S)-methyl 2-(7-(4-(allyloxy)-4-methylpiperidin-1-yl)-2-(4'-cyano-2'-((S)-pent-4-en-2-yloxy)-[1,1'-biphenyl]-3-yl)-5-methylpyrazolo[1,5-a]pyrimidin-6-yl)-2-(tert-butoxy)acetate using the same procedure as intermediate 170 in 16% yield. LCMS (M+1)=666.4.

EXAMPLE 87

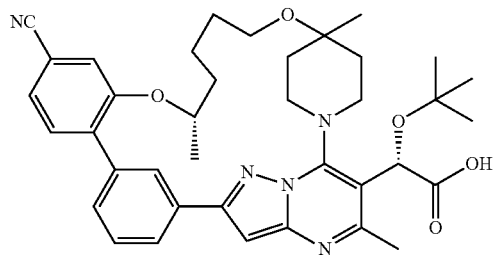 [SMILES: Cc1nc2cc3nn2c(c1[C@H](OC(C)(C)C)C(=O)O)N1CCC(C)(CC1)OCCCC[C@H](C)Oc1cc(C#N)ccc1-c1cccc-3c1]

(2S)-2-(tert-Butoxy)-2-[(22S)-18-cyano-4,22,28-trimethyl-21,27-dioxa-1,5,7,8-tetraazahexacyclo[26.2.2.1⁶,⁹.1¹⁰,¹⁴.0²,⁷.0¹⁵,²⁰]tetratriaconta-2,4,6(34),8,10(33), 11, 13, 15 (20),16,18-decaen-3-yl]acetic acid: Prepared from methyl (2S)-2-(tert-butoxy)-2-[(22S)-18-cyano-4,22,28-trimethyl-21,27-dioxa-1,5,7,8-tetraazahexacyclo[26.2.2.1⁶,⁹.1¹⁰,¹⁴.0²,⁷.0¹⁵,²⁰]tetratriaconta-2,4,6(34),8,10(33),11, 13,15 (20),16,18-decaen-3-yl]acetate using the same procedure as example 81 in 19% yield. ¹H NMR (500 MHz, DMSO-d₆) δ 8.49 (br. s., 1H), 8.00 (d, J=7.3 Hz, 1H), 7.70 (s, 1H), 7.57 (t, J=7.2 Hz, 1H), 7.52-7.44 (m, 2H), 7.36 (d, J=7.3 Hz, 1H), 7.12 (s, 1H), 5.65 (br. s., 1H), 4.82 (br. s., 1H), 4.46 (t, J=12.1 Hz, 1H), 3.62-3.53 (m, 4H), 2.80 (d, J=9.5 Hz, 1H), 2.51 (br. s., 3H), 2.01-1.86 (m, 3H), 1.71 (br. s., 4H), 1.60-1.43 (m, 3H), 1.18 (br. s., 3H), 1.16 (s, 9H), 1.09 (d, J=5.5 Hz, 3H). LCMS (M+1)=652.7.

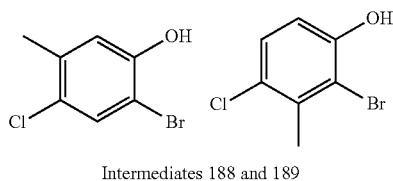

Intermediates 188 and 189

2-Bromo-4-chloro-5-methylphenol and 2-bromo-4-chloro-3-methylphenol: To a solution of 4-chloro-3-methylphenol (2.2 g, 15.4 mmol, 1 equiv) in AcOH (69 mL) was added slowly a solution of bromine (0.80 mL, 15.4 mmol, 1 equiv) in water (8 mL) with some AcOH (to solubolize bromine) After stirring 2 h, the reaction was concentrated under a stream of nitrogen. The residue was taken up in ether and washed with 1 N NaS₂O₃ and a saturated aqueous solution of NaHCO₃. The ether layer was dried (MgSO₄) and concentrated in vacuo. The crude product was purified by flash column chromatography (0-30% EtOAc in hexane) to provide the an inseperable mixture of the products as a colorless oil (2.7 g, 79%) and 2:1 ratio of 2-bromo-4-chloro-5-methylphenol: ¹H NMR (400 MHz, CDCl₃) δ 7.44 (s, 1H), 6.92 (s, 1H), 5.41 (br. s., 1H) and 2-bromo-4-chloro-3-methylphenol: ¹H NMR (400 MHz, CDCl₃) δ 7.24 (d, J=8.8 Hz, 1H), 6.86 (d, J=8.8 Hz, 1H), 5.67-5.52 (m, 1H).

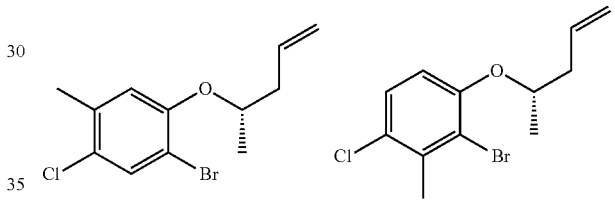

Intermediates 190 and 191

(S)-1-Bromo-5-chloro-4-methyl-2-(pent-4-en-2-yloxy) benzene and (S)-2-bromo-4-chloro-3-methyl-1-(pent-4-en-2-yloxy)benzene: Prepared from a 2:1 mixture of 2-bromo-4-chloro-5-methylphenol and 2-bromo-4-chloro-3-methylphenol using the same procedure as intermediate 7a to provide an inseperable mixture of the products in 90% yield and 2:1 ratio. (S)-1-bromo-5-chloro-4-methyl-2-(pent-4-en-2-yloxy)benzene: ¹H NMR (400 MHz, CDCl₃) δ 7.51 (s, 1H), 6.78 (s, 1H), 5.97-5.82 (m, 1H), 5.20-5.09 (m, 2H), 4.41 (qd, J=6.0, 3.3 Hz, 1H), 2.54 (s, 3H), 2.52-2.49 (m, 1H), 2.46-2.39 (m, 1H), 1.35 (dd, J=6.1, 1.6 Hz, 3H) and (S)-2-bromo-4-chloro-3-methyl-1-(pent-4-en-2-yloxy)benzene: ¹H NMR (400 MHz, CDCl₃) δ 7.25 (d, J=8.8 Hz, 1H), 6.72 (d, J=8.8 Hz, 1H), 5.97-5.82 (m, 1H), 5.20-5.09 (m, 2H), 4.41 (qd, J=6.0, 3.3 Hz, 1H), 2.54 (s, 3H), 2.52-2.49 (m, 1H), 2.46-2.39 (m, 1H), 1.35 (dd, J=6.1, 1.6 Hz, 3H).

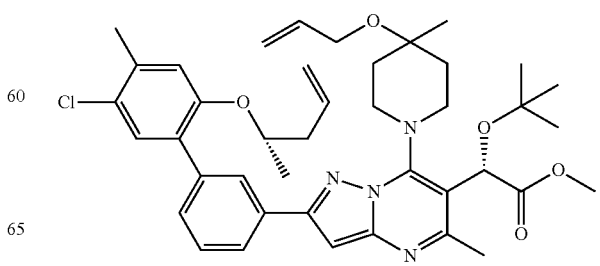

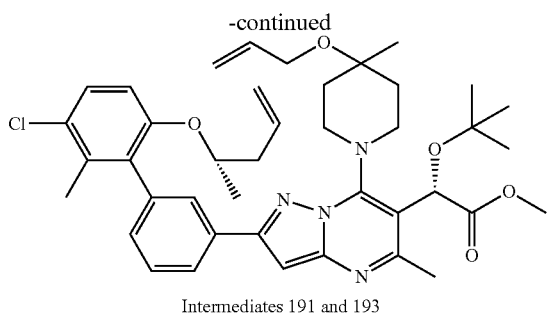

Intermediates 191 and 193

(S)-Methyl 2-(7-(4-(allyloxy)-4-methylpiperidin-1-yl)-2-(5'-chloro-4'-methyl-2'-((S)-pent-4-en-2-yloxy)-[1,1'-biphenyl]-3-yl)-5-methylpyrazolo[1,5-a]pyrimidin-6-yl)-2-(tert-butoxy)acetate and (S)-methyl 2-(7-(4-(allyloxy)-4-methylpiperidin-1-yl)-2-(3'-chloro-2'-methyl-6'-((S)-pent-4-en-2-yloxy)-[1,1'-biphenyl]-3-yl)-5-methylpyrazolo[1,5-a]pyrimidin-6-yl)-2-(tert-butoxy)acetate: Prepared from a 2:1 mixture of (S)-1-bromo-5-chloro-4-methyl-2-(pent-4-en-2-yloxy)benzene and (S)-2-bromo-4-chloro-3-methyl-1-(pent-4-en-2-yloxy)benzene using the same procedures as intermediate 182 and 168 to provide an inseperable mixture of the products in 98% yield and 2:1 ratio. (S)-Methyl 2-(7-(4-(allyloxy)-4-methylpiperidin-1-yl)-2-(5'-chloro-4'-methyl-2'-((S)-pent-4-en-2-yloxy)-[1,1'-biphenyl]-3-yl)-5-methylpyrazolo[1,5-a]pyrimidin-6-yl)-2-(tert-butoxy)acetate. LCMS (M+1)=715.4. (S)-Methyl 2-(7-(4-(allyloxy)-4-methylpiperidin-1-yl)-2-(3'-chloro-2'-methyl-6'-((S)-pent-4-en-2-yloxy)-[1,1'-biphenyl]-3-yl)-5-methylpyrazolo[1,5-a]pyrimidin-6-yl)-2-(tert-butoxy)acetate. LCMS (M+1)=715.4.

EXAMPLES 88, 89 AND 90

Prepared from a 2:1 mixture of (S)-methyl 2-(7-(4-(allyloxy)-4-methylpiperidin-1-yl)-2-(5'-chloro-4'-methyl-2'-((S)-pent-4-en-2-yloxy)-[1,1'-biphenyl]-3-yl)-5-methylpyrazolo[1,5-a]pyrimidin-6-yl)-2-(tert-butoxy)acetate and (S)-methyl 2-(7-(4-(allyloxy)-4-methylpiperidin-1-yl)-2-(3'-chloro-2'-methyl-6'-((S)-pent-4-en-2-yloxy)-[1,1'-biphenyl]-3-yl)-5-methylpyrazolo[1,5-a]pyrimidin-6-yl)-2-(tert-butoxy)acetate using the same procedures as intermediate 170 and example 81 to afford three compounds.

EXAMPLE 88

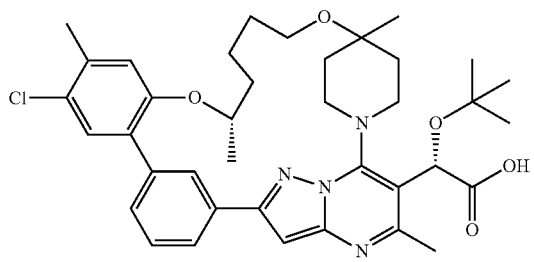 [SMILES: Cc1cc2c(cc1Cl)-c1cccc(c1)-c1cc3nc(C)c([C@H](OC(C)(C)C)C(=O)O)c(n3n1)N1CCC(C)(CC1)OCCCC[C@H](C)O2]

(2S)-2-(tert-Butoxy)-2-[(22S)-17-chloro-4,18,22,28-tetramethyl-21,27-dioxa-1,5,7,8-tetraazahexacyclo[26.2.2.$1^{6,9}.1^{10,14}.0^{2,7}.0^{15,20}$]tetratriaconta-2,4, 6(34), 8, 10(33), 11, 13, 15 (20),16,18-decaen-3-yl]acetic acid: 5% yield. $^1$H NMR (400 MHz, methanol-d$_4$) δ 8.51 (s, 1H), 7.80 (d, J=7.6 Hz, 1H), 7.45 (t, J=7.7 Hz, 1H), 7.26-7.18 (m, 2H), 6.99 (s, 1H), 6.85 (s, 1H), 5.72 (br. s., 1H), 4.60 (d, J=11.5 Hz, 2H), 3.68 (s, 2H), 2.90 (d, J=11.2 Hz, 1H), 2.59 (br. s., 3H), 2.38 (s, 3H), 2.04-1.88 (m, 4H), 1.81-1.66 (m, 4H), 1.65-1.45 (m, 4H), 1.24 (br. s., 3H), 1.19 (s, 9H), 1.08 (d, J=5.9 Hz, 4H). LCMS (M+1)=675.6.

EXAMPLE 89

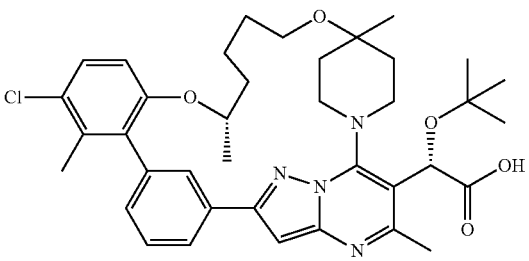 [SMILES: Cc1nc2cc3nn2c(c1[C@H](OC(C)(C)C)C(=O)O)N1CCC(C)(CC1)OCCCC[C@H](C)Oc1ccc(Cl)c(C)c1-c1cccc-3c1]

(2S)-2-(tert-Butoxy)-2-[(22S)-17-chloro-4,16,22,28-tetramethyl-21,27-dioxa-1,5,7,8-tetraazahexacyclo[26.2.2.$1^{6,9}.1^{10,14}.0^{2,7}.0^{15,20}$]tetratriaconta-2,4, 6(34), 8, 10(33), 11, 13, 15(20),16,18-decaen-3-yl]acetic acid: 2% yield. $^1$H NMR (400 MHz, Methanol-d$_4$) δ 8.08 (s, 1H), 7.79 (d, J=7.3 Hz, 1H), 7.47 (t, J=7.6 Hz, 1H), 7.31 (d, J=8.8 Hz, 1H), 7.05 (d, J=7.6 Hz, 1H), 6.91 (d, J=8.8 Hz, 1H), 6.80 (s, 1H), 5.72 (br. s., 1H), 4.54 (br. s., 2H), 3.49-3.39 (m, 2H), 2.87 (d, J=11.2 Hz, 1H), 2.63 (br. s., 3H), 2.05 (s, 3H), 1.99-1.91 (m, 4H), 1.68 (d, J=14.7 Hz, 4H), 1.52 (d, J=8.3 Hz, 4H), 1.27 (br. s., 3H), 1.22 (s, 12H), 1.11 (d, J=5.9 Hz, 3H). LCMS (M+1)=675.6.

EXAMPLE 90

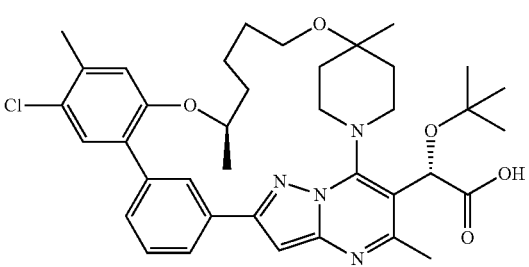 [SMILES: Cc1cc2c(cc1Cl)-c1cccc(c1)-c1cc3nc(C)c([C@H](OC(C)(C)C)C(=O)O)c(n3n1)N1CCC(C)(CC1)OCCCC[C@@H](C)O2]

(2S)-2-(tert-Butoxy)-2-[(22R)-17-chloro-4,18,22,28-tetramethyl-21,27-dioxa-1,5,7,8-tetraazahexacyclo[26.2.2.$1^{6,9}.1^{10,14}.0^{2,7}.0^{15,20}$]tetratriaconta-2,4, 6(34), 8, 10(33), 11, 13, 15 (20),16,18-decaen-3-yl]acetic acid: 2% yield. The inverted stereochemistry likely arises as a minor double inversion byproduct of the earlier Mitsunobu reaction and is carried through. $^1$H NMR (400 MHz, Methanol-d$_4$) δ 8.55 (br. s., 1H), 7.80 (t, J=6.7 Hz, 1H), 7.52-7.43 (m, 1H), 7.34-7.21 (m, 2H), 7.03 (d, J=7.8 Hz, 1H), 6.83 (d, J=4.2 Hz, 1H), 5.64 (br. s., 1H), 4.61 (d, J=12.5 Hz, 2H), 3.44 (br. s., 2H), 3.03 (d, J=13.4 Hz, 1H), 2.62 (br. s., 3H), 2.40 (s, 3H), 1.93 (br. s., 8H), 1.76 (d, J=12.2 Hz, 4H), 1.28 (br. s., 3H), 1.21 (s, 9H), 1.08 (d, J=5.9 Hz, 3H). LCMS (M+1)=675.6.

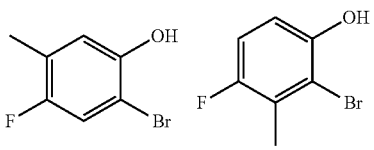

Intermediates 194 and 195

2-Bromo-4-fluoro-5-methylphenol and 2-bromo-4-fluoro-3-methylphenol: Prepared from 4-fluoro-3-methylphenol using the same procedures as intermediates 188 and 189 in 59% yield and 2:1 ratio. 2-bromo-4-fluoro-5-methylpheno: $^1$H NMR (400 MHz, CDCl$_3$) δ 7.14 (d, J=8.5 Hz, 1H), 6.87 (s, 1H), 5.22 (s, 1H) and 2-bromo-4-fluoro-3-methylphenol: $^1$H NMR (400 MHz, CDCl$_3$) δ 6.98-6.91 (m, 1H), 6.88-6.85 (m, 2H), 5.38 (s, 1H).

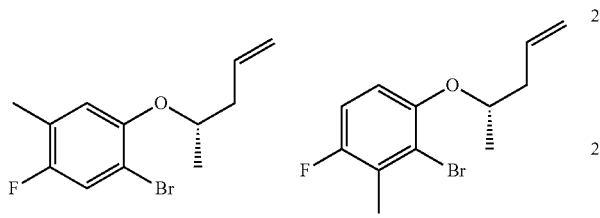

Intermediates 196 and 197

(S)-1-Bromo-5-fluoro-4-methyl-2-(pent-4-en-2-yloxy) benzene and (S)-2-bromo-4-fluoro-3-methyl-1-(pent-4-en-2-yloxy)benzene: Prepared from a 2:1 mixture of 2-bromo-4-fluoro-5-methylphenol and 2-bromo-4-fluoro-3-methylphenol using the same procedure as intermediate 185 to provide an inseperable mixture of the products in 88% yield and 2:1 ratio. Used in the subsequent step without further purification.

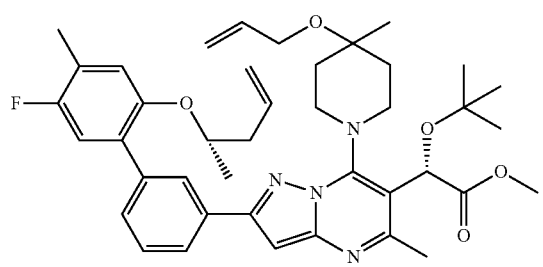

Intermediates 198 and 199

(S)-Methyl 2-(7-(4-(allyloxy)-4-methylpiperidin-1-yl)-2-(5'-fluoro-4'-methyl-2'-((S)-pent-4-en-2-yloxy)-[1,1'-biphenyl]-3-yl)-5-methylpyrazolo[1,5-a]pyrimidin-6-yl)-2-(tert-butoxy)acetate and(S)-methyl 2-(7-(4-(allyloxy)-4-methylpiperidin-1-yl)-2-(3'-fluoro-2'-methyl-6'-((S)-pent-4-en-2-yloxy)-[1,1'-biphenyl]-3-yl)-5-methylpyrazolo[1,5-a] pyrimidin-6-yl)-2-(tert-butoxy)acetate: Prepared from a 2:1 mixture of (S)-1-bromo-5-fluoro-4-methyl-2-(pent-4-en-2-yloxy)benzene and (S)-2-bromo-4-fluoro-3-methyl-1-(pent-4-en-2-yloxy)benzene using the same procedures as intermediate 182 and 168 to provide an inseperable mixture of the products in 63% yield and 2:1 ratio. (S)-methyl 2-(7-(4-(allyloxy)-4-methylpiperidin-1-yl)-2-(5'-fluoro-4'-methyl-2'45)-pent-4-en-2-yloxy)-[1,1'-biphenyl]-3-yl)-5-methylpyrazolo[1,5-a]pyrimidin-6-yl)-2-(tert-butoxy)acetate. LCMS (M+1)=699.45. (S)-methyl 2-(7-(4-(allyloxy)-4-methylpiperidin-1-yl)-2-(3'-fluoro-2'-methyl-6'-((S)-pent-4-en-2-yloxy)-[1,1'-biphenyl]-3-yl)-5-methylpyrazolo[1,5-a]pyrimidin-6-yl)-2-(tert-butoxy)acetate. LCMS (M+1)=699.45.

EXAMPLE 91

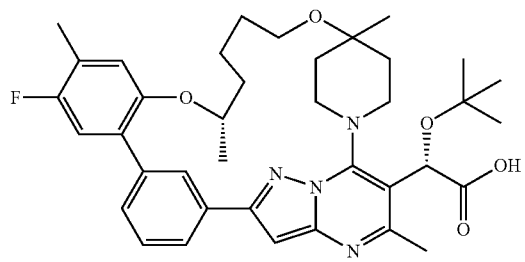 [SMILES: Cc1cc2c(cc1F)-c1cccc(c1)-c1cc3nc(C)c([C@H](OC(C)(C)C)C(=O)O)c(n3n1)N1CCC(C)(CC1)OCCCC[C@H](C)O2]

(2S)-2-(tert-Butoxy)-2-[(22S)-17-fluoro-4,18,22,28-tetramethyl-21,27-dioxa-1,5,7,8-tetraazahexacyclo[26.2.2. 1$^{6,9}$.1$^{10,14}$.0$^{2,7}$.0$^{15,20}$]tetratriaconta-2,4,6(34),8,10(33), 11, 13, 15(20),16,18-decaen-3-yl]acetic acid: Prepared from a 2:1 mixture of (S)-methyl 2-(7-(4-(allyloxy)-4-methylpiperidin-1-yl)-2-(5'-fluoro-4'-methyl-2'-((S)-pent-4-en-2-yloxy)-[1,1'-biphenyl]-3-yl)-5-methylpyrazolo[1,5-a]pyrimidin-6-yl)-2-(tert-butoxy)acetate and (S)-methyl 2-(7-(4-(allyloxy)-4-methylpiperidin-1-yl)-2-(3'-fluoro-2'-methyl-6'-((S)-pent-4-en-2-yloxy)-[1,1'-biphenyl]-3-yl)-5-methylpyrazolo[1,5-a]pyrimidin-6-yl)-2-(tert-butoxy)acetate using the same procedures as intermediates 170 and example 81 in 9% yield. $^1$H NMR (400 MHz, Methanol-d$_4$) δ 8.53 (s, 1H), 7.73 (d, J=7.8 Hz, 1H), 7.37 (t, J=7.7 Hz, 1H), 7.19 (d, J=7.6 Hz, 1H), 6.92-6.82 (m, 2H), 6.78 (s, 1H), 5.54 (s, 1H), 4.62-4.43 (m, 2H), 3.83 (d, J=10.5 Hz, 1H), 3.67-3.58 (m, 1H), 3.38 (d, J=6.8 Hz, 1H), 2.87 (d, J=12.2 Hz, 1H), 2.58 (s, 3H), 2.24 (s, 3H), 1.93-1.84 (m, 3H), 1.78-1.59 (m, 5H), 1.57-1.42 (m, 3H), 1.14 (s, 12H), 1.02 (d, J=5.9 Hz, 3H). LCMS (M+1)=659.6.

Intermediate 200

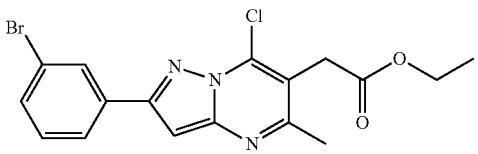

Ethyl 2-(2-(3-bromophenyl)-7-chloro-5-methylpyrazolo [1,5-a]pyrimidin-6-yl)acetate :Prepared according to the procedure for intermediate 4. $^1$H NMR (500 MHz, CDCl$_3$) δ 8.20 (t, J=1.7 Hz, 1H), 7.95 (qd, J=0.8, 7.8 Hz, 1H), 7.56 (ddd, J=1.0, 2.0, 8.0 Hz, 1H), 7.36 (t, J=7.9 Hz, 1H), 6.94 (s, 1H), 4.25 (q, J=7.1 Hz, 2H), 3.93 (s, 2H), 2.65 (s, 3H), 1.32 (t, J=7.1 Hz, 3H).

Intermediate 201

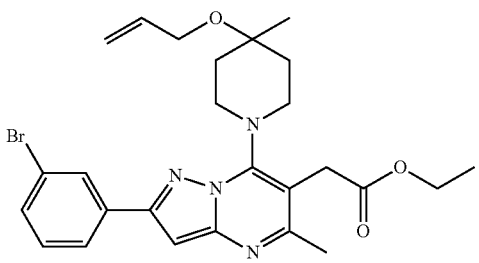

Ethyl 2-(7-(4-(allyloxy)-4-methylpiperidin-1-yl)-2-(3-bromophenyl)-5-methylpyrazolo[1,5-a]pyrimidin-6-yl)acetate: A mixture of ethyl 2-(2-(3-bromophenyl)-7-chloro-5-methylpyrazolo[1,5-a]pyrimidin-6-yl)acetate (28 g, 68.5 mmol) in DMF (150 ml) was treated with 4-(allyloxy)-4-methylpiperidine.HCl (14.3 g, 74.6 mmol) and Hunig's Base (35.9 ml, 206 mmol), and the mixture was heated (60° C. oil bath) for 16 h. At this point LCMS indicates completion of reaction. Mixture was then cooled, diluted with Et₂O and washed with water (3×100 mL) and brine (100 mL), then dried (Na₂SO₄), filtered, and concentrated under reduced pressure. The residue was then purified by Biotage (5-50% EtOAc/hexane) to afford ethyl 2-(7-(4-(allyloxy)-4-methylpiperidin-1-yl)-2-(3-bromophenyl)-5-methylpyrazolo[1,5-a]pyrimidin-6-yl)acetate (32.6 g, 61.8 mmol, 90% yield) as viscous oil. $^1$H NMR (500 MHz, CDCl₃) δ 8.16 (t, J=1.7 Hz, 1H), 7.94 (dt, J=7.8, 1.3 Hz, 1H), 7.54-7.49 (m, 1H), 7.37-7.30 (m, 1H), 6.79 (s, 1H), 6.13-5.99 (m, 1H), 5.51-5.40 (m, 1H), 5.26 (dd, J=10.4, 1.4 Hz, 1H), 4.24 (q, J=7.1 Hz, 2H), 4.03 (dt, J=5.2, 1.6 Hz, 2H), 3.82 (br. s, 4H), 3.32 (br. s., 2H), 2.54 (s, 3H), 1.99 (d, J=13.2 Hz, 2H), 1.86 (br. s., 2H), 1.36 (s, 3H), 1.31 (t, J=7.1 Hz, 3H). LCMS (M+H)=528.8.

Intermediate 202

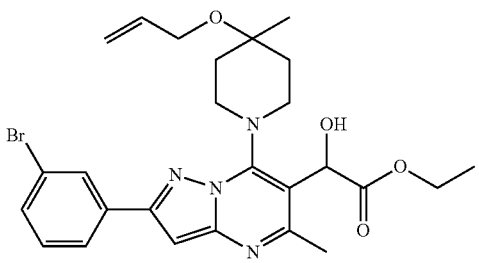

Ethyl 2-(7-(4-(allyloxy)-4-methylpiperidin-1-yl)-2-(3-bromophenyl)-5-methylpyrazolo[1,5-d]pyrimidin-6-yl)-2-hydroxyacetate: To a stirred solution of 1M KHMDS/THF (49.3 mL, 49.3 mmol) in THF (150 mL) at −78° C. was added dropwise a THF (100 mL) solution of ethyl 2-(7-(4-(allyloxy)-4-methylpiperidin-1-yl)-2-(3-bromophenyl)-5-methylpyrazolo[1,5-a]pyrimidin-6-yl)acetate (20 g, 37.9 mmol) over 5 min. After 30 min, a THF (100 mL) solution of 3-phenyl-2-(phenylsulfonyl)-1,2-oxaziridine (12.88 g, 49.3 mmol) was added and stirred for additional 30 min at −78° C. Then, the resulting dark reaction mixture was quenched with sat. NH₄Cl (50 mL), diluted with EtOAc (200 mL), washed with water (100 mL), brine (100 mL), dried (Na₂SO₄), filtered and concentrated. The residue was then purified by Biotage(5-50% EtOAc/hexane) to afford ethyl 2-(7-(4-(allyloxy)-4-methylpiperidin-1-yl)-2-(3-bromophenyl)-5-methylpyrazolo[1,5-a]pyrimidin-6-yl)-2-hydroxyacetate (17 g, 31.3 mmol, 82% yield) as white foam. Impurities were present by NMR. Used as is in the next step without further purification. $^1$H NMR (500 MHz, CDCl₃) δ 8.16 (t, J=1.7 Hz, 1H), 7.99-7.92 (m, 1H), 7.58-7.50 (m, 2H), 7.34 (t, J=7.9 Hz, 1H), 6.83 (s, 1H), 6.18-6.06 (m, 1H), 5.57 (d, J=5.4 Hz, 1H), 5.48 (d, J=17.0 Hz, 1H), 5.27 (d, J=10.2 Hz, 1H), 4.83 (br. s., 2H), 4.35 (dq, J=10.8, 7.1 Hz, 1H), 4.23 (dq, J=10.9, 7.1 Hz, 1H), 4.06-3.99 (m, 2H), 2.65 (s, 3H), 2.00 (d, J=14.2 Hz, 2H), 1.84 (d, J=13.4 Hz, 2H), 1.36 (s, 3H), 1.29-1.26 (m, 3H). LCMS (M+H)=545.3.

Intermediate 203

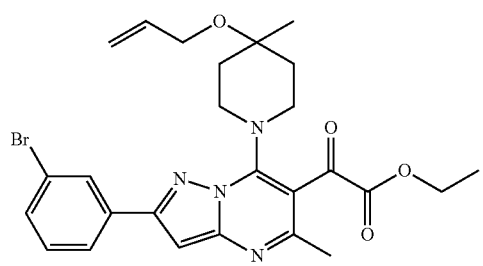

Ethyl 2-(7-(4-(allyloxy)-4-methylpiperidin-1-yl)-2-(3-bromophenyl)-5-methylpyrazolo[1,5-d]pyrimidin-6-yl)-2-oxoacetate: To a solution of ethyl 2-(7-(4-(allyloxy)-4-methylpiperidin-1-yl)-2-(3-bromophenyl)-5-methylpyrazolo[1,5-a]pyrimidin-6-yl)-2-hydroxyacetate (32 g, 58.9 mmol) in dry DCM (500 mL) was added Dess-Martin periodinane (24.97 g, 58.9 mmol). The resulting bright orange-red solution was stirred for 90 min. The reaction was quenched by stirring with a saturated solution of Na₂S₂O₃ (100 mL) and sat. NaHCO₃ (100 mL) for 25 min to quench any unreacted Dess-Martin reagent. The reaction mixture was poured into a separatory funnel and organic layer separated. The aqueous layer was further extracted with EtOAc. The two organic components were separately washed with brine, then combined, dried (Na₂SO₄), filtered, and concentrated under reduced pressure. The residue was then purified via Biotage (5-40%) EtOAc/hexane to afford ethyl 2-(7-(4-(allyloxy)-4-methylpiperidin-1-yl)-2-(3-bromophenyl)-5-methylpyrazolo[1,5-a]pyrimidin-6-yl)-2-oxoacetate (22.6 g, 41.7 mmol, 70.9% yield) as off-white solid. $^1$H NMR (500 MHz, CDCl₃) δ 8.12 (t, J=1.7 Hz, 1H), 7.91 (dt, J=7.8, 1.3 Hz, 1H), 7.56 (ddd, J=8.0, 2.0, 0.9 Hz, 1H), 7.37 (t, J=7.9 Hz, 1H), 6.82 (s, 1H), 6.00 (ddt, J=17.2, 10.4, 5.2 Hz, 1H), 5.44-5.36 (m, 1H), 5.24-5.17 (m, 1H), 4.46-4.35 (m, 2H), 3.98 (dt, J=5.1, 1.5 Hz, 2H), 3.80-3.71 (m, 2H), 3.69-3.60 (m, 2H), 2.60 (s, 3H), 2.03-1.88 (m, 4H), 1.46-1.40 (m, 3H), 1.31 (s, 3H). LCMS (M+H)=543.3.

Intermediate 204

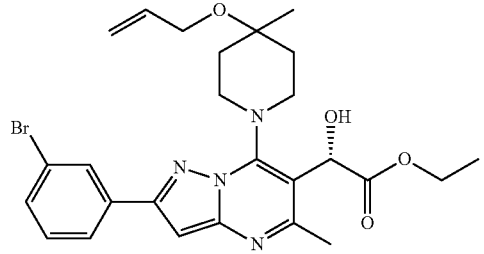

(S)-Ethyl 2-(7-(4-(allyloxy)-4-methylpiperidin-1-yl)-2-(3-bromophenyl)-5-methylpyrazolo[1,5-d]pyrimidin-6-yl)-2-hydroxyacetate: To a stirred yellow solution of ethyl 2-(7-(4-(allyloxy)-4-methylpiperidin-1-yl)-2-(3-bromophenyl)-5-methylpyrazolo[1,5-a]pyrimidin-6-yl)-2-oxoacetate (22 g, 40.6 mmol) in anhydrous toluene (800 mL) was added 1M (R)-1-methyl-3,3-diphenylhexahydropyrrolo[1,2-c][1,3,2]oxazaborole/toluene (16.25 mL, 16.25 mmol). The mixture was cooled to −35° C. and catechoborane (7.11 mL, 56.9 mmol) was added over 5 min. After 30 min, the reaction mixture was slowly warmed to −15° C. and stirred for additional 2 h. A this point LCMS indicated approx 60% conversion, so mixture was cooled to −35° C. and 3.5 mL of catechoborane was added and stirred at −15° C. for 2 h. At his point LCMS indicates completion of reaction. Mixture was then dluted with EtOAc (1 L) and sat. Na$_2$CO$_3$ (300 mL). The mixture was stirred vigorously for 30 min, and the organic phase washed with sat Na$_2$CO$_3$ (2×200 mL) each time vigorously stirring for 30 min, dried (Na$_2$SO$_4$), filtered, concentrated and the residue was purified by silica gel chromatography (5-70% EtOAc/hexane) to afford desired (S)-ethyl 2-(7-(4-(allyloxy)-4-methylpiperidin-1-yl)-2-(3-bromophenyl)-5-methylpyrazolo[1,5-a]pyrimidin-6-yl)-2-hydroxyacetate (17 g, 31.3 mmol, 77% yield) as off-white solid. $^1$H NMR (500 MHz, CDCl$_3$) δ 8.19-8.10 (m, 1H), 7.95 (d, J=7.9 Hz, 1H), 7.58-7.52 (m, 1H), 7.33 (t, J=7.8 Hz, 1H), 6.86-6.82 (m, 1H), 6.10 (dd, J=10.8, 5.1 Hz, 1H), 5.57 (d, J=5.2 Hz, 1H), 5.48 (d, J=16.9 Hz, 1H), 5.27 (d, J=10.2 Hz, 1H), 4.35 (dq, J=10.8, 7.2 Hz, 1H), 4.23 (dq, J=10.7, 7.1 Hz, 1H), 4.03 (dt, J=5.2, 1.5 Hz, 2H), 2.65 (s, 3H), 2.00 (d, J=14.5 Hz, 2H), 1.84 (br. s., 2H), 1.36 (s, 3H), 1.29-1.24 (m, 3H). LCMS (M+H)=543.4.

Intermediate 205

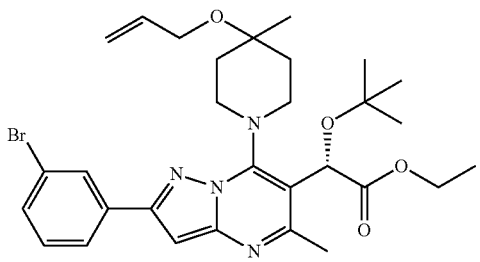

(S)-Ethyl 2-(7-(4-(allyloxy)-4-methylpiperidin-1-yl)-2-(3-bromophenyl)-5-methylpyrazolo[1,5-a]pyrimidin-6-yl)-2-(tert-butoxy)acetate: To a stirred solution of (S)-ethyl 2-(7-(4-(allyloxy)-4-methylpiperidin-1-yl)-2-(3-bromophenyl)-5-methylpyrazolo[1,5-a]pyrimidin-6-yl)-2-hydroxyacetate (8.5 g, 15.64 mmol) in DCM (250 mL) and t-butyl acetate (175 mL) was added perchloric acid (4.03 mL, 46.9 mmol) at rt. After 3 h, the reaction mixture was diluted with DCM (100 mL), carefully quenched with sat. NaHCO$_3$ (50 mL), organic layer separated and washed with brine (100 mL), dried (Na$_2$SO$_4$), filtered and concentrated to give yellow liquid. This was purified by flash column chromatograpgy on silica gel column using (10-50% EtOAc/Hex as eluant) to afford the desired (S)-ethyl 2-(7-(4-(allyloxy)-4-methylpiperidin-1-yl)-2-(3-bromophenyl)-5-methylpyrazolo[1,5-a]pyrimidin-6-yl)-2-(tert-butoxy)acetate (5 g, 8.34 mmol, 53.3% yield) as light yellow solid. 3 g of starting material was also recovered. $^1$H NMR (500 MHz, CDCl$_3$) δ 8.23-8.11 (m, 1H), 7.94 (d, J=7.7 Hz, 1H), 7.56-7.51 (m, 1H), 7.33 (t, J=7.9 Hz, 1H), 6.81 (s, 1H), 6.10 (br. s., 1H), 6.00 (br. s., 1H), 5.49 (d, J=16.6 Hz, 1H), 5.28 (d, J=10.2 Hz, 1H), 4.30-4.14 (m, 2H), 4.10-4.00 (m, 2H), 2.65 (s, 3H), 2.09-1.85 (m, 3H), 1.74 (br. s., 1H), 1.38 (s, 3H), 1.28-1.16 (m, 12H). 4 missing piperidine hydrogens. LCMS (M+H)=601.5.

Intermediate 206

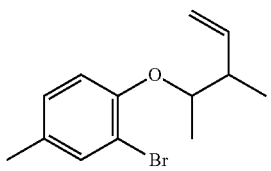

2-Bromo-4-methyl-1-((3-methylpent-4-en-2-yl)oxy)benzene: To a solution of 2-bromo-4-methylphenol (1 g, 5.35 mmol) and 3-methylpent-4-en-2-ol (2.68 g, 26.7 mmol) in THF (20 mL) was added Ph$_3$P (7.01 g, 26.7 mmol) followed by DEAD (4.23 mL, 26.7 mmol) and the resulting mixture was stirred at room temp for 16 h. Water was then added and the mixture was extracted with ether (2×50 mL), dried (Na$_2$SO$_4$), filtered and concentrated. The residue was then purified by Biotage (0-20% EtOAc/hexane) to afford 2-bromo-4-methyl-1-((3-methylpent-4-en-2-yl)oxy)benzene (860 mg, 3.19 mmol, 59.8% yield) as yellow oil. Product is approx 2:1 mixture of trans/cis isomers. $^1$H NMR (400 MHz, CDCl$_3$) δ 7.38 (d, J=2.0 Hz, 1H), 7.08-7.01 (m, 1H), 6.83-6.79 (m, 1H), 6.02-5.89 (m, 1H), 5.16 (q, J=1.8 Hz, 0.5H), 5.14-5.08 (m, 1.5H), 4.31-4.37 (m, 0.3H), 4.28-4.19 (m, 0.7H), 2.64-2.50 (m, 1H), 2.29 (s, 3H), 1.30-1.24 (m, 3H), 1.19-1.14 (m, 3H).

Intermediate 207

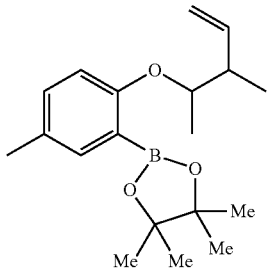

4,4,5,5-Tetramethyl-2-(5-methyl-2-((3-methylpent-4-en-2-yl)oxy)phenyl)-1,3,2-dioxaborolane: To a solution of 2-bromo-4-methyl-1-((3-methylpent-4-en-2-yl)oxy)benzene (820 mg, 3.05 mmol) in THF (15.200 mL) at −78° C. was added 1.6M n-BuLi/THF (2.285 mL, 3.66 mmol) and the mixture was stirred for 30 min. 2-Isopropoxy-4,4,5,5-tetramethyl-1,3,2-dioxaborolane (0.746 mL, 3.66 mmol) was then added and after 30 min, bath removed and reaction allowed to warm to rt. After 3 h, partitioned between EtOAc and water. EtOAc layer was dried (Na$_2$SO$_4$), filtered and concentrated. Crude was used as-is in the next step without further purification.

Intermediate 208

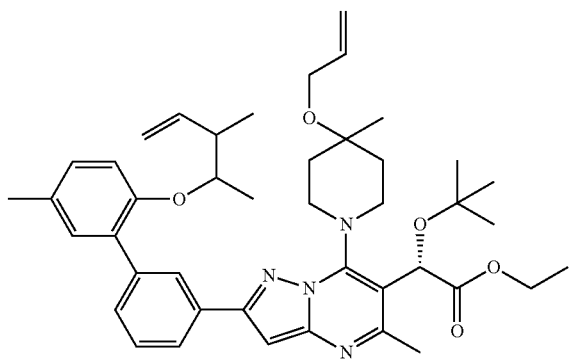

(2S)-Ethyl 2-(7-(4-(allyloxy)-4-methylpiperidin-1-yl)-5-methyl-2-(5'-methyl-2'-((3-methylpent-4-en-2-yl)oxy)-[1,1'-biphenyl]-3-yl)-pyrazolo[1,5-d]pyrimidin-6-yl)-2-(tert-butoxy)acetate: A solution of ((S)-ethyl 2-(7-(4-(allyloxy)-4-methylpiperidin-1-yl)-2-(3-bromophenyl)-5-methylpyrazolo[1,5-a]pyrimidin-6-yl)-2-(tert-butoxy) acetate (300 mg, 0.500 mmol), 4,4,5,5-tetramethyl-2-(5-methyl-2-((3-methylpent-4-en-2-yl)oxy)phenyl)-1,3,2-dioxaborolane (316 mg, 1.001 mmol) and 2.0 M aq. $Na_2CO_3$ (0.751 mL, 1.501 mmol) in DMF (5 mL) was degassed for 10 min. $Pd(Ph_3P)_4$ (40.5 mg, 0.035 mmol), was added and the degassing was continued for another 5 min. The reaction was then heated at 90° C. for 5 h. At this point LCMS indicates completion of reaction. The mixture was then cooled to room temp and diluted with water (25 mL) and extracted with $Et_2O$ (2×50 mL). The combined extracts were dried ($Na_2SO_4$), filtered, and concentrated under reduced pressure, and the residue was purified by biotage (0-25% EtOAc/hexane) to afford (2S)-ethyl 2-(7-(4-(allyloxy)-4-methylpiperidin-1-yl)-5-methyl-2-(5'-methyl-2'43-methylpent-4-en-2-yl)oxy)-[1,1'-biphenyl]-3-yl)pyrazolo[1,5-a]pyrimidin-6-yl)-2-(tert-butoxy)acetate (260 mg, 0.367 mmol, 73.3% yield) as viscous oil (inseperable mixture of diastereomers). $^1$H NMR (500 MHz, $CDCl_3$) δ 8.13 (br. s., 1H), 8.04 (br. s., 1H), 7.59-7.53 (m, 1H), 7.51-7.44 (m, 1H), 7.24 (s, 1H), 7.13 (d, J=8.2 Hz, 1H), 6.96-6.91 (m, 1H), 6.85 (s, 1H), 6.09-5.97 (m, 2H), 5.85-5.68 (m, 1H), 5.43 (d, J=16.7 Hz, 1H), 5.20-5.08 (m, 1H), 5.02-4.92 (m, 2H), 4.33-4.11 (m, 4H), 4.03 (d, J=4.3 Hz, 2H), 2.66-2.61 (m, 3H), 2.49-2.41 (m, 1H), 2.38 (s, 3H), 2.07-1.95 (m, 2H), 1.85-1.69 (m, 1H), 1.39 (br. s., 3H), 1.28-1.22 (m, 12H), 1.17-1.12 (m, 3H), 1.01-0.94 (m, 3H). 4 missing piperidine hydrogens. LCMS (M+H)=709.4.

Intermediate 209

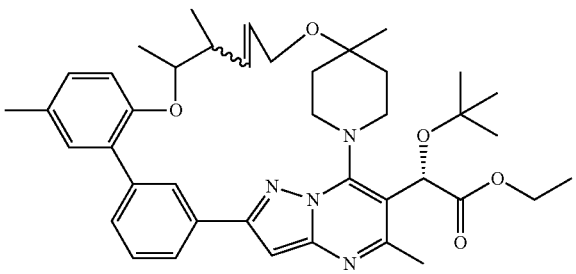

Ethyl (2S)-2-(tert-butoxy)-2-[4,17,22,23,28-pentamethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetate: To a mixture of (2S)-ethyl 2-(7-(4-(allyloxy)-4-methylpiperidin-1-yl)-5-methyl-2-(5'-methyl-2'-((3-methylpent-4-en-2-yl)oxy)-[1,1'-biphenyl]-3-yl)pyrazolo[1,5-a]pyrimidin-6-yl)-2-(tert-butoxy)acetate (250 mg, 0.353 mmol) and CuI (67.2 mg, 0.353 mmol) in DCE (200 mL) at 70° C. was added (1,3-dimesityl-imidazolidin-2-ylidene)(2-isopropoxybenzylidene)ruthenium(VI) chloride (22.10 mg, 0.035 mmol) and the resulting mixture was refluxed for 2 h. At this point LCMS indicates completion of reaction. Mixture was then concentrated and used as is in the next step without further purification. LCMS (M+H)=681.4.

Intermediate 210

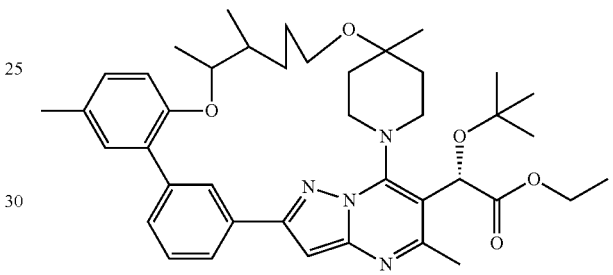

Ethyl (2S)-2-(tert-butoxy)-2-{4,17,22,23,28-pentamethyl-21,27-dioxa-1,5,7,8-tetraazahexacyclo[26.2.2.1$^{6,9}$.1$^{9,14}$.0$^{2,7}$.0$^{15,20}$]tetratriaconta-2,4, 6(34), 8, 10(33), 11,13, 15 (20),16,18-decaen-3-yl}acetate: To a mixture of ethyl (2S)-2-(tert-butoxy)-2-[4,17,22,23,28-pentamethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetate (250 mg, 0.367 mmol) in MeOH (10 mL) was added $NaBH_4$ (69.5 mg, 1.836 mmol) (gas evolution) and the mixture was stirred at room temp for 1 h. More $NaBH_4$ (2×70 mg) was then added and the mixture was stirred for another 2 h. Mixture was then quenched with water (20 mL), extracted with EtOAc (50 mL), dried ($Na_2SO_4$), filtered and concentrated. The crude was then used as is in the next step without further purification. LCMS (M+H)=683.7

EXAMPLES 92, 93, 94 AND 95

To a solution of ethyl (2S)-2-(tert-butoxy)-2-{4,17,22,23,28-pentamethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl}acetate (100 mg, 0.146 mmol) in MeOH (4 mL) was added 1N NaOH (0.439 mL, 0.439 mmol) and the resulitng mixture was heated at 75° C. for 5 h. Mixture was then cooled and purified by prep HPLC to afford 4 diastereomers.

EXAMPLE 92

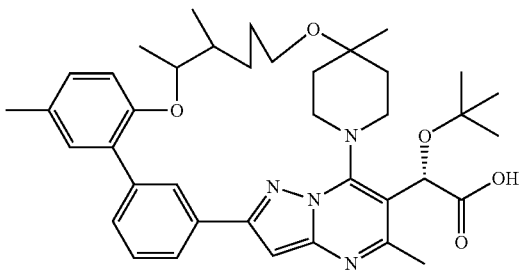 [SMILES: Cc1ccc2c(c1)-c1cccc(c1)-c1cc3nc(C)c([C@H](OC(C)(C)C)C(=O)O)c(n3n1)N1CCC(C)(CC1)OCCCC(C)C(C)O2]

(2S)-2-(tert-Butoxy)-2-{4,17,22,23,28-penta-methyl-21,27-dioxa-1,5,7,8-tetraazahexacyclo[26.2.2.1$^{6,9}$.1$^{10,14}$.0$^{2,7}$.0$^{15,20}$]tetratriaconta-2,4, 6(34), 8, 10(33), 11, 13, 15 (20),16,18-decaen-3-yl}acetic acid: Diastereomer 1, First eluting, (2.1 mg, 3.21 µmol, 2.190% yield). $^1$H NMR (500 MHz, DMSO-d$_6$) δ 8.53 (s, 1H), 7.90 (d, J=7.3 Hz, 1H), 7.51 (t, J=7.5 Hz, 1H), 7.35 (d, J=7.3 Hz, 1H), 7.18-7.11 (m, 2H), 7.09-7.02 (m, 2H), 5.59 (br. s., 1H), 4.56 (t, J=12.4 Hz, 1H), 4.46 (d, J=5.5 Hz, 1H), 3.92 (s, 1H), 3.60 (d, J=10.7 Hz, 4H), 2.82 (d, J=11.0 Hz, 1H), 2.29 (s, 3H), 2.09 (br. s., 1H), 2.03 (d, J=8.5 Hz, 1H), 2.00-1.86 (m, 3H), 1.64 (d, J=13.7 Hz, 2H), 1.56 (br. s., 2H), 1.35 (br. s., 1H), 1.19 (s, 3H), 1.16 (br. s., 9H), 1.04 (br. s., 1H), 0.95 (d, J=5.5 Hz, 3H), 0.82 (d, J=6.4 Hz, 3H). LCMS (M+H)=655.0.

EXAMPLE 93

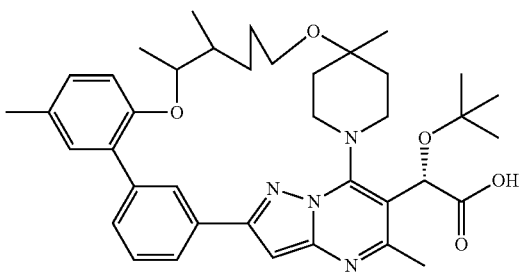 [SMILES: Cc1ccc2c(c1)-c1cccc(c1)-c1cc3nc(C)c([C@H](OC(C)(C)C)C(=O)O)c(n3n1)N1CCC(C)(CC1)OCCCC(C)C(C)O2]

(2S)-2-(tert-Butoxy)-2-{4,17,22,23,28-penta-methyl-21,27-dioxa-1,5,7,8-tetraazahexacyclo[26.2.2.1$^{6,9}$.1$^{10,14}$.0$^{2,7}$.0$^{15,20}$]tetratriaconta-2,4, 6(34), 8, 10(33), 11, 13, 15 (20),16,18-decaen-3-yl}acetic acid: Diastereomer 2, second eluting, (7.3 mg, 0.011 mmol, 7.61% yield) $^1$H NMR (500 MHz, DMSO-d$_6$) δ 8.50 (s, 1H), 7.92 (d, J=7.3 Hz, 1H), 7.51 (t, J=7.6 Hz, 1H), 7.31 (d, J=7.3 Hz, 1H), 7.14 (d, J=7.9 Hz, 1H), 7.10 (d, J=4.9 Hz, 2H), 7.04 (d, J=8.2 Hz, 1H), 5.70 (br. s., 1H), 4.67 (d, J=7.3 Hz, 2H), 3.62 (t, J=11.7 Hz, 1H), 3.46 (br. s., 2H), 3.41-3.20 (m, 4H), 2.68 (d, J=9.2 Hz, 1H), 2.29 (s, 3H), 2.15 (d, J=14.0 Hz, 1H), 2.04 (d, J=12.2 Hz, 1H), 1.83 (d, J=13.1 Hz, 1H), 1.72 (br. s., 1H), 1.68-1.52 (m, 3H), 1.45 (br. s., 1H), 1.30 (br. s., 1H), 1.19 (br. s., 3H), 1.17 (s, 9H), 1.01 (d, J=5.8 Hz, 3H), 0.69 (d, J=6.7 Hz, 3H). LCMS (M+H)=655.7.

EXAMPLE 94

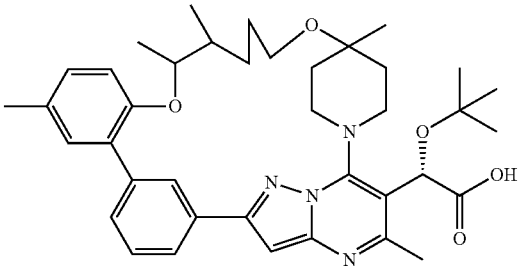 [SMILES: Cc1ccc2c(c1)-c1cccc(c1)-c1cc3nc(C)c([C@H](OC(C)(C)C)C(=O)O)c(n3n1)N1CCC(C)(CC1)OCCCC(C)C(C)O2]

(2S)-2-(tert-Butoxy)-2-{4,17,22,23,28-penta-methyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33), 11, 13, 15 (20),16,18-decaen-3-yl}acetic acid: Diastereomer 3, third eluting, (7 mg, 10.69 µmol, 7.30% yield) $^1$H NMR (500 MHz, DMSO-d$_6$) δ 8.13 (s, 1H), 7.85 (d, J=7.6 Hz, 1H), 7.54 (t, J=7.5 Hz, 1H), 7.34 (d, J=7.3 Hz, 1H), 7.14 (d, J=7.6 Hz, 1H), 7.06 (s, 1H), 7.02-6.96 (m, 2H), 5.87 (s, 1H), 4.34 (t, J=11.9 Hz, 1H), 4.01 (t, J=6.0 Hz, 1H), 3.78 (t, J=11.3 Hz, 1H), 3.55-3.35 (m, 2H), 2.97 (br. s., 1H), 2.74 (d, J=6.4 Hz, 1H), 2.56 (s, 3H), 2.29 (s, 3H), 1.91 (d, J=13.4 Hz, 1H), 1.83 (d, J=13.4 Hz, 1H), 1.75-1.64 (m, 2H), 1.63-1.54 (m, 1H), 1.52 (br. s., 1H), 1.46 (br. s., 3H), 1.21 (s, 9H), 1.18 (s, 3H), 0.84 (d, J=5.8 Hz, 6H). LCMS (M+H)=655.6.

EXAMPLE 95

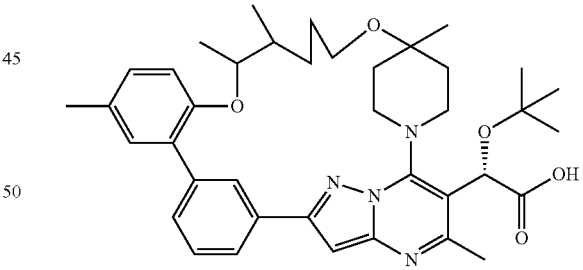

(2S)-2-(tert-Butoxy)-2-{4,17,22,23,28-penta-methyl-21,27-dioxa-1,5,7,8-tetraazahexacyclo[26.2.2.$^{6,9}$.1$^{10,14}$.0$^{2,7}$.0$^{15,20}$]tetratriaconta-2,4,6(34),8,10(33), 11, 13, 15 (20),16,18-decaen-3-yl}acetic acid: Diastereomer 4, fourth eluting, (19.9 mg, 0.030 mmol, 20.75% yield). $^1$H NMR (500 MHz, DMSO-d$_6$) δ 8.25 (s, 1H), 7.87 (d, J=7.9 Hz, 1H), 7.52 (t, J=7.6 Hz, 1H), 7.31 (d, J=7.3 Hz, 1H), 7.14 (d, J=8.5 Hz, 1H), 7.05 (s, 1H), 7.03-6.98 (m, 2H), 5.89 (br. s., 1H), 4.47 (br. s., 1H), 4.20-4.12 (m, 1H), 4.02 (br. s., 2H), 2.87 (br. s., 1H), 2.75 (s, 1H), 2.57 (s, 3H), 2.28 (s, 3H), 2.04 (d, J=13.4 Hz, 2H), 1.74 (br. s., 4H), 1.59-1.50 (m, 1H), 1.45 (br.

s., 1H), 1.22 (s, 9H), 1.20 (br. s., 3H), 1.02 (d, J=5.8 Hz, 3H), 0.68 (d, J=6.4 Hz, 3H). LCMS (M+H)=655.7.

Intermediate 211

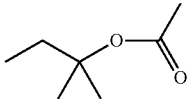

Tert-Pentyl Acetate: To a solution of 2-methylbutan-2-ol (10 g, 113 mmol) in DCM (100 mL) was added DMAP (0.693 g, 5.67 mmol) and TEA (17.39 mL, 125 mmol). Mixture was then cooled to 0° C. and acetic anhydride (15.56 mL, 125 mmol) was added and the mixture was stirred at room temp for 24 h. The mixture was then washed with sat.NaHCO$_3$ (100 mL), 1N HCl (100 mL), 10% NaOH (100 mL), brine (100 mL), dried (Na$_2$SO$_4$), filtered and concentrated to afford dark oil which was dilstilled by short path distillation (product distilled at 90-95° C.) to afford tert-pentyl acetate (8 g, 61.5 mmol, 54.2% yield) as colorless oil. $^1$H NMR (500 MHz, CDCl$_3$) δ 1.98 (s, 3H), 1.78 (q, J=7.5 Hz, 2H), 1.43 (s, 6H), 0.89 (t, J=7.5 Hz, 3H).

Intermediate 212

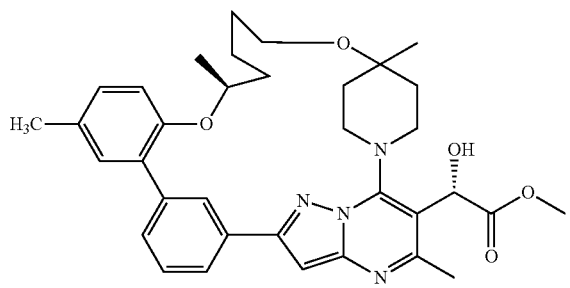

Methyl (2S)-2-hydroxy-2-[(22S)-4,17,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate: To a solution of methyl (2S)-2-(tert-butoxy)-2-[(22S)-4,17,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15 (20),16,18-decaen-3-yl]acetate (88 mg, 0.134 mmol) in DCM (3 mL) at room temp was added TFA (0.311 mL, 4.03 mmol) and the mixture was stirred at room temp for 16 h. Then, mixture was concentrated and purified by biotage (0-40% EtOAc/hexane) to afford methyl (2S)-2-hydroxy-2-[(22S)-4,17,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15 (20),16,18-decaen-3-yl]acetate (60 mg, 0.100 mmol, 74.6% yield) as viscous oil. $^1$H NMR (500 MHz, CDCl$_3$) δ 8.53-8.42 (m, 1H), 7.79 (d, J=7.7 Hz, 1H), 7.50 (t, J=7.6 Hz, 1H), 7.36 (d, J=7.6 Hz, 1H), 7.16-7.11 (m, 2H), 6.96-6.85 (m, 2H), 5.56 (s, 1H), 4.62-4.38 (m, 2H), 4.15 (q, J=7.1 Hz, 1H), 3.89-3.83 (m, 1H), 3.81 (s, 3H), 3.47 (br. s., 1H), 3.41-3.29 (m, 1H), 3.18 (d, J=10.9 Hz, 1H), 2.76 (d, J=11.8 Hz, 1H), 2.66 (s, 2H), 2.36 (s, 3H), 2.05-1.96 (m, 1H), 1.90 (t, J=12.5 Hz, 2H), 1.82-1.72 (m, 2H), 1.68-1.56 (m, 2H), 1.50 (br. s., 2H), 1.29 (t, J=7.1 Hz, 2H), 1.24 (s, 3H), 1.15 (d, J=6.0 Hz, 3H). LCMS (M+H)=599.4.

Intermediate 213

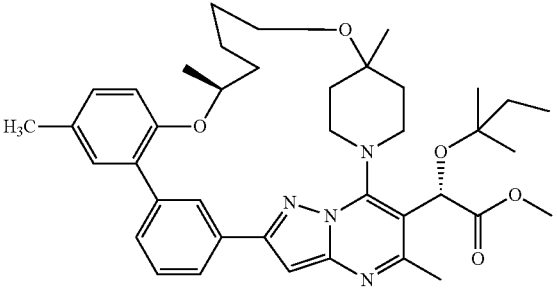 [SMILES: CCC(C)(C)O[C@H](C(=O)O)c1c(C)nc2cc3nn2c1N1CCC(C)(CC1)OCCCC[C@H](C)Oc1ccc(C)cc1-c1cccc-3c1]

Methyl (2S)-2-[(2-methylbutan-2-yl)oxy 1-24(228)-4,17,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10 (33), 11, 13, 15 (20),16,18-decaen-3-yl]acetate: To a stirred solution of methyl (2S)-2-hydroxy-2-[(22S)-4,17,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate (50 mg, 0.084 mmol) in DCM (2 mL) and tert-pentyl acetate (0.692 mL, 5.85 mmol) at rt was added 70 wt % perchloric acid (0.022 mL, 0.251 mmol). After 3 h, the reaction mixture was diluted with DCM (25 mL), carefully quenched with sat. NaHCO$_3$ (5 mL), organic layer separated and washed with brine (10 mL), dried (Na$_2$SO$_4$), filtered and concentrated to give yellow liquid. This was purified by flash column chromatograpgy on silica gel column using (10-50% EtOAc/Hex as eluant) to afford the desired methyl (25)-2-[(2-methylbutan-2-yl)oxy]-2-[(22S)-4,17,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate (10 mg, 0.015 mmol, 17.90% yield) as viscous oil. $^1$H NMR (500 MHz, CDCl$_3$) δ 7.82-7.76 (m, 1H), 7.50 (t, J=7.7 Hz, 1H), 7.39-7.34 (m, 1H), 7.18 (d, J=1.9 Hz, 1H), 7.13 (dd, J=8.5, 2.0 Hz, 1H), 6.92 (d, J=8.5 Hz, 1H), 6.90 (s, 1H), 5.90 (s, 1H), 4.66-4.59 (m, 1H), 4.58-4.52 (m, 1H), 3.84-3.79 (m, 1H), 3.77 (s, 3H), 3.50 (td, J=7.7, 3.1 Hz, 1H), 3.44-3.35 (m, 1H), 3.27 (d, J=12.3 Hz, 1H), 2.89 (d, J=11.3 Hz, 1H), 2.61 (s, 3H), 2.36 (s, 3H), 2.07-1.96 (m, 3H), 1.89-1.80 (m, 1H), 1.79-1.70 (m, 3H), 1.63-1.47 (m, 6H), 1.26 (s, 3H), 1.23 (s, 3H), 1.17 (d, J=6.0 Hz, 3H), 1.15 (s, 3H), 0.83 (t, J=7.5 Hz, 3H). LCMS (M+H)=669.4. 35 mg of starting material was also recovered.

EXAMPLE 96

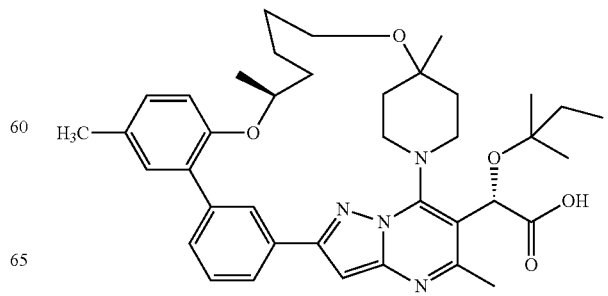

(2S)-2-[(2-Methylbutan-2-yl)oxy]-2-[(22S)-4,17,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33), 11, 13, 15 (20),16,18-decaen-3-yl]acetic acid: To a solution of methyl (2S)-2-[(2-methylbutan-2-yl)oxy]-2-[(22S)-4,17,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate (10 mg, 0.015 mmol) in MeOH (1 mL) was added 1N NaOH (0.150 mL, 0.150 mmol) solution and the resulting mixture was heated at 75° C. for 3 h. Then, the mixture was cooled and purified by prep HPLC to afford (2S)-2-[(2-methylbutan-2-yl)oxy]-2-[(22S)-4,17,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid (6.4 mg, 9.77 µmol, 65.4% yield). $^1$H NMR (500 MHz, DMSO-d$_6$) δ 8.50 (s, 1H), 7.92 (d, J=8.2 Hz, 1H), 7.51 (t, J=7.6 Hz, 1H), 7.33 (d, J=7.0 Hz, 1H), 7.17-7.08 (m, 3H), 7.05 (d, J=8.5 Hz, 1H), 5.65 (br. s., 1H), 4.62 (d, J=6.1 Hz, 1H), 4.49 (t, J=12.5 Hz, 1H), 3.64-3.54 (m, 1H), 3.48-3.42 (m, 2H), 2.80 (d, J=10.4 Hz, 1H), 2.29 (s, 3H), 2.03-1.86 (m, 3H), 1.72-1.62 (m, 4H), 1.60-1.41 (m, 5H), 1.19 (s, 3H), 1.15 (s, 3H), 1.11-1.03 (m, 6H), 0.72 (t, J=7.3 Hz, 3H). 4 missing piperidine hydrogens. LCMS (M+H)=655.8.

Intermediate 214

1-Methylcyclobutanol: Ref: PCT 2010009195: To a solution of cyclobutanone (5 g, 71.3 mmol) in diethyl ether (400 mL) at 0° C. was added dropwise 3M MeMgBr/diethyl ether (47.6 mL, 143 mmol) and the resulting mixture was stirred for 3 h at 0° C. Then, the reaction mixture was poured over cooled 1N HCl and extracted twice with ether, dried (Na$_2$SO$_4$), filtered and concentrated to afford 1-methylcyclobutanol (6.1 g, 70.8 mmol, 99% yield) as colorless oil. $^1$H NMR (500 MHz, CDCl$_3$) δ 2.17-1.97 (m, 4H), 1.90-1.67 (m, 2H), 1.61-1.47 (m, 1H), 1.39 (t, J=0.8 Hz, 3H).

Intermediate 215

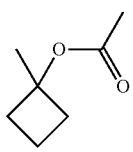

1-Methylcyclobutyl acetate: To a solution of 1-methylcyclobutanol (6.2 g, 72.0 mmol) in DCM (50 mL) was added DMAP (0.440 g, 3.60 mmol) and TEA (15.05 mL, 108 mmol). Then, the mixture was cooled to 0° C. and acetic anhydride (13.46 mL, 108 mmol) was added and stirred at room temp for 24 h. The mixture was then washed with sat.NaHCO$_3$ (100 mL), 1N HCl (100 mL), 10% NaOH (100 mL), brine (100 mL), dried (Na$_2$SO$_4$), filtered and concentrated to afford 1-methylcyclobutyl acetate (8 g, 62.4 mmol, 87% yield) as light yellow oil which was used in the next step as is without further purification. $^1$H NMR (500 MHz, CDCl$_3$) δ 2.36-2.26 (m, 2H), 2.18-2.11 (m, 2H), 2.01-1.98 (m, 3H), 1.87-1.76 (m, 1H), 1.72-1.63 (m, 1H), 1.55 (s, 3H).

EXAMPLE 97

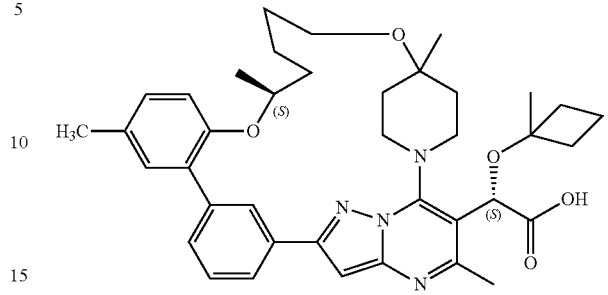

(2S)-2-(1-Methylcyclobutoxy)-2-[(22S)-4,17,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4, 6(34), 8, 10(33), 11, 13, 15 (20),16,18-decaen-3-yl]acetic acid: To a stirred solution of methyl (2S)-2-hydroxy-2-[(22S)-4,17,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetate (40 mg, 0.067 mmol) in DCM (2 mL) and 1-methylcyclobutyl acetate (599 mg, 4.68 mmol) at rt was added 70 wt % perchloric acid (0.017 mL, 0.200 mmol). After 3 h, the reaction mixture was diluted with DCM (25 mL), carefully quenched with sat. NaHCO$_3$ (5 mL), organic layer separated and washed with brine (10 mL), dried (Na$_2$SO$_4$), filtered and concentrated to give yellow paste. The crude was then tretated with 1N NaOH (0.334 mL, 0.334 mmol) in MeOH (1 mL) at 75° C. for 3 h. Mixture was then cooled and purified by prep HPLC to afford (2S)-2-(1-methylcyclobutoxy)-2-[(22S)-4,17,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid (15.8 mg, 0.024 mmol, 36.2% yield). $^1$H NMR (500 MHz, DMSO-d$_6$) δ 8.52 (s, 1H), 7.91 (d, J=7.9 Hz, 1H), 7.51 (t, J=7.6 Hz, 1H), 7.33 (d, J=7.6 Hz, 1H), 7.17-7.11 (m, 2H), 7.08 (s, 1H), 7.05 (d, J=8.2 Hz, 1H), 5.49 (s, 1H), 4.62 (d, J=5.5 Hz, 1H), 4.45 (t, J=12.2 Hz, 1H), 3.61-3.53 (m, 1H), 3.40-3.20 (m, 7H), 2.83 (d, J=10.4 Hz, 1H), 2.29 (s, 3H), 2.22 (q, J=10.0 Hz, 1H), 2.01-1.86 (m, 4H), 1.82 (br. s., 1H), 1.70-1.62 (m, 5H), 1.58-1.41 (m, 4H), 1.28 (s, 3H), 1.17 (s, 3H), 1.07 (d, J=5.8 Hz, 3H). LCMS (M+H)=653.6.

Intermediate 216

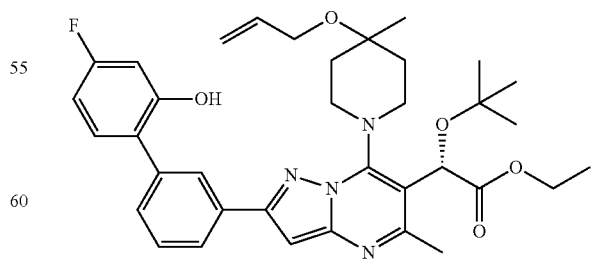

(S)-Ethyl 2-(7-(4-(allyloxy)-4-methylpiperidin-1-yl)-2-(4'-fluoro-2'-hydroxy-[1,1'-biphenyl]-3-yl)-5-methylpyrazolo[1,5-a]pyrimidin-6-yl)-2-(tert-butoxy)acetate: To (S)- ethyl 2-(7-(4-(allyloxy)-4-methylpiperidin-1-yl)-2-(3-bromophenyl)-5-methylpyrazolo[1,5-a]pyrimidin-6-yl)-2-(tert-butoxy)acetate (0.38 g, 0.63 mmol, 1 equiv), (4-fluoro-2-hydroxyphenyl)boronic acid (148 mg, 0.95 mmol, 1.5 equiv), and Pd(PPh$_3$)$_4$ (73 mg, 0.063 mmol, 0.1 equiv) was added DMF (6.3 mL that had been degassed by sparging with nitrogen for 10 min) Na$_2$CO$_3$ (0.63 mL of a 2 M aqueous solution, 1.27 mmol, 2 equiv) was added and the reaction was heated to 90° C. for 18 h. Upon cooling to ambient temperature, the reaction was diluted with EtOAc and washed with water. The EtOAc layer was dried (Na$_2$SO$_4$) and concentrated in vacuo. The crude product was purified by flash column chromatography (0-100% EtOAc in hexane) to provide the product as a yellow glass (0.27 g, 68%). LCMS (M+1)=631.4.

droimidazol-2-ylidene[2-(isopropoxy)-5-(N,N-dimethylaminosulfonyl)phenyl]methyleneruthenium(II) dichloride (0.5 mg, 0.0007 mmol, 0.005 equiv) was added. The pale green yellow solution was refluxed for 18 h. More 1,3-bis(2,4,6-trimethylphenyl)-4,5-dihydroimidazol-2-ylidene[2-(isopropoxy)-5-(N,N-dimethylaminosulfonyl)phenyl]methyleneruthenium(II) dichloride (5 mg, 0.007 mmol, 0.05 equiv) was added. After 3 h, 2-mercaptonicotinic acid (5 mg, 0.2 equiv) was added and the reaction was removed from heat. Upon cooling, the reaction was concentrated in vacuo. The crude product was purified by flash column chromatography (0-30% EtOAc in hexane) to provide the product as a tan glass (33 mg, 34%). LCMS (M+1)=671.4.

EXAMPLE 98

Intermediate 217

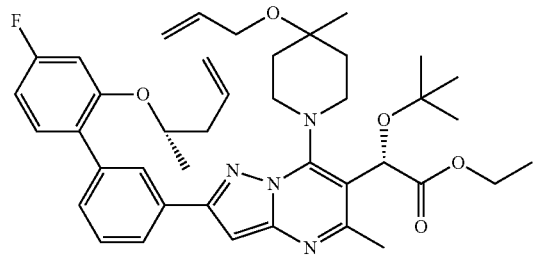

(S)-Ethyl 2-(7-(4-(allyloxy)-4-methylpiperidin-1-yl)-2-(4'-fluoro-2'-((S)-pent-4-en-2-yloxy)-[1,1'-biphenyl]-3-yl)-5-methylpyrazolo[1,5-a]pyrimidin-6-yl)-2-(tert-butoxy)acetate: To a solution of (S)-ethyl 2-(7-(4-(allyloxy)-4-methylpiperidin-1-yl)-2-(4'-fluoro-2'-hydroxy-[1,1'-biphenyl]-3-yl)-5-methylpyrazolo[1,5-a]pyrimidin-6-yl)-2-(tert-butoxy)acetate (0.27 g, 0.43 mmol, 1 equiv), (R)-pent-4-en-2-ol (0.132 mL, 1.28 mmol, 3 equiv), and PPh$_3$ (0.23 g, 0.86 mmol, 2 equiv) in THF (2.1 mL) was added DIAD (0.166 mL, 0.86 mmol, 2 equiv). After stirring 18 h, diluted with EtOAc and washed with water. The EtOAc layer was dried (Na$_2$SO$_4$) and concentrated in vacuo. The crude product was purified by flash column chromatography (0-100% EtOAc in hexane) to provide the product as a colorless glass (0.29 g, 97%). LCMS (M+1)=699.45.

Intermediate 218

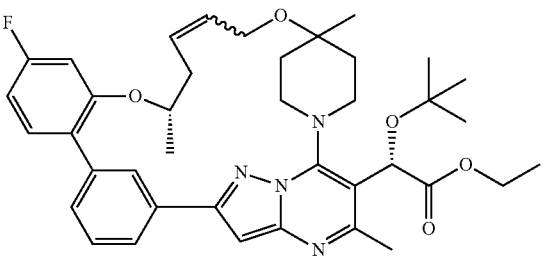

(S)-Ethyl-2-(7-(4-(allyloxy)-4-methylpiperidin-1-yl)-2-(4'-fluoro-2'-((S)-pent-4-en-2-yloxy)-[1,1'-biphenyl]-3-yl)-5-methylpyrazolo[1,5-a]pyrimidin-6-yl)-2-(tert-butoxy)acetate: A solution of (S)-ethyl 2-(7-(4-(allyloxy)-4-methylpiperidin-1-yl)-2-(4'-fluoro-2'-((S)-pent-4-en-2-yloxy)-[1,1'-biphenyl]-3-yl)-5-methylpyrazolo[1,5-a]pyrimidin-6-yl)-2-(tert-butoxy)acetate (0.10 g, 0.14 mmol, 1 equiv) in toluene (29 mL) was heated to reflux for 30 min to degas the solvent. 1,3-Bis(2,4,6-trimethylphenyl)-4,5-dihy-

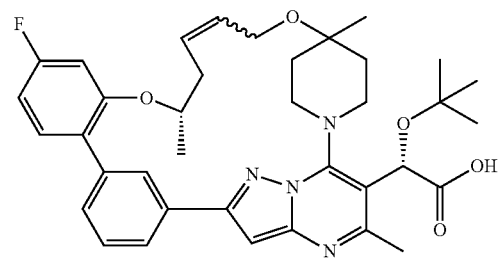 [SMILES: Cc1nc2cc3nn2c(c1[C@H](OC(C)(C)C)C(=O)O)N1CCC(C)(CC1)OCC=CC[C@H](C)Oc1cc(F)ccc1-c1cccc-3c1]

(S)-2-(7-(4-(Allyloxy)-4-methylpiperidin-1-yl)-2-(4'-fluoro-2'-((S)-pent-4-en-2-yloxy)-[1,1'-biphenyl]-3-yl)-5-methylpyrazolo[1,5-a]pyrimidin-6-yl)-2-(tert-butoxy)acetic Acid: To a solution of (S)-ethyl-2-(7-(4-(allyloxy)-4-methylpiperidin-1-yl)-2-(4'-fluoro-2'-((S)-pent-4-en-2-yloxy)-[1,1'-biphenyl]-3-yl)-5-methylpyrazolo[1,5-a]pyrimidin-6-yl)-2-(tert-butoxy)acetate (32 mg, 0.048 mmol, 1 equiv) in MeOH (1.0 mL) and water (0.1 mL) was added LiOH.H$_2$O (60 mg, 1.43 mmol, 30 equiv). The reaction was heated to 60° C. for 2 h. Upon cooling to ambient temperature, the reaction was then filtered and purified via preparative HPLC with the following conditions: Column. XBridge Phenyl, 19×mm, 5-1 μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min. Product (7 mg, 23%) isolated. $^1$H NMR (600 MHz, DMSO-d$_6$) δ 8.41 (s, 1H), 7.89 (d, J=7.7 Hz, 1H), 7.52 (t, J=7.7 Hz, 1H), 7.36-7.30 (m, 2H), 7.10 (d, J=11.6 Hz, 1H), 7.04 (s, 1H), 6.88-6.81 (m, 1H), 6.31 (d, J=6.1 Hz, 1H), 5.58 (s, 1H), 4.66-4.60 (m, 1H), 4.53 (q, J=7.0 Hz, 1H), 4.37 (t, J=12.1 Hz, 1H), 3.64-3.55 (m, 4H), 2.88 (br. s., 1H), 2.53 (s, 3H), 2.40-2.32 (m, 1H), 2.31-2.24 (m, 1H), 1.96-1.59 (m, 4H), 1.32 (s, 3H), 1.16 (s, 9H), 1.13 (d, J=6.1 Hz, 3H). LCMS (M+1)=643.5.

Intermediate 219

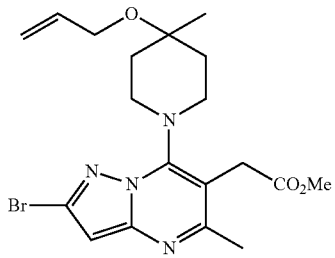

Methyl 2-(7-(4-(allyloxy)-4-methylpiperidin-1-yl)-2-bromo-5-methylpyrazolo[1,5-a]pyrimidin-6-yl)acetate: A solution of methyl 2-(2-bromo-7-chloro-5-methylpyrazolo[1,5-a]pyrimidin-6-yl)acetate (prepared according to the procedure for intermediate 4 starting from 3-bromo-1H-pyrazol-5-amine; 13.4 g, 41.9 mmol, 1 equiv), 4-(allyloxy)-4-methylpiperidine (7.16 g, 46.1 mmol, 1.1 equiv), and DIEA (17.6 mL, 101 mmol, 2.4 equiv) in DMF (84 mL) was heated at 60° C. for 2 h. The reaction was then added to water and extracted with ether (×2). Combined ether extracts dried (MgSO$_4$) and concentrated in vacuo. The crude product was purified by silica gel flash chromatography (0-50% EtOAc/hex) to provide methyl 2-(7-(4-(allyloxy)-4-methylpiperidin-1-yl)-2-bromo-5-methylpyrazolo[1,5-a]pyrimidin-6-yl)acetate (17.7 g, 97%). $^1$H NMR (500 MHz, CDCl$_3$) δ 6.52 (s, 1H), 6.02 (ddt, J=17.2, 10.4, 5.2 Hz, 1H), 5.43 (dd, J=17.2, 1.6 Hz, 1H), 5.22 (dq, J=10.4, 1.5 Hz, 1H), 3.99 (dt, J=5.2, 1.6 Hz, 2H), 3.77 (s, 3H), 3.79-3.76 (m, 2H), 3.70-3.56 (m, J=7.4 Hz, 2H), 3.33 (br. s., 2H), 2.50 (s, 3H), 1.97-1.89 (m, 2H), 1.87-1.78 (m, J=9.3 Hz, 2H), 1.32 (s, 3H). LCMS (M+1)=437.20.

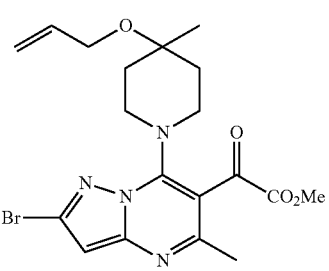

Intermediate 220

Methyl 2-(7-(4-(allyloxy)-4-methylpiperidin-1-yl)-2-bromo-5-methylpyrazolo[1,5-a]pyrimidin-6-yl)-2-oxoacetate: A solution of methyl 2-(7-(4-(allyloxy)-4-methylpiperidin-1-yl)-2-bromo-5-methylpyrazolo[1,5-a]pyrimidin-6-yl)acetate (17.7 g, 40.5 mmol, 1 equiv) in THF (200 mL) was cooled to −78° C. (IPA/CO$_2$). KHMDS (72 mL of a 0.91 M solution in THF, 64.9 mmol, 1.6 equiv) was added dropwise over ~2 min. Reaction turned a deep orange color. After 30 min, 3-phenyl-2-(phenylsulfonyl)-1,2-oxaziridine (15.9 g, 60.8 mmol, 1.2 equiv) was added in a single portion. The reaction significantly darkened. After 30 min, the reaction was added to saturated aqueous sodium bicarbonate and extracted with ether (×2). The combined ether extracts were dried (MgSO$_4$) and concentrated in vacuo to provide the crude product as a brown oil. This was taken up in DCM (200 mL) and Dess-Martin periodinane (20.6 g, 48.6 mmol, 1.2 equiv). After 30 min, the reaction was added to saturated aqueous sodium bicarbonate and extracted with DCM (×3). Combined DCM extracts were dried (Na$_2$SO$_4$) and concentrated in vacuo to provide the crude product. The crude product was purified via silica gel flash chromatography (0-50% EtOAc/hex) to provide methyl 2-(7-(4-(allyloxy)-4-methylpiperidin-1-yl)-2-bromo-5-methylpyrazolo[1,5-a]pyrimidin-6-yl)-2-oxoacetate (9.2 g, 50%). $^1$H NMR (500 MHz, CDCl$_3$) δ 6.55 (s, 1H), 6.07-5.87 (m, 1H), 5.38 (dq, J=17.2, 1.7 Hz, 1H), 5.20 (dq, J=10.4, 1.6 Hz, 1H), 3.95-3.92 (m, 5H), 3.69 (d, J=12.6 Hz, 2H), 3.59-3.50 (m, 2H), 2.56 (s, 3H), 1.96-1.82 (m, 4H), 1.28 (s, 3H). LCMS (M+1)=450.95.

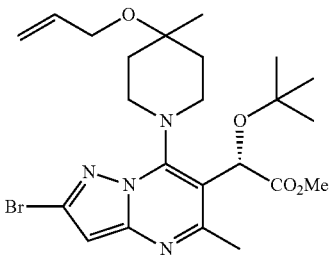

Intermediate 221

(S)-Methyl 2-(7-(4-(allyloxy)-4-methylpiperidin-1-yl)-2-bromo-5-methylpyrazolo[1,5-a]pyrimidin-6-yl)-2-(tert-butoxy)acetate: A solution of methyl 2-(7-(4-(allyloxy)-4-methylpiperidin-1-yl)-2-bromo-5-methylpyrazolo[1,5-a]pyrimidin-6-yl)-2-oxoacetate (9.20 g, 20.3 mmol, 1 equiv) and (R)-1-methyl-3,3-diphenylhexahydropyrrolo[1,2-c][1,3,2]oxazaborole (12.2 mL of a 1 M solution in toluene, 12.2 mmol, 0.6 equiv) in toluene (200 mL) was cooled to −25° C. (MeCN/CO$_2$). Catecholborane (6.8 mL of a 50% solution in toluene, 28.4 mmol, 1.4 equiv) was then added and temperature was held between −15° C. and −25° C. for 18 h. At this point, more and (R)-1-methyl-3,3-diphenylhexahydropyrrolo[1,2-c][1,3,2]oxazaborole (4 mL of a 1 M solution in toluene, 4 mmol, 0.2 equiv) and catecholborane (3 mL of a 50% solution in toluene, 12.5 mmol, 0.6 equiv) were added. The reaction was then stirred a further 4 h. The reaction was then quenched with 10% aqueous K$_2$CO$_3$ (100 mL) and EtOAc (100 mL) and removed from cooling bath. After stirring 45 min, the mixture was added to water and extracted with ether (×4). The combined ether extracts were dried (MgSO$_4$) and concentrated in vacuo to provide the crude product as a yellow foam. This was taken up in DCM (50 mL) and tBuOAc (150 mL). To this solution was added 70% perchloric acid (3.7 mL, 60.9 mmol, 3 equiv) to give a cloudy orange solution. After stirring 3 h, the reaction was added cautiously to saturated aqueous sodium bicarbonate and extracted with DCM (×3). The combined DCM extracts were dried (Na$_2$SO$_4$) and concentrated in vacuo to provide the crude product. The crude product was purified via silica gel flash chromatography (0-100% EtOAc/hex) to provide (S)-methyl 2-(7-(4-(allyloxy)-4-methylpiperidin-1-yl)-2-bromo-5-methylpyrazolo[1,5-a]pyrimidin-6-yl)-2-(tert-butoxy)acetate (3.56 g, 34%) $^1$H NMR (500 MHz, CDCl$_3$) δ 6.54 (s, 1H), 6.09-5.97 (m, 1H), 5.83 (br. s., 1H), 5.48 (d, J=17.8 Hz, 1H), 5.24 (d, J=9.8 Hz, 1H), 4.50-3.00 (very broad m, 4H), 4.05-3.98 (m, 2H), 3.76 (s, 3H), 2.59 (s, 3H), 2.04-1.90 (m, 2H), 1.36 (s, 3H), 1.24 (s, 9H). LCMS (M+1)=509.09.

And recovered (S)-Methyl 2-(7-(4-(allyloxy)-4-methylpiperidin-1-yl)-2-bromo-5-methylpyrazolo[1,5-a]pyrimidin-6-yl)-2-hydroxyacetate (4.53 g, 49%). $^1$H NMR (500 MHz, CDCl$_3$) δ 6.57 (s, 1H), 6.12-5.97 (m, 1H), 5.56-5.47 (m, 2H), 5.28-5.22 (m, 1H), 4.50-3.00 (very broad m, 4H), 4.00 (dt, J=5.0, 1.6 Hz, 2H), 3.82 (s, 3H), 2.59 (s, 3H), 2.01-1.91 (m, 2H), 1.80 (d, J=11.7 Hz, 2H), 1.33 (s, 3H). LCMS (M+1)=453.00.

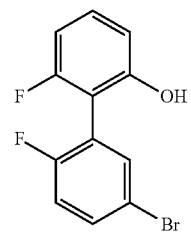

Intermediate 222

5'-Bromo-2',6-difluoro-[1,1'-biphenyl]-2-ol: (2-Fluoro-6-hydroxyphenyl)boronic acid (50 mg, 0.321 mmol, 1.0 equiv), $Pd(PPh_3)_4$ (37.1 mg, 0.032 mmol, 0.1 equiv) and aqueous $Na_2CO_3$ (2 M, 401 µl, 0.802 mmol, 2.5 equiv) were mixed with toluene (2 mL) in a sealed microwave tube. 4-Bromo-1-fluoro-2-iodobenzene (96 mg, 0.321 mmol, 1.0 equiv) in MeOH (1.00 mL) was added to the above mixture. The resulted mixture was heated at 105° C. overnight. TLC showed the starting material disappeared and a new spot was produced. The reaction was allowed to cool to ambient temperature and then loaded on 12 g ISCO column and purified by 30% EtOAc/hexane to afford 5'-bromo-2',6-difluoro-[1,1'-biphenyl]-2-ol (81 mg, 89%). $^1$H NMR (400 MHz, CHLOROFORM-d) δ 7.54 (dd, J=6.3, 2.5 Hz, 1H), 7.48 (ddd, J=8.7, 4.5, 2.6 Hz, 1H), 7.21 (td, J=8.2, 6.7 Hz, 1H), 7.07 (t, J=8.9 Hz, 1H), 6.81 (d, J=8.3 Hz, 1H), 6.71 (t, J=8.8 Hz, 1H). LCMS (M+1)=286.1.

Intermediate 223

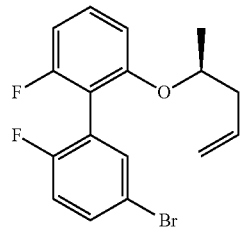

5-Bromo-2,2'-difluoro-6'-((S)-pent-4-en-2-yloxy)-1,1'-biphenyl: 5'-Bromo-2',6-difluoro-[1,1'-biphenyl]-2-ol (520 mg, 1.82 mmol., 1.0 equiv) were mixed with (R)-pent-4-en-2-ol (314 mg, 3.65 mmol, 2.0 equiv) and $Ph_3P$ (957 mg, 3.65 mmol, 2.0 equiv) in THF (6 mL). To this solution was added DEAD (1661 µl, 3.65 mmol, 2.0 equiv) dropwise and stirred overnight. The solution was mixed with silica gel and concentrated and purified by 40 g ISCO column with 0-10% EtOAc/hexane to afford 5-bromo-2,2'-difluoro-6'-((S)-pent-4-en-2-yloxy)-1,1'-biphenyl (500 mg, 78%). $^1$H NMR (400 MHz, CDCl$_3$) δ 7.52-7.42 (m, 2H), 7.34-7.28 (m, 1H), 7.03 (t, J=9.0 Hz, 1H), 6.81-6.74 (m, 2H), 5.81-5.62 (m, 1H), 5.12-4.96 (m, 2H), 4.41 (dq, J=11.7, 5.9 Hz, 1H), 2.44-2.18 (m, 2H), 1.23 (dd, J=7.3, 6.3 Hz, 3H). LCMS (M+1)=353.1.

Intermediate 224

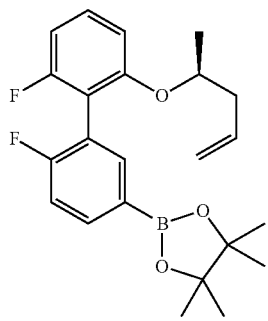

2-(2',6-Difluoro-6'-((S)-pent-4-en-2-yloxy)-[1,1'-biphenyl]-3-yl)-4,4,5,5-tetramethyl-1,3,2-dioxaborolane: A mixture of 5-bromo-2,2'-difluoro-6'-((S)-pent-4-en-2-yloxy)-1,1'-biphenyl (300 mg, 0.849 mmol, 1.0 equiv), 4,4,4',4',5,5,5',5'-octamethyl-2,2'-bi(1,3,2-dioxaborolane) (324 mg, 1.274 mmol, 1.5 equiv), potassium acetate (167 mg, 1.699 mmol, 2.0 equiv) and dioxane (8494 ni) was de-oxygenated by vacuum/nitrogen purge and treated with Pd(dppf)Cl$_2$CH$_2$Cl$_2$ (34.7 mg, 0.042 mmol, 0.05 equiv). The mixture was stirred at reflux under nitrogen for 2 h, cooled and used in the next reaction without further purification. LCMS (M+1)=401.2.

Intermediate 225

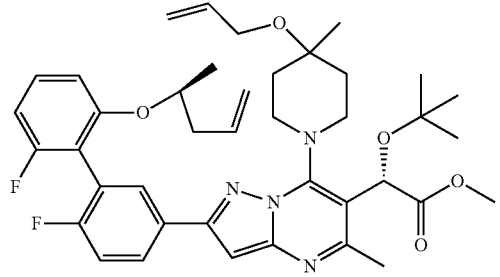

(2S)-Methyl 2-(7-(4-(allyloxy)-4-methylpiperidin-1-yl)-2-(2',6-difluoro-6'-((S)-pent-4-en-2-yloxy)-[1,1'-biphenyl]-3-yl)-5-methylpyrazolo[1,5-d]pyrimidin-6-yl)-2-(tert-butoxy)acetate: To solution of above crude product was added (S)-methyl 2-(7-(4-(allyloxy)-4-methylpiperidin-1-yl)-2-bromo-5-methylpyrazolo[1,5-a]pyrimidin-6-yl)-2-(tert-butoxy)acetate (100 mg, 0.196 mmol, 1.0 equiv), PdCl$_2$(dppf)-CH$_2$Cl$_2$ (16.03 mg, 0.020 mmol, 0.1 equiv), DMF (0.5 mL) and 2 M K$_3$PO$_4$ (0.294 mL, 0.589 mmol, 3.0 equiv). The mixture was stirred at 90° C. for 2 h, cooled, diluted with EtOAc and washed with saturated NaHCO$_3$. The organic solution was dried over MgSO$_4$ and concentrated with silica gel and purified on 24 g ISCO column to afford (2S)-methyl 2-(7-(4-(allyloxy)-4-methylpiperidin-1-yl)-2-(2',6-difluoro-6'-((S)-pent-4-en-2-yloxy)-[1,1'-biphenyl]-3-yl)-5-methylpyrazolo[1,5-a]pyrimidin-6-yl)-2-(tert-butoxy)acetate (100 mg, 72.5% yield) as a pale yellow oil. $^1$H NMR (400 MHz, CDCl$_3$) δ 8.06 (br. s., 1H), 7.92 (br. s., 1H), 7.35-7.28 (m, 1H), 7.21 (t, J=8.8 Hz, 1H), 6.86-6.73 (m, 3H), 6.09-5.86 (m, 2H), 5.77-5.60 (m, 1H), 5.40 (d, J=17.3 Hz, 1H), 5.11 (br. s., 1H), 5.04-4.92 (m, 2H), 4.47-4.34 (m, 1H), 4.00 (br. s., 2H), 3.74 (s, 3H), 2.60 (s, 3H), 2.41-2.31 (m, 1H), 2.29-2.18 (m, 1H), 2.09-2.06 (m, 2H), 2.03-1.90 (m, 2H), 1.71 (br. s., 1H), 1.62-1.59 (m, 1H), 1.27 (s, 3H), 1.25 (s, 9H), 1.24-1.21 (m, 3H). LCMS (M+1)=703.4.

Intermediate 226

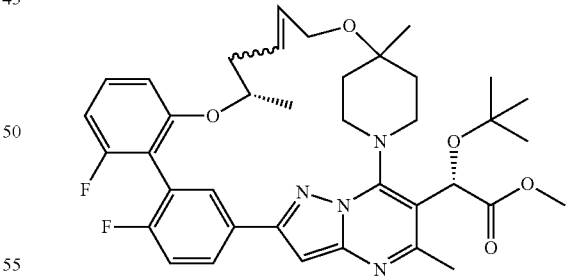

Methyl (2S)-[(22S)-13,16-difluoro-4,22,28-trimethyl-21,27-dioxa-1,5,7,8-tetraazahexacyclo[26.2.2. $1^{6,9}.1^{10,14}.0^{2,7}.0^{15,20}$]tetratriaconta-2,4,6(34),8,10(33),11,13,15,17,19,24-undecaen-3-yl][(2-methyl-2-propanyl)oxy]acetate: To a solution of (2S)-methyl 2-(7-(4-(allyloxy)-4-methylpiperidin-1-yl)-2-(2',6-difluoro-6'-((S)-pent-4-en-2-yloxy)-[1,1'-biphenyl]-3-yl)-5-methylpyrazolo[1,5-a]pyrimidin-6-yl)-2-(tert-butoxy)acetate (100 mg, 0.142 mmol, 1.0 equiv) in DCE (70 mL) was added Hoveyda-Grubbs Catalyst 2$^{nd}$ Generation (8.92 mg, 0.014 mmol, 0.1 equiv) and stirred for 5 h at 90° C. Then, the solvent was evaporated and the residue was used in the next step without further purification. LCMS (M+1)=675.4.

EXAMPLE 99

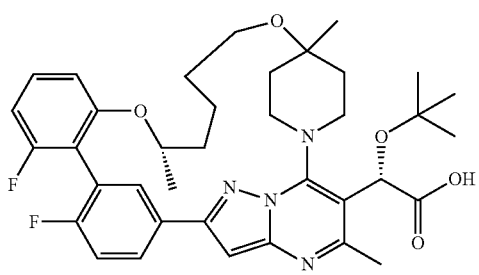 [SMILES: Cc1nc2cc3nn2c(c1[C@H](OC(C)(C)C)C(=O)O)N1CCC(C)(CC1)OCCCC[C@H](C)Oc1cccc(F)c1-c1cc-3ccc1F]

(2S)-[(22S)-16-Chloro-4,13,22,28-tetramethyl-21,27-di-oxa-1,5,7,8-tetraazahexacyclo[26.2.2.1$^{6,9}$.1$^{10,14}$.0$^{2,7}$.0$^{15,20}$] tetratriaconta-2,4,6(34),8,10(33),11,13,15,17,19-decaen-3-yl][(2-methyl-2-propanyl)oxy]acetic acid: The residue from the last step was dissolved in methanol (2 mL) and to this solution was added sodium borohydride (28.0 mg, 0.741 mmol, 5 equiv) in several batches until the alkene was completely reduced. The reaction was quenched with 0.5 M HCl and extracted with ethyl acetate. The organic layer was collected and concentrated down to a grey solid. This solid was redissolved in methanol (1.5 mL), THF (1 mL) and water (0.8 mL). To this solution was added LiOH (89 mg, 3.70 mmol, 25 equiv) and stirred at 60° C. for 2 h. After filtration, the solution was purified by HPLC, Column. XBridge C18, 19×200 mm, 5-mm particles; Mobile Phase A: 5:95 acetonitrile:water with 10-mM ammonium acetate; Mobile Phase B: 95:5 acetonitrile:water with 10-mM ammoniumacetate; Gradient: 40-80% B over 20 minutes, then a 5-minute hold at 100% B; Flow: 20 mL/min. Fractions containing the desired product were combined and dried via centrifugal evaporation to afford (2S)-[(22S)-16-chloro-4,13,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15,17,19-decaen-3-yl][(2-methyl-2-propanyl)oxy]acetic acid (6.7 mg, 10.11 µmol, 7% yield). $^1$H NMR (500 MHz, DMSO-d$_6$) δ 8.20 (d, J=6.7 Hz, 1H), 8.03 (br. s., 1H), 7.47-7.35 (m, 2H), 7.11-7.03 (m, 2H), 6.88 (t, J=8.7 Hz, 1H), 5.61 (br. s., 1H), 4.68 (br. s., 1H), 4.50 (t, J=11.7 Hz, 1H), 3.39 (br. s., 2H), 3.30 (br. s., 2H), 2.80-2.69 (m, 1H), 2.52-2.50 (m, 3H), 1.95-1.83 (m, 3H), 1.61 (br. s., 5H), 1.41 (br. s., 2H), 1.15 (br. s., 12H), 1.10 (d, J=5.2 Hz, 3H). LCMS (ESI, M+1): 663.3.

Intermediate 227

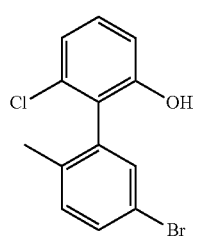

5'-Bromo-6-chloro-2'-methyl-[1,1'-biphenyl]-2-ol: (2-Chloro-6-hydroxyphenyl)boronic acid (250 mg, 1.450 mmol, 1 equiv), Pd(PPPh$_3$)$_4$ (168 mg, 0.145 mmol, 0.1 equiv) and aqueous Na$_2$CO$_3$ (2 M, 1.8 ml, 3.63 mmol, 2.5 equiv) were mixed with toluene (2 mL) in a sealed microwave tube. 4-Bromo-2-iodo-1-methylbenzene (431 mg, 1.450 mmol, 1.0 equiv) in MeOH (1.00 mL) was to the above mixture. The mixture was heated at 105° C. overnight. Then, the crude reaction mixture was loaded on 12 g column and purified at 30% EtOAc/hexane to afford 5'-bromo-6-chloro-2'-methyl-[1,1'-biphenyl]-2-ol (345 mg, 80%). LCMS (M+1)=299.0.

Intermediate 228

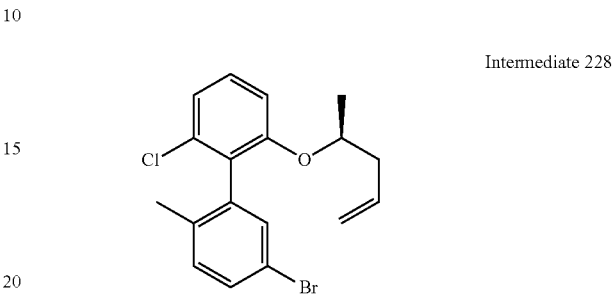

5-Bromo-2'-chloro-2-methyl-6'-((S)-pent-4-en-2-yloxy)-1,1'-biphenyl: 5'-Bromo-6-chloro-2'-methyl-[1,1'-biphenyl]-2-ol (540 mg, 1.82 mmol, 1.0 equiv) were mixed with (R)-pent-4-en-2-ol (313 mg, 3.63 mmol, 2.0 equiv) and Ph$_3$P (952 mg, 3.63 mmol, 2.0 equiv) in THF (6 ml). To this solution was added DEAD (1653 µl, 3.63 mmol, 2.0 equiv) dropwise and stirred overnight. The solution was mixed with silica gel and concentrated and purified by 40 g ISCO column with 0-10% EtOAc/hex to afford 5-bromo-2'-chloro-2-methyl-6'-((S)-pent-4-en-2-yloxy)-1,1'-biphenyl (350 mg, 52.7%). $^1$H NMR (400 MHz, CDCl$_3$) δ 7.39 (dd, J=8.2, 2.1 Hz, 1H), 7.25-7.21 (m, 2H), 7.14 (d, J=7.5 Hz, 1H), 7.07 (d, J=8.0 Hz, 1H), 6.86 (dd, J=8.0, 5.3 Hz, 1H), 5.66-5.50 (m, 1H), 5.05-4.90 (m, 2H), 4.35-4.24 (m, 1H), 2.30-2.12 (m, 2H), 2.01 (s, 3H), 1.16 (dd, J=11.0, 6.0 Hz, 3H). LCMS (M+1)=365.0.

Intermediate 229

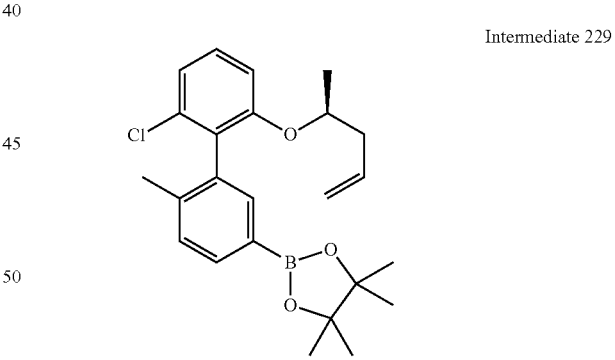

2-(2'-Chloro-6-methyl-6'-((S)-pent-4-en-2-yloxy)-[1,1'-biphenyl]-3-yl)-4,4,5,5-tetramethyl-1,3,2-dioxaborolane: A mixture of 5-bromo-2'-chloro-2-methyl-6'-((S)-pent-4-en-2-yloxy)-1,1'-biphenyl (400 mg, 1.094 mmol, 1.0 equiv), 4,4,4',4',5,5,5',5'-octamethyl-2,2'-bi(1,3,2-dioxaborolane) (417 mg, 1.641 mmol, 1.5 equiv), potassium acetate (215 mg, 2.188 mmol, 2.0 equiv) and dioxane (1.1 ml) was de-oxygenated by vacuum/nitrogen purge and treated with Pd(dppf)Cl$_2$.CH$_2$Cl$_2$ (44.7 mg, 0.055 mmol, 0.05 equiv). The mixture was stirred at reflux under nitrogen overnight. It was cooled down to room temperature and used for next reaction without further purification. LCMS (M+1)=413.2.

Intermediate 230

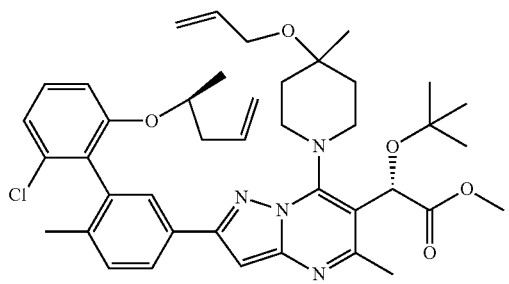

(2S)-Methyl 2-(7-(4-(allyloxy)-4-methylpiperidin-1-yl)-2-(2'-chloro-6-methyl-6'-((S)-pent-4-en-2-yloxy)-[1,1'-biphenyl]-3-yl)-5-methylpyrazolo[1,5-a]pyrimidin-6-yl)-2-(tert-butoxy)acetate: To the crude reaction mixture of the previous step was added (S)-methyl 2-(7-(4-(allyloxy)-4-methylpiperidin-1-yl)-2-bromo-5-methylpyrazolo[1,5-a]pyrimidin-6-yl)-2-(tert-butoxy)acetate (130 mg, 0.254 mmol, 1.0 equiv), PdCl$_2$(dppf)-CH$_2$Cl$_2$ (21 mg, 0.025 mmol, 0.1 equiv), DMF (2 mL) and 2 M K$_3$PO$_4$ (0.382 mL, 0.763 mmol, 3.0 equiv). The mixture was stirred at 90° C. for 1 h, cooled, diluted with EtOAc and washed with saturated NaHCO$_3$. The organic solution was dried over MgSO$_4$ and concentrated with silica gel and purified on 24 g ISCO column to afford (2S)-methyl 2-(7-(4-(allyloxy)-4-methylpiperidin-1-yl)-2-(2'-chloro-6-methyl-6'-((S)-pent-4-en-2-yloxy)-[1,1'-biphenyl]-3-yl)-5-methylpyrazolo[1,5-a]pyrimidin-6-yl)-2-(tert-butoxy)acetate (120 mg, 0.168 mmol, 66%) as pale yellow oil. LCMS (M+1)=715.3.

Intermediate 231

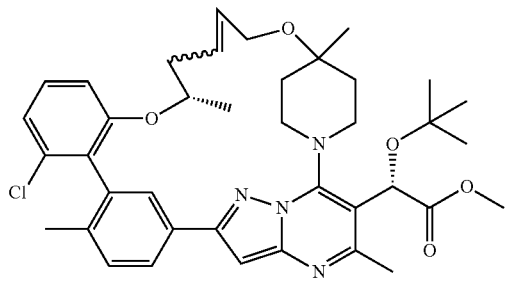

Methyl (2S)-[(22S)-16-chloro-4,13,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15,17,19,24-undecaen-3-yl][(2-methyl-2-propanyl)oxy]acetate: To a solution of (2S)-methyl 2-(7-(4-(allyloxy)-4-methylpiperidin-1-yl)-2-(2'-chloro-6-methyl-6'-((S)-pent-4-en-2-yloxy)-[1,1'-biphenyl]-3-yl)-5-methylpyrazolo[1,5-a]pyrimidin-6-yl)-2-(tert-butoxy)acetate (100 mg, 0.140 mmol, 1.0 equiv) in DCE (7 mL) was added Hoveyda-Grubbs Catalyst 2$^{nd}$ Generation (8.76 mg, 0.014 mmol, 0.1 equiv) and stirred for 3 h at 95° C. The solvent was evaporated to give a grey solid which was used in the next step without further purification. LCMS (M+1)=687.3.

EXAMPLES 100 AND 101

The crude product from the previous step was dissolved in 2 mL methanol. To this solution was added sodium borohydride (27.5 mg, 0.728 mmol, 5 equiv) in several batches until the alkene was reduced. The reaction was quenched with 0.5 M HCl and extracted with ethyl acetate. The organic layer was collected and concentrated down to a grey solid. This solid was redissolved in 1.5 mL methanol, 1 mL THF and 0.8 mL water. To this solution was added LiOH (89 mg, 3.70 mmol, 25 equiv) and stirred at 60° C. for 2 h. After filtration, the solution was purified by HPLC (Column XBridge C18, 19×200 mm, 5-µm particles; Mobile Phase A: 5:95 acetonitrile:water with 10-mM ammonium acetate; Mobile Phase B: 95:5 acetonitrile:water with 10-mM ammoniumacetate; Gradient: 40-80% B over 20 minutes, then a 5-minute hold at 100% B; Flow: 20 mL/min.) to afford two atropisomers.

EXAMPLE 100

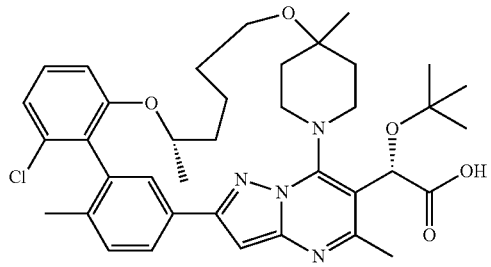 [SMILES: Cc1ccc2cc1-c1c(Cl)cccc1O[C@@H](C)CCCCOC1(C)CCN(CC1)c1c([C@H](OC(C)(C)C)C(=O)O)c(C)nc3cc-2nn13]

(2S)-[(22S)-16-Chloro-4,13,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4, 6(34), 8, 10(33),11,13,15,17,19-decaen-3-yl][(2-methyl-2-propanyl)oxy]acetic acid: $^1$H NMR (400 MHz, METHANOL-d$_4$) δ 7.83 (d, J=1.5 Hz, 1H), 7.64 (dd, J=7.9, 1.6 Hz, 1H), 7.33-7.23 (m, 2H), 7.00 (t, J=7.8 Hz, 2H), 6.75 (s, 1H), 5.91 (s, 1H), 4.73 (t, J=11.5 Hz, 1H), 4.55 (t, J=6.4 Hz, 1H), 3.65 (t, J=11.1 Hz, 1H), 3.44-3.30 (m, 3H), 2.78 (d, J=11.5 Hz, 1H), 2.58 (s, 3H), 1.99 (s, 3H), 1.95-1.87 (m, 2H), 1.80-1.58 (m, 4H), 1.53 (dd, J=8.4, 4.8 Hz, 1H), 1.49-1.34 (m, 3H), 1.21 (s, 9H), 1.17 (s, 3H), 1.12 (d, J=5.9 Hz, 3H). LCMS (M+1)=675.3.

EXAMPLE 101

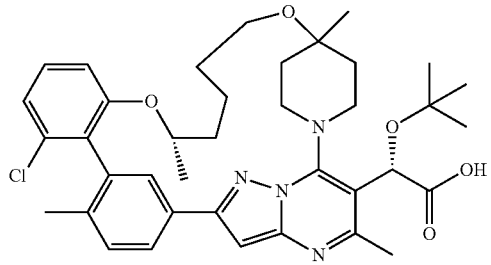 [SMILES: Cc1ccc2cc1-c1c(Cl)cccc1O[C@@H](C)CCCCOC1(C)CCN(CC1)c1c([C@H](OC(C)(C)C)C(=O)O)c(C)nc3cc-2nn13]

(2S)-[(22S)-16-Chloro-4,13,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15,17,19-decaen-3-yl][(2-methyl-2-propanyl)oxy]acetic Acid: $^1$H NMR (400 MHz, METHANOL-d$_4$) δ 7.71-7.62 (m, 2H), 7.41 (d, J=7.8 Hz, 1H), 7.34-7.25 (m, 2H), 7.03 (d, J=7.6 Hz, 1H), 6.68 (s, 1H), 5.93 (s, 1H), 4.36-4.22 (m, 1H), 4.10-3.91 (m, 2H), 3.36 (d, J=9.0 Hz, 3H), 2.66 (s, 3H), 2.61 (d, J=9.5 Hz, 1H), 2.07 (s, 3H), 2.03 (d, J=5.6 Hz, 1H), 1.76 (d, J=11.0 Hz, 3H), 1.58 (dd, J=13.3, 4.0 Hz, 2H), 1.43-1.28 (m, 3H), 1.25 (s, 9H), 1.21 (s, 3H), 0.85 (d, J=6.1 Hz, 3H). LCMS (M+1)=675.3.

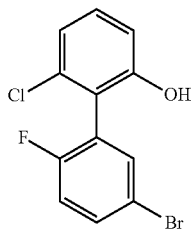

Intermediate 232

5'-Bromo-6-chloro-2'-fluoro-[1,1'-biphenyl]-2-ol: (2-Chloro-6-hydroxyphenyl)boronic acid (250 mg, 1.450 mmol, 1.0 equiv), Pd(PPh$_3$)$_4$ (168 mg, 0.145 mmol, 0.1 equiv) and aqueous Na$_2$CO$_3$ (2 M, 1.8 mL, 3.63 mmol, 2.5 equiv) were mixed with toluene (3 mL) in a sealed microwave tube. 4-Bromo-1-fluoro-2-iodobenzene (436 mg, 1.450 mmol) in MeOH (1.50 mL) was added to the above mixture. The mixture was heated at 105° C. overnight. Then, the reaction mixture was loaded on 12 g column and purified using 30% EtOAc/Hex to afford 5'-bromo-6-chloro-2'-fluoro-[1,1'-biphenyl]-2-ol (400 mg, 91% yield). $^1$H NMR (400 MHz, CDCl$_3$) δ 7.57 (ddd, J=8.8, 4.5, 2.5 Hz, 1H), 7.47 (dd, J=6.3, 2.5 Hz, 1H), 7.24 (t, J=8.2 Hz, 1H), 7.17-7.06 (m, 2H), 6.90 (d, J=8.0 Hz, 1H). LCMS (M+1)=302.9.

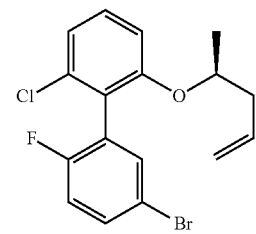

Intermediate 233

5-Bromo-2'-chloro-2-fluoro-6'-((S)-pent-4-en-2-yloxy)-1,1'-biphenyl: 5'-Bromo-6-chloro-2'-fluoro-[1,1'-biphenyl]-2-ol (750 mg, 2.49 mmol, 1.0 equiv) were mixed with (R)-pent-4-en-2-ol (428 mg, 4.97 mmol, 2.0 equiv) and PPh$_3$ (1305 mg, 4.97 mmol, 2.0 equiv) in tetrahydrofuran (8 mL). To this solution was added DEAD (2266 µl, 4.97 mmol, 2.0 equiv) dropwise and stirred overnight. The solution was mixed with silica gel and concentrated and purified by 40 g ISCO column with 0-10% EtOAc/hexane to afford 5-bromo-2'-chloro-2-fluoro-6'-((S)-pent-4-en-2-yloxy)-1,1'-biphenyl (385 mg, 42%). $^1$H NMR (400 MHz, CDCl$_3$) δ 7.49-7.44 (m, 1H), 7.41-7.36 (m, 1H), 7.29 (s, 1H), 7.11-6.99 (m, 2H), 6.87 (dd, J=8.3, 2.0 Hz, 1H), 5.73-5.56 (m, 1H), 5.07-4.93 (m, 2H), 4.36 (dq, J=8.8, 6.0 Hz, 1H), 2.37-2.16 (m, 2H), 1.20 (dd, J=6.0, 3.0 Hz, 3H). LCMS (M+1)=369.0.

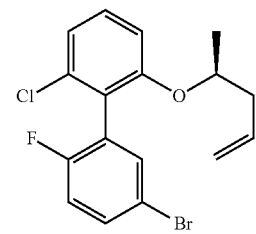

Intermediate 234

2-(2'-Chloro-6-fluoro-6'-((S)-pent-4-en-2-yloxy)-[1,1'-biphenyl]-3-yl)-4,4,5,5-tetramethyl-1,3,2-dioxaborolane: A mixture of 5-bromo-2'-chloro-2-fluoro-6'-((S)-pent-4-en-2-yloxy)-1,1'-biphenyl (220 mg, 0.595 mmol, 1.0 equiv), 4,4,4',4',5,5,5',5'-octamethyl-2,2'-bi(1,3,2-dioxaborolane) (227 mg, 0.893 mmol, 1.5 equiv), potassium acetate (117 mg, 1.190 mmol, 2.0 equiv) and 1,4-dioxane (6 mL) were de-oxygenated by vacuum/nitrogen purge and treated with Pd(dppf)Cl$_2$CH$_2$Cl$_2$ (24.30 mg, 0.030 mmol, 0.05 equiv). The mixture was stirred at reflux under nitrogen until all the starting material was consumed. It was cooled down to room temperature and used in the next stepwithout further purification. LCMS (M+1)=417.2.

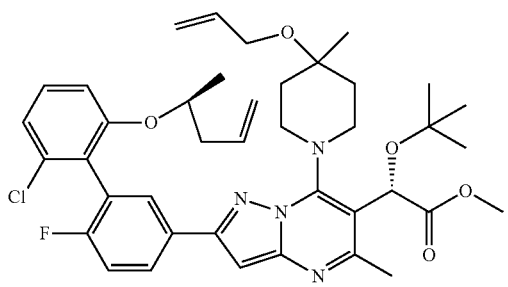

Intermediate 235

(2S)-Methyl 2-(7-(4-(allyloxy)-4-methylpiperidin-1-yl)-2-(2'-chloro-6-fluoro-6'-((S)-pent-4-en-2-yloxy)-[1,1'-biphenyl]-3-yl)-5-methylpyrazolo[1,5-a]pyrimidin-6-yl)-2-(tert-butoxy)acetate: To 3.0 mL solution of above crude product was added (S)-methyl 2-(7-(4-(allyloxy)-4-methylpiperidin-1-yl)-2-bromo-5-methylpyrazolo[1,5-a]pyrimidin-6-yl)-2-(tert-butoxy)acetate (150 mg, 0.294 mmol, 1.0 equiv), PdCl$_2$(dppf)-CH$_2$Cl$_2$ (24.05 mg, 0.029 mmol, 0.1 equiv), DMF (3 mL) and 2 M K$_3$PO$_4$ (442 µl, 0.883 mmol, 3.0 equiv). The mixture was stirred at 90° C. for 2 h, cooled, diluted with EtOAc and washed with saturated NaHCO$_3$. The organic solution was dried over MgSO$_4$ and concentrated with silica gel and purified on 24 g ISCO column to afford (2S)-methyl 2-(7-(4-(allyloxy)-4-methylpiperidin-1-yl)-2-(2'-chloro-6-fluoro-6'-((S)-pent-4-en-2-yloxy)-[1,1'-biphenyl]-3-yl)-5-methylpyrazolo[1,5-a]pyrimidin-6-yl)-2-(tert-butoxy)acetate (100 mg, 0.139 mmol, 47%) as a pale yellow oil. LCMS (M+1)=719.3.

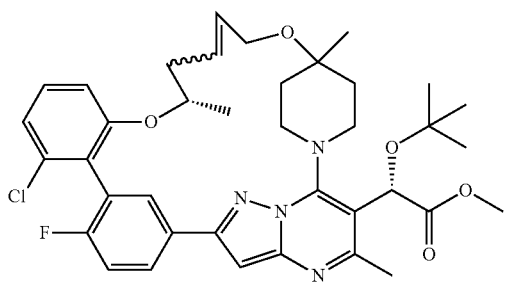

Intermediate 236

Methyl (2S)-[(22S)-16-chloro-13-fluoro-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4, 6(34), 8, 10(33), 11, 13, 15, 17, 19,24-undecaen-3-yl][(2-methyl-2-propanyl)oxy] acetate: To a solution of (2S)-methyl 2-(7-(4-(allyloxy)-4-methylpiperidin-1-yl)-2-(2'-chloro-6-fluoro-6'-((S)-pent-4-en-2-yloxy)-[1,1'-biphenyl]-3-yl)-5-methylpyrazolo[1,5-a]

pyrimidin-6-yl)-2-(tert-butoxy)acetate (120 mg, 0.167 mmol, 1.0 equiv) in DCE (83 mL) was added Hoveyda-Grubbs Catalyst 2$^{nd}$ Generation (10.45 mg, 0.017 mmol, 0.1 equiv) and stirred for 2 h at 95° C. The solvent was evaporated and the residue was used as is. LCMS (M+1)=687.3.

EXAMPLE 102

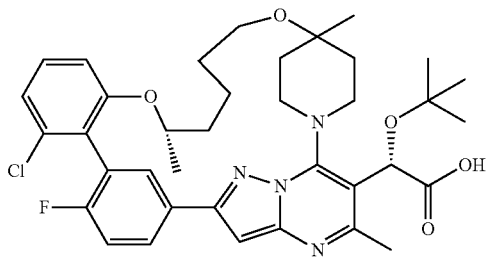 [SMILES: Cc1nc2cc3nn2c(c1[C@H](OC(C)(C)C)C(=O)O)N1CCC(C)(CC1)OCCCC[C@H](C)Oc1cccc(Cl)c1-c1cc-3ccc1F]

(2S)-[(22S)-16-Chloro-13-fluoro-4,22,28-trimethyl-21,27-dioxa-1,5,7,8-tetraazahexacyclo[26.2.2. 1$^{6,9}$.1$^{10,14}$.0$^{2,7}$.0$^{15,20}$]tetratriaconta-2,4, 6(34), 8, 10(33),11, 13,15,17,19-decaen-3-yl][(2-methyl-2-propanyl)oxy]acetic acid: The residue from the last step was dissolved in 2 mL methanol. To this solution was added sodium borohydride (32.8 mg, 0.868 mmol, 5.0 equiv) in several batches until the alkene was reduced. The reaction was quenched by 0.5 M HCl and extracted with ethyl acetate. The organic layer was collected and concentrated down to a grey solid which was redissolved in 1.5 mL methanol, 1 mL THF and 0.8 mL water. To this solution was added LiOH (89 mg, 3.70 mmol, 25 equiv) and stirred at 60° C. for 2 h to give the title compound. LCMS (M+1)=679.3.

Intermediate 237

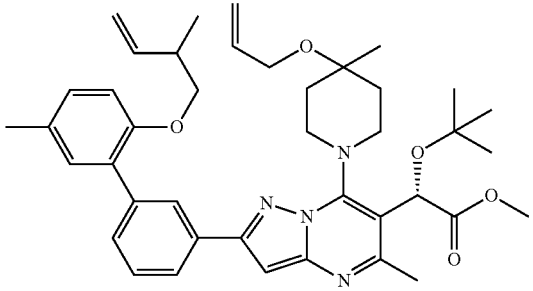

(2S)-Methyl 2-(7-(4-(allyloxy)-4-methylpiperidin-1-yl)-5-methyl-2-(5'-methyl-2'-((2-methylbut-3-en-1-yl)oxy)-[1,1'-biphenyl]-3-yl)pyrazolo[1,5-d]pyrimidin-6-yl)-2-(tert-butoxy)acetate: A solution of methyl (2S)-2-(tert-butoxy)-2-{2-[3-(2-hydroxy-5-methylphenyl)phenyl]-5-methyl-7-[4-methyl-4-(prop-2-en-1-yloxy)piperidin-1-yl]pyrazolo[1,5-a]pyrimidin-6-yl}acetate (0.297 g, 0.485 mmol) in dry THF (5 mL) was treated sequentially with 2-methylbut-3-en-1-ol (0.167 g, 1.939 mmol), Ph$_3$P (0.509 g, 1.939 mmol) and DEAD (0.307 ml, 1.939 mmol), and the reaction was stirred for 16 h. The reaction was diluted with water (20 mL), extracted into Et$_2$O (2×20 mL), dried (MgSO$_4$), filtered, and concentrated. The residue was purified by flash column chromatography (40 g SiO$_2$, 0-100% (38.1 CV), EtOAc in hexanes) to afford the desired product (0.300 g, 0.419 mmol, 86% yield). $^1$H NMR (500 MHz, CDCl$_3$) δ: 8.12 (s, 1H), 8.03 (d, J=6.8 Hz, 1H), 7.57 (d, J=7.6 Hz, 1H), 7.50-7.41 (m, 1H), 7.23 (d, J=1.9 Hz, 1H), 7.16-7.09 (m, 1H), 6.90 (d, J=8.4 Hz, 1H), 6.83 (s, 1H), 6.08-5.90 (m, 2H), 5.78 (ddd, J=17.3, 10.4, 6.9 Hz, 1H), 5.41 (dd, J=17.2, 1.3 Hz, 1H), 5.18-5.07 (m, 1H), 5.02 (dt, J=17.3, 1.3 Hz, 1H), 4.97 (dq, J=10.5, 1.2 Hz, 1H), 4.01 (d, J=4.9 Hz, 2H), 3.87 (dd, J=8.8, 6.1 Hz, 1H), 3.79-3.75 (m, 1H), 3.74 (s, 3H), 2.61 (s, 4H), 2.36 (s, 3H), 2.05-1.92 (m, 2H), 1.81-1.67 (m, 1H), 1.42-1.35 (m, 2H), 1.26 (s, 9H), 1.04 (dd, J=6.8, 0.6 Hz, 3H). LCMS (M+H)=681.6.

Intermediate 238

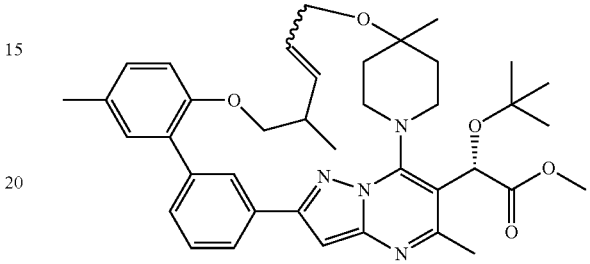

Methyl (2S)-2-(tert-butoxy)-2-[(24E/Z)-4,17,23,28-tetramethyl-21,27-dioxa-1,5,7,8-tetraazahexacyclo[26.2.2. 1$^{6,9}$.1$^{10,14}$.0$^{2,7}$.0$^{15,20}$]tetratriaconta-2,4,6(34),8,10(33), 11,13,15 (20),16,18,24-undecaen-3-yl]acetate: A solution of (2S)-methyl 2-(7-(4-(allyloxy)-4-methylpiperidin-1-yl)-5-methyl-2-(5'-methyl-2'42-methylbut-3-en-1-yl)oxy)-[1,1'-biphenyl]-3-yl)pyrazolo[1,5-a]pyrimidin-6-yl)-2-(tert-butoxy)acetate (0.300 g, 0.441 mmol) in DCE (110 ml) was heated (85° C.) then treated with Hoveyda-Grubbs cat., 2nd gen. (0.019 g, 0.031 mmol), and stirred for 2 h, then cooled and stirred for 16 h. The solvent was removed and the residue was purified by biotage (12 g SiO$_2$, 0% (3 CV), 0-60% (15 CV), 60% (2 CV), EtOAc in hexanes) to afford the desired product (0.203 g, 0.311 mmol, 70.6% yield) as a 1:1 mixture of diasteriomers. LCMS (M+H)=653.6.

Intermediate 239

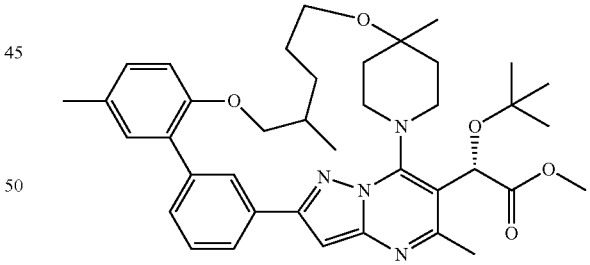

Methyl (2S)-2-(tert-butoxy)-2-{4,17,23,28-tetramethyl-21,27-dioxa-1,5,7,8-tetraazahexacyclo [26.2.2.1$^{6,9}$.1$^{10,14}$.0$^{2,7}$.0$^{16,20}$]tetratriaconta-2,4,6(34),8,10 (33), 11,13,15 (20),16,18-decaen-3-yl}acetate. A solution of methyl (2S)-2-(tert-butoxy)-2-[(24E/Z)-4,17,23,28-tetramethyl-21,27-dioxa-1,5,7,8-tetraazahexacyclo[26.2.2. 1$^{6,9}$.1$^{10,14}$.0$^{2,7}$.0$^{16,20}$]tetratriaconta-2,4,6(34),8,10(33), 11,13, 15 (20),16,18,24-undecaen-3-yl]acetate: (0.203 g, 0.311 mmol) in MeOH (4 mL) was treated with 10 wt % Pd/C (0.033 g, 0.031 mmol), and then three times evacuated and back-filled with H$_2$ gas (balloon). The reaction was stirred for 2.5 hrs, then the reaction was filtered (0.45 μm syringe tip filter), and concentrated to afford the desired product (0.191 g, 0.292 mmol, 94% yield) as a pale yellow oil and mixture of diastereomers. LCMS (M+H)=655.4.

EXAMPLES 103 AND 104

A solution of methyl (2S)-2-(tert-butoxy)-2-{4,17,23,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl}acetate (0.191 g, 0.292 mmol) in MeOH (2 mL) was treated with 5.0 M NaOH (0.3 mL, 1.458 mmol), resulting in a thick gummy deposit, so THF (2 mL) was added, and the solution was then heated (75° C.) for 2 h. The reaction was cooled and then diluted with CH$_2$Cl$_2$ (15 mL) and washed with 1.0 N HCl (5 mL), then brine, concentrated, and purified by prep-HPLC to afford two diasteriomers.

EXAMPLE 103

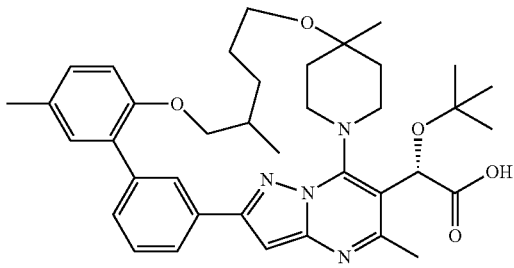 [SMILES: Cc1ccc2c(c1)-c1cccc(c1)-c1cc3nc(C)c([C@H](OC(C)(C)C)C(=O)O)c(n3n1)N1CCC(C)(CC1)OCCCC(C)CO2]

(2S)-2-(tert-Butoxy)-2-{4,17,23,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl}acetic acid: (early eluting diasteriomer, 0.0125 g, 0.019 mmol, 13.24% yield). $^1$H NMR (500 MHz, DMSO-d$_6$) δ: 8.58 (s, 1H), 7.89 (d, J=7.0 Hz, 1H), 7.51 (t, J=7.6 Hz, 1H), 7.36 (d, J=7.3 Hz, 1H), 7.17 (s, 1H), 7.14 (d, J=7.9 Hz, 1H), 7.07-7.02 (m, 2H), 5.59 (s, 1H), 4.50-4.40 (m, 1H), 4.16 (t, J=7.5 Hz, 1H), 2.93-2.85 (m, 1H), 2.35 (br. s., 1H), 2.29 (s, 3H), 1.99-1.88 (m, 3H), 1.82 (br. s., 1H), 1.73-1.49 (m, 4H), 1.37 (br. s., 1H), 1.19 (s, 3H), 1.15 (s, 9H), 0.81 (d, J=6.7 Hz, 3H). Note: piperidine protons broaden into baseline, and/or are solvent obscured. LCMS (M+H)=641.7.

EXAMPLE 104

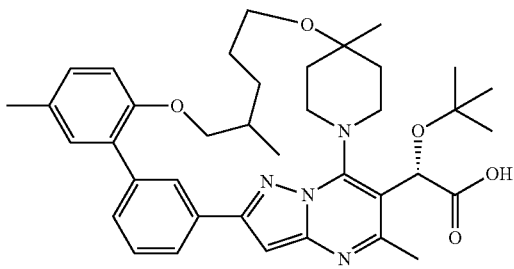 [SMILES: Cc1ccc2c(c1)-c1cccc(c1)-c1cc3nc(C)c([C@H](OC(C)(C)C)C(=O)O)c(n3n1)N1CCC(C)(CC1)OCCCC(C)CO2]

(2S)-2-(tert-Butoxy)-2-{4,17,23,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33), 11, 13, 15 (20),16,18-decaen-3-yl}acetic acid: (later eluting diasteriomer, 0.015 g, 0.023 mmol, 15.57% yield). $^1$H NMR (500 MHz, DMSO-d$_6$) δ: 8.47 (s, 1H), 7.92 (d, J=7.6 Hz, 1H), 7.50 (t, J=7.6 Hz, 1H), 7.29 (d, J=7.3 Hz, 1H), 7.17-7.07 (m, 3H), 7.04 (d, J=8.5 Hz, 1H), 5.69 (s, 1H), 4.65-4.55 (m, 1H), 4.32 (d, J=9.5 Hz, 1H), 3.52 (d, J=11.6 Hz, 1H), 2.71 (d, J=11.6 Hz, 1H), 2.28 (s, 3H), 2.19 (d, J=13.4 Hz, 1H), 2.03 (d, J=13.4 Hz, 1H), 1.86-1.76 (m, 2H), 1.75-1.52 (m, 3H), 1.46 (br. s., 1H), 1.18 (s, 3H), 1.16 (s, 9H), 0.74 (d, J=6.7 Hz, 3H). Note: piperidine protons broaden into baseline, and/or are solvent obscured. LCMS (M+H)=641.6.

EXAMPLE 105

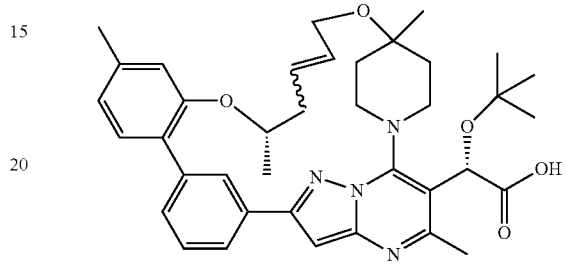

(2S)-2-(tert-Butoxy)-2-[(22S)-4,18,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33), 11, 13, 15(20),16,18,24-undecaen-3-yl]acetic acid: A mixture of methyl (2S)-2-(tert-butoxy)-2-[(22S)-4,18,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetate (8 mg, 0.012 mmol), NaOH (0.061 mL, 0.061 mmol) in MeOH (1.5 mL) was refluxed for 3 h. It was then filtered and prep-HPLC to isolate 1.4 mg (18%) of the desired product. $^1$H NMR (500 MHz, DMSO-d$_6$) δ 8.43 (s, 1H), 7.92 (d, J=7.9 Hz, 1H), 7.51 (t, J=7.6 Hz, 1H), 7.28 (d, J=7.6 Hz, 1H), 7.14 (d, J=7.6 Hz, 1H), 7.09 (s, 1H), 6.99 (s, 1H), 6.82 (d, J=7.3 Hz, 1H), 6.30 (br. s., 1H), 5.75-5.59 (m, 2H), 4.77 (t, J=11.6 Hz, 1H), 4.58 (br. s., 1H), 4.01-3.92 (m, 1H), 3.91-3.83 (m, 1H), 3.60-3.20 (m, 2H), 2.75 (d, J=7.3 Hz, 1H), 2.51 (s, 3H), 2.40-2.26 (m, 4H), 2.17 (br. s., 1H), 2.03 (d, J=13.7 Hz, 1H), 1.86 (d, J=12.5 Hz, 1H), 1.68-1.53 (m, 2H), 1.22 (s, 3H), 1.16 (s, 9H), 1.05 (d, J=6.1 Hz, 3H). LCMS (M+1)=639.3.

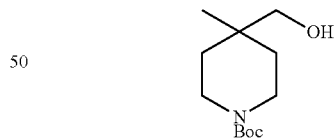

Intermediate 240 tert-Butyl 4-(hydroxymethyl)-4-methylpiperidine-1-carboxylate: A suspension of 1-(tert-butoxycarbonyl)-4-methylpiperidine-4-carboxylic acid (0.750 g, 3.08 mmol) in THF (5 mL) at rt under N$_2$ was treated with 2M THF solution of BH$_3$·SMe$_2$ (1.541 mL, 3.08 mmol). After 18 h, the reaction was cooled in an ice bath and quenched by the addition of 5 mL of 1N NaOH. Partitioned between ether and water. Organic phase dried (MgSO$_4$), filtered, and concentrated in vacuo to give 700 mg (99%) of tert-butyl 4-(hydroxymethyl)-4-methylpiperidine-1-carboxylate as a colorless oil. $^1$H NMR (400 MHz, CDCl$_3$) δ 3.86-3.64 (m, 3H), 3.41 (s, 2H), 3.15 (ddd, J=13.6, 10.2, 3.5 Hz, 2H), 1.94-1.80 (m, 1H), 1.52-1.43 (m, 10H), 1.31 (dt, J=13.5, 3.8 Hz, 2H), 1.01 (s, 3H).

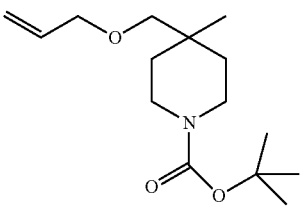

Intermediate 241 tert-Butyl 4-((allyloxy)methyl)-4-methylpiperidine-1-carboxylate: To a solution of e tert-butyl 4-(hydroxymethyl)-4-methylpiperidine-1-carboxylate (479 mg, 2.089 mmol) in DMA (3 mL) was added 60 wt % sodium hydride (125 mg, 3.13 mmol). Reaction immediately turned yellow. Stirred for 5 min and added 3-bromoprop-1-ene (1263 mg, 10.44 mmol). After 3 h, partitioned between EtOAc and sat.aq.NH$_4$Cl. The organic phase was washed with water (3×), brine and dried (MgSO$_4$), filtered, and concentrated to give 471 mg (75%) of tert-butyl 4-((allyloxy)methyl)-4-methylpiperidine-1-carboxylate as a colorless oil. $^1$H NMR (400 MHz, CDCl$_3$) δ 5.91 (ddt, J=17.2, 10.5, 5.3 Hz, 1H), 5.29 (dq, J=17.1, 1.7 Hz, 1H), 5.19 (dq, J=10.4, 1.5 Hz, 1H), 3.98 (dt, J=5.3, 1.5 Hz, 2H), 3.62 (br. s., 2H), 3.23-3.14 (m, 4H), 1.56-1.49 (m, 2H), 1.48 (s, 9H), 1.37-1.28 (m, 2H), 1.02 (s, 3H). LCMS (M+1)=270.25.

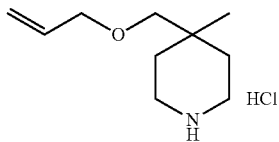

Intermediate 242

4-((Allyloxy)methyl)-4-methylpiperidine: tert-Butyl 4-((allyloxy)methyl)-4-methylpiperidine-1-carboxylate (300 mg, 1.114 mmol) was placed in a 25 mL RBF. A 2N solution of HCl/ether was added (7 mL) and the vessel was sealed with a septa. The colorless homogeneous solution was stirred for 24 h. An aliquot was removed and analyzed by 1H NMR which indicated that the reaction was complete. The reaction mixture was concentrated in vacuo to give 221 mg (96%) of 4-((allyloxy)methyl)-4-methylpiperidine as a white sticky solid. $^1$H NMR (500 MHz, DMSO-d$_6$) δ 8.88-8.42 (m, 2H), 5.90 (ddt, J=17.3, 10.5, 5.2 Hz, 1H), 5.35-5.12 (m, 2H), 3.96 (dt, J=5.2, 1.5 Hz, 2H), 3.24-3.16 (m, 2H), 3.12-2.93 (m, 4H), 1.70 (ddd, J=14.3, 10.0, 4.3 Hz, 2H), 1.43 (dt, J=14.2, 4.4 Hz, 2H), 0.98 (s, 3H).

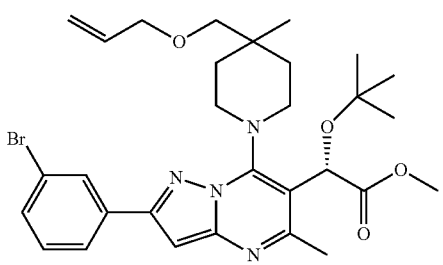

Intermediate 240

(S)-Methyl 2-(7-(4-((allyloxy)methyl)-4-methylpiperidin-1-yl)-2-(3-bromophenyl)-5-methylpyrazolo[1,5-a]pyrimidin-6-yl)-2-(tert-butoxy)acetate Intermediate 61 (558 mg, 1.195 mmol) was dissolved in DMF (100 mL). After flushing with N$_2$, 4-((allyloxy)methyl)-4-methylpiperidine, hydrochloride and Hunig's Base (0.626 mL, 3.59 mmol) were added to the reaction mixture. After stirring for 18 h at rt, the reaction was heated at 50° C. for 3 h. The reaction mixture was diluted with EtOAc. It was then added water. The organic layer was separated and dried over MgSO$_4$, filtered and concentrated to obtain 230 mg oil, which was then purified by prep HPLC (NH$_4$OAc/CH$_3$CN, 90%-100% B) to isolate 200 mg (28%) of the desired product as a white solid. $^1$H NMR (500 MHz, CDCl$_3$) δ 8.18 (s, 1H), 7.93 (d, J=7.7 Hz, 1H), 7.67-7.52 (m, 1H), 7.35 (t, J=7.9 Hz, 1H), 6.81 (s, 1H), 6.06 (s, 1H), 6.03-5.93 (m, 1H), 5.35 (dd, J=17.3, 1.5 Hz, 1H), 5.21 (dd, J=10.5, 1.7 Hz, 1H), 4.72-4.29 (m, 1H), 4.08 (br. s., 2H), 3.75 (s, 3H), 3.58-2.87 (m, 5H), 2.63 (s, 3H), 1.99-1.90 (m, 1H), 1.82 (ddd, J=13.0, 9.4, 4.0 Hz, 1H), 1.52 (d, J=13.4 Hz, 2H), 1.31-1.25 (m, 9H), 1.23 (br. s., 3H). LCMS (M+1)=599.15.

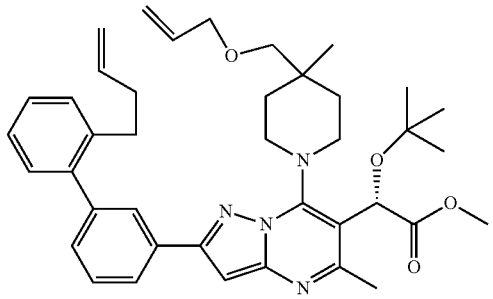

Intermediate 241

(S)-Methyl 2-(7-(4-((allyloxy)methyl)-4-methylpiperidin-1-yl)-2-(2'-(but-3-en-1-yl)-[1,1'-biphenyl]-3-yl)-5-methylpyrazolo[1,5-a]pyrimidin-6-yl)-2-(tert-butoxy)acetate:

A mixture of (2-(but-3-en-1-yl)phenyl)boronic acid (66.1 mg, 0.300 mmol), intermediate 240 (120 mg, 0.200 mmol), 2.0 M aqueous K$_2$CO$_3$ (0.200 mL, 0.400 mmol) in DMF (2 mL). The reaction was sparged with nitrogen for 10 minutes, treated with tetrakis(triphenylphosphine)palladium(0) (23.13 mg, 0.020 mmol) then sparged with nitrogen for 1 min. The reaction tube was sealed and then heated at 90° C. in a microwave tube for 1 h. The reaction was concentrated, then diluted with water (15 mL) and extracted wtih EtOAc. The EtOAc layer was washed with brine, then dried (Na$_2$SO$_4$), filtered, and concentrated under reduced pressure. The residue was purified by biotage (0%-20% EtOAc in hexanes) to isolate 100 mg (77%) of the desired product as an off-white foam. $^1$H NMR (500 MHz, CDCl$_3$) δ 8.02 (d, J=7.9 Hz, 1H), 7.98 (s, 1H), 7.53 (t, J=7.6 Hz, 1H), 7.39-7.30 (m, 5H), 6.84 (s, 1H), 6.07 (s, 1H), 5.99-5.84 (m, 1H), 5.74 (ddt, J=17.0, 10.3, 6.6 Hz, 1H), 5.35-5.26 (m, 1H), 5.18 (d, J=9.3 Hz, 1H), 4.97-4.86 (m, 2H), 4.60-2.80 (m, 2 H), 4.00 (br. s., 2H), 3.74 (s, 3H), 3.58-2.87 (m, 4H), 2.80-2.70 (m, 2H), 2.63 (s, 3H), 2.34-2.24 (m, 2H), 1.96-1.86 (m, 1H), 1.85-1.74 (m, 1H), 1.65-1.47 (m, 2H), 1.33-1.17 (m, 12H). LCMS (M+1)=651.41.

Intermediate 242

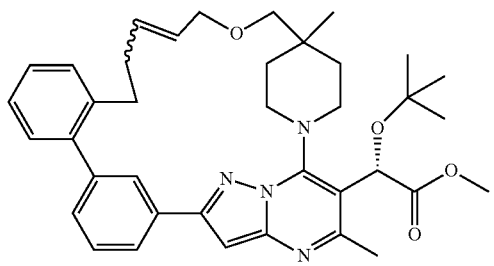

Methyl (2S)-2-(tert-butoxy)-2-[(23E)-4,28-dimethyl-26-oxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11, 13, 15(20),16,18,23-undecaen-3-yl]acetate: A mixture of intermediate 241 (80 mg, 0.123 mmol), (1,3-dimesitylimidazolidin-2-ylidene)(2-isopropoxybenzylidene)ruthenium(VI) chloride (7.70 mg, 0.012 mmol) in DCE (100 mL) was heated at 70° C. for 3 h. It was then concentrated and purified by biotage, eluting with 20% EtOAc/hexane to iafford 75 mg (98%) of the desired product as an oil. It was a mixture of isomers. LCMS (M+1)=623.4.

Intermediate 243

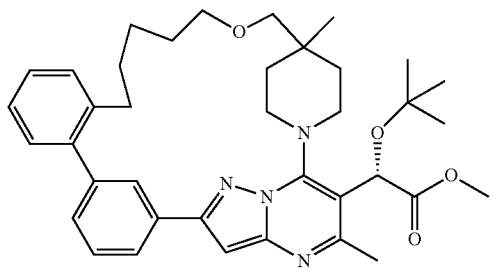

Methyl (2S)-2-(tert-butoxy)-2-{4,28-dimethyl-26-oxa-1,5,7,8-tetraazahexacyclo[26.2.2.1$^{6,9}$.1$^{10,14}$.0$^{2,7}$.0$^{15,20}$]tetratriaconta-2,4,6(34),8,10(33), 11,13,15 (20), 16,18-decaen-3-yl}acetate: A mixture of intermediate 242 (75 mg, 0.120 mmol), 10% Pd/C (12.82 mg, 0.012 mmol) in MeOH (1 mL) was stirred at rt for 1 h. It was then filtered and concentrated to obtain 70 mg (98%) of the desired product as a white solid. $^1$H NMR (400 MHz, CDCl$_3$) δ 8.07 (t, J=1.5 Hz, 1H), 7.81-7.71 (m, 1H), 7.51 (t, J=7.8 Hz, 1H), 7.37-7.33 (m, 2H), 7.30 (d, J=1.2 Hz, 1H), 7.27-7.21 (m, 2H), 6.83 (s, 1H), 5.92 (s, 1H), 4.36 (t, J=10.1 Hz, 1H), 3.86-3.79 (m, 1H), 3.75 (s, 3H), 3.50 (d, J=9.3 Hz, 1H), 3.46-3.35 (m, 2H), 3.31 (d, J=9.0 Hz, 1H), 3.23 (d, J=11.5 Hz, 1H), 2.96 (d, J=12.2 Hz, 1H), 2.80-2.70 (m, 2H), 2.61 (s, 3H), 2.06 (d, J=13.4 Hz, 1H), 1.77-1.30 (m, 9H), 1.28-1.26 (m, 12H). LCMS (M+1)=625.5.

EXAMPLE 106

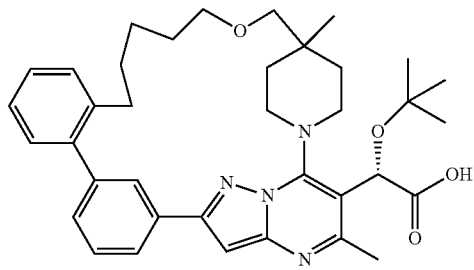 [SMILES: Cc1nc2cc3nn2c(c1[C@H](OC(C)(C)C)C(=O)O)N1CCC(C)(CC1)COCCCCCc1ccccc1-c1cccc-3c1]

(2S)-2-(tert-Butoxy)-2-{4,28-dimethyl-26-oxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl}acetic acid: Example 104 was prepared using intermediate 243 by following to the procedure to prepare example 26. $^1$H NMR (400 MHz, CDCl$_3$) δ 8.05 (s, 1H), 7.75 (d, J=7.5 Hz, 1H), 7.50 (t, J=7.7 Hz, 1H), 7.34 (d, J=3.5 Hz, 2H), 7.31-7.21 (m, 3H), 6.83 (s, 1H), 5.84 (br. s., 1H), 4.41 (t, J=10.2 Hz, 1H), 3.92-3.83 (m, 1H), 3.47-3.32 (m, 4H), 3.24 (d, J=9.3 Hz, 1H), 3.01 (d, J=12.5 Hz, 1H), 2.80-2.69 (m, 2H), 2.60 (s, 3H), 2.13 (br. s., 1H), 1.76-1.32 (m, 9H), 1.31-1.23 (m, 12H). LCMS (M+H)=611.3.

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:

1. A compound of Formula I

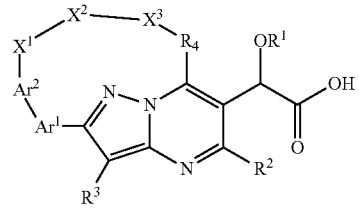

where:
R$^1$ is hydrogen, alkyl, or cycloalkyl;
R$^2$ is hydrogen or alkyl;
R$^3$ is hydrogen, alkyl or halo;
R$^4$ is cycloalkyl or Ar$^3$;
or R$^4$ is azetidinyl, pyrrolidinyl, piperidinyl, piperazinyl, morpholinyl, homopiperidinyl, homopiperazinyl, or homomorpholinyl, and is substituted with 0-3 alkyl substituents;
R$^5$ is hydrogen or alkyl;
Ar$^1$ is phenyl substituted with 0-3 substituents selected from cyano, halo, alkyl, haloalkyl, alkoxy, and haloalkoxy;
Ar$^2$ is phenyl, pyridinyl, pyridazinyl, pyrimidinyl, pyrazinyl, or trizainyl, and is substituted with 0-3 substituents selected from cyano, halo, alkyl, haloalkyl, alkoxy, haloalkoxy, and CON(R$^5$)$_2$;
Ar$^3$ is phenyl, chromanyl, or dihydrobenzoxazinyl, and is substituted with 0-3 substituents selected from cyano, halo, alkyl, haloalkyl, alkoxy, and haloalkoxy;
X$^1$ is CH, CH$_2$, O, S, or NR$^5$;
X$^2$ is alkylene or alkenylene; and
X$^3$ is CH, CH$_2$, CH$_2$O, O, S, or NR$^5$;
or a pharmaceutically acceptable salt thereof.

2. A compound of claim 1 where R$^1$ is alkyl; R$^2$ is alkyl; R$^3$ is hydrogen; R$^4$ is Ar$^3$ or is azetidinyl, pyrrolidinyl, piperidinyl, piperazinyl, morpholinyl, homopiperidinyl, homopiperazinyl, or homomorpholinyl substituted with 0-3 alkyl substituents; Ar$^1$ is phenyl substituted with 0-3 substituents selected from cyano, halo, alkyl, haloalkyl, alkoxy, and haloalkoxy; Ar$^2$ is phenyl substituted with 0-3 substituents selected from selected from cyano, halo, alkyl, haloalkyl, alkoxy, haloalkoxy, and CON(R$^5$)$_2$; Ar$^3$ is dihydrobenzoxazinyl substituted with 0-3 substituents selected from cyano, halo, alkyl, haloalkyl, alkoxy, and haloalkoxy; $X^1$ is $CH_2$ or O; $X^2$ is alkylene or alkenylene; and $X^3$ is CH, $CH_2$ or O; or a pharmaceutically acceptable salt thereof.

3. A compound of claim 2 where $R^1$ is alkyl; $R^2$ is alkyl; $R^3$ is hydrogen; $R^4$ is piperidinyl substituted with 0-1 alkyl substituents; $Ar^1$ is phenyl; $Ar^2$ is phenyl substituted with 0-3 substituents selected from cyano, halo, alkyl, haloalkyl, alkoxy, haloalkoxy, and $CON(R^5)_2$; $X^1$ is $CH_2$ or O; $X^2$ is alkylene or alkenylene; and $X^3$ is CH, $CH_2$ or O; or a pharmaceutically acceptable salt thereof.

4. A compound of claim 1 where $R^1$ is alkyl, $R^2$ is alkyl and $R^3$ is hydrogen.

5. A compound of claim 1 where $R^4$ is piperidinyl substituted with 0-3 alkyl substituents.

6. A compound of claim 1 where $Ar^1$ is phenyl.

7. A compound of claim 1 where $Ar^2$ is phenyl substituted with 0-3 substituents selected from cyano, halo, alkyl, haloalkyl, alkoxy, haloalkoxy, and $CON(R^5)_2$.

8. A compound of claim 1 where $Ar^3$ is chromanyl or dihydrobenzoxazinyl, and is substituted with 0-3 substituents selected from cyano, halo, alkyl, haloalkyl, alkoxy, and haloalkoxy.

9. A compound of claim 1 where $X^1$ is $CH_2$ or O; $X^2$ is alkylene or alkenylene; and $X^3$ is CH, $CH_2$ or O.

10. A compound of claim 1 selected from the group consisting of (2S)-2-(tert-Butoxy)-2-[(22Z)-32-chloro-4-methyl-28-oxa-5,7,8,25-tetraazaheptacyclo[23.6.2.$1^{6,9}.1^{10,14}.1^{15,19}.0^{2,7}.0^{29,33}$]hexatriaconta-1(31),2,4,6 (36),8,10(35),11,13,15(34),16,18,22,29,32-tetradecaen-3-yl]acetic acid;

(2S)-2-(tert-Butoxy)-2-[(22E)-32-chloro-4-methyl-28-oxa-5,7,8,25-tetraazaheptacyclo[23.6.2.$1^{6,9}.1^{10,14}.1^{15,19}.0^{2,7}.0^{29,33}$]hexatriaconta-1(31),2,4,6 (36),8,10(35),11,13,15(34),16,18,22,29,32-tetradecaen-3-yl]acetic acid;

(2S)-2-(tert-Butoxy)-2-{32-chloro-4-methyl-20,28-dioxa-5,7,8,25-tetraazaheptacyclo[23.6.2.$1^{6,9}.1^{10,14}.1^{15,19}.0^{2,7}.0^{29,33}$]hexatriaconta-1(31),2,4,6 (36),8,10(35),11,13,15(34),16,18,29,32-tridecaen-3-yl}acetic acid;

(2S)-2-(tert-Butoxy)-2-[(33-chloro-4-methyl-29-oxa-5,7,8,26-tetraazaheptacyclo[24.6.2.$1^{6,9}.1^{10,14}.0^{2,7}.0^{15,20}.0^{30,34}$]hexatriaconta-1(32),2,4,6 (36),8,10(35),11,13,15(20),16,18,23,30,33-tetradecaen-3-yl]acetic acid;

(2S)-2-(tert-Butoxy)-2-{35-chloro-4-methyl-21,31-dioxa-5,7,8,28-tetraazaheptacyclo[26.6.2.$1^{6,9}.1^{10,14}.0^{2,7}.0^{15,20}.0^{32,36}$]octatriaconta-1(34),2,4,6 (38),8,10(37),11,13,15(20),16,18,32,35-tridecaen-3-yl}acetic acid;

(2S)-2-(tert-Butoxy)-2-{32-fluoro-4-methyl-29-oxa-5,7,8,26-tetraazaheptacyclo[24.6.2.$1^{6,9}.1^{10,14}.0^{2,7}.0^{15,20}.0^{30,34}$]hexatriaconta-1(32),2,4,6 (36),8,10(35),11,13,15(20),16,18,30,33-tridecaen-3-yl}acetic acid;

(2S)-2-(tert-Butoxy)-2-{4,32-dimethyl-29-oxa-5,7,8,26-tetraazaheptacyclo[24.6.2.$1^{6,9}.1^{10,14}.0^{2,7}.0^{15,20}.0^{30,34}$]hexatriaconta-1(32),2,4,6(36),8,10(35),11,13,15(20),16,18,30,33-tridecaen-3-yl}acetic acid;

(2S)-2-(tert-butoxy)-2-{4-methyl-29-oxa-5,7,8-triazaheptacyclo[24.6.2.$1^{6,9}.1^{10,14}.0^{2,7}.0^{15,20}.0^{30,34}$]hexatriaconta-1(32),2,4,6(36),8,10(35),11,13,15(20),16,18,30,33-tridecaen-3-yl}acetic acid;

(2S)-2-(tert-butoxy)-2-{4-methyl-29-oxa-5,7,8-triazaheptacyclo[24.6.2.$1^{6,9}.1^{10,14}.0^{2,7}.0^{15,20}.0^{30,34}$]hexatriaconta-1(32),2,4,6(36),8,10(35),11,13,15(20),16,18,30,33-tridecaen-3-yl}acetic acid;

(2S)-2-(tert-Butoxy)-2-{4-methyl-28-oxa-5,7,8-triazaheptacyclo[23.6.2.$1^{6,9}.1^{10,14}.0^{2,7}.0^{15,20}.0^{29,33}$]pentatriaconta-1(31),2,4,6(35),8,10(34),11,13,15(20),16,18,29,32-tridecaen-3-yl}acetic acid;

(2S)-2-(tert-Butoxy)-2-{4-methyl-28-oxa-5,7,8-triazaheptacyclo[23.6.2.$1^{6,9}.1^{10,14}.0^{2,7}.0^{15,20}.0^{29,33}$]pentatriaconta-1(31),2,4,6(35),8,10(34),11,13,15(20),16,18,29,32-tridecaen-3-yl}acetic acid;

(2S)-2-(tert-Butoxy)-2-[(26R)-4-methyl-21,29-dioxa-5,7,8-triazaheptacyclo[24.6.2.$1^{6,9}.1^{10,14}.0^{2,7}.0^{15,20}.0^{30,34}$]hexatriaconta-1(32),2,4,6(36),8,10(35),11,13,15(20),16,18,30,33-tridecaen-3-yl]acetic acid;

(2S)-2-(tert-Butoxy)-2-[(26S)-4-methyl-21,29-dioxa-5,7,8-triazaheptacyclo[24.6.2.$1^{6,9}.1^{10,14}.0^{2,7}.0^{15,20}.0^{30,34}$]hexatriaconta-1(32),2,4,6(36),8,10(35),11,13,15 (20),16,18,30,33-tridecaen-3-yl]acetic acid;

(2S)-2-(tert-Butoxy)-2-[(26S)-4-methyl-21,29-dioxa-5,7,8-triazaheptacyclo[24.6.2.$1^{6,9}.1^{10,14}.0^{2,7}.0^{15,20}.0^{30,34}$]hexatriaconta-1(32),2,4,6(36),8,10(35),11,13,15(20),16,18,23,30,33-tetradecaen-3-yl]acetic acid;

(2S)-2-(tert-Butoxy)-2-[(26S)-4-methyl-21,29-dioxa-5,7,8-triazaheptacyclo[24.6.2.$1^{6,9}.1^{10,14}.0^{2,7}.0^{15,20}.0^{30,34}$]hexatriaconta-1(32),2,4,6(36),8,10(35),11,13,15(20),16,18,23,30,33-tetradecaen-3-yl]acetic acid;

(2S)-2-(tert-Butoxy)-2-{31-fluoro-4-methyl-29-oxa-5,7,8,26-tetraazaheptacyclo[24.6.2.$1^{6,9}.1^{10,14}.0^{2,7}.0^{15,20}.0^{30,34}$]hexatriaconta-1(32),2,4,6 (36),8,10(35),11,13,15(20),16,18,30,33-tridecaen-3-yl}acetic acid;

(2S)-2-(tert-Butoxy)-2-{33-chloro-4-methyl-29-oxa-5,7,8,26-tetraazaheptacyclo[24.6.2.$1^{6,9}.1^{10,14}.0^{2,7}.0^{15,20}.0^{30,34}$]hexatriaconta-1(32),2,4,6 (36),8,10(35),11,13,15(20),16,18,30,33-tridecaen-3-yl}acetic acid;

(2S)-2-(tert-Butoxy)-2-[4,27-dimethyl-26-oxa-1,5,7,8-tetraazahexacyclo[25.2.2.$1^{6,9}.1^{10,14}.0^{2,7}.0^{15,20}$]tritriaconta-2,4,6(33),8,10(32),11,13,15(20),16,18,23-undecaen-3-yl]acetic acid;

(2S)-2-(tert-Butoxy)-2-{4,27-dimethyl-26-oxa-1,5,7,8-tetraazahexacyclo[25.2.2.$1^{6,9}.1^{10,14}.0^{2,7}.0^{15,20}$]tritriaconta-2,4,6(33),8,10(32),11,13,15 (20),16,18-decaen-3-yl}acetic acid;

(2S)-2-(tert-Butoxy)-2-[(23E)-4,27-dimethyl-21,26-dioxa-1,5,7,8-tetraazahexacyclo[25.2.2.$1^{6,9}.1^{10,14}.0^{2,7}.0^{15,20}$]tritriaconta-2,4,6(33),8,10(32),11,13,15(20),16,18,23-undecaen-3-yl]acetic acid;

(2S)-2-(tert-Butoxy)-2-{4,27-dimethyl-21,26-dioxa-1,5,7,8-tetraazahexacyclo[25.2.2.$1^{6,9}.1^{10,14}.0^{2,7}.0^{15,20}$]tritriaconta-2,4,6(33),8,10(32),11,13,15(20),16,18-decaen-3-yl}acetic acid;

(2S)-2-(tert-Butoxy)-2-[(22R)-4,22,27-trimethyl-21,26-dioxa-1,5,7,8-tetraazahexacyclo[25.2.2.$1^{6,9}.1^{10,14}.0^{2,7}.0^{15,20}$]tritriaconta-2,4,6(33),8,10(32),11,13,15(20),16,18,23-undecaen-3-yl]acetic acid;

(2S)-2-(tert-Butoxy)-2-[(22S)-4,22,27-trimethyl-21,26-dioxa-1,5,7,8-tetraazahexacyclo[25.2.2.$1^{6,9}.1^{10,14}.0^{2,7}.0^{15,20}$]tritriaconta-2,4,6(33),8,10(32),11,13,15(20),16,18,23-undecaen-3-yl]acetic acid;

(2S)-2-(tert-Butoxy)-2-[(22S)-4,22,27-trimethyl-21,26-dioxa-1,5,7,8-tetraazahexacyclo[25.2.2.$1^{6,9}.1^{10,14}.0^{2,7}.0^{15,20}.0^{30,34}$]tritriaconta-2,4,6(33),8,10 (32),11,13,15(20),16,18-decaen-3-yl]acetic acid;

(2S)-2-(tert-Butoxy)-2-[(22R)-4,22,27-trimethyl-21,26-dioxa-1,5,7,8-tetraazahexacyclo[25.2.2.

1⁶,⁹.1¹⁰,¹⁴.0²,⁷.0¹⁵,²⁰]tritriaconta-2,4,6(33),8,10(32),
11,13,15(20),16,18-decaen-3-yl]acetic acid;
(2S)-2-(tert-Butoxy)-2-[4,28-dimethyl-21,27-dioxa-1,5,
7,8-tetraazahexacyclo[26.2.2.1⁶,⁹.1¹⁰,¹⁴.0²,⁷.0¹⁵,²⁰]tetratriaconta-2,4,6(34),8,10(33),11,13,15(20),16,18,24-undecaen-3-yl]acetic acid;
(2S)-2-(tert-Butoxy)-2-{4,28-dimethyl-21,27-dioxa-1,5,
7,8-tetraazahexacyclo[26.2.2.1⁶,⁹.1¹⁰,¹⁴.0²,⁷.0¹⁵,²⁰]tetratriaconta-2,4,6(34),8,10(33),11,13,15(20),16,18-decaen-3-yl}acetic acid;
(2S)-2-(tert-Butoxy)-2-[(22R)-4,22,28-trimethyl-21,27-dioxa-1,5,7,8-tetraazahexacyclo[26.2.2.
1⁶,⁹.1¹⁰,¹⁴.0²,⁷.0¹⁵,²⁰]tetratriaconta-2,4,6(34),8,10(33),
11,13,15(20),16,18-decaen-3-yl]acetic acid;
(2S)-2-(tert-Butoxy)-2-[(22S)-4,22,28-trimethyl-21,27-dioxa-1,5,7,8-tetraazahexacyclo[26.2.2.
1⁶,⁹.1¹⁰,¹⁴.0²,⁷.0¹⁵,²⁰]tetratriaconta-2,4,6(34),8,10(33),
11,13,15(20),16,18-decaen-3-yl]acetic acid;
(2S)-2-(tert-Butoxy)-2-{4,28-dimethyl-27-oxa-1,5,7,8-tetraazahexacyclo[26.2.2.1⁶,⁹.1¹⁰,¹⁴.0²,⁷.0¹⁵,²⁰]tetratriaconta-2,4,6(34),8,10(33),11,13,15(20),16,18-decaen-3-yl}acetic acid;
(2S)-2-(tert-Butoxy)-2-[17-chloro-4,27-dimethyl-21,26-dioxa-1,5,7,8-tetraazahexacyclo[25.2.2.
1⁶,⁹.1¹⁰,¹⁴.0²,⁷.0¹⁵,²⁰]tritriaconta-2,4,6(33),8,10(32),
11,13,15(20),16,18,23-undecaen-3-yl]acetic acid;
(2S)-2-(tert-Butoxy)-2-{17-chloro-4,27-di-q
methyl-21,26-dioxa-1,5,7,8-tetraazahexacyclo[25.2.2.
1⁶,⁹.1¹⁰,¹⁴.0²,⁷.0¹⁵,²⁰]tritriaconta-2,4,6(33),8,10(32),
11,13,15(20),16,18-decaen-3-yl}acetic acid;
(2S)-2-(tert-Butoxy)-2-[4,17,27-trimethyl-21,26-dioxa-1,
5,7,8-tetraazahexacyclo[25.2.2.1⁶,⁹.1¹⁰,¹⁴.0²,⁷.0¹⁵,²⁰]
tritriaconta-2,4,6(33),8,10(32),11,13,15(20),16,18,23-undecaen-3-yl]acetic acid;
(2S)-2-(tert-Butoxy)-2-{4,17,27-trimethyl-
21,26-dioxa-1,5,7,8-tetraazahexacyclo[25.2.2.
1⁶,⁹.1¹⁰,¹⁴.0²,⁷.0¹⁵,²⁰]tritriaconta-2,4,6(33),8,10(32),
11,13,15(20),16,18,24-undecaen-3-yl}acetic acid;
(2S)-2-(tert-Butoxy)-2-{4,17,27-trimethyl-
21,26-dioxa-1,5,7,8-tetraazahexacyclo[25.2.2.
1⁶,⁹.1¹⁰,¹⁴.0²,⁷.0¹⁵,²⁰]tritriaconta-2,4,6(33),8,10(32),
11,13,15(20),16,18-decaen-3-yl}acetic acid;
(2S)-2-(tert-Butoxy)-2-[(23E)-4,27-dimethyl-
26-oxa-1,5,7,8,17-pentaazahexacyclo[25.2.2.
1⁶,⁹.1¹⁰,¹⁴.0²,⁷.0¹⁵,²⁰]tritriaconta-2,4,6(33),8,10(32),
11,13,15(20),16,18,23-undecaen-3-yl]acetic acid;
(2S)-2-(tert-Butoxy)-2-[(23Z)-4,27-dimethyl-26-
oxa-1,5,7,8,17-pentaazahexacyclo[25.2.2.
1⁶,⁹.1¹⁰,¹⁴.0²,⁷.0¹⁵,²⁰]tritriaconta-2,4,6(33),8,10(32),
11,13,15(20),16,18,23-undecaen-3-yl]acetic acid;
(2S)-2-(tert-Butoxy)-2-{4,27-dimethyl-26-oxa-1,5,7,8,
17-pentaazahexacyclo[25.2.2.1⁶,⁹.1¹⁰,¹⁴.0²,⁷.0¹⁵,²⁰]tritriaconta-2,4,6(33),8,10(32),11,13,15(20),16,18-decaen-3-yl}acetic acid;
(2S)-2-(tert-Butoxy)-2-[(23Z,25E)-4,27-dimethyl-1,5,7,
8-tetraazahexacyclo[25.2.2.1⁶,⁹.1¹⁰,¹⁴.0²,⁷.0¹⁵,²⁰]tritriaconta-2,4,6(33),8,10(32),11,13,15(20),16,18,23,25-dodecaen-3-yl]acetic acid;
(2S)-2-(tert-Butoxy)-2-[(23E,25E)-4,27-dimethyl-1,5,7,
8-tetraazahexacyclo[25.2.2.1⁶,⁹.1¹⁰,¹⁴.0²,⁷.0¹⁵,²⁰]tritriaconta-2,4,6(33),8,10(32),11,13,15(20),16,18,23,25-dodecaen-3-yl]acetic acid;
(2S)-2-(tert-Butoxy)-2-{4,27-dimethyl-1,5,7,8-tetraazahexacyclo[25.2.2.1⁶,⁹.1¹⁰,¹⁴.0²,⁷.0¹⁵,²⁰]tritriaconta-2,
4,6(33),8,10(32),11,13,15(20),16,18-decaen-3-yl}acetic acid;

(2S)-2-(tert-Butoxy)-2-[(23Z,25E)-17-chloro-4,27-dimethyl-21-oxa-1,5,7,8-tetraazahexacyclo[25.2.2.
1⁶,⁹.1¹⁰,¹⁴.0²,⁷.0¹⁵,²⁰]tritriaconta-2,4,6(33),8,10(32),
11,13,15(20),16,18,23,25-dodecaen-3-yl]acetic acid;
(2S)-2-(tert-Butoxy)-2-[(23E,25E)-17-chloro-4,27-dimethyl-21-oxa-1,5,7,8-tetraazahexacyclo[25.2.2.
1⁶,⁹.1¹⁰,¹⁴.0²,⁷.0¹⁵,²⁰]tritriaconta-2,4,6(33),8,10(32),
11,13,15(20),16,18,23,25-dodecaen-3-yl]acetic acid;
(2S)-2-(tert-Butoxy)-2-{17-chloro-4,27-di-
methyl-21-oxa-1,5,7,8-tetraazahexacyclo[25.2.2.
1⁶,⁹.1¹⁰,¹⁴.0²,⁷.0¹⁵,²⁰]tritriaconta-2,4,6(33),8,10(32),
11,13,15(20),16,18-decaen-3-yl}acetic acid;
(2S)-2-(tert-Butoxy)-2-[(25E)-17-chloro-4,27-
dimethyl-21-oxa-1,5,7,8-tetraazahexacyclo[25.2.2.
1⁶,⁹.1¹⁰,¹⁴.0²,⁷.0¹⁵,²⁰]tritriaconta-2,4,6(33),8,10(32),
11,13,15(20),16,18,25-undecaen-3-yl]acetic acid;
(2S)-2-(tert-Butoxy)-2-{4,27-dimethyl-26-oxa-1,5,7,8,
19-pentaazahexacyclo[25.2.2.1⁶,⁹.1¹⁰,¹⁴.0²,⁷.0¹⁵,²⁰]tritriaconta-2,4,6(33),8,10(32),11,13,15(20),16,18-decaen-3-yl}acetic acid;
(2S)-2-(tert-Butoxy)-2-[(23Z)-18-fluoro-4,27-dimethyl-
21,26-dioxa-1,5,7,8-tetraazahexacyclo[25.2.2.
1⁶,⁹.1¹⁰,¹⁴.0²,⁷.0¹⁵,²⁰]tritriaconta-2,4,6(33),8,10(32),
11,13,15(20),16,18,23-undecaen-3-yl]acetic acid;
(2S)-2-(tert-Butoxy)-2-[(23E)-18-fluoro-4,27-dimethyl-
21,26-dioxa-1,5,7,8-tetraazahexacyclo[25.2.2.
1⁶,⁹.1¹⁰,¹⁴.0²,⁷.0¹⁵,²⁰]tritriaconta-2,4,6(33),8,10(32),
11,13,15(20),16,18,23-undecaen-3-yl]acetic acid;
(2S)-2-(tert-Butoxy)-2-{18-fluoro-4,27-dimethyl-
21,26-dioxa-1,5,7,8-tetraazahexacyclo[25.2.2.
1⁶,⁹.1¹⁰,¹⁴.0²,⁷.0¹⁵,²⁰]tritriaconta-2,4,6(33),8,10(32),
11,13,15(20),16,18-decaen-3-yl}acetic acid;
(2S)-2-(tert-Butoxy)-2-[(23E)-4,27-dimethyl-1,5,7,8,17-pentaazahexacyclo[25.2.2.1⁶,⁹.1¹⁰,¹⁴.0²,⁷.0¹⁵,²⁰]tritriaconta-2,4,6(33),8,10(32),11,13,15 (20),16,18,23-undecaen-3-yl]acetic acid;
(2S)-2-(tert-Butoxy)-2-[(23Z)-4,27-dimethyl-1,5,7,8,17-pentaazahexacyclo[25.2.2.1⁶,⁹.1¹⁰,¹⁴.0²,⁷.0¹⁵,²⁰]tritriaconta-2,4,6(33),8,10(32),11,13,15 (20),16,18,23-undecaen-3-yl]acetic acid;
(2S)-2-(tert-Butoxy)-2-{4,27-dimethyl-1,5,7,8,17-pentaazahexacyclo[25.2.2.1⁶,⁹.1¹⁰,¹⁴.0²,⁷.0¹⁵,²⁰]tritriaconta-2,4,6(33),8,10(32),11,13,15(20),16,18-decaen-3-yl}acetic acid;
(2S)-2-(tert-Butoxy)-2-[(22S,24E)-4,17,22,28-tetramethyl-21,27-dioxa-1,5,7,8-tetraazahexacyclo[26.2.2.
1⁶,⁹.1¹⁰,¹⁴.0²,⁷.0¹⁵,²⁰]tetratriaconta-2,4,6(34),8,10(33),
11,13,15(20),16,18,24-undecaen-3-yl]acetic acid;
(2S)-2-(tert-Butoxy)-2-[(22S,24Z)-4,17,22,28-tetramethyl-21,27-dioxa-1,5,7,8-tetraazahexacyclo[26.2.2.
1⁶,⁹.1¹⁰,¹⁴.0²,⁷.0¹⁵,²⁰]tetratriaconta-2,4,6(34),8,10(33),
11,13,15(20),16,18,24-undecaen-3-yl]acetic acid;
(2S)-2-(tert-Butoxy)-2-[(22S)-4,17,22,28-tetramethyl-21,
27-dioxa-1,5,7,8-tetraazahexacyclo[26.2.2.
1⁶,⁹.1¹⁰,¹⁴.0²,⁷.0¹⁵,²⁰]tetratriaconta-2,4,6(34),8,10(33),
11,13,15(20),16,18-decaen-3-yl]acetic acid;
(2S)-2-(tert-Butoxy)-2-[(22R)-4,22,27-trimethyl-21,26-dioxa-1,5,7,8,17-pentaazahexacyclo[25.2.2.
1⁶,⁹.1¹⁰,¹⁴.0²,⁷.0¹⁵,²⁰]tritriaconta-2,4,6(33),8,10(32),
11,13,15(20),16,18,23-undecaen-3-yl]acetic acid;
(2S)-2-(tert-Butoxy)-2-[(22S)-4,22,27-trimethyl-21,26-dioxa-1,5,7,8,17-pentaazahexacyclo[25.2.2.
1⁶,⁹.1¹⁰,¹⁴.0²,⁷.0¹⁵,²⁰]tritriaconta-2,4,6(33),8,10(32),
11,13,15(20),16,18,23-undecaen-3-yl]acetic acid;
(2S)-2-(tert-Butoxy)-2-[(22R)-4,17,22,27-tetramethyl-
21,26-dioxa-1,5,7,8-tetraazahexacyclo[25.2.2.

1⁶,⁹.1¹⁰,¹⁴.0²,⁷.0¹⁵,²⁰]tritriaconta-2,4,6(33),8,10(32), 11,13,15(20),16,18,23-undecaen-3-yl]acetic acid;
(2S)-2-(tert-Butoxy)-2-[(22S)-4,17,22,27-tetramethyl-21, 26-dioxa-1,5,7,8-tetraazahexacyclo[25.2.2. 1⁶,⁹.1¹⁰,¹⁴.0²,⁷.0¹⁵,²⁰]tritriaconta-2,4,6(33),8,10(32), 11,13,15(20),16,18,23-undecaen-3-yl]acetic acid;
(2S)-2-(tert-Butoxy)-2-[(22R)-4,17,22,27-tetramethyl-21,26-dioxa-1,5,7,8-tetraazahexacyclo[25.2.2. 1⁶,⁹.1¹⁰,¹⁴.0²,⁷.0¹⁵,²⁰]tritriaconta-2,4,6(33),8,10(32), 11,13,15(20),16,18-decaen-3-yl]acetic acid;
(2S)-2-(tert-Butoxy)-2-[(22S)-4,17,22,27-tetramethyl-21, 26-dioxa-1,5,7,8-tetraazahexacyclo[25.2.2. 1⁶,⁹.1¹⁰,¹⁴.0²,⁷.0¹⁵,²⁰]tritriaconta-2,4,6(33),8,10(32), 11,13,15(20),16,18-decaen-3-yl]acetic acid;
(2S)-2-(tert-Butoxy)-2-[17-fluoro-4,27-dimethyl-21,26-dioxa-1,5,7,8-tetraazahexacyclo[25.2.2. 1⁶,⁹.1¹⁰,¹⁴.0²,⁷.0¹⁵,²⁰]tritriaconta-2,4,6(33),8,10(32), 11,13,15(20),16,18,23-undecaen-3-yl]acetic acid;
(2S)-2-(tert-Butoxy)-2-{17-fluoro-4,27-dimethyl-21,26-dioxa-1,5,7,8-tetraazahexacyclo[25.2.2. 1⁶,⁹.1¹⁰,¹⁴.0²,⁷.0¹⁵,²⁰]tritriaconta-2,4,6(33),8,10(32), 11,13,15(20),16,18-decaen-3-yl}acetic acid;
(2S)-2-(tert-Butoxy)-2-[(22S)-4,17,22,29-tetramethyl-21,28-dioxa-1,5,7,8-tetraazahexacyclo[27.2.2.1⁶,⁹.1¹⁰,¹⁴.0²,⁷.0¹⁵,²⁰]pentatriaconta-2,4,6(35), 8,10(34),11,13,15(20),16,18,25-undecaen-3-yl]acetic acid;
(2S)-2-(tert-Butoxy)-2-[(22S)-4,17,22,29-tetramethyl-21,28-dioxa-1,5,7,8-tetraazahexacyclo[27.2.2.1⁶,⁹.1¹⁰,¹⁴.0²,⁷.0¹⁵,²⁰]pentatriaconta-2,4,6(35), 8,10(34),11,13,15(20),16,18-decaen-3-yl]acetic acid;
(2S)-2-(tert-Butoxy)-2-[(22S)-18-chloro-4,17,22,28-tetramethyl-21,27-dioxa-1,5,7,8-tetraazahexacyclo[26.2.2.1⁶,⁹.1¹⁰,¹⁴.0²,⁷.0¹⁵,²⁰]tetratriaconta-2,4,6(34), 8,10(33),11,13,15(20),16,18,24-undecaen-3-yl]acetic acid;
(2S)-2-(tert-butoxy)-2-[(22S)-18-chloro-4,17,22,28-tetramethyl-21,27-dioxa-1,5,7,8-tetraazahexacyclo[26.2.2.1⁶,⁹.1¹⁰,¹⁴.0²,⁷.0¹⁵,²⁰]tetratriaconta-2,4,6(34), 8,10(33),11,13,15(20),16,18-decaen-3-yl]acetic acid;
(2S)-2-(tert-Butoxy)-2-[(22S,24E)-16-fluoro-4,17,22,28-tetramethyl-21,27-dioxa-1,5,7,8-tetraazahexacyclo[26.2.2.1⁶,⁹.1¹⁰,¹⁴.0²,⁷.0¹⁵,²⁰]tetratriaconta-2,4,6(34), 8,10(33),11,13,15(20),16,18,24-undecaen-3-yl]acetic acid;
(2S)-2-(tert-Butoxy)-2-[(22S,24Z)-16-fluoro-4,17,22,28-tetramethyl-21,27-dioxa-1,5,7,8-tetraazahexacyclo[26.2.2.1⁶,⁹.1¹⁰,¹⁴.0²,⁷.0¹⁵,²⁰]tetratriaconta-2,4,6(34), 8,10(33),11,13,15(20),16,18,24-undecaen-3-yl]acetic acid;
(2S)-2-(tert-Butoxy)-2-[(22S)-16-fluoro-4,17,22,28-tetramethyl-21,27-dioxa-1,5,7,8-tetraazahexacyclo[26.2.2.1⁶,⁹.1¹⁰,¹⁴.0²,⁷.0¹⁵,²⁰]tetratriaconta-2,4,6(34), 8,10(33),11,13,15(20),16,18-decaen-3-yl]acetic acid;
(2S)-2-(tert-Butoxy)-2-[(22S)-17-isocyano-4,22,28-trimethyl-21,27-dioxa-1,5,7,8-tetraazahexacyclo[26.2.2. 1⁶,⁹.1¹⁰,¹⁴.0²,⁷.0¹⁵,²⁰]tetratriaconta-2,4,6(34),8,10(33), 11,13,15(20),16,18,24-undecaen-3-yl]acetic acid;
(2S)-2-(tert-Butoxy)-2-[(22S)-17-carbamoyl-4,22,27-trimethyl-21,26-dioxa-1,5,7,8-tetraazahexacyclo[25.2.2.1⁶,⁹.1¹⁰,¹⁴.0²,⁷.0¹⁵,²⁰]tritriaconta-2,4,6(33),8, 10(32),11,13,15(20),16,18,23-undecaen-3-yl]acetic acid;
(2S)-2-(tert-Butoxy)-2-[(22S)-17-cyano-4,22,28-trimethyl-21,27-dioxa-1,5,7,8-tetraazahexacyclo[26.2.2. 1⁶,⁹.1¹⁰,¹⁴.0²,⁷.0¹⁵,²⁰]tetratriaconta-2,4,6(34),8,10(33), 11,13,15(20),16,18-decaen-3-yl]acetic acid;
(2S)-2-(tert-Butoxy)-2-[(22S)-4,18,22,28-tetramethyl-21,27-dioxa-1,5,7,8-tetraazahexacyclo[26.2.2.1⁶,⁹.1¹⁰,¹⁴.0²,⁷.0¹⁵,²⁰]tetratriaconta-2,4,6(34), 8,10(33),11,13,15(20),16,18-decaen-3-yl]acetic acid;
(2S)-2-(tert-Butoxy)-2-[(22S)-4,17,18,22,28-pentamethyl-21,27-dioxa-1,5,7,8-tetraazahexacyclo[26.2.2. 1⁶,⁹.1¹⁰,¹⁴.0²,⁷.0¹⁵,²⁰]tetratriaconta-2,4,6(34),8,10(33), 11,13,15(20),16,18,24-undecaen-3-yl]acetic acid;
(2S)-2-(tert-Butoxy)-2-[(22S)-4,17,18,22,28-pentamethyl-21,27-dioxa-1,5,7,8-tetraazahexacyclo[26.2.2. 1⁶,⁹.1¹⁰,¹⁴.0²,⁷.0¹⁵,²⁰]tetratriaconta-2,4,6(34),8,10(33), 11,13,15(20),16,18-decaen-3-yl]acetic acid;
(2S)-2-(tert-Butoxy)-2-[(22S)-4,16,22,28-tetramethyl-21,27-dioxa-1,5,7,8-tetraazahexacyclo[26.2.2.1⁶,⁹.1¹⁰,¹⁴.0²,⁷.0¹⁵,²⁰]tetratriaconta-2,4,6(34), 8,10(33),11,13,15(20),16,18-decaen-3-yl]acetic acid;
(2S)-2-(tert-Butoxy)-2-[(22S)-18-fluoro-4,17,22,28-tetramethyl-21,27-dioxa-1,5,7,8-tetraazahexacyclo[26.2.2.1⁶,⁹.1¹⁰,¹⁴.0²,⁷.0¹⁵,²⁰]tetratriaconta-2,4,6(34), 8,10(33),11,13,15(20),16,18,24-undecaen-3-yl]acetic acid;
(2S)-2-(tert-Butoxy)-2-[(22S)-18-fluoro-4,17,22,28-tetramethyl-21,27-dioxa-1,5,7,8-tetraazahexacyclo[26.2.2.1⁶,⁹.1¹⁰,¹⁴.0²,⁷.0¹⁵,²⁰]tetratriaconta-2,4,6(34), 8,10(33),11,13,15(20),16,18-decaen-3-yl]acetic acid;
(2S)-2-(tert-Butoxy)-2-[(22S)-4,22,28-trimethyl-17-(trifluoromethyl)-21,27-dioxa-1,5,7,8-tetraazahexacyclo[26.2.2.1⁶,⁹.1¹⁰,¹⁴.0²,⁷.0¹⁵,²⁰]tetratriaconta-2,4,6(34), 8,10(33),11,13,15(20),16,18-decaen-3-yl]acetic acid;
(2S)-2-(tert-Butoxy)-2-[(22S)-17-fluoro-4,22,28-trimethyl-21,27-dioxa-1,5,7,8-tetraazahexacyclo[26.2.2. 1⁶,⁹.1¹⁰,¹⁴.0²,⁷.0¹⁵,²⁰]tetratriaconta-2,4,6(34),8,10(33), 11,13,15(20),16,18-decaen-3-yl]acetic acid;
(2S)-2-(tert-Butoxy)-2-[(22S)-17-chloro-4,22,28-trimethyl-21,27-dioxa-1,5,7,8-tetraazahexacyclo[26.2.2. 1⁶,⁹.1¹⁰,¹⁴.0²,⁷.0¹⁵,²⁰]tetratriaconta-2,4,6(34),8,10(33), 11,13,15(20),16,18-decaen-3-yl]acetic acid;
(2S)-2-(tert-Butoxy)-2-[(22S)-18-fluoro-4,22,28-trimethyl-21,27-dioxa-1,5,7,8-tetraazahexacyclo[26.2.2. 1⁶,⁹.1¹⁰,¹⁴.0²,⁷.0¹⁵,²⁰]tetratriaconta-2,4,6(34),8,10(33), 11,13,15(20),16,18-decaen-3-yl]acetic acid;
(2S)-2-(tert-Butoxy)-2-[(22S)-16-fluoro-4,22,28-trimethyl-21,27-dioxa-1,5,7,8-tetraazahexacyclo[26.2.2. 1⁶,⁹.1¹⁰,¹⁴.0²,⁷.0¹⁵,²⁰]tetratriaconta-2,4,6(34),8,10(33), 11,13,15(20),16,18-decaen-3-yl]acetic acid;
(2S)-2-(tert-Butoxy)-2-[(22S)-16-chloro-4,22,28-trimethyl-21,27-dioxa-1,5,7,8-tetraazahexacyclo[26.2.2. 1⁶,⁹.1¹⁰,¹⁴.0²,⁷.0¹⁵,²⁰]tetratriaconta-2,4,6(34),8,10(33), 11,13,15(20),16,18-decaen-3-yl]acetic acid;
(2S)-2-(tert-Butoxy)-2-[(22S)-18-chloro-4,22,28-trimethyl-21,27-dioxa-1,5,7,8-tetraazahexacyclo[26.2.2. 1⁶,⁹.1¹⁰,¹⁴.0²,⁷.0¹⁵,²⁰]tetratriaconta-2,4,6(34),8,10(33), 11,13,15(20),16,18-decaen-3-yl]acetic acid;
(2S)-2-(tert-Butoxy)-2-[(22S)-18-cyano-4,22,28-trimethyl-21,27-dioxa-1,5,7,8-tetraazahexacyclo[26.2.2. 1⁶,⁹.1¹⁰,¹⁴.0²,⁷.0¹⁵,²⁰]tetratriaconta-2,4,6(34),8,10(33), 11,13,15(20),16,18-decaen-3-yl]acetic acid;
(2S)-2-(tert-Butoxy)-2-[(22S)-17-chloro-4,18,22,28-tetramethyl-21,27-dioxa-1,5,7,8-tetraazahexacyclo[26.2.2.1⁶,⁹.1¹⁰,¹⁴.0²,⁷.0¹⁵,²⁰]tetratriaconta-2,4,6(34), 8,10(33),11,13,15(20),16,18-decaen-3-yl]acetic acid;
(2S)-2-(tert-Butoxy)-2-[(22S)-17-chloro-4,16,22,28-tetramethyl-21,27-dioxa-1,5,7,8-tetraazahexacyclo[26.2.2.1⁶,⁹.1¹⁰,¹⁴.0²,⁷.0¹⁵,²⁰]tetratriaconta-2,4,6(34), 8,10(33),11,13,15(20),16,18-decaen-3-yl]acetic acid;

(2S)-2-(tert-Butoxy)-2-[(22R)-17-chloro-4,18,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-Butoxy)-2-[(22S)-17-fluoro-4,18,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-Butoxy)-2-{4,17,22,23,28-pentamethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl}acetic acid;

(2S)-2-(tert-Butoxy)-2-{4,17,22,23,28-pentamethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl}acetic acid;

(2S)-2-(tert-Butoxy)-2-{4,17,22,23,28-pentamethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl}acetic acid;

(2S)-2-(tert-Butoxy)-2-{4,17,22,23,28-pentamethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl}acetic acid;

(2S)-2-[(2-Methylbutan-2-yl)oxy]-2-[(22S)-4,17,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(1-Methylcyclobutoxy)-2-[(22S)-4,17,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-[(2-Methylbutan-2-yl)oxy]-2-[(22S)-4,17,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-[(22S)-16-Chloro-4,13,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15,17,19-decaen-3-yl][(2-methyl-2-propanyl)oxy]acetic acid;

(2S)-[(22S)-16-Chloro-4,13,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15,17,19-decaen-3-yl][(2-methyl-2-propanyl)oxy]acetic acid;

(2S)-[(22S)-16-Chloro-4,13,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15,17,19-decaen-3-yl][(2-methyl-2-propanyl)oxy]acetic acid;

(2S)-[(22S)-16-Chloro-13-fluoro-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15,17,19-decaen-3-yl][(2-methyl-2-propanyl)oxy]acetic acid;

(2S)-2-(tert-Butoxy)-2-{4,17,23,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl}acetic acid;

(2S)-2-(tert-Butoxy)-2-{4,17,23,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl}acetic acid;

(2S)-2-(tert-butoxy)-2-[(22S,24E)-4,18,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetic acid; and (2S)-2-(tert-Butoxy)-2-{4,28-dimethyl-26-oxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl}acetic acid or a pharmaceutically acceptable salt thereof.

11. A compound of claim 1 selected from the group consisting of (2S)-2-(tert-butoxy)-2-[(22S)-4,17,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-butoxy)-2-[(22S)-16-chloro-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-butoxy)-2-[(22S)-16-fluoro-4,17,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-butoxy)-2-[(22S)-16-fluoro-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-butoxy)-2-[(22S)-17-fluoro-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-butoxy)-2-[(22S)-18-fluoro-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-butoxy)-2-[(22S,24E)-16-fluoro-4,17,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetic acid;

(2S)-2-(tert-butoxy)-2-[(22S,24E)-4,17,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18,24-undecaen-3-yl]acetic acid;

(2S)-2-(tert-butoxy)-2-[(22S)-4,17,18,22,28-pentamethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

(2S)-2-(tert-butoxy)-2-[(22S)-18-chloro-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid and (2S)-2-(tert-butoxy)-2-[(22S)-17-cyano-4,22,28-trimethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

or a pharmaceutically acceptable salt thereof.

12. The compound of claim 1: (2S)-2-(tert-butoxy)-2-[(22S)-4,17,22,28-tetramethyl-21,27-dioxa-1,5,7,8-tetraazahexacyclo[26.2.2.1$^{6,9}$.1$^{10,14}$.0$^{2,7}$.0$^{15,20}$]tetratriaconta-2,4,6(34),8,10(33),11,13,15(20),16,18-decaen-3-yl]acetic acid;

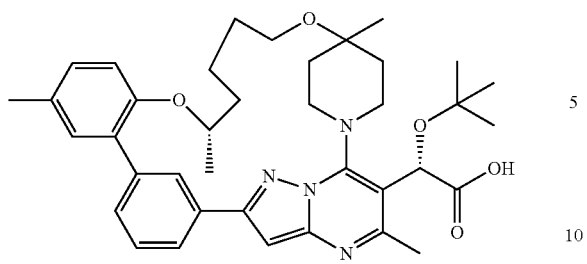

or a pharmaceutically acceptable salt thereof.

13. A pharmaceutical composition comprising a therapeutic amount of a compound of claim 1 and a pharmaceutically acceptable carrier.

14. A method for treating HIV infection comprising administering a therapeutically effective amount of a compound of claim 1, or a pharmaceutically acceptable salt thereof, to a patient in need thereof.

15. The method of claim 14 further comprising administering a therapeutically effective amount of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

* * * * *